(12) United States Patent  
Schirmer et al.

(10) Patent No.: US 8,323,924 B2
(45) Date of Patent: Dec. 4, 2012

(54) METHODS AND COMPOSITIONS FOR PRODUCING HYDROCARBONS

(75) Inventors: Andreas Schirmer, South San Francisco, CA (US); Mathew Rude, South San Francisco, CA (US); Shane Brubaker, Oakland, CA (US)

(73) Assignee: LS9, Inc., South San Francisco, CA (US)

( * ) Notice: Subject to any disclaimer, the term of this patent is extended or adjusted under 35 U.S.C. 154(b) by 238 days.

(21) Appl. No.: 12/710,237

(22) Filed: Feb. 22, 2010

(65) Prior Publication Data

US 2010/0249470 A1 Sep. 30, 2010

Related U.S. Application Data

(63) Continuation-in-part of application No. PCT/US2009/044403, filed on May 18, 2009.

(60) Provisional application No. 61/053,955, filed on May 16, 2008.

(51) Int. Cl.
C12P 1/00 (2006.01)

(52) U.S. Cl. ....... 435/41; 435/183; 435/189; 435/252.3; 536/23.2

(58) Field of Classification Search .................. 435/41, 435/252.3, 189, 183; 536/23.2
See application file for complete search history.

(56) References Cited

U.S. PATENT DOCUMENTS

| | | | |
|---|---|---|---|
| 5,000,000 | A | 3/1991 | Ingram et al. |
| 5,028,539 | A | 7/1991 | Ingram et al. |
| 5,424,202 | A | 6/1995 | Ingram et al. |
| 5,482,846 | A | 1/1996 | Ingram et al. |
| 5,602,030 | A | 2/1997 | Ingrahm et al. |
| 5,807,893 | A | 9/1998 | Voelker et al. |
| 7,056,714 | B2 | 6/2006 | Rosazza et al. |
| 7,118,896 | B2 | 10/2006 | Kalscheuer |
| 7,169,588 | B2 | 1/2007 | Burch et al. |
| 7,425,433 | B2 | 9/2008 | Rosazza et al. |
| 7,897,369 | B2 | 3/2011 | Schmidt-Dannert et al. |
| 2003/0097686 | A1 | 5/2003 | Knauf et al. |
| 2003/0129601 | A1 | 7/2003 | Cole |
| 2003/0233675 | A1 | 12/2003 | Cao et al. |
| 2004/0180400 | A1 | 9/2004 | Rosazza et al. |
| 2004/0197896 | A1 | 10/2004 | Cole |
| 2007/0281345 | A1 | 12/2007 | Binder |
| 2008/0221310 | A1 | 9/2008 | O'Sullivan et al. |
| 2009/0047721 | A1 | 2/2009 | Trimbur et al. |
| 2009/0084025 | A1 | 4/2009 | Bhatia et al. |
| 2009/0117629 | A1 | 5/2009 | Schmidt-Dannert et al. |
| 2010/0105955 | A1 | 4/2010 | Alibhai et al. |
| 2010/0105963 | A1 | 4/2010 | Hu |
| 2010/0221798 | A1 | 9/2010 | Schirmer et al. |
| 2010/0242345 | A1 | 9/2010 | Keasling et al. |
| 2010/0249470 | A1 | 9/2010 | Schirmer et al. |
| 2010/0251601 | A1 | 10/2010 | Hu et al. |
| 2011/0124071 | A1 | 5/2011 | Schirmer et al. |

FOREIGN PATENT DOCUMENTS

| | | |
|---|---|---|
| WO | WO-2007/003736 | 1/2007 |
| WO | WO-2007/136762 A2 | 11/2007 |
| WO | WO-2008/058788 | 5/2008 |
| WO | WO-2008/-119082 | 10/2008 |
| WO | WO 2009/042950 A1 | 4/2009 |
| WO | WO-2009/140695 | 11/2009 |
| WO | WO-2009/140696 | 11/2009 |
| WO | WO-2010/042664 | 4/2010 |
| WO | WO-2010/062480 A2 | 6/2010 |
| WO | WO 2008/119082 A2 | 10/2010 |
| WO | WO 2011/062987 A2 | 5/2011 |

OTHER PUBLICATIONS

Atsumi, et al., "Non-fermentative Pathways for Synthesis of Branched-chain Higher Alcohols as Biofuelds," Nature, vol. 451, Jan. 2008, 5 pages.
Bergler, et al., "Protein EnvM Is the NADH-dependent Enoyl-ACP Reductase (FabI) of *Escherichia coli*\*," The Journal of Biological Chemistry, vol. 269, No. 8, Issue Feb. 1994, pp. 5943-5946, 4 pages.
Black, et al., "Cloning, Sequencing, and Expression of the fadD Gene of *Escherichia Coli* Encoding Acyl Coenzyme A Synthetase\*," The Journal of Biological Chemistry, vol. 267, No. 35, Issue of Dec. 1992, pp. 25513-25520, 8 pages.
Campbell, et al., "A New *Escherichia coli* Metabolic Competency: Growth on Fatty Acids by a Novel Anaerobic β-oxidation Pathway," Molecular Microbiology, 2003, 47(3), pp. 793-805, 13 pages.
Caviglia, et al., "Rat Long Chain Acyl-CoA Synthetase 5, but Not 1, 2, 3, or 4, Complements *Escherichia coli* fadD\*," The Journal of Biological Chemistry, vol. 279, No. 12, Issue of Mar. 2004, pp. 11163-11169, 7 pages.
Datsenko, et al., "One-step Inactivation of Chromosomal Genes in *Escherichia coli* K-12 using PCR Products," Proc. Natl. Acad. Sci, USA 97, 2000, pp. 6640-6645, 6 pages.
He, et al., "*Nocardia* sp. Carboxylic Acid Reductase: Cloning, Expression, and Characterization of a New Aldehyde Oxidoreductase Family," Applied and Environmental Microbiology, Mar. 2004, pp. 1874-1881, 8 pages.
Hoffmeister, et al., "Mitochondrial *trans*—2-Enoyl-CoA Reductase of Wax Ester Fermentation from *Euglena gracilis* Defines a New Family of Enzymes Involved in Lipid Synthesis\*," The Journal of Biological Chemistry, vol. 280, No. 6, Issue of Feb. 2005, pp. 4329-4338, 10 pages.
Inui, et al., "Fatty Acid Synthesis in Mitochondria of *Euglena gracilis*," Eur. J. Biochem. 142, 1984, pp. 121-126, 6 pages. Johnson, et al., "Genetic Analysis of the Role of *Saccharomyces cerevisiae* Acyl-CoA Synthetase Genes in Regulating Protein N-Myristoylation\*," The Journal of Biological Chemistry, vol. 269, No. 27, Issue of Jul. 1994, pp. 18037-18046, 10 pages.
Knoll, et al., "Biochemical Studies of Three *Saccharomyces cerevisiae* Acyl-CoA Synthetases, Faa1p, Faa2p, and Faa3p\*," The Journal of Biological Chemistry, vol. 269, No. 23, Issue of Jun. 1994, pp. 16348-16356, 9 pages.
Li, et al., "Purification, Characterization, and Properties of an Aryl Aldehyde Oxidoreductase from *Nocardia* Sp. Strain NRRL 5646," Journal of Bacteriology, Jun. 1997, pp. 3482-3487, 6 pages.
Mackey, et al., "Detection of Rhythmic Bioluminescense from Luciferase Reporters in Cyanobacteria," Methods in Molecular Biology, vol. 362, 2007, 16 pages.
Marrakchi, et al., "A New Mechanism for Anaerobic Unsaturated Fatty Acid Formation in *Streptococcus pneumoniae*\*," The Journal of Biological Chemistry, vol. 277, No. 47, Issue of Nov. 2002, pp. 44809-44816, 6 pages.

(Continued)

Primary Examiner — Tekchand Saidha
(74) Attorney, Agent, or Firm — Linda R. Judge; LS9, Inc.

(57) ABSTRACT

Compositions and methods for producing aldehydes, alkanes, and alkenes are described herein. The aldehydes, alkanes, and alkenes can be used in biofuels.

12 Claims, 62 Drawing Sheets

OTHER PUBLICATIONS

Mayer, et al., "Identification of Amino Acid Residues Involved in Substrate Specificity of Plant Acyl-ACP Thioesterases Using a Bioinformatics-guided Approach," BMC Plant Biology, Jan. 2007, 11 pages.

Morgan-Kiss, et al., "The *Lactococcus lactis* FabF Fatty Acid Synthetic Enzyme can Functionally Replace both the FabB and FabF Proteins of *Escherichia coli* and the FabH Protein of *Lactococcus lactis*," Arch Microbiol., 2008, 190, pp. 427-437, 11 pages.

Naccarato, et al., "In Vivo and in Vitro Biosynthesis of Free Fatty Alcohols in *Exscherichia coli* K-12," Lipids vol. 9, No. 6, 1973, 10 pages.

Reiser, et al., "Isolation of Mutants of *Acinetobacter calcoaceticus* Deficient in Wax Ester Synthesis of Complementation of One Mutation with a Gene Encoding a Fatty Acyl Coenzyme A Reductase," Journal of Bacteriology, May 1997, pp. 2969-2975, 7 pages.

Shockey, et al., "Arabidopsis Contains Nine Long-Chain Acyl-Coenzyme A Synthetase Genes that Participate in Fatty Acid and Glycerolipid Metabolism," Plant Physiology, Aug. 2002, vol. 129, pp. 1710-1722, 13 pages.

Spencer, et al., "Thioesterases I and II of *Escherichia coli*," The Journal of Biological Chemistry, vol. 253, No. 17, Issue Sep. 1978, pp. 5922-5926, 5 pages.

Tucci, et al., "A Novel Prokaryotic *trans*—2-enoyl-CoA reductase from the Spirochete *Treponema denticola*," FEBS Letters 581, 2007, pp. 1561-1566, 6 pages.

Venkitasubramanian, et al., "Reduction of Carboxylic Acids by *Nocardia* Aldehyde Oxidoreductase Requires a Phosphopantetheinylated Enzyme*," The Journal of Biological Chemistry, vol. 282, No. 1, pp. 478-485, Jan. 2007, 8 pages.

Doss, R., P. et al., "Composition and Enzymatic Activity of the Extracellular Matrix Secreted by Germlings of Botrytis Cinerea," Applied and Environmental Microbiology, Feb. 1999, vol. 65(2), pp. 404-408.

Fleischmant et al., Accession No. YP_889972/GI:118469671, 2006, 3 pages.

International Search Report and Written Opinion of the International Searching Authority of the United States Patent and Trademark Office for PCT/US2009/059903, mailing date of Jun. 2, 2010, 13 pages.

International Search Report and Written Opinion of the International Searching Authority of the United States Patent and Trademark Office for PCT/US2009/59904, mailing date of Apr. 5, 2010, 11 pages.

NCBI Reference Sequence YP_889972.1, Putative Long-Chain Fatty-Acid-CoA Ligase [*Mycobacterium smegmatis* Str. MC2 155], retrieved from http://www.ncbi.nlm.nih.gov/protein/118469671, 4 pages.

NCBI Reference, Putative Alcohol Dehydrogenase [*Acinetobacter* sp. ADP1], 2010, retrieved from http://www.ncbi.nlm.nih.gov/protein/49532534.

Jiang, et al., "Inhibition of Fatty Acid Synthesis in *Escherichia coli* in the Absence of Phospholipid Synthesis and Release of Inhibition by Thioesterase Action," Journal of Bacteriology, vol. 176, No. 10, May 1994, pp. 2814-2821.

Kalscheuer, et al., "Microdiesel: *Escherichia coli* Engineered for Fuel Production," Microbiology, 2006, 152, pp. 2529-2536.

Lykidis, et al., "Genomic Prospecting for Microbial Biodiesel Production," NN, Jun. 2008, 41 pages.

Morgan-Kiss et al., "The *Escherichia coli fadK* (ydiD) Gene Encodes an Anerobically Regulated Short Chain Acyl-CoA Synthetase*," The Journal of Biological Chemistry, vol. 279, No. 36, Sep. 2004, pp. 37324-37333.

Partial International Search Report from the International Search Authority of the European Patent Office, for PCT/US2008/058788, mailing date May 11, 2008, 4 pages.

Voelker, et al., "Alteration of the Specifity and Regulation of Fatty Acid Synthesis of *Escherichia coli* by Expression of a Plant Medium-Chain Acyl-Acyl Carrier Protein Thioesterase," Journal of Bacteriology, vol. 176, No. 23, Dec. 1994, pp. 7320-7327.

Yuan-Zheng, et al., Metabolic Engineering of *Aeromonas hydrophila* for the Enhanced Production of poly(3-hydroxybutyrate-co-3-hydroxyhexanoate), Appl. Microbiol. Biotechnol., 2006, 69, pp. 537-532.

Zheng, et al., "Thioesterase II of *Escherichia coli* Plays an Important Role in 3-Hydroxydecanoic Acid Production," Applied and Environmental Microbiology, vol. 70, No. 7, Jul. 2004, pp. 3807-3813, 7 pages.

Zhang, et al., "Molecular Effect of FadD on the Regulation and Metabolism of Fatty Acid in *Escherichia Coli*," FEMS Microbiol Lett, 259, 2006, pp. 249-253.

Database EMBL (Online), Jul. 1996, "*Synechococcus*, PC07942 Ribosomal Protein S1 of 30S Ribosome (rpsl), ORF271, ORF231, ORF341, Carboxyltransferase alpha subunit (accA), ORF245, ORF227, and GTP cyclohydrolase I (folE) genes, complete cds, and ORF205 gene, partial cds.," XP002564232, 4 pages.

Chang et al.,:Genetic and Biochemical Analysis of *Escherichia Coli* Strains Having a Mutation in the Structural Gene (poxB) for Pyruvate Oxidase, J. Bacteriol. 154 (2):756-62 (1983).

Mat-Jan et al., "Mutants of *Escherichia coli* Deficient in the Fermentative Lactate Dehydrogenase," J. Bacteriol. 171(1):342-8 (1989).

Bunch et al., "The IdhA gene encoding the fermentative lactate dehydrogenase of *Escherichia coli*," Microbiol. 143(1):187-95 (1997).

Abdel-Hamid et al., "Pyruvate oxidase contributes to the aerobic growth efficiency of *Escherichia coli*," Micribiol. 147 (6):1483-98 (2001).

Knothe, G. "Dependence of biodiesel fuel properties on the structure of fatty acid alkyl esters," Fuel Processing Technology 86:1059-1070, 2005.

McCue, L. et al., "Phylogenetic footprinting of transcription factor binding sites in proteobacterial genomes," Nucleic Acids Res., 29(3):774-82 (2001).

Jarboe, L.R. et al., "Development of Ethanologenic Bacteria," Adv. Biochem. Engin./Biotechnol. 108:237-261 (2007).

Peterson & Ingram, "Anaerobic Respiration in Engineered *Escherichia coli* with an Internal Electron Acceptor to Produce Fuel Ethanol," Ann. N.Y. Acad. Sci. 1125:363-372 (2008).

Yomano, L.P. et al., "Re-Engineering *Escherichia coli* for ethanol production," Biotechnol. Lett. 30:2097-2103 (2008).

Cheng, J. et al., "Mammalian Wax Biosynthesis," J. Biol. Chem. 279(36):37798-37807, 2004.

Kalscheuer, R. And Steinbuchel, A., "A Novel Bifunctional Wax Ester Synthase/Acyl-CoA:Diacylglycerol Acyltransferase Mediates Wax Ester and Triacylglycerol Biosynthesis in Acinetobacter Calcoaceticus ADPI," J. Biol. Chem. 278:8075-8082, 2003.

Cho, H. et al., "Defective Export of a Periplasmic Enzyme Disrupts Regulation of Fatty Acid Synthesis," J. Biol. Chem., 270:4216-4219 (1995).

Aliverti et al., "Structural and functional diversity of ferredoxin-NADP(+) reductases", ABB 474: 283-291 (2008).

Allen et al., "Structure and regulation of the omega-3 polyunsaturated fatty acid synthase genes from the deep-sea bacterium *Photobacterium profundum* strain SS9", Microbiol. 148(6): 1903-1913 (2002).

Black et al., "Cloning, Sequencing, and Expression of the fadD Gene of *Escherichia coli* Encoding Acyl Coenzyme A Synthetase," J. Biol. Chem. 267(35): 25513-25520 (1992).

Bundy et al., "Investigating the specificity of regulators of degradation of hydrocarbons and hydrocarbon-based compounds using structure-activity relationships" Biodegradation, 11, 2000.

Chassagnole et al., "Dynamic Modeling of the Central Carbon Metabolism of *Escherichia coli*", Biotech & Engineering 79(1): 59-73 (2002).

Cheng et al., "Mammalian Wax Biosynthesis, II, Expression Cloning of Wax Synthase cDNAs Encoding a Member of the Acyltransferase Enzyme Family*," *J. Biol. Chem.*, 279(36): 37798-37807 (2004).

Cho et al., "Defective Export of a Periplasmic Enzyme Disrupts Regulation of Fatty Acid Synthesis," *J. Biol. Chem.*, 270: 4216-4219 (1995).

Coleman et al., "Enzymes of triacylglycerol synthesis and their regulation" *Progress in Lipid Research* 43:134-176 (2004).

Database EMBL (online): "*Synechococcus*, PCC7942 Ribosomal Protein S1 of 30S Ribosome (rpls): ORF271, ORF231, ORF341, Carboxyltransferase alpha subunit (accA) ORF245, ORF227, and GTP cyclohydrolase I (folE) genes, complete cds, and ORF205 gene, partial cds," XP002564232 (1996).

Davis, J.B., "Microbial Incorporation of Fatty Acids Derived From n-Alkanes Into Glycerides and Waxes" *Applied Microbiology* 12(3): 210-214 (1964).

Dellomonaco et al., "Engineered Respiro-Fermentative Metabolism for the Production of Biofuels and Biochemicals from Fatty Acid-Rich Feedstocks", *Applied & Environmental Microbiology* 76(15): 5067-5078 (2010).

Grahame et al., "Partial ReactionsCatalyzed byProtein Components of the Acetyl-CoA Decarbonylase Synthase Enzyme Complex from *Methanosarcina barkeri*", *J.Biol.Chem.*271(14): 8352-8358.

Holtzapple et al., "Biosynthesis of Isoprenoid Wax Ester in Marinobacter hydrocarbonoclasticus DSM 8798: Identification and Characterization of Isoprenoid Coenzyme A Synthetase and Wax Ester Synthases", *J.Bacteriology* 189(10): 3804-3812 (2007).

Hu et at, Microalgal triacylglycerols as feedstocks for biofuel production: perspectives and advances, *The Plant Journal* 54; 621-639 (2008).

Huber et al., "Production of Liquid Alkanes by Aqueous-Phase Processing of Biomass-Derived Carbohydrates", *Science* 308: 1446-1450 (2005).

Kalscheuer et al., "A Novel Bifunctional Wax Ester Synthase/Acyl-CoA:Diacylglycerol Acyltransferase Mediates Wax Ester & Triacylglycerol Biosynthesis in Acinetobacter calcoaceticus ADP1," *J. Biol. Chem.*, 278(10): 8075-8082 (2003).

Keasling et al., "Metabolic engineering delivers next-generation biofuels", *Nature Biotechnology* 26(3):298-299 (2008).

Knudsen et al,. "Transacylation as a chain-termination mechanism in fatty acid synthesis by mammalian fatty acid synthetase. Synthesis of medium-chain-length ($C_8$-$C_{12}$) acyl-CoA esters by goat mammary-gland fatty acid synthetase", *Biochem. J.* 202: 139-143 (1982).

Krebs at at, "Cyanobacterial alkane biosynthesis further expands the catalytic repertoire of the ferritin-like 'di-iron-carboxylate' proteins" *COCB* 15: 1-13 (2011).

Lendenmann et al., "Kinetics of the Simultaneous Utilization of Sugar Mixtures by *Escherichia coli* in Continuous Culture", *Appl. Environ. Microbiol.* 62(5): 1493-1499 (1996).

Lennen et al., "A Process for Microbial Hydrocarbon Synthesis: Overproduction of Fatty Acids in *Escherichia coil* and Catalytic Conversion to Alkane", *Biotech.Bioengineering* 106(2):193-202 (2010).

Li at al., "The Gene Encoding the Biotin Carboxylase Subunit of *Escherichia coil* Acetyl-CoA carboxylase", *J.Biol.Chem.* 267(2): 855-863 (1992).

Li et al., "The carboxylic acid reduction pathway in *Nocardia*. Purification and characterization of the aldehyde reductase", *J. of Industrial Microbiology & Biotechnology* 25: 328-332 (2000).

Li et al., "Conversion of Fatty Aldehydes to Alka(e)nes and Formate by a Cyanobacterial Aldehyde Decarbonylase: Cryptic Redox by an Unusual Dimetal Oxygenase", *J. Am. Chem. Soc.* 133: 6158-6161 (2011).

Li et al., "Growth Rate Regulation of Escherichia coli Acetyl Coenzyme A Carboxylase, Which Catalyzes the First Committed Step of Lipid Biosynthesis", *J. of Bacteriology* 175(2): 332-340 (1993).

Lu et al., "Overproduction of free fatty acids in *E. coli*: Implications for biodiesel production", *Metabolic Engineering* 10: 333-339 (2008).

Miller et al., "A Highly Catalytic and Selective Conversion of Carboxylic Acids to 1-Alkenes of One Less Carbon Atom," *J. Org. Chem*, 58(1): 18-20 (1993).

Mohan et al., "An *Escherichia coli* Gene (*FabZ*) Encoding (3*R*)-Hydroxymyristoyl Acyl Carrier Protein Dehydrase. Relation to fubA and Suppression of Mutations in Lipid a Biosynthesis", *J.BiolChem* 269(52): 32896-32903 (1994).

Rude et al., "Terminal Olefin (1-Alkene) Biosynthesis by a Novel P450 Fatty Acid Decarboxylase from *Jeotgalicoccus* Species", *Appl. Environ.Microbiol.* 77(5): 1718-1727 (2011).

Rude et al., "New microbial fuels: a biotech perspective", *Current Opinion in Microbiology* 12: 274-281 (2009).

Schirmer et al., "Microbial Biosynthesis of Alkanes", *Science* 329:559-562 (2010).

Schneider-Belhaddad et al., "Solubilization, Partial Purification, and Characterization of a Fatty Aldehyde Decarbonylase from a Higher Plant, *Pisum sativum*", *Archives of Biochem. and Biophysics* 377(2): 341-349 (2000).

Schweizer et al., "Microbial Type I Fatty Acid Syntheses (FAS): Major Players in a Network of Cellular FAS Systems", Microbiol. Mol.Biol.Rev. 68(3): 501-517 (2004).

Ta et al., "Cloning, Sequencing, and Overexpression oaf [2Fe-2S] Ferredoxin Gene from *Escherichia coli*", *J.Biol.Chem.* 267(16):11120-11125 (1992).

Zhang et al., "Inhibiting Bacterial Fatty Acid Synthesis", *J.Biol. Chem.* 281(26): 17541-17544 (2006).

Zhang et al., "Structural Basis for Catalytic and Inhibitory Mechanisms of β-Hydroxyacyl-acyl Carrier Protein Dehydratase (FabZ)", *J.Biol.Chem.* 283(9):5370-5379 (2008).

Zhu et al., "Functions of the *Clostridium acetobutylicum* FabF and FabZ proteins in unsaturated fatty acid biosynthesis", *BMC Microbiology* 9:119 (2009).

Zimhony et al., "Characterization of *Mycobacterium smegmatis* Expressing the *Mycobacterium tuberculosis* Fatty Acid Synthase I (*fas*1) Gene", *J.Bacteriol.* 186(13):4051-4055 (2004).

International Search Report and Written Opinion from PCT/US2010/050026, mailed Jan. 6, 2011.

Chen, et al., "Biosynthesis of Ansatrienin (mycotrienin) and naphthomycin, Identification and Analysis of Two Separate Biosynthetic Gene Clusters in *Streptomyces collinus* Tu 1892," Eur. J. Biochem. 261, 1999, pp. 98-107.

Cropp, et al., "Identification of a Cyclohexylcarbonyl CoA Biosynthetic Gene Cluster and Application in the Production of Doramectin," Nature Biotechnology, vol. 18, Sep. 2000, 4 pages.

Database UniProt, Online, Nov. 1996, XP002545841, Retrieved from EBI Accession No. Uniprot:Q54764, 1 page.

Database UniProt, Online, Nov. 1996, XP002564231, Retrieved from EBI Accession No. Uniprot:Q54765, 1 page.

Database Uniprot, Online, Nov. 1996, XP002564232, Retrieved from EBI Accession No. Uniprot:Q54765, 4 pages.

De Mendoza, et al., "Thermal Regulation of Membrane Fluidity in *Escherichia coli*, Effects of Overproduction of β-Ketoacyl-Acyl Carrier Protein Synthase I*," The Journal of Biological Chemistry, vol. 258, No. 4, Issue of Feb. 1983, pp. 2098-2101.

Denoya, et al., "A Second Branded-Chain α-Keto Acid Dehydrogenase Gene Cluster (bkdFGH) from *Streptomyces avermitilis*: Its Relationship to Avermectin Biosynthesis and the Construction of a bkdF Mutant Suitable for the Production of Novel Antiparasitic Avermectins," Journal of Bacteriology, Jun. 1995, pp. 3504-3511.

Fehler, et al., "Biosynthesis of Hydrocarbons in *Anabaena variabilis*. Incorporation of [*methyl*-14C]- and [*methyl*-$2H_2$] Methionine into 7- and 8-Methylheptadecanes", Biochemistry, vol. 9, No. 2, Jan. 1970, pp. 418-422.

Han, et al., "A Novel Alternate Anaplerotic Pathway to the Glyoxylate Cycle in StreptOrnycetes," Journal of Bacteriology, Aug. 1997, pp. 5157-5164.

Han, et al., "Biosynthesis of Alkanes in Nostoc Muscorum," Journal of the American Chemical Society, 91:18, Aug. 1969, pp. 5156-5159.

Heath, et al., "Lipid Biosynthesis as a Target for Antibacterial Agents," Progress in Lipid Research 40, 2001, pp. 467-497.

International Search Report and Written Opinion of the Searching Authority of the European Patent Office for PCT/US2009/044403, mailing date Sep. 25, 2009, 12 pages.

International Search Report of the International Searching Authority of the European Patent Office for PCT/US2009/044409, mailing date Jan. 29, 2010, 4 pages.

Juttner, et al., "Environmental Factors Affecting the Formation of Mesityloxide, Dimethylallylic Alcohol and Other Volatile Compounds Excreted by *Anabaena cylindrica*," Journal of General Microbiology, 1983, 129, 407-412.

Juttner, et al., "The reducing capacities of cyanobacteria for aldehydes and ketones," Applied Microbiology and Biotechnology, 25: 52-54, 1986.

Ladygina, et al., "A Review of Microbial Synthesis of Hydrocarbons," Process Biochemistry, 41, 2006, pp. 1001-1014.

Li, et al., "Alteration of the Fatty Acid Profile of *Streptomyces coelicolor* by Replacement of the Initiation Enzyme 3-Ketoacyl Acyl Carrier Protein Synthase III (FabH)," Journal of Bacteriology, Jun. 2005, pp. 3795-3799.

Marrakchi, et al., "Mechanistic Diversity and Regulation of Type II Fatty Acid Synthesis," Biochemical Society Transactions, 2002, vol. 30, Part 6, pp. 1050-1055.

Palaniappan, et al., "Enhancement and Selective Production of Phoslactomycin B, a Protein Phosphatase lla Inhibitor, through Identification and Engineering of the Corresponding Biosynthetic Gene Cluster," The Journal of Biological Chemistry, vol. 278, No. 37, Issue of Sep. 2003, pp. 35552-35557.

Patton, et al., "A Novel $\Delta^3$, $\Delta^2$-Enoyl-CoA Isomerase Involved in the Biosynthesis of the Cyclohexanecarboxylic Acid-Derived Moiety of the Polyketide Ansatrienin A ,," Biochemistry 2000, 39, pp. 7595-7604.

Phung, et al, "Genes for Fatty Acid Biosynthesis in the Cyanobacterium *Synechococcus* sp. Strain PCC 7942," Jan. 1995, Abstracts of the General Meeting of the American Society of Microbiology, The Society, Washington, DC, p. 524.

Rock, et al., Increased Unsaturated Fatty Acid Production Associated with a Suppressor of the fabA6(Ts) Mutation in *Escherichia coli*, Journal of Bacteriology, Sep. 1996, vol. 178, No. 18, pp. 5382-5387.

Zang, et al., "Optimum Conditions for Transformation of *Synechocystis* sp. PCC 6803," The Journal of Microbiology, Jun. 2007, vol. 45, No. 3, pp. 241-245.

Zhang, et al., "The FabR (YijC) Transcription Factor Regulates Unsaturated Fatty Acid Biosynthesis in *Escherichia coli*\*," The Journal of Biological Chemistry, vol. 277, No. 18, Issue of May 2002, pp. 15558-15565.

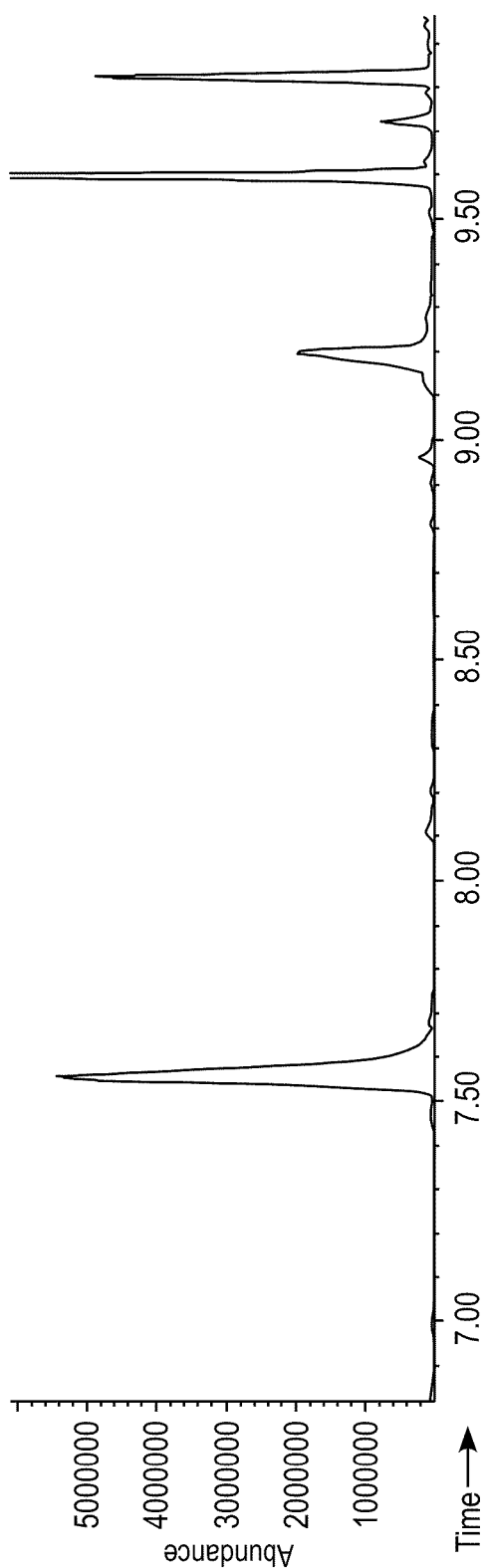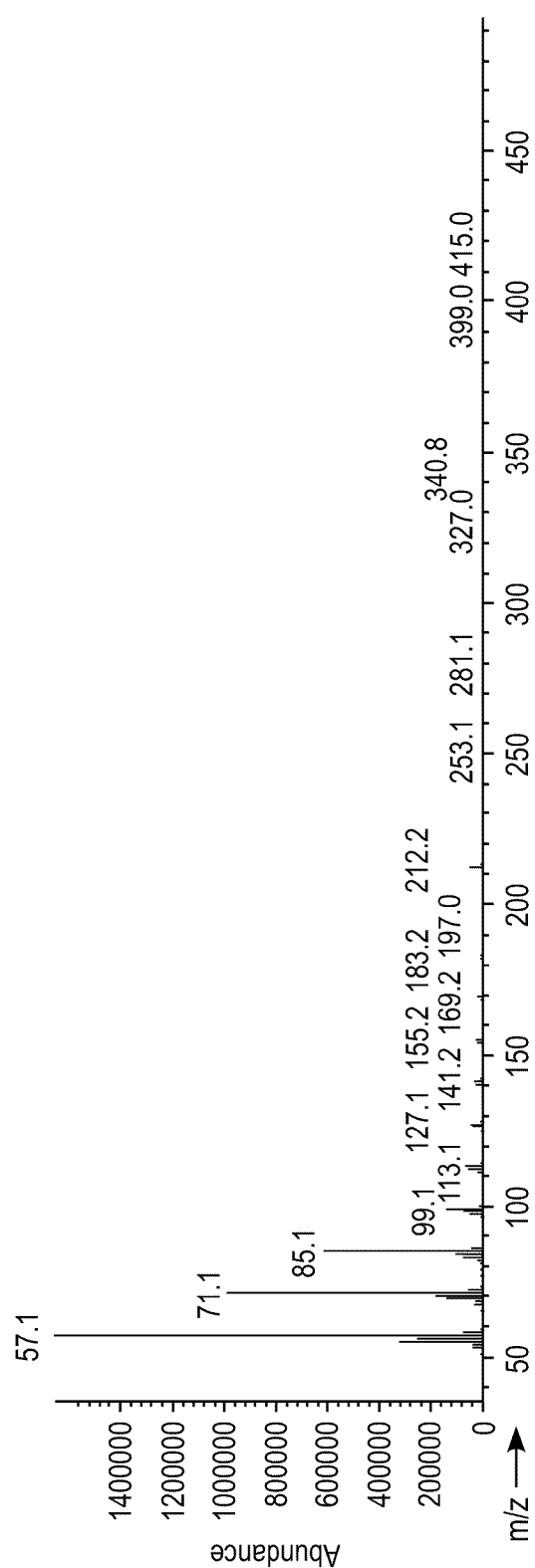
FIG. 1A
FIG. 1B

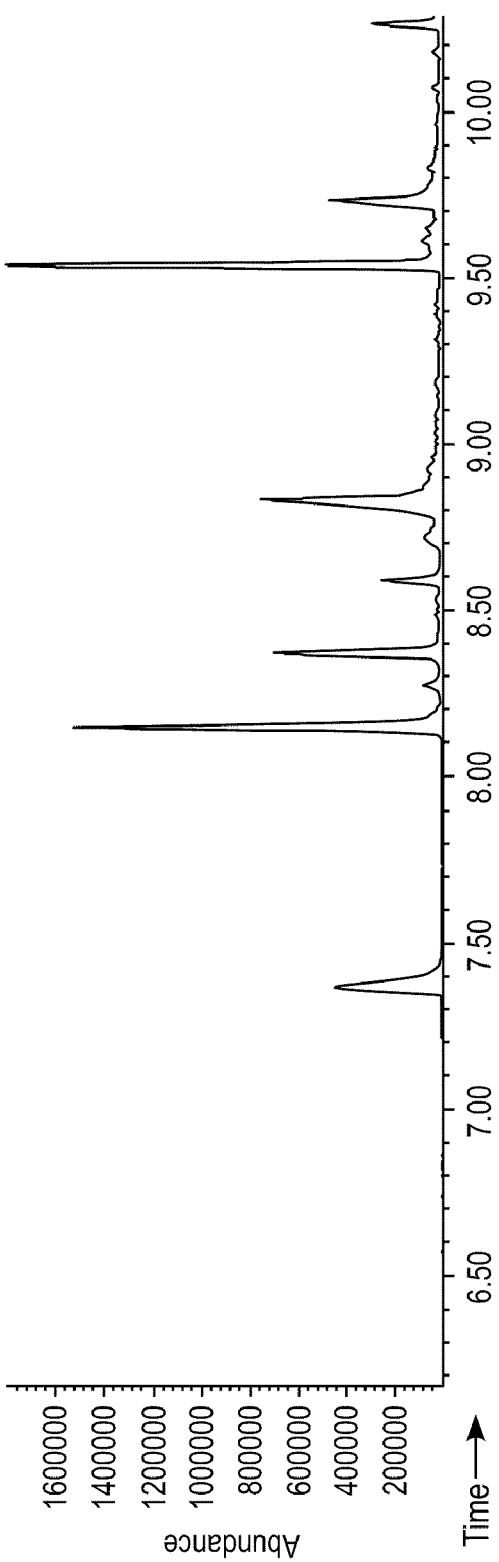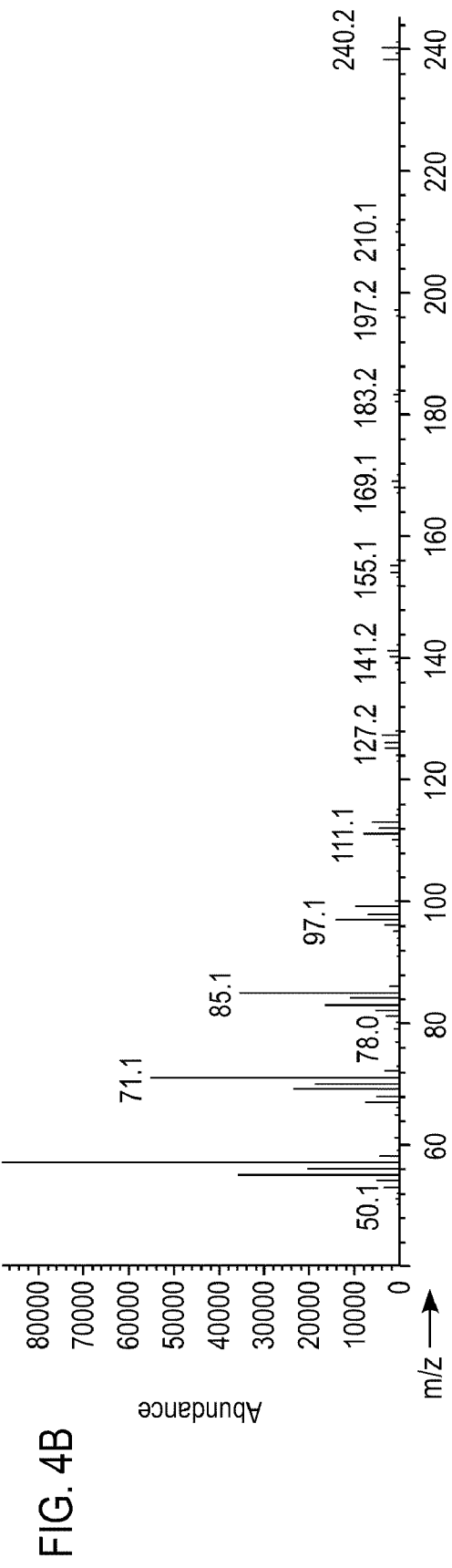
FIG. 4A
FIG. 4B

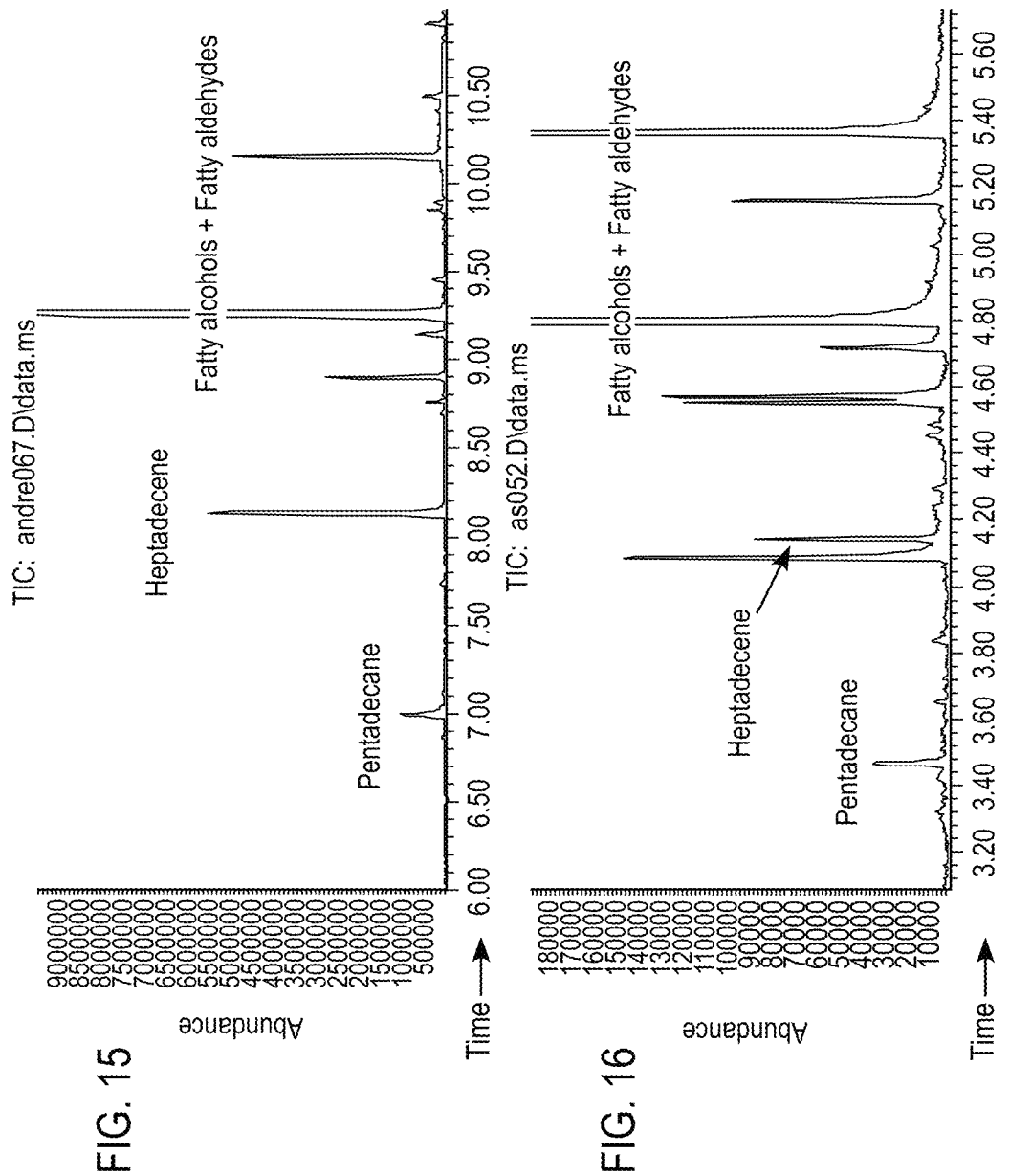

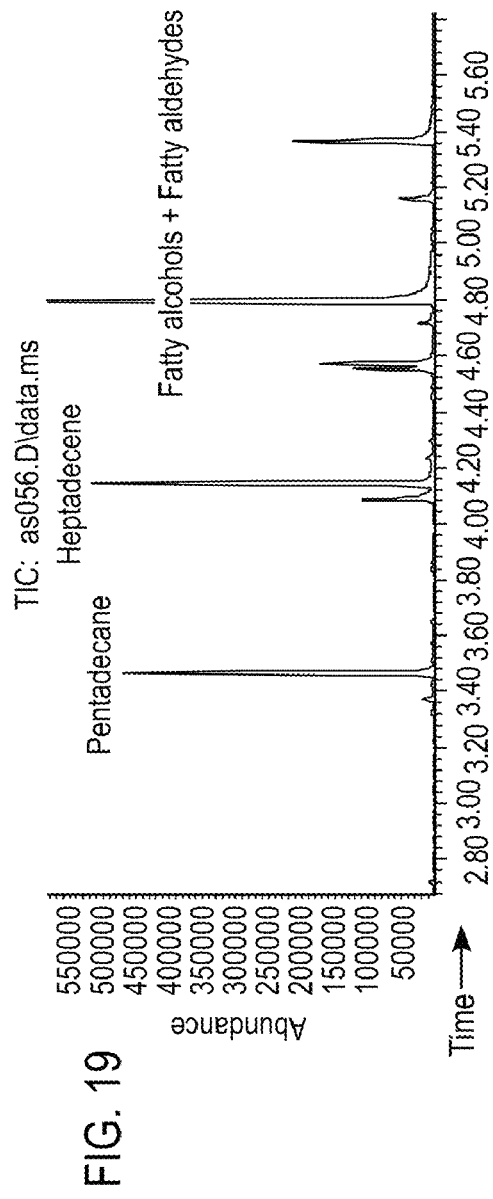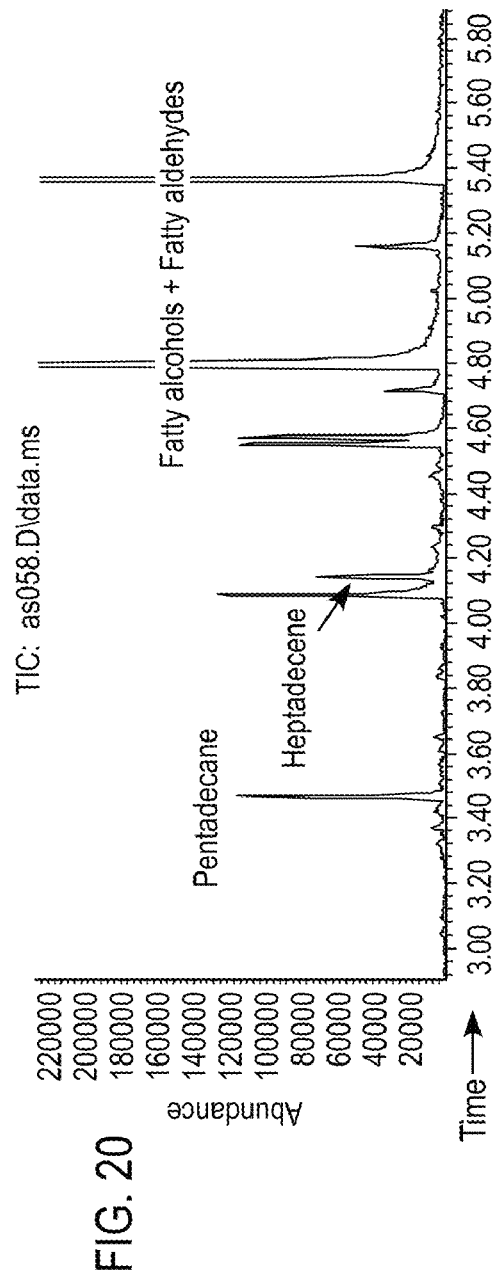

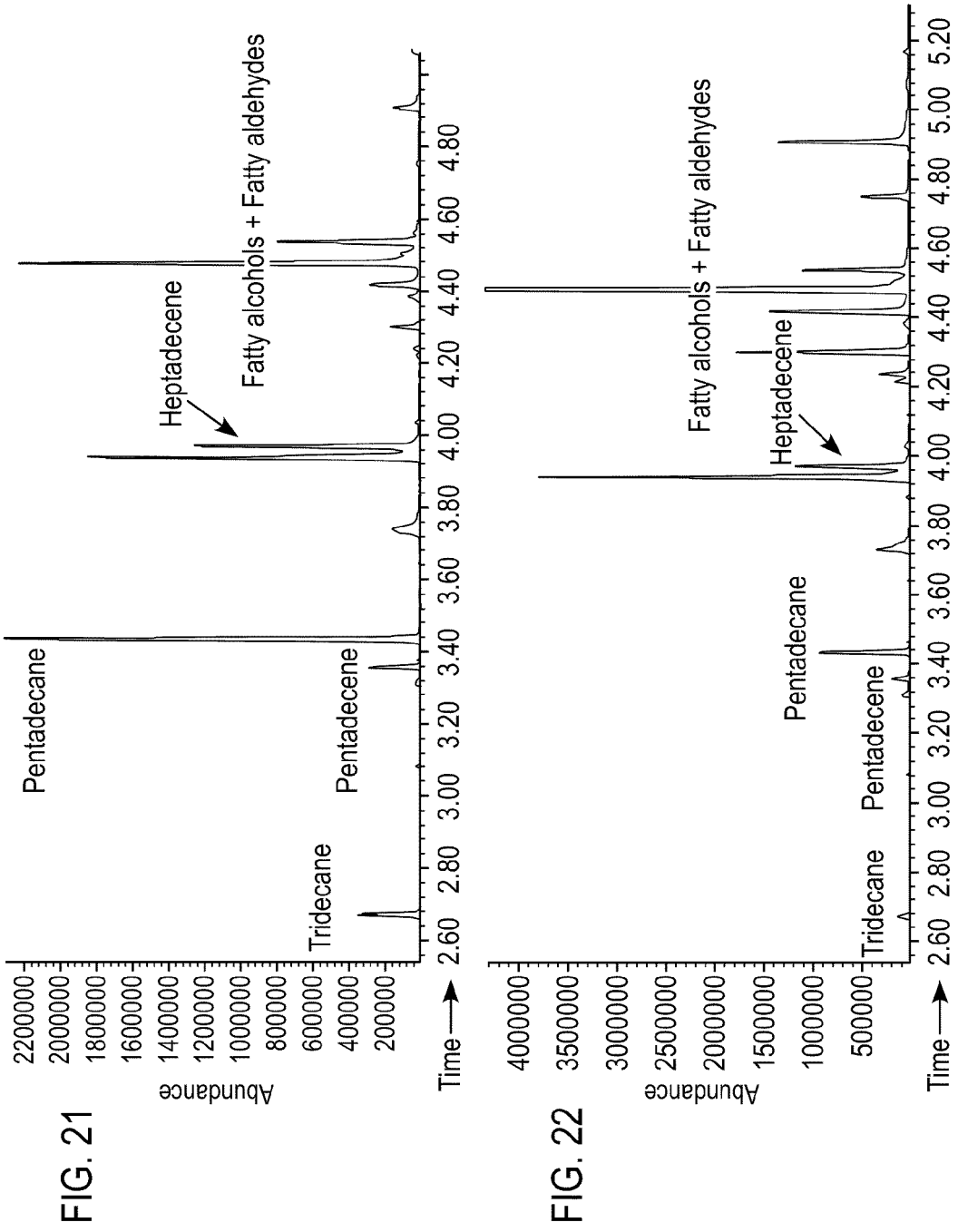

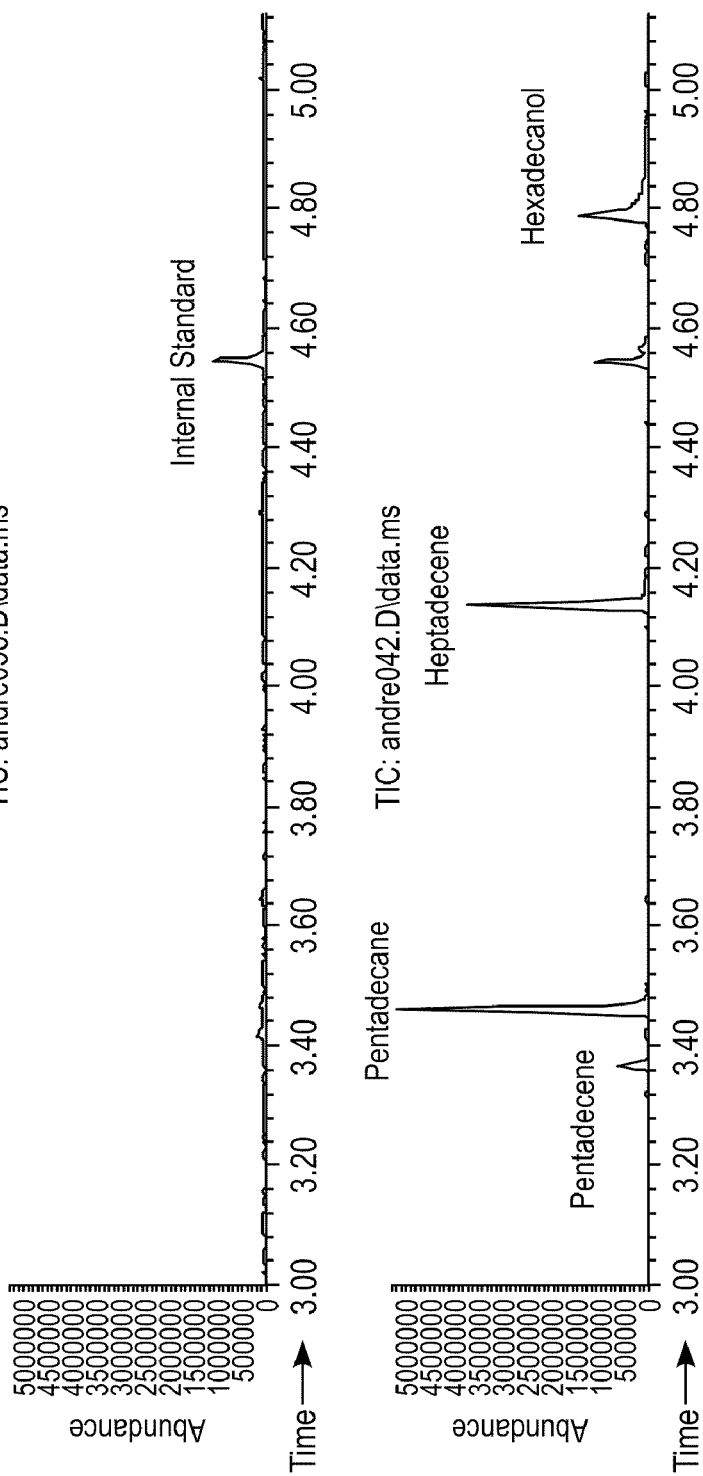

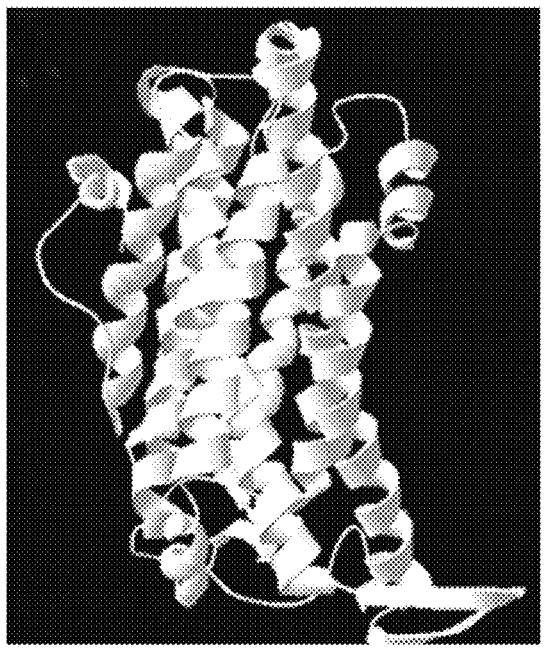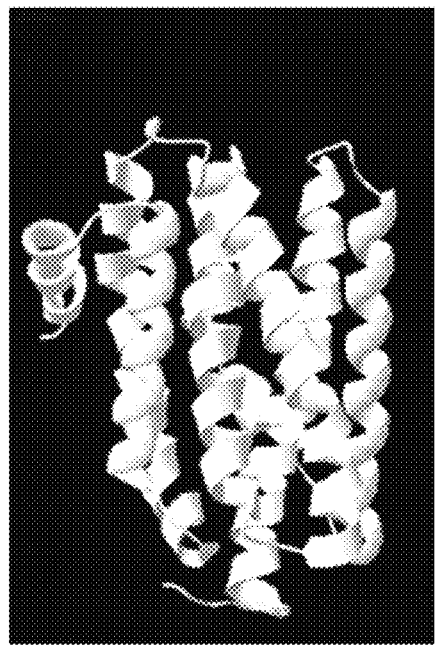
FIG. 29A    FIG. 29B
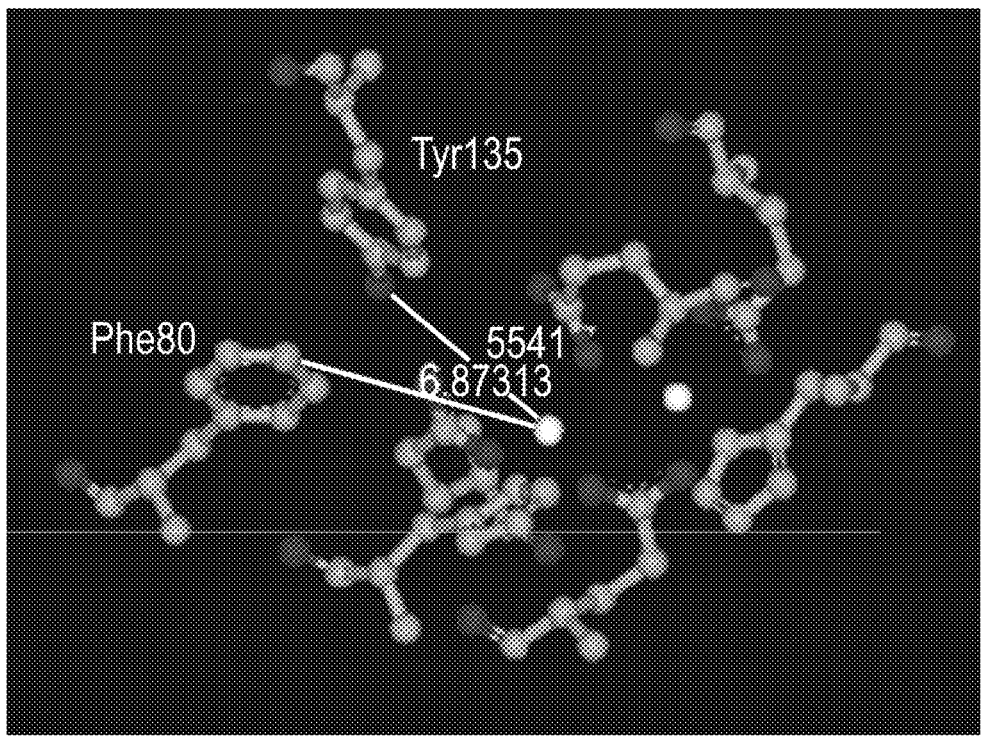
FIG. 29C

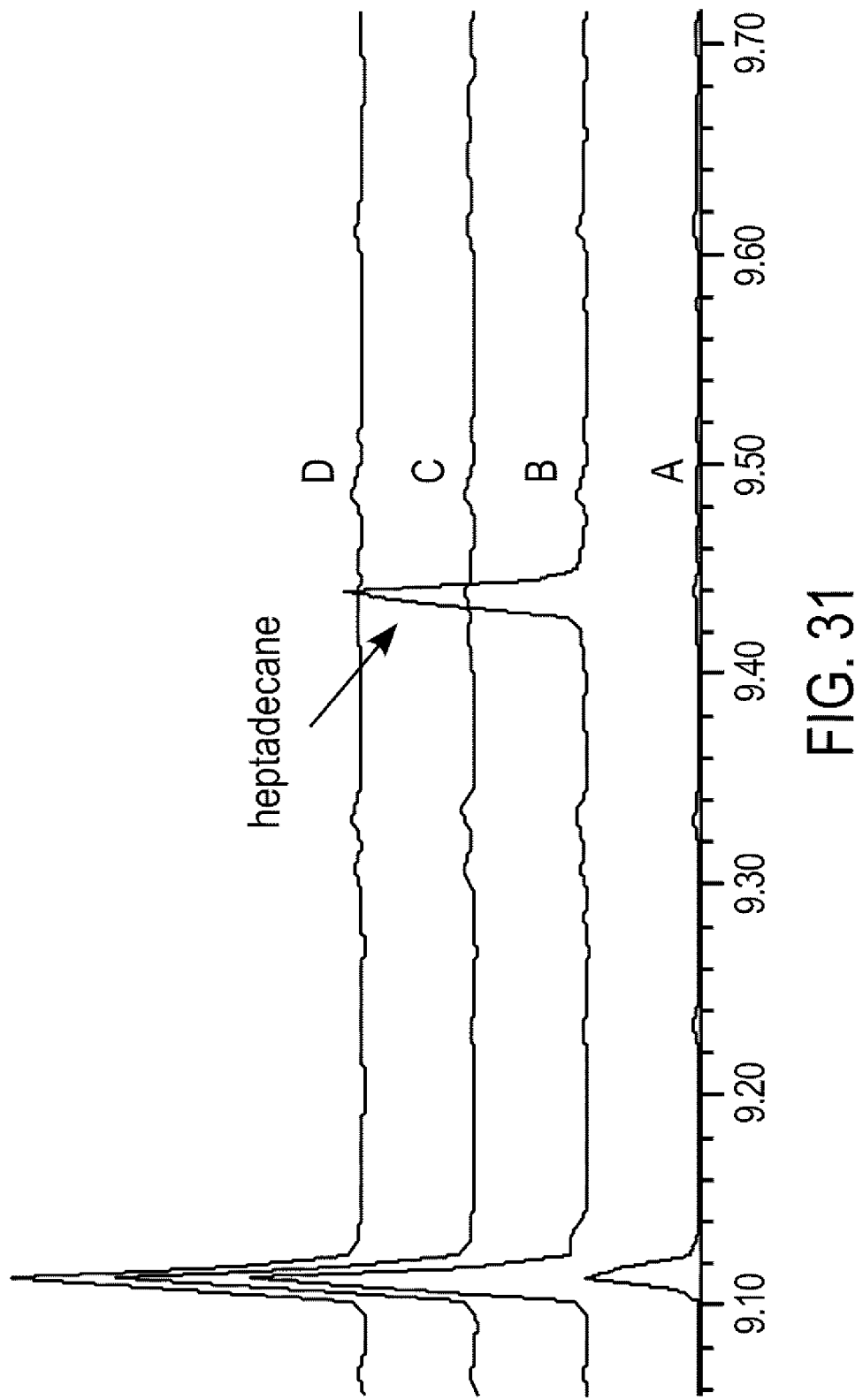

FIG. 38A

Accession Numbers as of April 10, 2009

| Accession Number | % Identity | % Similarity | Alignment Length |
|---|---|---|---|
| gi\|135970898\|gb\|EBL05614.1\| | 59.5 | 74.3 | 237 |
| gi\|134964254\|gb\|EBE59803.1\| | 57.6 | 74.2 | 229 |
| gi\|142528845\|gb\|ECY73505.1\| | 60.4 | 77.9 | 222 |
| gi\|135713677\|gb\|EBJ38387.1\| | 61.1 | 78.7 | 221 |
| gi\|141225813\|gb\|ECQ49060.1\| | 59.7 | 77.8 | 221 |
| gi\|144115151\|gb\|EDI97334.1\| | 67.7 | 80.9 | 220 |
| gi\|142133005\|gb\|ECV83152.1\| | 67.3 | 80.9 | 220 |
| gi\|137965371\|gb\|EBX01252.1\| | 67.3 | 80.9 | 220 |
| gi\|134786157\|gb\|EBD42319.1\| | 67.3 | 80.9 | 220 |
| gi\|136216894\|gb\|EBM66672.1\| | 62.3 | 77.7 | 220 |
| gi\|143271262\|gb\|EDE04654.1\| | 63.0 | 78.5 | 219 |
| gi\|135973786\|gb\|EBL07573.1\| | 63.0 | 78.1 | 219 |
| gi\|140222739\|gb\|ECK35865.1\| | 63.0 | 77.6 | 219 |
| gi\|139710482\|gb\|ECG93903.1\| | 62.6 | 78.1 | 219 |
| gi\|140109767\|gb\|ECJ60294.1\| | 62.6 | 78.5 | 219 |
| gi\|137939755\|gb\|EBW86789.1\| | 62.6 | 78.1 | 219 |
| gi\|140086977\|gb\|ECJ44922.1\| | 62.6 | 78.1 | 219 |
| gi\|143729007\|gb\|EDG48416.1\| | 62.6 | 78.1 | 219 |
| gi\|143217179\|gb\|EDD66368.1\| | 62.6 | 78.1 | 219 |
| gi\|138728422\|gb\|ECB60007.1\| | 62.6 | 78.1 | 219 |
| gi\|143540790\|gb\|EDF53461.1\| | 62.6 | 78.1 | 219 |
| gi\|143580323\|gb\|EDF73830.1\| | 62.6 | 78.1 | 219 |
| gi\|137317024\|gb\|EBT41871.1\| | 62.6 | 78.1 | 219 |
| gi\|143567212\|gb\|EDF67415.1\| | 62.6 | 78.1 | 219 |
| gi\|140726723\|gb\|ECN09681.1\| | 62.6 | 78.1 | 219 |
| gi\|136249402\|gb\|EBM88688.1\| | 62.6 | 78.1 | 219 |
| gi\|141156650\|gb\|ECQ02018.1\| | 62.6 | 78.1 | 219 |
| gi\|143550472\|gb\|EDF58473.1\| | 62.6 | 78.1 | 219 |
| gi\|139581046\|gb\|ECG04925.1\| | 62.6 | 78.1 | 219 |
| gi\|141904835\|gb\|ECU06854.1\| | 62.6 | 78.1 | 219 |
| gi\|143596624\|gb\|EDF78559.1\| | 62.1 | 78.1 | 219 |
| gi\|142808717\|gb\|EDA73967.1\| | 62.1 | 78.1 | 219 |
| gi\|137639134\|gb\|EBV19468.1\| | 62.1 | 78.1 | 219 |
| gi\|140970945\|gb\|ECO75236.1\| | 62.1 | 77.6 | 219 |
| gi\|137724335\|gb\|EBV66164.1\| | 62.1 | 78.1 | 219 |
| gi\|143095952\|gb\|EDC78454.1\| | 66.1 | 80.3 | 218 |
| gi\|135919851\|gb\|EBK71172.1\| | 66.1 | 80.3 | 218 |
| gi\|143083445\|gb\|EDC69308.1\| | 66.1 | 80.3 | 218 |
| gi\|137949431\|gb\|EBW92260.1\| | 63.1 | 77.6 | 214 |

FIG. 38B

| | | | |
|---|---|---|---|
| gi\|136336883\|gb\|EBN48108.1\| | 62.2 | 78.0 | 214 |
| gi\|136008042\|gb\|EBL28916.1\| | 62.2 | 78.0 | 214 |
| gi\|134796061\|gb\|EBD49256.1\| | 60.8 | 76.6 | 214 |
| gi\|143142117\|gb\|EDD12240.1\| | 60.8 | 76.6 | 214 |
| gi\|141842906\|gb\|ECT63492.1\| | 60.3 | 77.6 | 214 |
| gi\|137436109\|gb\|EBU09046.1\| | 60.3 | 77.1 | 214 |
| gi\|142796298\|gb\|EDA64685.1\| | 71.0 | 83.3 | 210 |
| gi\|138143480\|gb\|EBX98705.1\| | 70.5 | 83.3 | 210 |
| gi\|136004890\|gb\|EBL27104.1\| | 68.6 | 82.4 | 210 |
| gi\|142206956\|gb\|ECW39307.1\| | 67.1 | 82.4 | 210 |
| gi\|135813588\|gb\|EBK00762.1\| | 62.4 | 78.6 | 210 |
| gi\|137008728\|gb\|EBR69250.1\| | 62.7 | 79.0 | 209 |
| gi\|141443295\|gb\|ECR86509.1\| | 63.0 | 78.9 | 208 |
| gi\|135999440\|gb\|EBL23890.1\| | 63.1 | 79.1 | 206 |
| gi\|136001501\|gb\|EBL25083.1\| | 62.6 | 77.7 | 206 |
| gi\|137008499\|gb\|EBR69124.1\| | 62.3 | 77.5 | 204 |
| gi\|135813080\|gb\|EBK00444.1\| | 60.8 | 77.5 | 204 |
| gi\|139947991\|gb\|ECI56786.1\| | 63.6 | 79.8 | 198 |
| gi\|136255251\|gb\|EBM92608.1\| | 61.1 | 77.3 | 198 |
| gi\|141717528\|gb\|ECS91623.1\| | 58.6 | 76.8 | 198 |
| gi\|141153056\|gb\|ECP99448.1\| | 59.3 | 75.3 | 194 |
| gi\|140654921\|gb\|ECM59517.1\| | 67.9 | 81.9 | 193 |
| gi\|140993407\|gb\|ECO91072.1\| | 63.9 | 79.6 | 191 |
| gi\|143171676\|gb\|EDD33295.1\| | 63.9 | 79.6 | 191 |
| gi\|143659341\|gb\|EDG12240.1\| | 59.5 | 75.8 | 190 |
| gi\|138539256\|gb\|ECA29247.1\| | 68.1 | 81.9 | 188 |
| gi\|141964470\|gb\|ECU48335.1\| | 64.5 | 80.3 | 183 |
| gi\|139227663\|gb\|ECE28885.1\| | 63.9 | 79.2 | 183 |
| gi\|135926500\|gb\|EBK75672.1\| | 58.2 | 76.4 | 182 |
| gi\|140708786\|gb\|ECM97174.1\| | 68.4 | 81.4 | 177 |
| gi\|139523141\|gb\|ECF65392.1\| | 62.6 | 79.3 | 174 |
| gi\|137874181\|gb\|EBW49523.1\| | 61.5 | 76.4 | 174 |
| gi\|143221750\|gb\|EDD69688.1\| | 60.9 | 75.9 | 174 |
| gi\|140086962\|gb\|ECJ44914.1\| | 63.4 | 80.2 | 172 |
| gi\|142781070\|gb\|EDA53384.1\| | 61.8 | 77.1 | 170 |
| gi\|139775004\|gb\|ECH37282.1\| | 61.0 | 76.3 | 169 |
| gi\|136260534\|gb\|EBM96169.1\| | 61.0 | 75.7 | 169 |
| gi\|137441185\|gb\|EBU11854.1\| | 58.1 | 75.5 | 167 |
| gi\|136330550\|gb\|EBN43814.1\| | 65.1 | 80.7 | 166 |
| gi\|139650149\|gb\|ECG51660.1\| | 67.3 | 80.6 | 165 |
| gi\|143638003\|gb\|EDF99869.1\| | 63.6 | 80.0 | 165 |
| gi\|137949739\|gb\|EBW92432.1\| | 61.7 | 75.9 | 162 |
| gi\|143382653\|gb\|EDE68551.1\| | 63.9 | 81.0 | 158 |

FIG. 38C

| | | | |
|---|---|---|---|
| gi\|138989189\|gb\|ECC70595.1\| | 63.9 | 80.4 | 158 |
| gi\|138408887\|gb\|EBZ46853.1\| | 64.1 | 78.2 | 156 |
| gi\|137230040\|gb\|EBS93199.1\| | 61.3 | 76.1 | 155 |
| gi\|141605381\|gb\|ECS53894.1\| | 65.6 | 81.8 | 154 |
| gi\|137858747\|gb\|EBW40699.1\| | 64.9 | 81.8 | 154 |
| gi\|140209383\|gb\|ECK27191.1\| | 66.0 | 79.1 | 153 |
| gi\|142753984\|gb\|EDA33411.1\| | 60.7 | 75.3 | 150 |
| gi\|137242084\|gb\|EBS99775.1\| | 64.9 | 82.4 | 148 |
| gi\|136229422\|gb\|EBM75188.1\| | 64.6 | 82.3 | 147 |
| gi\|140311369\|gb\|ECK89744.1\| | 73.3 | 85.6 | 146 |
| gi\|140866197\|gb\|ECO03647.1\| | 65.1 | 82.2 | 146 |
| gi\|139229558\|gb\|ECE29833.1\| | 61.4 | 76.6 | 145 |
| gi\|141659030\|gb\|ECS68172.1\| | 61.4 | 76.6 | 145 |
| gi\|139580852\|gb\|ECG04786.1\| | 65.3 | 81.9 | 144 |
| gi\|138338712\|gb\|EBZ05758.1\| | 65.3 | 81.9 | 144 |
| gi\|136204827\|gb\|EBM58548.1\| | 61.3 | 76.8 | 142 |
| gi\|139095530\|gb\|ECD38154.1\| | 64.0 | 81.3 | 139 |
| gi\|136351648\|gb\|EBN58190.1\| | 60.1 | 76.1 | 138 |
| gi\|138155154\|gb\|EBY06350.1\| | 67.9 | 80.3 | 137 |
| gi\|137644530\|gb\|EBV22059.1\| | 63.1 | 80.8 | 130 |
| gi\|143775710\|gb\|EDG72409.1\| | 61.5 | 79.2 | 130 |
| gi\|143500330\|gb\|EDF32920.1\| | 63.1 | 77.9 | 122 |
| gi\|139709584\|gb\|ECG93249.1\| | 71.1 | 85.1 | 121 |
| gi\|142537519\|gb\|ECY79816.1\| | 62.8 | 81.0 | 121 |
| gi\|137944410\|gb\|EBW89433.1\| | 64.2 | 78.3 | 120 |
| gi\|137387955\|gb\|EBT81682.1\| | 63.9 | 78.2 | 119 |
| gi\|139955976\|gb\|ECI62054.1\| | 71.2 | 84.8 | 118 |
| gi\|137251843\|gb\|EBT05348.1\| | 62.1 | 77.6 | 116 |
| gi\|138442523\|gb\|EBZ70326.1\| | 62.1 | 76.7 | 116 |
| gi\|141590592\|gb\|ECS49420.1\| | 60.7 | 78.6 | 112 |
| gi\|143187997\|gb\|EDD45026.1\| | 60.7 | 77.7 | 112 |
| gi\|143655969\|gb\|EDG10472.1\| | 61.5 | 78.0 | 109 |
| gi\|139459255\|gb\|ECF24788.1\| | 62.9 | 79.1 | 105 |
| gi\|141976584\|gb\|ECU56751.1\| | 62.9 | 79.1 | 105 |
| gi\|139233104\|gb\|ECE31190.1\| | 69.6 | 83.3 | 102 |
| gi\|139233107\|gb\|ECE31193.1\| | 70.3 | 82.2 | 101 |
| gi\|138582711\|gb\|ECA59616.1\| | 61.4 | 77.2 | 101 |
| gi\|138442855\|gb\|EBZ70514.1\| | 61.4 | 75.3 | 101 |
| gi\|137662676\|gb\|EBV31757.1\| | 60.4 | 76.2 | 101 |
| gi\|139846062\|gb\|ECH87248.1\| | 62.6 | 74.8 | 99 |
| gi\|136935327\|gb\|EBR27657.1\| | 60.6 | 74.5 | 94 |
| gi\|137466252\|gb\|EBU25703.1\| | 67.0 | 80.2 | 91 |
| gi\|137820604\|gb\|EBW18665.1\| | 63.7 | 80.2 | 91 |

FIG. 38D

| | | | |
|---|---|---|---|
| gi\|138539295\|gb\|ECA29276.1\| | 62.6 | 79.1 | 91 |
| gi\|136239262\|gb\|EBM81844.1\| | 64.7 | 81.2 | 85 |
| gi\|136294902\|gb\|EBN19768.1\| | 64.7 | 81.2 | 85 |
| gi\|137413136\|gb\|EBT96003.1\| | 61.2 | 76.5 | 85 |
| gi\|137641041\|gb\|EBV20354.1\| | 60.0 | 72.9 | 85 |
| gi\|142508710\|gb\|ECY58869.1\| | 64.3 | 82.1 | 84 |
| gi\|140096399\|gb\|ECJ51008.1\| | 62.2 | 81.7 | 82 |
| gi\|137938664\|gb\|EBW86178.1\| | 64.0 | 81.3 | 75 |
| gi\|137275448\|gb\|EBT18729.1\| | 58.1 | 70.3 | 74 |
| gi\|141955842\|gb\|ECU42610.1\| | 63.0 | 80.8 | 73 |
| gi\|139221707\|gb\|ECE24659.1\| | 66.2 | 83.1 | 71 |
| gi\|142508709\|gb\|ECY58868.1\| | 52.9 | 68.6 | 70 |
| gi\|137523719\|gb\|EBU55323.1\| | 65.2 | 82.6 | 69 |
| gi\|140781524\|gb\|ECN46583.1\| | 65.6 | 82.8 | 64 |
| gi\|137627577\|gb\|EBV13553.1\| | 60.0 | 73.3 | 60 |
| gi\|141951833\|gb\|ECU39722.1\| | 59.7 | 73.7 | 57 |
| gi\|137232510\|gb\|EBS94613.1\| | 59.7 | 73.7 | 57 |

Cut-off used: >50% Identity to and >25% length of synpcc7942_1593

FIG. 39A

Accession Numbers as of April 10, 2009

| Accession Number | % Identity | % Similarity | Alignment Length |
|---|---|---|---|
| gi\|143288250\|gb\|EDE13503.1\| | 71.3 | 80.5 | 87 |
| gi\|142342310\|gb\|ECX39602.1\| | 71.3 | 80.5 | 87 |
| gi\|137949588\|gb\|EBW92346.1\| | 70.7 | 85.9 | 92 |
| gi\|139984340\|gb\|ECI81897.1\| | 70.6 | 78.8 | 85 |
| gi\|140249046\|gb\|ECK54318.1\| | 69.7 | 82.0 | 267 |
| gi\|142111437\|gb\|ECV67406.1\| | 69.2 | 81.3 | 182 |
| gi\|142994709\|gb\|EDC04737.1\| | 68.8 | 81.2 | 138 |
| gi\|143066602\|gb\|EDC56955.1\| | 67.7 | 81.5 | 248 |
| gi\|138840827\|gb\|ECC11022.1\| | 67.1 | 78.8 | 146 |
| gi\|137829071\|gb\|EBW23606.1\| | 66.7 | 77.1 | 96 |
| gi\|142133008\|gb\|ECV83155.1\| | 66.5 | 79.5 | 337 |
| gi\|143095956\|gb\|EDC78458.1\| | 66.4 | 79.1 | 339 |
| gi\|144115152\|gb\|EDI97335.1\| | 66.4 | 79.4 | 339 |
| gi\|140732156\|gb\|ECN13587.1\| | 66.1 | 79.5 | 254 |
| gi\|136241230\|gb\|EBM83170.1\| | 66.0 | 78.6 | 103 |
| gi\|140001769\|gb\|ECI93451.1\| | 65.9 | 76.9 | 91 |
| gi\|139305662\|gb\|ECE48752.1\| | 65.9 | 80.0 | 205 |
| gi\|137634503\|gb\|EBV17219.1\| | 65.8 | 80.7 | 114 |
| gi\|138584841\|gb\|ECA61142.1\| | 65.5 | 81.9 | 116 |
| gi\|135919849\|gb\|EBK71170.1\| | 65.4 | 76.6 | 107 |
| gi\|141153057\|gb\|ECP99449.1\| | 65.4 | 79.6 | 280 |
| gi\|141976585\|gb\|ECU56752.1\| | 65.3 | 77.6 | 98 |
| gi\|142206955\|gb\|ECW39306.1\| | 65.3 | 78.5 | 340 |
| gi\|141804802\|gb\|ECT36785.1\| | 65.3 | 76.8 | 95 |
| gi\|138931154\|gb\|ECC47219.1\| | 65.1 | 76.7 | 86 |
| gi\|138408888\|gb\|EBZ46854.1\| | 65.1 | 78.0 | 255 |
| gi\|134743188\|gb\|EBD14908.1\| | 64.8 | 78.8 | 307 |
| gi\|138168794\|gb\|EBY16028.1\| | 64.8 | 77.6 | 304 |
| gi\|135749749\|gb\|EBJ60721.1\| | 64.8 | 79.1 | 105 |
| gi\|138338711\|gb\|EBZ05757.1\| | 64.6 | 80.0 | 175 |
| gi\|142827948\|gb\|EDA88477.1\| | 64.5 | 77.7 | 121 |
| gi\|138361576\|gb\|EBZ15968.1\| | 64.4 | 78.7 | 267 |
| gi\|140517919\|gb\|ECM08416.1\| | 64.4 | 77.4 | 115 |
| gi\|135813081\|gb\|EBK00445.1\| | 64.3 | 79.7 | 143 |
| gi\|137627576\|gb\|EBV13552.1\| | 64.3 | 80.1 | 171 |
| gi\|141161845\|gb\|ECQ05757.1\| | 64.2 | 77.1 | 109 |

FIG. 39B

| | | | |
|---|---|---|---|
| gi\|140992134\|gb\|ECO90156.1\| | 64.2 | 76.8 | 95 |
| gi\|137796334\|gb\|EBW04596.1\| | 64.2 | 78.9 | 279 |
| gi\|137619413\|gb\|EBV08950.1\| | 64.1 | 77.6 | 223 |
| gi\|140517917\|gb\|ECM08414.1\| | 64.1 | 79.6 | 181 |
| gi\|137232509\|gb\|EBS94612.1\| | 64.1 | 79.0 | 181 |
| gi\|135811491\|gb\|EBJ99446.1\| | 64.0 | 77.7 | 314 |
| gi\|141167040\|gb\|ECQ09480.1\| | 64.0 | 78.8 | 250 |
| gi\|143441820\|gb\|EDE97777.1\| | 64.0 | 78.2 | 261 |
| gi\|140311368\|gb\|ECK89743.1\| | 64.0 | 79.3 | 261 |
| gi\|140970943\|gb\|ECO75234.1\| | 64.0 | 76.6 | 111 |
| gi\|136817739\|gb\|EBQ60666.1\| | 63.8 | 78.5 | 340 |
| gi\|141717529\|gb\|ECS91624.1\| | 63.7 | 78.8 | 146 |
| gi\|137632337\|gb\|EBV16047.1\| | 63.7 | 77.7 | 256 |
| gi\|137662677\|gb\|EBV31758.1\| | 63.6 | 79.7 | 143 |
| gi\|140091056\|gb\|ECJ47190.1\| | 63.6 | 78.2 | 280 |
| gi\|143217178\|gb\|EDD66367.1\| | 63.5 | 78.8 | 137 |
| gi\|139984339\|gb\|ECI81896.1\| | 63.5 | 76.3 | 156 |
| gi\|139382506\|gb\|ECE73591.1\| | 63.4 | 78.9 | 194 |
| gi\|140096397\|gb\|ECJ51006.1\| | 63.4 | 79.7 | 153 |
| gi\|134606350\|gb\|EBC34611.1\| | 63.4 | 77.9 | 131 |
| gi\|140705175\|gb\|ECM95033.1\| | 63.4 | 77.0 | 191 |
| gi\|139846064\|gb\|ECH87250.1\| | 63.1 | 76.0 | 179 |
| gi\|137953535\|gb\|EBW94572.1\| | 63.1 | 78.0 | 241 |
| gi\|143738737\|gb\|EDG53066.1\| | 63.1 | 76.6 | 111 |
| gi\|141951832\|gb\|ECU39721.1\| | 63.1 | 76.6 | 111 |
| gi\|143271261\|gb\|EDE04653.1\| | 63.1 | 76.6 | 111 |
| gi\|139846065\|gb\|ECH87251.1\| | 63.0 | 78.8 | 146 |
| gi\|137251844\|gb\|EBT05349.1\| | 63.0 | 78.8 | 146 |
| gi\|136249401\|gb\|EBM88687.1\| | 63.0 | 78.8 | 146 |
| gi\|134628580\|gb\|EBC48074.1\| | 63.0 | 77.0 | 100 |
| gi\|136312048\|gb\|EBN31461.1\| | 62.9 | 76.2 | 143 |
| gi\|143221751\|gb\|EDD69689.1\| | 62.9 | 78.9 | 194 |
| gi\|141955844\|gb\|ECU42612.1\| | 62.9 | 75.7 | 140 |
| gi\|143395654\|gb\|EDE73119.1\| | 62.8 | 77.5 | 218 |
| gi\|142781071\|gb\|EDA53385.1\| | 62.8 | 79.3 | 164 |
| gi\|136303394\|gb\|EBN25555.1\| | 62.7 | 77.7 | 319 |
| gi\|143557688\|gb\|EDF62238.1\| | 62.6 | 77.9 | 131 |
| gi\|136008043\|gb\|EBL28917.1\| | 62.6 | 77.6 | 294 |
| gi\|143596625\|gb\|EDF78560.1\| | 62.6 | 77.0 | 318 |
| gi\|137641042\|gb\|EBV20355.1\| | 62.6 | 79.1 | 163 |

FIG. 39C

| | | | |
|---|---|---|---|
| gi\|136231267\|gb\|EBM76426.1\| | 62.5 | 76.7 | 339 |
| gi\|143175604\|gb\|EDD36054.1\| | 62.5 | 76.7 | 339 |
| gi\|142508708\|gb\|ECY58867.1\| | 62.5 | 76.7 | 339 |
| gi\|135926501\|gb\|EBK75673.1\| | 62.5 | 76.6 | 320 |
| gi\|141955884\|gb\|ECU42641.1\| | 62.4 | 77.8 | 189 |
| gi\|142821119\|gb\|EDA83282.1\| | 62.4 | 78.7 | 202 |
| gi\|134609411\|gb\|EBC36492.1\| | 62.4 | 75.8 | 194 |
| gi\|142885864\|gb\|EDB27722.1\| | 62.3 | 75.4 | 207 |
| gi\|136204828\|gb\|EBM58549.1\| | 62.3 | 77.0 | 318 |
| gi\|143580324\|gb\|EDF73831.1\| | 62.2 | 76.7 | 339 |
| gi\|143766375\|gb\|EDG67769.1\| | 62.2 | 77.0 | 339 |
| gi\|143500332\|gb\|EDF32922.1\| | 62.2 | 76.4 | 339 |
| gi\|139233105\|gb\|ECE31191.1\| | 62.1 | 76.5 | 132 |
| gi\|143738779\|gb\|EDG53089.1\| | 62.1 | 76.8 | 314 |
| gi\|134964255\|gb\|EBE59804.1\| | 62.1 | 77.1 | 153 |
| gi\|140863545\|gb\|ECO01751.1\| | 62.1 | 77.0 | 269 |
| gi\|137944409\|gb\|EBW89432.1\| | 62.0 | 78.5 | 158 |
| gi\|143411619\|gb\|EDE81261.1\| | 62.0 | 76.7 | 339 |
| gi\|142753988\|gb\|EDA33415.1\| | 62.0 | 77.0 | 339 |
| gi\|139580853\|gb\|ECG04787.1\| | 61.9 | 75.7 | 202 |
| gi\|141227933\|gb\|ECQ50606.1\| | 61.9 | 75.1 | 173 |
| gi\|143659340\|gb\|EDG12239.1\| | 61.8 | 78.3 | 157 |
| gi\|136935328\|gb\|EBR27658.1\| | 61.8 | 77.7 | 157 |
| gi\|137275449\|gb\|EBT18730.1\| | 61.8 | 77.5 | 204 |
| gi\|138585243\|gb\|ECA61437.1\| | 61.8 | 76.5 | 136 |
| gi\|139195947\|gb\|ECE06889.1\| | 61.7 | 76.2 | 269 |
| gi\|139424973\|gb\|ECF02640.1\| | 61.7 | 76.3 | 274 |
| gi\|141380828\|gb\|ECR42772.1\| | 61.7 | 75.8 | 227 |
| gi\|136351647\|gb\|EBN58189.1\| | 61.7 | 77.0 | 339 |
| gi\|136304410\|gb\|EBN26254.1\| | 61.6 | 75.7 | 185 |
| gi\|139948037\|gb\|ECI56814.1\| | 61.6 | 76.8 | 224 |
| gi\|135970899\|gb\|EBL05615.1\| | 61.6 | 76.8 | 211 |
| gi\|138627165\|gb\|ECA90647.1\| | 61.5 | 75.5 | 143 |
| gi\|137395720\|gb\|EBT86160.1\| | 61.5 | 74.8 | 143 |
| gi\|140086960\|gb\|ECJ44912.1\| | 61.5 | 77.1 | 249 |
| gi\|141024916\|gb\|ECP11582.1\| | 61.4 | 76.7 | 223 |
| gi\|139095531\|gb\|ECD38155.1\| | 61.4 | 76.7 | 210 |
| gi\|141659029\|gb\|ECS68171.1\| | 61.4 | 77.2 | 127 |
| gi\|139969430\|gb\|ECI71470.1\| | 61.4 | 76.7 | 215 |
| gi\|136986729\|gb\|EBR56775.1\| | 61.4 | 75.7 | 202 |

FIG. 39D

| | | | |
|---|---|---|---|
| gi\|143634197\|gb\|EDF97600.1\| | 61.3 | 76.7 | 313 |
| gi\|135973785\|gb\|EBL07572.1\| | 61.3 | 76.3 | 279 |
| gi\|143200944\|gb\|EDD54508.1\| | 61.3 | 74.6 | 173 |
| gi\|137787263\|gb\|EBV99371.1\| | 61.2 | 76.3 | 232 |
| gi\|139204136\|gb\|ECE12313.1\| | 61.2 | 76.7 | 219 |
| gi\|136001500\|gb\|EBL25082.1\| | 61.2 | 76.3 | 219 |
| gi\|141874476\|gb\|ECT85572.1\| | 61.2 | 76.4 | 237 |
| gi\|137905325\|gb\|EBW67375.1\| | 61.1 | 74.9 | 175 |
| gi\|140089341\|gb\|ECJ46519.1\| | 61.1 | 75.4 | 203 |
| gi\|140855194\|gb\|ECN95754.1\| | 61.1 | 75.9 | 203 |
| gi\|134965622\|gb\|EBE60718.1\| | 61.1 | 75.8 | 339 |
| gi\|141527125\|gb\|ECS15588.1\| | 61.1 | 76.0 | 208 |
| gi\|136218988\|gb\|EBM68086.1\| | 61.0 | 73.4 | 154 |
| gi\|142364499\|gb\|ECX54765.1\| | 60.9 | 76.1 | 330 |
| gi\|141603393\|gb\|ECS53340.1\| | 60.8 | 74.8 | 143 |
| gi\|136216893\|gb\|EBM66671.1\| | 60.8 | 76.3 | 245 |
| gi\|143743653\|gb\|EDG56305.1\| | 60.8 | 73.7 | 148 |
| gi\|140222741\|gb\|ECK35867.1\| | 60.7 | 73.0 | 163 |
| gi\|142389887\|gb\|ECX71634.1\| | 60.6 | 74.8 | 198 |
| gi\|139315697\|gb\|ECE51398.1\| | 60.6 | 76.4 | 241 |
| gi\|136255250\|gb\|EBM92607.1\| | 60.5 | 76.0 | 291 |
| gi\|137387954\|gb\|EBT81681.1\| | 60.5 | 76.6 | 124 |
| gi\|139229559\|gb\|ECE29834.1\| | 60.4 | 75.3 | 202 |
| gi\|140866196\|gb\|ECO03646.1\| | 60.1 | 74.6 | 303 |
| gi\|139229561\|gb\|ECE29836.1\| | 60.0 | 74.0 | 100 |
| gi\|140957440\|gb\|ECO66006.1\| | 59.9 | 75.9 | 274 |
| gi\|143567213\|gb\|EDF67416.1\| | 59.8 | 74.8 | 286 |
| gi\|139955973\|gb\|ECI62051.1\| | 59.8 | 72.2 | 97 |
| gi\|140726724\|gb\|ECN09682.1\| | 59.7 | 73.4 | 154 |
| gi\|139775003\|gb\|ECH37281.1\| | 59.6 | 73.7 | 99 |
| gi\|137949740\|gb\|EBW92433.1\| | 58.7 | 71.7 | 92 |
| gi\|139650150\|gb\|ECG51661.1\| | 57.7 | 73.2 | 97 |
| gi\|142528844\|gb\|ECY73504.1\| | 56.7 | 70.0 | 90 |

Cut-off used: >50% Identity to and >25% length of synpcc7942_1594

FIG. 40A

Accession Numbers are from NCBI, GenBank, Release 159.0 as of April 15, 2007
EC Numbers are from KEGG, Release 42.0 as of April 2007 (plus daily updates up to March, 2008)

| CATEGORY | GENE | NAME | ACCESSION | EC NUMBER | MODIFICATION | USE | ORGANISM |
|---|---|---|---|---|---|---|---|
| 1. Fatty Acid Production Increase / Product Production Increase | | | | | | | |
| increase acyl-CoA | | | | | | | |
| reduce catabolism of derivatives and intermediates | | | | | | | |
| reduce feedback inhibition | | | | | | | |
| attenuate other pathways that consume fatty acids | | | | | | | |
| | accA | Acetyl-CoA carboxylase, subunit A (carboxyltransferase alpha) | AAC73296, NP_414727 | 6.4.1.2 | Over-express | increase Malonyl-CoA production | Escherichia coli, Lactococci |
| | accB | Acetyl-CoA carboxylase, subunit B (BCCP: biotin carboxyl carrier protein) | NP_417721 | 6.4.1.2 | Over-express | increase Malonyl-CoA production | Escherichia coli, Lactococci |
| | accC | Acetyl-CoA carboxylase, subunit C (biotin carboxylase) | NP_417722 | 6.4.1.2, 6.3.4.14 | Over-express | increase Malonyl-CoA production | Escherichia coli, Lactococci |
| | accD | Acetyl-CoA carboxylase, subunit D (carboxyltransferase beta) | NP_416819 | 6.4.1.2 | Over-express | increase Malonyl-CoA production | Escherichia coli, Lactococci |
| | aceE | pyruvate dehydrogenase, subunit E1 | NP_414656, AAC73226 | 1.2.4.1 | Over-express | increase Acetyl-CoA production | Escherichia coli |
| | aceF | pyruvate dehydrogenase, subunit E2 | NP_414657 | 2.3.1.12 | Over-express | increase Acetyl-CoA production | Escherichia coli |

FIG. 40B

| | | | | | | |
|---|---|---|---|---|---|---|
| ackA | acetate kinase | AAC75356, NP_416799 | 2.7.2.1 | Delete or reduce | increase Acetyl-CoA production | Escherichia coli |
| ackB | acetate kinase AckB | BAB81430 | 2.7.2.1 | Delete or reduce | increase Acetyl-CoA production | Escherichia coli |
| acpP | acyl carrier protein | AAC74178 | NONE | Over-express | increase Acetyl-CoA production | Escherichia coli |
| fadD | acyl-CoA synthase | AP_002424 | 2.3.1.86, 6.2.1.3 | Over-express | increase Fatty acid production | Escherichia coli W3110 |
| adhE | alcohol dehydrogenase | CAA47743 | 1.1.1.1, 1.2.1.10 | Delete or reduce | increase Acetyl-CoA production | Escherichia coli W3111 |
| cer1 | Aldehyde decarbonylase | BAA11024 | 4.1.99.5 | Over-express | increase Acetyl-CoA production | Arabidopsis thaliana |
| fabA | beta-hydroxydecanoyl thioester dehydrase | NP_415474 | 4.2.1.60 | express | fatty acyl-CoA production | E. coli K12 |
| fabD | [acyl-carrier-protein] S-malonyltransferase | AAC74176 | 2.3.1.39 | Over-express | increase Acetyl-CoA production | E. coli K12 |
| fabF | 3-oxoacyl-[acyl-carrier-protein] synthase II | AAC74179 | 2.3.1.179 | Delete or OverExpress | increase Acetyl-CoA production | E. coli K12 |
| fabG | 3-oxoacyl-[acyl-carrier protein] reductase | AAC74177 | 1.1.1.100 | Over-express | increase Acetyl-CoA production | E. coli K12 |
| fabH | 3-oxoacyl-[acyl-carrier-protein] synthase III | AAC74175 | 2.3.1.180 | Over-express | increase Acetyl-CoA production | E. coli K12, lactococci |
| fabI | enoyl-[acyl-carrier-protein] reductase, NADH-dependent | NP_415804 | 1.3.1.9 | express | fatty acyl-CoA production | E. coli K12, lactococci |
| fabR | Transcriptional Repressor | NP_418398 | NONE | Delete or reduce | modulate unsaturated fatty acid production | E. coli K12 |
| fabZ | (3R)-hydroxymyristol acyl carrier protein dehydratase | NP_414722 | 4.2.1.- | | | E. coli K12 |

FIG. 40C

| | | | | | | |
|---|---|---|---|---|---|---|
| | fadE | acyl-CoA dehydrogenase | AAC73325 | 1.3.99.3, 1.3.99.- | Delete or reduce | increase Acetyl-CoA production | |
| | acr1 | Fatty Acyl-CoA reductase | YP_047869, AAC45217 | | Over-express | for fatty alcohol production | Acinetobacter sp., i.e. calcoaceticus |
| | GST, gshB | Glutathione synthase | P04425 | 1.2.1.42 | Delete or reduce | increase Acyl-CoA | E. coli K12 |
| | gpsA | biosynthetic sn-glycerol 3-phosphate dehydrogenase | AAC76632, NP_418065 | 6.3.2.3 | Delete or reduce | increase Acetyl-CoA production | E. coli K12 |
| | ldhA | lactate dehydrogenase | AAC74462, NP_415898 | EC: 1.1.1.94 | Delete or reduce | increase Acetyl-CoA production | E. coli K12 |
| | Lipase | Triglyceride Lipase | CAA89087, CAA98876 | EC: 1.1.1.27, 1.1.1.28 | express | increase Fatty acid production | Saccharomyces cerevisiae |
| | panD | Malonyl-CoA decarboxylase | AAA26500 | 3.1.1.13 | Over-express | | Saccharopolyspora erythraea |
| | panK a.k.a. coaA | aspartate 1-decarboxylase | BAB96708 | 4.1.1.9, 4.1.1.41 | Over-express | increase Acyl-CoA | Escherichia coli W3110 |
| | panK a.k.a. coaA | pantothenate kinase | AAC76952 | 4.1.1.11 | Over-express | increase Acetyl-CoA production | E.coli |
| | panK a.k.a. coaA, R106K | pantothenate kinase | AAC76952 | 2.7.1.33 | Express, Over-express, R106K mutation | increase Acetyl-CoA production | E. coli |
| | pdh | Pyruvate dehydrogenase | BAB34380, AAC73226, NP_415392 | 2.7.1.33 | Over-express | increase Acetyl-CoA production | |
| | pflB | formate acetyltransferase (pyruvate formate lyase) | AAC73989, P09373 | 1.2.4.1 | Delete or reduce | increase Acetyl-CoA production | |
| | plsB | acyltransferase | AAC77011 | EC: 2.3.1.54 | D311E mutation | reduce limits on Acyl-CoA pool | E. coli K12 |
| | | | | 2.3.1.15 | | | |

FIG. 40D

| | | | | | | |
|---|---|---|---|---|---|---|
| | poxB | pyruvate oxidase | AAC73958, NP_415392 | 1.2.2.2 | Delete or reduce | increase Acetyl-CoA production | |
| | pta | phosphotransacetylase | AAC75357, NP_416800 | 2.3.1.8 | Delete or reduce | increase Acetyl-CoA production | |
| | udhA | pyridine nucleotide transhydrogenase | CAA46822 | 1.6.1.1 | Over-express | conversion NADH to NADPH or vice versa | E. coli |
| | | fused 3-hydroxybutyryl-CoA epimerase/delta(3)-cis-delta(2)-trans-enoyl-CoA isomerase/enoyl-CoA hydratase and 3-hydroxyacyl-CoA dehydrogenase | | 4.2.1.17, 5.1.2.3, 5.3.3.8, 1.1.1.35 | | | |
| | fadB | 3-hydroxyacyl-CoA dehydrogenase; K01692 enoyl-CoA hydratase; K01782 3-hydroxybutyryl-CoA epimerase | AP_003956 | | Delete or reduce | Block fatty acid degradation | |
| | fadJ | | AAC75401 | 1.1.1.35, 4.2.1.17, 5.1.2.3 | Delete or reduce | Block fatty acid degradation | E. coli |
| | fadA | 3-ketoacyl-CoA thiolase | BAE77458 | 2.3.1.16 | Delete or reduce | Block fatty acid degradation | E. coli |
| | fadI | beta-ketoacyl-CoA thiolase | AAC75402 | 2.3.1.16 | Delete or reduce | Block fatty acid degradation | E. coli |
| | YdiO | acyl-coA dehydrogenase | YP_852786 | 1.3.99.- | Delete or reduce | Block fatty acid degradation | E. coli |
| 2. Structure Control | | | | | | | |
| 2A. Chain Length Control | | | | | | | |
| 2 | tesA | thioesterase | P0ADA1 | 3.1.2.-, 3.1.1.5 | Delete and/or express | C18 Chain Length | |

FIG. 40E

| | | | | | |
|---|---|---|---|---|---|
| tesA without leader sequence | thioesterase | AAC73596, NP_415027 | 3.1.2.-, 3.1.1.5 | express or overexpress | C18:1 | E.coli |
| tesA without leader sequence:L109P | thioesterase | P0ADA1 | 3.1.2.-, 3.1.1.5 | Express and/or overexpress mutation L109P | <C18 Chain Length | E. coli |
| fatB1 (umbellulari a) | thioesterase | Q41635 | 3.1.2.14 | express or overexpress | C12:0 | Umbellularia californica |
| fatB2 (umbellulari a)DELETE umbelluria) | thioesterase | AAC49269 | 3.1.2.14 | express or overexpress | C8:0 - C10:0 | Cuphea hookeriana |
| fatB3 | thioesterase | AAC72881 | 3.1.2.14 | express or overexpress | C14:0 - C16:0 | Cuphea hookeriana |
| fatB (cinnamonu m) | thioesterase | Q39473 | 3.1.2.14 | express or overexpress | C14:0 | Cinnamomum camphora |
| fatB[M141 T]* | thioesterase | CAA85388 | 3.1.2.14 | express or overexpress | C16:1 | Arabidopsis thaliana |
| fatA1 (Helianthus) | thioesterase | AAL79361 | 3.1.2.14 | express or overexpress | *C18:1* | Helianthus annuus |
| atfata (ARABID OPSIS FATA ACYL- | thioesterase | NP_189147, NP_193041 | 3.1.2.14 | express or overexpress | C18:1 | Arabidopsis thaliana |

FIG. 40F

| ACP THIOESTERASE | | | | | | | |
|---|---|---|---|---|---|---|---|
| fatA | thioesterase | CAC39106 | 3.12.14 | express or overexpress | C18:1 | | Brassica juncea |
| fatA (cuphea) | thioesterase | AAC72883 | 3.12.14 | express or overexpress | C18:1 | | Cuphea hookeriana |
| 2B. Branching Control | | | | | | | |
| attenuate FabH | | | | | | | |
| express FabH from S. glaucescens or S. coelicolor and knock out endogenous eFabH | | | | | | increase branched chain fatty acid derivatives | |
| express FabH from B. subtilis and knock out endogenous eFabH | | | | | | | |

FIG. 40G

| | | | | | | |
|---|---|---|---|---|---|---|
| bdk-E3-dihydrolipoyl dehydrogenase subunit | | | | | | |
| bkd-E1-alpha/beta subunit | decarboxylase subunits of branched-chain α-ketoacid dehydrogenase complex | | EC 1.2.4.4 | | | |
| bkd-E2-dihydrolipoyl transacylase subunit | | | EC 1.2.4.4 | | | |
| bkdA1 | branched-chain α-ketoacid dehydrogenase a-subunit (E1a) | NP_628006 | EC 1.2.4.4 | express or Over-Express | make branched-chain acyl-CoA precursors | Streptomyces coelicolor |
| bkdB1 | branched-chain α-ketoacid dehydrogenase a-subunit (E1b) | NP_628005 | EC 1.2.4.4 | express or Over-Express | make branched-chain acyl-CoA precursors | Streptomyces coelicolor |
| bkdC1 | dihydrolipoyl transacetylase (E2) | NP_628004 | EC 2.3.1.168 | express or Over-Express | make branched-chain acyl-CoA precursors | Streptomyces coelicolor |
| bkdA2 | branched-chain α-ketoacid dehydrogenase a-subunit (E1a) | NP_733618 | EC 1.2.4.4 | express or Over-Express | make branched-chain acyl-CoA precursors | Streptomyces coelicolor |
| bkdB2 | branched-chain α-ketoacid dehydrogenase b-subunit (E1b) | NP_628019 | EC 1.2.4.4 | express or Over-Express | make branched-chain acyl-CoA precursors | Streptomyces coelicolor |
| bkdC2 | dihydrolipoyl transacetylase (E2) | NP_628018 | EC 2.3.1.168 | express or Over-Express | make branched-chain acyl-CoA precursors | Streptomyces coelicolor |

FIG. 40H

| | | | | | |
|---|---|---|---|---|---|
| bkdA | branched-chain a-ketoacid dehydrogenase a-subunit (E1a) | BAC72074 | EC 1.2.4.4 | express or Over-Express | make branched-chain acyl-CoA precursors | Streptomyces avermitilis |
| bkdB | branched-chain a-ketoacid dehydrogenase b-subunit (E1b) | BAC72075 | EC 1.2.4.4 | express or Over-Express | make branched-chain acyl-CoA precursors | Streptomyces avermitilis |
| bkdC | dihydrolipoyl transacetylase (E2) | BAC72076 | EC 2.3.1.168 | express or Over-Express | make branched-chain acyl-CoA precursors | Streptomyces avermitilis |
| bkdF | branched-chain a-ketoacid dehydrogenase a-subunit (E1a) | BAC72088 | EC 1.2.4.4 | express or Over-Express | make branched-chain acyl-CoA precursors | Streptomyces avermitilis |
| bkdG | branched-chain a-ketoacid dehydrogenase b-subunit (E1b) | BAC72089 | EC 1.2.4.4 | express or Over-Express | make branched-chain acyl-CoA precursors | Streptomyces avermitilis |
| bkdH | dihydrolipoyl transacetylase (E2) | BAC72090 | EC 2.3.1.168 | express or Over-Express | make branched-chain acyl-CoA precursors | Streptomyces avermitilis |
| bkdAA | branched-chain a-ketoacid dehydrogenase a-subunit (E1a) | NP_390285 | EC 1.2.4.4 | express or Over-Express | make branched-chain acyl-CoA precursors | Bacillus subtilis |
| bkdAB | branched-chain a-ketoacid dehydrogenase b-subunit (E1b) | NP_390284 | EC 1.2.4.4 | express or Over-Express | make branched-chain acyl-CoA precursors | Bacillus subtilis |
| bkdB | dihydrolipoyl transacetylase (E2) | NP_390283 | EC 2.3.1.168 | express or Over-Express | make branched-chain acyl-CoA precursors | Bacillus subtilis |

FIG. 40I

| | | | | | |
|---|---|---|---|---|---|
| bkdA1 | branched-chain a-ketoacid dehydrogenase a-subunit (E1a) | AAA65614 | EC 1.2.4.4 | express or Over-Express | make branched-chain acyl-CoA precursors | Pseudomonas putida |
| bkdA2 | branched-chain a-ketoacid dehydrogenase b-subunit (E1b) | AAA65615 | EC 1.2.4.4 | express or Over-Express | make branched-chain acyl-CoA precursors | Pseudomonas putida |
| bkdC | dihydrolipoyl transacetylase (E2) | AAA65617 | EC 2.3.1.168 | express or Over-Express | make branched-chain acyl-CoA precursors | Pseudomonas putida |
| lpd | dihydrolipoamide dehydrogenase (E3) | NP_414658 | 1.8.1.4 | express or Over-Express | make branched-chain acyl-CoA precursors | Escherichia coli |
| IlvE | branched-chain amino acid aminotransferase | YP_026247 | 2.6.1.42 | express or Over-Express | make branched a-ketoacids | Escherichia coli |
| IlvE | branched-chain amino acid aminotransferase | AAF34406 | 2.6.1.42 | express or Over-Express | make branched a-ketoacids | Lactococcus lactis |
| IlvE | branched-chain amino acid aminotransferase | NP_745648 | 2.6.1.42 | express or Over-Express | make branched a-ketoacids | Pseudomonas putida |
| IlvE | branched-chain amino acid aminotransferase | NP_629657 | 2.6.1.42 | express or Over-Express | make branched a-ketoacids | Streptomyces coelicolor |
| ccr | crotonyl-CoA reductase | NP_630556 | 1.6.5.5,1.1.1.1 | express or Over-Express | Converting crotonyl-CoA to butyryl-CoA | Streptomyces coelicolor |
| ccr | crotonyl-CoA reductase | AAD53915 | 1.6.5.5,1.1.1.1 | express or Over-Express | Converting crotonyl-CoA to butyryl-CoA | Streptomyces cinnamonensis |
| IcmA, isobutyryl-CoA mutase A | isobutyryl-CoA mutase, subunit A | NP_629554 | 5.4.99.2 | express or Over-Express | converting butyryl-CoA to isobutyryl-CoA | Streptomyces coelicolor |

FIG. 40J

| | | | | | |
|---|---|---|---|---|---|
| IcmA, isobutyryl-CoA mutase | isobutyryl-CoA mutase, subunit A | AAC08713 | 5.4.99.2 | express or Over-Express | converting butyryl-CoA to isobutyryl-CoA | *Streptomyces cinnamonensis* |
| IcmB, isobutyryl-CoA mutase | isobutyryl-CoA mutase, subunit B | NP_630904 | 5.4.99.2 | express or Over-Express | converting butyryl-CoA to isobutyryl-CoA | *Streptomyces coelicolor* |
| IcmB, isobutyryl-CoA mutase | isobutyryl-CoA mutase, subunit B | CAB59633 | 5.4.99.2 | express or Over-Express | converting butyryl-CoA to isobutyryl-CoA | *Streptomyces cinnamonensis* |
| FabHs, ACPs and fabF genes with specificity for branched chain acyl-CoAs | | | | | | |
| IlvE | branched-chain amino acid aminotransferase | CAC12788 | EC2.6.1.42 | over express | branched chain amino acid amino transferase | Staphylococcus carnosus |
| FabH1 | beta-ketoacyl-ACP synthase III | NP_626634 | 2.3.1.180 | express or Over-Express | initiation of branched-chain fatty acid biosynthesis | *Streptomyces coelicolor* |

FIG. 40K

| | | | | | |
|---|---|---|---|---|---|
| ACP | acyl-carrier protein | NP_626635 | NONE | initiation and elongation of branched-chain fatty acid biosynthesis | Streptomyces coelicolor |
| FabF | beta-ketoacyl-ACP synthase II | NP_626636 | 2.3.1.179 | elongation of branched-chain fatty acid biosynthesis | Streptomyces coelicolor |
| FabH3 | beta-ketoacyl-ACP synthase III | NP_823466 | 2.3.1.180 | initiation of branched-chain fatty acid biosynthesis | Streptomyces avermitilis |
| FabC3 (ACP) | acyl-carrier protein | NP_823467 | NONE | initiation and elongation of branched-chain fatty acid biosynthesis | Streptomyces avermitilis |
| FabF | beta-ketoacyl-ACP synthase II | NP_823468 | 2.3.1.179 | elongation of branched-chain fatty acid biosynthesis | Streptomyces avermitilis |
| FabH_A | beta-ketoacyl-ACP synthase III | NP_389015 | 2.3.1.180 | initiation of branched-chain fatty acid biosynthesis | Bacillus subtillis |
| FabH_B | beta-ketoacyl-ACP synthase III | NP_388898 | 2.3.1.180 | initiation of branched-chain fatty acid biosynthesis | Bacillus subtillis |

(express or Over-Express for each row)

FIG. 40L

| | | | | | | | |
|---|---|---|---|---|---|---|---|
| | ACP | acyl-carrier protein | NP_389474 | NONE | express or Over-Express | initiation and elongation of branched-chain fatty acid biosynthesis | *Bacillus subtillis* |
| | FabF | beta-ketoacyl-ACP synthase II | NP_389016 | 2.3.1.179 | express or Over-Express | elongation of branched-chain fatty acid biosynthesis | *Bacillus subtillis* |
| | SmalDRAFT_0818 | beta-ketoacyl-ACP synthase III | ZP_01643059 | 2.3.1.180 | express or Over-Express | initiation of branched-chain fatty acid biosynthesis | *Stenotrophomonas maltophilia* |
| | SmalDRAFT_0821 | acyl-carrier protein | ZP_01643063 | NONE | express or Over-Express | initiation and elongation of branched-chain fatty acid biosynthesis | *Stenotrophomonas maltophilia* |
| | SmalDRAFT_0822 | beta-ketoacyl-ACP synthase II | ZP_01643064 | 2.3.1.179 | express or Over-Express | elongation of branched-chain fatty acid biosynthesis | *Stenotrophomonas maltophilia* |
| | FabH | beta-ketoacyl-ACP synthase III | YP_123672 | 2.3.1.180 | express or Over-Express | initiation of branched-chain fatty acid biosynthesis | *Legionella pneumophila* |
| | ACP | acyl-carrier protein | YP_123675 | NONE | express or Over-Express | initiation and elongation of branched-chain fatty acid | *Legionella pneumophila* |

FIG. 40M

| | | | | | |
|---|---|---|---|---|---|
| | | | | biosynthesis | |
| FabF | beta-ketoacyl-ACP synthase II | YP_123676 | 2.3.1.179 | express or Over-Express | elongation of branched-chain fatty acid biosynthesis | *Legionella pneumophila* |
| FabH | beta-ketoacyl-ACP synthase III | NP_415609 | 2.3.1.180 | delete or reduce | initiation of branched-chain fatty acid biosynthesis | *Escherichia coli* |
| FabF | beta-ketoacyl-ACP synthase II | NP_415613 | 2.3.1.179 | delete or reduce | elongation of branched-chain fatty acid biosynthesis | *Escherichia coli* |
| *To Produce Cyclic Fatty Acids* | | | | | | |
| AnsJ | dehydratase (putative) | not available | not available | express or Over-Express | cyclohexylcarbonyl-CoA boiosynthesis | *Streptomyces collinus* |
| AnsK | CoA ligase (putative) | not available | not available | express or Over-Express | cyclohexylcarbonyl-CoA boiosynthesis | *Streptomyces collinus* |
| AnsL | dehydrogenase (putative) | not available | not available | express or Over-Express | cyclohexylcarbonyl-CoA boiosynthesis | *Streptomyces collinus* |
| ChcA | enoyl-CoA reductase | U72144 | EC 1.3.1.34 | express or Over-Express | cyclohexylcarbonyl-CoA boiosynthesis | *Streptomyces collinus* |
| AnsM | oxidorecutase (putative) | not available | not available | express or Over-Express | cyclohexylcarbonyl-CoA | *Streptomyces collinus* |

FIG. 40N

| | | | | | |
|---|---|---|---|---|---|
| | | | | boiosynthesis | |
| PlmJ | dehydratase (putative) | AAQ84158 | not available | express or Over-Express | cyclohexylcarbonyl-CoA boiosynthesis | Streptomyces sp. HK803 |
| PlmK | CoA ligase (putative) | AAQ84158 | not available | express or Over-Express | cyclohexylcarbonyl-CoA boiosynthesis | Streptomyces sp. HK803 |
| PlmL | dehydrogenase (putative) | AAQ84159 | not available | express or Over-Express | cyclohexylcarbonyl-CoA boiosynthesis | Streptomyces sp. HK803 |
| ChcA | enoyl-CoA reductase | AAQ84160 | EC 1.3.1.34 | express or Over-Express | cyclohexylcarbonyl-CoA boiosynthesis | Streptomyces sp. HK803 |
| PlmM | oxidorecutase (putative) | AAQ84161 | not available | express or Over-Express | cyclohexylcarbonyl-CoA boiosynthesis | Streptomyces sp. HK803 |
| ChcB | enoyl-CoA isomerase | AF268489 | not available | express or Over-Express | cyclohexylcarbonyl-CoA boiosynthesis | Streptomyces collinus |
| ChcB/CaiD | enoyl-CoA isomerase | NP 629292 | 4.2.1.- | express or Over-Express | cyclohexylcarbonyl-CoA boiosynthesis | Streptomyces coelicolor |
| ChcB/CaiD | enoyl-CoA isomerase | NP 824296 | 4.2.1.- | express or Over-Express | cyclohexylcarbonyl-CoA boiosynthesis | Streptomyces avermitilis |
| 2C. Saturation Level Control | | | | | | |
| Sfa | Suppressor of FabA | AAN79592, AAC44390 | NONE | Over-express | increase monounsaturated | E.coli |

FIG. 40O

| | | | | | | |
|---|---|---|---|---|---|---|
| | also see FabA in sec. 1 | | | | fatty acids | |
| | | suppressors of the secG null mutation | ABD18647.1 | NONE | express | produce unsaturated fatty acids | |
| GnsA | | suppressors of the secG null mutation | ABD18647.1 | NONE | Over-express | increase unsaturated fatty acid esters | *E.coli* |
| GnsB | | suppressors of the secG null mutation | AAC74076.1 | NONE | Over-express | increase unsaturated fatty acid esters | *E.coli* |
| | also see section 2A - items with :0 are unsaturated (no double bonds) and with :1 are saturated (1 double bond) | | | | | | |
| fabB | | 3-oxoacyl-[acyl-carrier-protein] synthase I | BAA16180 | EC:2.3.1.41 | overexpress | modulate unsaturated fatty acid production | *Escherichia coli* |
| fabK | | trans-2-enoyl-ACP reductase II | AAF98273 | 1.3.1.9 | express | modulate unsaturated fatty acid production | *Streptococcus pneumoniae* |

FIG. 40P

| | | | | | |
|---|---|---|---|---|---|
| fabI | enoyl-(acyl carrier protein) reductase | AAU39821 | 1.3.1.9 | express | modulate unsaturated fatty acid production | Bacillus licheniformis DSM13 |
| fabM | trans-2, cis-3-decenoyl-ACP isomerase | DAA05501 | 4.2.1.17 | Over-express | modulate unsaturated fatty acid production | Streptococcus mutans |
| 3. Final Product Output | | | | | | |
| 3A. Wax Output | | | | | | |
| AT3G51970 | long-chain-alcohol O-fatty-acyltransferase | NP_190765 | 2.3.1.26 | express | wax production | Arabidopsis thaliana |
| | thioesterase (see chain length control section) | | | express | increase fatty acid production | |
| | fatty alcohol forming acyl-CoA reductase | | 1.1.1.* | express | convert acyl-coa to fatty alcohol | |
| acr1 | acyl-CoA reductase (ACR1) | YP_047869 | 1.2.1.42 | express | convert acyl-coa to fatty alcohol | Acinetobacter sp. ADP1 |
| yqhD | alcohol dehydrogenase | AP_003562 | 1.1.-.- | express | increase | E. coli W3110 |
| ELO1 | Fatty acid elongase | BAD98251 | 2.3.1.- | express | produce very long chain length fatty acids | Pichia angusta |
| plsC | acyltransferase | AAA16514 | 2.3.1.51 | express | | Saccharomyces cerevisiae |
| DAGAT/DGAT | diacylglycerol acyltransferase | AAF19262 | 2.3.1.20 | express | wax production | Arabidopsis thaliana |
| hWS | acyl-CoA wax alcohol acyltransferase | AAX48018 | 2.3.1.20 | express | wax production | Homo sapiens |

FIG. 40Q

| | | | | | |
|---|---|---|---|---|---|
| aft1 | bifunctional wax ester synthase/acyl-CoA:diacylglycerol acyltransferase | AAO17391 | 2.3.1.20, 2.3.1.75 | express | wax production | Acinetobacter sp. ADP1 |
| mWS | wax ester synthase (simmondsia) | AAD38041 | 2.3.1.-, 2.3.1.75 | express | wax production | Simmondsia chinensis |
| 3B. Fatty Alcohol Output | | | | | | |
| | various thioesterases (refer to Sec. 2A) | | | | produce | |
| acr1 | acyl-CoA reductase | YP_047869 | 1.2.1.42 | express | produce | Acinetobacter sp. ADP1 |
| yqhD | alcohol dehydrogenase | AP_003562 | 1.1.-.- | express | produce | Escherichia coli W3110 |
| BmFAR | FAR (fatty alcohol forming acyl-CoA reductase) | BAC79425 | 1.1.1.* | express | reduce fatty acyl-CoA to fatty alcohol | Bombyx mori |
| Akr1a4 | Mammalian microsomal aldehyde reductase | NP_067448 | 1.1.1.2 | express | produce | Mus musculus |
| GTNG_1865 | Long-chain aldehyde dehydrogenase | YP_001125970 | 1.2.1.3 | express | produce | Geobacillus thermodenitrificans NG80-2 |
| FadD | acyl-CoA synthase | NP_416319 | EC 6.2.1.3 | express | produce more | E. Coli K12 |
| To make Butanol | | | | | | |
| atoB | acetyl-CoA acetyltransferase | YP_049388 | 2.3.1.9 | express | produce | Erwinia carotovora |
| hbd | Beta-hydroxybutyryl-CoA dehydrogenase | BAD51424 | 1.1.1.157 | express | produce | Butyrivibrio fibrisolvens |
| CPE0095 | crotonase | BAB79801 | 4.2.1.55 | express | produce | Clostridium perfringens |

FIG. 40R

| | | | | | |
|---|---|---|---|---|---|
| | bcd | butyryl-CoA dehydrogenase | AAM14583 | 1.3.99.2 | express | produce | *Clostridium beijerinckii* |
| | ALDH | coenzyme A-acylating aldehyde dehydrogenase | AAT66436 | 1.2.1.3 | express | produce | *Clostridium beijerinckii* |
| | AdhE | aldehyde-alcohol dehydrogenase | AAN80172 | 1.1.1.1 1.2.1.10 | express | produce | *Escherichia coli CFT073* |
| 3C. Fatty Acid Ester Output | | | | | | | |
| | thioesterase | see chain length control section | | | | | |
| | acr1 | acyl-CoA reductase | YP_047869 | 1.2.1.42 | express | produce | *Acinetobacter sp. ADP1* |
| | yqhD | alcohol dehydrogenase | AP_003562 | 1.1.-.- | express | produce | *E. Coli K12* |
| | AAT | alcohol O-acetyltransferase | AAG13130 | 2.3.1.84 | express | produce | *Fragaria x ananassa* |
| 4. Export | | | | | | | |
| | Wax ester exporter (FATP family, Fatty Acid (long chain) Transport Protein) | | NP_524723 | NONE | express | export wax | *Drosophila melanogaster* |
| | ABC transport protein | putative alkane transporter | AAN73268 | NONE | express | export products | *Rhodococcus erythropolis* |
| | CER5 | wax transporter | At1g51500, AY734542, At3g21090, At1g51460 | NONE | express | export products | *Arabidopsis thaliana* |

FIG. 40S

| | | | | | | | |
|---|---|---|---|---|---|---|---|
| | AtMRP5 | Arabidopsis thaliana multidrug resistance-associated | NP_171908 | NONE | express | export products | *Arabidopsis thaliana* |
| | AmiS2 | ABC transporter AmiS2 | JC5491 | NONE | express | export products | *Rhodococcus sp.* |
| | AtPGP1 | ARABIDOPSIS THALIANA P GLYCOPROTEIN1 | NP_181228 | NONE | express | export products | *Arabidopsis thaliana* |
| | AcrA | putative multidrug-efflux transport protein acrA | CAF23274 | NONE | express | export products | *Candidatus Protochlamydia amoebophila UWE25* |
| | AcrB | probable multidrug-efflux transport protein, acrB | CAF23275 | NONE | express | export products | *Candidatus Protochlamydia amoebophila UWE25* |
| | TolC | Outer membrane protein [Cell envelope biogenesis, | ABD59001 | NONE | express | export products | *Francisella tularensis subsp. novicida* |
| | AcrE | transmembrane protein affects septum formation and cell membrane permeability | YP_312213 | NONE | express | export products | *Shigella sonnei Ss046* |
| | AcrF | Acriflavine resistance protein F | P24181 | NONE | express | export products | *Escherichia coli* |
| | tll1618 | multidrug efflux transporter | NP_682408.1 | NONE | express | export products | *Thermosynechoc occus elongatus BP-1]* |
| | tll1619 | multidrug efflux transporter | NP_682409.1 | NONE | express | export products | *Thermosynechoc occus elongatus BP-1]* |
| | tll0139 | multidrug efflux transporter | NP_680930.1 | NONE | express | export products | *Thermosynechoc occus elongatus BP-1]* |

FIG. 40T

| 5. Fermentation | | | | | | |
|---|---|---|---|---|---|---|
| | replication checkpoint genes | | | | | |
| | umuD | DNA polymerase V, subunit | YP_310132 | 3.4.21.- | | increase output efficiency |
| | umuD | DNA polymerase V, subunit | YP_310132 | 3.4.21.- | Over-express | increase output efficiency | Shigella sonnei Ss046 |
| | umuC | DNA polymerase V, subunit | ABC42261 | 2.7.7.7 | Over-express | increase output efficiency | Escherichia coli |
| | NADH:NADPH transhydrogenase (alpha and beta subunits) (pntA, pntB) | | P07001, P0AB70 | 1.6.1.2 | express | increase output efficiency | Shigella flexneri |

METHODS AND COMPOSITIONS FOR PRODUCING HYDROCARBONS

CROSS-REFERENCE TO RELATED APPLICATIONS

This application is a continuation-in-part of International Application No. PCT/US09/44403, filed May 18, 2009, which claims the benefit of U.S. Provisional Application No. 61/053,955, filed May 16, 2008, the contents of all of which are hereby incorporated in their entirety herein.

BACKGROUND OF THE INVENTION

Petroleum is a limited, natural resource found in the Earth in liquid, gaseous, or solid forms. Petroleum is primarily composed of hydrocarbons, which are comprised mainly of carbon and hydrogen. It also contains significant amounts of other elements, such as, nitrogen, oxygen, or sulfur, in different forms.

Petroleum is a valuable resource, but petroleum products are developed at considerable costs, both financial and environmental. First, sources of petroleum must be discovered. Petroleum exploration is an expensive and risky venture. The cost of exploring deep water wells can exceed $100 million. Moreover, there is no guarantee that these wells will contain petroleum. It is estimated that only 40% of drilled wells lead to productive wells generating commercial hydrocarbons. In addition to the economic cost, petroleum exploration carries a high environmental cost. For example, offshore exploration disturbs the surrounding marine environments.

After a productive well is discovered, the petroleum must be extracted from the Earth at great expense. During primary recovery, the natural pressure underground is sufficient to extract about 20% of the petroleum in the well. As this natural pressure falls, secondary recovery methods are employed, if economical. Generally, secondary recovery involves increasing the well's pressure by, for example, water injection, natural gas injection, or gas lift. Using secondary recovery methods, an additional 5% to 15% of petroleum is recovered. Once secondary recovery methods are exhausted, tertiary recovery methods can be used, if economical. Tertiary methods involve reducing the viscosity of the petroleum to make it easier to extract. Using tertiary recovery methods, an additional 5% to 15% of petroleum is recovered. Hence, even under the best circumstances, only 50% of the petroleum in a well can be extracted. Petroleum extraction also carries an environmental cost. For example, petroleum extraction can result in large seepages of petroleum rising to the surface. Moreover, offshore drilling involves dredging the seabed which disrupts or destroys the surrounding marine environment.

Since petroleum deposits are not found uniformly throughout the Earth, petroleum must be transported over great distances from petroleum producing regions to petroleum consuming regions. In addition to the shipping costs, there is also the environmental risk of devastating oil spills.

In its natural form, crude petroleum extracted from the Earth has few commercial uses. It is a mixture of hydrocarbons (e.g., paraffins (or alkanes), olefins (or alkenes), alkynes, napthenes (or cylcoalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.).

Hence, crude petroleum must be refined and purified before it can be used commercially. Due to its high energy density and its easy transportability, most petroleum is refined into fuels, such as transportation fuels (e.g., gasoline, diesel, aviation fuel, etc.), heating oil, liquefied petroleum gas, etc.

Crude petroleum is also a primary source of raw materials for producing petrochemicals. The two main classes of raw materials derived from petroleum are short chain olefins (e.g., ethylene and propylene) and aromatics (e.g., benzene and xylene isomers). These raw materials are derived from longer chain hydrocarbons in crude petroleum by cracking it at considerable expense using a variety of methods, such as catalytic cracking, steam cracking, or catalytic reforming. These raw materials are used to make petrochemicals, which cannot be directly refined from crude petroleum, such as monomers, solvents, detergents, or adhesives.

One example of a raw material derived from crude petroleum is ethylene. Ethylene is used to produce petrochemicals such as, polyethylene, ethanol, ethylene oxide, ethylene glycol, polyester, glycol ether, ethoxylate, vinyl acetate, 1,2-dichloroethane, trichloroethylene, tetrachloroethylene, vinyl chloride, and polyvinyl chloride. An additional example of a raw material is propylene, which is used to produce isopropyl alcohol, acrylonitrile, polypropylene, propylene oxide, propylene glycol, glycol ethers, butylene, isobutylene, 1,3-butadiene, synthetic elastomers, polyolefins, alpha-olefins, fatty alcohols, acrylic acid, acrylic polymers, allyl chloride, epichlorohydrin, and epoxy resins.

These petrochemicals can then be used to make specialty chemicals, such as plastics, resins, fibers, elastomers, pharmaceuticals, lubricants, or gels. Particular specialty chemicals which can be produced from petrochemical raw materials are: fatty acids, hydrocarbons (e.g., long chain, branched chain, saturated, unsaturated, etc.), fatty alcohols, esters, fatty aldehydes, ketones, lubricants, etc.

Specialty chemicals have many commercial uses. Fatty acids are used commercially as surfactants, for example, in detergents and soaps. They can also be used as additives in fuels, lubricating oils, paints, lacquers, candles, salad oil, shortening, cosmetics, and emulsifiers. In addition, fatty acids are used as accelerator activators in rubber products. Fatty acids can also be used as a feedstock to produce methyl esters, amides, amines, acid chlorides, anhydrides, ketene dimers, and peroxy acids and esters.

Hydrocarbons have many commercial uses. For example, shorter chain alkanes are used as fuels. Methane and ethane are the main constituents of natural gas. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. Alkanes that contain approximately thirty-five carbons are found in bitumen, which is used for road surfacing. In addition, longer chain alkanes can be cracked to produce commercially useful shorter chain hydrocarbons.

Like short chain alkanes, short chain alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers.

Fatty alcohols have many commercial uses. The shorter chain fatty alcohols are used in the cosmetic and food industries as emulsifiers, emollients, and thickeners. Due to their amphiphilic nature, fatty alcohols behave as nonionic surfactants, which are useful as detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats.

Esters have many commercial uses. For example, biodiesel, an alternative fuel, is comprised of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

Aldehydes are used to produce many specialty chemicals. For example, aldehydes are used to produce polymers, resins (e.g., Bakelite), dyes, flavorings, plasticizers, perfumes, pharmaceuticals, and other chemicals. Some are used as solvents, preservatives, or disinfectants. Some natural and synthetic compounds, such as vitamins and hormones, are aldehydes. In addition, many sugars contain aldehyde groups.

Ketones are used commercially as solvents. For example, acetone is frequently used as a solvent, but it is also a raw material for making polymers. Ketones are also used in lacquers, paints, explosives, perfumes, and textile processing. In addition, ketones are used to produce alcohols, alkenes, alkanes, imines, and enamines.

In addition, crude petroleum is a source of lubricants. Lubricants derived petroleum are typically composed of olefins, particularly polyolefins and alpha-olefins. Lubricants can either be refined from crude petroleum or manufactured using raw materials refined from crude petroleum.

Obtaining these specialty chemicals from crude petroleum requires a significant financial investment as well as a great deal of energy. It is also an inefficient process because frequently the long chain hydrocarbons in crude petroleum are cracked to produce smaller monomers. These monomer are then used as the raw material to manufacture the more complex specialty chemicals.

In addition to the problems with exploring, extracting, transporting, and refining petroleum, petroleum is a limited and dwindling resource. One estimate of world petroleum consumption is 30 billion barrels per year. By some estimates, it is predicted that at current production levels, the world's petroleum reserves could be depleted before the year 2050.

Finally, the burning of petroleum based fuels releases greenhouse gases (e.g., carbon dioxide) and other forms of air pollution (e.g., carbon monoxide, sulfur dioxide, etc.). As the world's demand for fuel increases, the emission of greenhouse gases and other forms of air pollution also increases. The accumulation of greenhouse gases in the atmosphere leads to an increase global warming. Hence, in addition to damaging the environment locally (e.g., oil spills, dredging of marine environments, etc.), burning petroleum also damages the environment globally.

Due to the inherent challenges posed by petroleum, there is a need for a renewable petroleum source which does not need to be explored, extracted, transported over long distances, or substantially refined like petroleum. There is also a need for a renewable petroleum source that can be produced economically without creating the type of environmental damage produced by the petroleum industry and the burning of petroleum based fuels. For similar reasons, there is also a need for a renewable source of chemicals that are typically derived from petroleum.

SUMMARY OF THE INVENTION

The invention is based, at least in part, on the identification of cyanobacterial genes that encode hydrocarbon biosynthetic polypeptides. Accordingly, in one aspect, the invention features a method of producing a hydrocarbon, the method comprising producing in a host cell a polypeptide comprising the amino acid sequence of SEQ ID NO:2, 4, 6, 8, 10, 12, 14, 16, 18, 20, 22, 24, 26, 28, 30, 32, 34, or 36, or a variant thereof, and isolating the hydrocarbon from the host cell.

In some embodiments, the polypeptide comprises an amino acid sequence having at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99% identity to SEQ ID NO:2, 4, 6, 8, 10, 12, 14, 16, 18, 20, 22, 24, 26, 28, 30, 32, 34, or 36.

In some embodiments, the polypeptide comprises the amino acid sequence of SEQ ID NO:2, 4, 6, 8, 10, 12, 14, 16, 18, 20, 22, 24, 26, 28, 30, 32, 34, or 36 with one or more amino acid substitutions, additions, insertions, or deletions. In some embodiments, the polypeptide has decarbonylase activity. In yet other embodiments, the polypeptide comprises the amino acid sequence of SEQ ID NO:2, 4, 6, 8, 10, 12, 14, 16, 18, 20, 22, 24, 26, 28, 30, 32, 34, or 36, with one or more conservative amino acid substitutions. For example, the polypeptide comprises one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. In some embodiments, the polypeptide has decarbonylase activity.

In other embodiments, the polypeptide comprises the amino acid sequence of: (i) SEQ ID NO:37 or SEQ ID NO:38 or SEQ ID NO:39; or (ii) SEQ ID NO:40 and any one of (a) SEQ ID NO:37, (b) SEQ ID NO:38, and (c) SEQ ID NO:39; or (iii) SEQ ID NO:41 or SEQ ID NO:42 or SEQ ID NO:43 or SEQ ID NO:44. In certain embodiments, the polypeptide has decarbonylase activity.

In another aspect, the invention features a method of producing a hydrocarbon, the method comprising expressing in a host cell a polynucleotide comprising a nucleotide sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 3, 5, 7, 9, 11, 13, 15, 17, 19, 21, 23, 25, 27, 29, 31, 33, or 35. In some embodiments, the nucleotide sequence is SEQ ID NO:1, 3, 5, 7, 9, 11, 13, 15, 17, 19, 21, 23, 25, 27, 29, 31, 33, or 35. In some embodiments, the method further comprises isolating the hydrocarbon from the host cell.

In other embodiments, the nucleotide sequence hybridizes to a complement of SEQ ID NO:1, 3, 5, 7, 9, 11, 13, 15, 17, 19, 21, 23, 25, 27, 29, 31, 33, or 35, or to a fragment thereof, for example, under low stringency, medium stringency, high stringency, or very high stringency conditions.

In other embodiments, the nucleotide sequence encodes a polypeptide comprising: (i) the amino acid sequence of SEQ ID NO:2, 4, 6, 8, 10, 12, 14, 16, 18, 20, 22, 24, 26, 28, 30, 32, 34, or 36; or (ii) the amino acid sequence of SEQ ID NO:2, 4, 6, 8, 10, 12, 14, 16, 18, 20, 22, 24, 26, 28, 30, 32, 34, or 36 with one or more amino acid substitutions, additions, insertions, or deletions. In some embodiments, the polypeptide comprises the amino acid sequence of SEQ ID NO:2, 4, 6, 8, 10, 12, 14, 16, 18, 20, 22, 24, 26, 28, 30, 32, 34, or 36 with one or more conservative amino acid substitutions. In some embodiments, the polypeptide has decarbonylase activity.

In other embodiments, the nucleotide sequence encodes a polypeptide having the same biological activity as a polypeptide comprising the amino acid sequence of SEQ ID NO:2, 4, 6, 8, 10, 12, 14, 16, 18, 20, 22, 24, 26, 28, 30, 32, 34, or 36. In some embodiments, the nucleotide sequence is SEQ ID NO:1, 3, 5, 7, 9, 11, 13, 15, 17, 19, 21, 23, 25, 27, 29, 31, 33, or 35 or a fragment thereof. In other embodiments, the nucleotide sequence hybridizes to a complement of SEQ ID NO:1, 3, 5, 7, 9, 11, 13, 15, 17, 19, 21, 23, 25, 27, 29, 31, 33, or 35 or to a fragment thereof, for example, under low stringency, medium stringency, high stringency, or very high stringency conditions. In some embodiments, the biological activity is decarbonylase activity.

In some embodiments, the method comprises transforming a host cell with a recombinant vector comprising a nucleotide sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 3, 5, 7, 9, 11, 13, 15, 17, 19, 21, 23, 25, 27, 29, 31, 33, or 35. In some embodiments, the recombinant vector further comprises a promoter operably linked to the nucleotide sequence. In some embodiments, the promoter is a developmentally-regulated, an organelle-specific, a tissue-specific, an inducible, a constitutive, or a cell-specific promoter. In particular embodiments, the recombinant vector comprises at least one sequence selected from the group consisting of (a) a regulatory sequence operatively coupled to the nucleotide sequence; (b) a selection marker operatively coupled to the nucleotide sequence; (c) a marker sequence operatively coupled to the nucleotide sequence; (d) a purification moiety operatively coupled to the nucleotide sequence; (e) a secretion sequence operatively coupled to the nucleotide sequence; and (f) a targeting sequence operatively coupled to the nucleotide sequence. In certain embodiments, the nucleotide sequence is stably incorporated into the genomic DNA of the host cell, and the expression of the nucleotide sequence is under the control of a regulated promoter region.

In any of the aspects described herein, the host cell can be selected from the group consisting of a mammalian cell, plant cell, insect cell, yeast cell, fungus cell, filamentous fungi cell, and bacterial cell.

In some embodiments, the host cell is a Gram-positive bacterial cell. In other embodiments, the host cell is a Gram-negative bacterial cell.

In some embodiments, the host cell is selected from the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces.*

In particular embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell. In other embodiments, the host cell is an *Actinomycetes* cell.

In some embodiments, the host cell is a CHO cell, a COS cell, a VERO cell, a BHK cell, a HeLa cell, a Cv1 cell, an MDCK cell, a 293 cell, a 3T3 cell, or a PC12 cell.

In particular embodiments, the host cell is an *E. coli* cell, such as a strain B, a strain C, a strain K, or a strain W *E. coli* cell.

In other embodiments, the host cell is a cyanobacterial host cell. In particular embodiments, the cyanobacterial host cell is a cell listed in Table 1.

In some embodiments, the hydrocarbon is secreted from by the host cell.

In certain embodiments, the host cell overexpresses a substrate described herein. In some embodiments, the method further includes transforming the host cell with a nucleic acid that encodes an enzyme described herein, and the host cell overexpresses a substrate described herein. In other embodiments, the method further includes culturing the host cell in the presence of at least one substrate described herein. In some embodiments, the substrate is a fatty acid derivative, an acyl-ACP, a fatty acid, an acyl-CoA, a fatty aldehyde, a fatty alcohol, or a fatty ester.

In some embodiments, the fatty acid derivative substrate is an unsaturated fatty acid derivative substrate, a monounsaturated fatty acid derivative substrate, or a saturated fatty acid derivative substrate. In other embodiments, the fatty acid derivative substrate is a straight chain fatty acid derivative substrate, a branched chain fatty acid derivative substrate, or a fatty acid derivative substrate that includes a cyclic moiety.

In certain embodiments of the aspects described herein, the hydrocarbon produced is an alkane. In some embodiments, the alkane is a $C_3$-$C_{25}$ alkane. For example, the alkane is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ alkane. In some embodiments, the alkane is tridecane, methyltridecane, nonadecane, methylnonadecane, heptadecane, methylheptadecane, pentadecane, or methylpentadecane.

In some embodiments, the alkane is a straight chain alkane, a branched chain alkane, or a cyclic alkane.

In certain embodiments, the method further comprises culturing the host cell in the presence of a saturated fatty acid derivative, and the hydrocarbon produced is an alkane. In certain embodiments, the saturated fatty acid derivative is a $C_6$-$C_{26}$ fatty acid derivative substrate. For example, the fatty acid derivative substrate is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty acid derivative substrate. In particular embodiments, the fatty acid derivative substrate is 2-methylicosanal, icosanal, octadecanal, tetradecanal, 2-methyloctadecanal, stearaldehyde, or palmitaldehyde.

In some embodiments, the method further includes isolating the alkane from the host cell or from the culture medium. In other embodiments, the method further includes cracking or refining the alkane.

In certain embodiments of the aspects described herein, the hydrocarbon produced is an alkene. In some embodiments, the alkene is a $C_3$-$C_{25}$ alkene. For example, the alkene is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ alkene. In some embodiments, the alkene is pentadecene, heptadecene, methylpentadecene, or methylheptadecene.

In some embodiments, the alkene is a straight chain alkene, a branched chain alkene, or a cyclic alkene.

In certain embodiments, the method further comprises culturing the host cell in the presence of an unsaturated fatty acid derivative, and the hydrocarbon produced is an alkene. In certain embodiments, the unsaturated fatty acid derivative is a $C_6$-$C_{26}$ fatty acid derivative substrate. For example, the fatty acid derivative substrate is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ unsaturated fatty acid derivative substrate. In particular embodiments, the fatty acid derivative substrate is octadecenal, hexadecenal, methylhexadecenal, or methyloctadecenal.

In another aspect, the invention features a genetically engineered microorganism comprising an exogenous control sequence stably incorporated into the genomic DNA of the microorganism. In one embodiment, the control sequence is integrated upstream of a polynucleotide comprising a nucleotide sequence having at least about 70% sequence identity to SEQ ID NO:1, 3, 5, 7, 9, 11, 13, 15, 17, 19, 21, 23, 25, 27, 29, 31, 33, or 35. In some embodiments, the nucleotide sequence has at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 3, 5, 7, 9, 11, 13, 15, 17, 19, 21, 23, 25, 27, 29, 31, 33, or 35. In some embodiments, the nucleotide sequence is SEQ ID NO:1, 3, 5, 7, 9, 11, 13, 15, 17, 19, 21, 23, 25, 27, 29, 31, 33, or 35.

In some embodiments, the polynucleotide is endogenous to the microorganism. In some embodiments, the microorganism expresses an increased level of a hydrocarbon relative to a wild-type microorganism. In some embodiments, the microorganism is a cyanobacterium.

In another aspect, the invention features a method of making a hydrocarbon, the method comprising culturing a genetically engineered microorganism described herein under conditions suitable for gene expression, and isolating the hydrocarbon.

In another aspect, the invention features a method of making a hydrocarbon, comprising contacting a substrate with (i) a polypeptide having at least 70% identity to the amino acid sequence of SEQ ID NO:2, 4, 6, 8, 10, 12, 14, 16, 18, 20, 22, 24, 26, 28, 30, 32, 34, or 36, or a variant thereof; (ii) a polypeptide encoded by a nucleotide sequence having at least 70% identity to SEQ ID NO:1, 3, 5, 7, 9, 11, 13, 15, 17, 19, 21, 23, 25, 27, 29, 31, 33, or 35, or a variant thereof; (iii) a polypeptide comprising the amino acid sequence of SEQ ID NO:37, 38, or 39; (iv) a polypeptide comprising the amino acid sequence of SEQ ID NO:40 and any one of (a) SEQ ID NO:37, (b) SEQ ID NO:38, and (c) SEQ ID NO:39; or (v) SEQ ID NO:41, 42, 43, or 44. In some embodiments, the polypeptide has decarbonylase activity.

In some embodiments, the polypeptide has at least about 80%, at least about 85%, at least about 90%, at least about 91%, at least about 92%, at least about 93%, at least about 94%, at least about 95%, at least about 96%, at least about 97%, at least about 98%, or at least about 99% identity to SEQ ID NO:2, 4, 6, 8, 10, 12, 14, 16, 18, 20, 22, 24, 26, 28, 30, 32, 34, or 36. In some embodiments, the polypeptide has the amino acid sequence of SEQ ID NO:2, 4, 6, 8, 10, 12, 14, 16, 18, 20, 22, 24, 26, 28, 30, 32, 34, or 36.

In some embodiments, the polypeptide is encoded by a nucleotide sequence having at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 3, 5, 7, 9, 11, 13, 15, 17, 19, 21, 23, 25, 27, 29, 31, 33, or 35. In some embodiments, the polypeptide is encoded by a nucleotide sequence having SEQ ID NO:1, 3, 5, 7, 9, 11, 13, 15, 17, 19, 21, 23, 25, 27, 29, 31, 33, or 35.

In some embodiments, the biological substrate is a fatty acid derivative, an acyl-ACP, a fatty acid, an acyl-CoA, a fatty aldehyde, a fatty alcohol, or a fatty ester.

In some embodiments, the substrate is a saturated fatty acid derivative, and the hydrocarbon is an alkane, for example, a $C_3$-$C_{25}$ alkane. For example, the alkane is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ alkane. In some embodiments, the alkane is tridecane, methyltridecane, nonadecane, methylnonadecane, heptadecane, methylheptadecane, pentadecane, or methylpentadecane.

In some embodiments, the alkane is a straight chain alkane, a branched chain alkane, or a cyclic alkane.

In some embodiments, the saturated fatty acid derivative is 2-methylicosanal, icosanal, octadecanal, tetradecanal, 2-methyloctadecanal, stearaldehyde, or palmitaldehyde.

In other embodiments, the biological substrate is an unsaturated fatty acid derivative, and the hydrocarbon is an alkene, for example, a $C_3$-$C_{25}$ alkene. For example, the alkene is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ alkene. In some embodiments, the alkene is pentadecene, heptadecene, methylpentadecene, or methylheptadecene.

In some embodiments, the alkene is a straight chain alkene, a branched chain alkene, or a cyclic alkene.

In some embodiments, the unsaturated fatty acid derivative is octadecenal, hexadecenal, methylhexadecenal, or methyloctadecenal.

In another aspect, the invention features a hydrocarbon produced by any of the methods or microorganisms described herein. In particular embodiments, the hydrocarbon is an alkane or an alkene having a $\delta^{13}C$ of about −15.4 or greater. For example, the alkane or alkene has a $\delta^{13}C$ of about −15.4 to about −10.9, for example, about −13.92 to about −13.84. In other embodiments, the alkane or alkene has an $f_M{}^{14}C$ of at least about 1.003. For example, the alkane or alkene has an $f_M{}^{14}C$ of at least about 1.01 or at least about 1.5. In some embodiments, the alkane or alkene has an $f_M{}^{14}C$ of about 1.111 to about 1.124.

In another aspect, the invention features a biofuel that includes a hydrocarbon produced by any of the methods or microorganisms described herein. In particular embodiments, the hydrocarbon is an alkane or alkene having a $\delta^{13}C$ of about −15.4 or greater. For example, the alkane or alkene has a $\delta^{13}C$ of about −15.4 to about −10.9, for example, about −13.92 to about −13.84. In other embodiments, the alkane or alkene has an $f_M{}^{14}C$ of at least about 1.003. For example, the alkane or alkene has an $f_M{}^{14}C$ of at least about 1.01 or at least about 1.5. In some embodiments, the alkane or alkene has an $f_M{}^{14}C$ of about 1.111 to about 1.124. In some embodiments, the biofuel is diesel, gasoline, or jet fuel.

In another aspect, the invention features an isolated nucleic acid consisting of no more than about 500 nucleotides of SEQ ID NO:1, 3, 5, 7, 9, 11, 13, 15, 17, 19, 21, 23, 25, 27, 29, 31, 33, or 35. In some embodiments, the nucleic acid consists of no more than about 300 nucleotides, no more than about 350 nucleotides, no more than about 400 nucleotides, no more than about 450 nucleotides, no more than about 550 nucleotides, no more than about 600 nucleotides, or no more than about 650 nucleotides, of SEQ ID NO:1, 3, 5, 7, 9, 11, 13, 15, 17, 19, 21, 23, 25, 27, 29, 31, 33, or 35. In some embodiments, the nucleic acid encodes a polypeptide having decarbonylase activity.

In another aspect, the invention features an isolated nucleic acid consisting of no more than about 99%, no more than about 98%, no more than about 97%, no more than about 96%, no more than about 95%, no more than about 94%, no more than about 93%, no more than about 92%, no more than about 91%, no more than about 90%, no more than about 85%, or no more than about 80% of the nucleotides of SEQ ID NO:1, 3, 5, 7, 9, 11, 13, 15, 17, 19, 21, 23, 25, 27, 29, 31, 33, or 35. In some embodiments, the nucleic acid encodes a polypeptide having decarbonylase activity.

In another aspect, the invention features an isolated polypeptide consisting of no more than about 200, no more than about 175, no more than about 150, or no more than about 100 of the amino acids of SEQ ID NO:2, 4, 6, 8, 10, 12, 14, 16, 18, 20, 22, 24, 26, 28, 30, 32, 34, or 36. In some embodiments, the polypeptide has decarbonylase activity.

In another aspect, the invention features an isolated polypeptide consisting of no more than about 99%, no more than about 98%, no more than about 97%, no more than about 96%, no more than about 95%, no more than about 94%, no more than about 93%, no more than about 92%, no more than about 91%, no more than about 90%, no more than about 85%, or no more than about 80% of the amino acids of SEQ ID NO:2, 4, 6, 8, 10, 12, 14, 16, 18, 20, 22, 24, 26, 28, 30, 32, 34, or 36. In some embodiments, the polypeptide has decarbonylase activity.

DEFINITIONS

Throughout the specification, a reference may be made using an abbreviated gene name or polypeptide name, but it is understood that such an abbreviated gene or polypeptide name represents the genus of genes or polypeptides. Such gene names include all genes encoding the same polypeptide and homologous polypeptides having the same physiological function. Polypeptide names include all polypeptides that have the same activity (e.g., that catalyze the same fundamental chemical reaction).

The accession numbers referenced herein are derived from the NCBI database (National Center for Biotechnology Information) maintained by the National Institute of Health, U.S.A. Unless otherwise indicated, the accession numbers are as provided in the database as of April 2009.

EC numbers are established by the Nomenclature Committee of the International Union of Biochemistry and Molecular Biology (NC-IUBMB) (available at http://www.chem.qmul.ac.uk/iubmb/enzyme/). The EC numbers referenced herein are derived from the KEGG Ligand database, maintained by the Kyoto Encyclopedia of Genes and Genomics, sponsored in part by the University of Tokyo. Unless otherwise indicated, the EC numbers are as provided in the database as of March 2008.

The articles "a" and "an" are used herein to refer to one or to more than one (i.e., to at least one) of the grammatical object of the article. By way of example, "an element" means one element or more than one element.

The term "about" is used herein to mean a value ±20% of a given numerical value. Thus, "about 60%" means a value of between 60±(20% of 60) (i.e., between 48 and 70).

As used herein, the term "aldehyde" means a hydrocarbon having the formula RCHO characterized by an unsaturated carbonyl group (C=O). In a preferred embodiment, the aldehyde is any aldehyde made from a fatty acid or fatty acid derivative. In one embodiment, the R group is at least about 1, 2, 3, 4, 5, 6, 7, 8, 9, 10, 11, 12, 13, 14, 15, 16, 17, 18, 19, or 20 carbons in length.

As used herein, an "aldehyde biosynthetic gene" or an "aldehyde biosynthetic polynucleotide" is a nucleic acid that encodes an aldehyde biosynthetic polypeptide.

As used herein, an "aldehyde biosynthetic polypeptide" is a polypeptide that is a part of the biosynthetic pathway of an aldehyde. Such polypeptides can act on a biological substrate to yield an aldehyde. In some instances, the aldehyde biosynthetic polypeptide has reductase activity.

As used herein, the term "alkane" means a hydrocarbon containing only single carbon-carbon bonds.

As used herein, an "alkane biosynthetic gene" or an "alkane biosynthetic polynucleotide" is a nucleic acid that encodes an alkane biosynthetic polypeptide.

As used herein, an "alkane biosynthetic polypeptide" is a polypeptide that is a part of the biosynthetic pathway of an alkane. Such polypeptides can act on a biological substrate to yield an alkane. In some instances, the alkane biosynthetic polypeptide has decarbonylase activity.

As used herein, an "alkene biosynthetic gene" or an "alkene biosynthetic polynucleotide" is a nucleic acid that encodes an alkene biosynthetic polypeptide.

As used herein, an "alkene biosynthetic polypeptide" is a polypeptide that is a part of the biosynthetic pathway of an alkene. Such polypeptides can act on a biological substrate to yield an alkene. In some instances, the alkene biosynthetic polypeptide has decarbonylase activity.

As used herein, the term "attenuate" means to weaken, reduce or diminish. For example, a polypeptide can be attenuated by modifying the polypeptide to reduce its activity (e.g., by modifying a nucleotide sequence that encodes the polypeptide).

As used herein, the term "biodiesel" means a biofuel that can be a substitute of diesel, which is derived from petroleum. Biodiesel can be used in internal combustion diesel engines in either a pure form, which is referred to as "neat" biodiesel, or as a mixture in any concentration with petroleum-based diesel. Biodiesel can include esters or hydrocarbons, such as aldehydes and alkanes.

As used therein, the term "biofuel" refers to any fuel derived from biomass. Biofuels can be substituted for petroleum based fuels. For example, biofuels are inclusive of transportation fuels (e.g., gasoline, diesel, jet fuel, etc.), heating fuels, and electricity-generating fuels. Biofuels are a renewable energy source.

As used herein, the term "biomass" refers to a carbon source derived from biological material. Biomass can be converted into a biofuel. One exemplary source of biomass is plant matter. For example, corn, sugar cane, or switchgrass can be used as biomass. Another non-limiting example of biomass is animal matter, for example cow manure. Biomass also includes waste products from industry, agriculture, forestry, and households. Examples of such waste products that can be used as biomass are fermentation waste, straw, lumber, sewage, garbage, and food leftovers. Biomass also includes sources of carbon, such as carbohydrates (e.g., monosaccharides, disaccharides, or polysaccharides).

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). These include, for example, various monosaccharides, such as glucose, fructose, mannose, and galactose; oligosaccharides, such as fructo-oligosaccharide and galacto-oligosaccharide; polysaccharides such as xylose and arabinose; disaccharides, such as sucrose, maltose, and turanose; cellulosic material, such as methyl cellulose and sodium carboxymethyl cellulose; saturated or unsaturated fatty acid esters, such as succinate, lactate, and acetate; alcohols, such as ethanol or mixtures thereof. The carbon source can also be a product of photosynthesis, including, but not limited to, glucose. A preferred carbon source is biomass. Another preferred carbon source is glucose.

As used herein, a "cloud point lowering additive" is an additive added to a composition to decrease or lower the cloud point of a solution.

As used herein, the phrase "cloud point of a fluid" means the temperature at which dissolved solids are no longer completely soluble. Below this temperature, solids begin precipitating as a second phase giving the fluid a cloudy appearance. In the petroleum industry, cloud point refers to the temperature below which a solidified material or other heavy hydrocarbon crystallizes in a crude oil, refined oil, or fuel to form a cloudy appearance. The presence of solidified materials influences the flowing behavior of the fluid, the tendency of the fluid to clog fuel filters, injectors, etc., the accumulation of solidified materials on cold surfaces (e.g., a pipeline or heat exchanger fouling), and the emulsion characteristics of the fluid with water.

A nucleotide sequence is "complementary" to another nucleotide sequence if each of the bases of the two sequences matches (i.e., is capable of forming Watson Crick base pairs). The term "complementary strand" is used herein interchangeably with the term "complement". The complement of a nucleic acid strand can be the complement of a coding strand or the complement of a non-coding strand.

As used herein, the term "conditions sufficient to allow expression" means any conditions that allow a host cell to produce a desired product, such as a polypeptide, aldehyde, or alkane described herein. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source, such as glucose, fructose, cellulose, or the like, that can be metabolized by a host cell directly. In addition, enzymes can be used in the medium to facilitate the mobilization (e.g., the depolymerization of starch or cellulose to fermentable sugars) and subsequent metabolism of the carbon source.

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as, but not limited to, TLC, HPLC, GC/FID, GC/MS, LC/MS, MS, can be used.

It is understood that the polypeptides described herein may have additional conservative or non-essential amino acid substitutions, which do not have a substantial effect on the polypeptide functions. Whether or not a particular substitution will be tolerated (i.e., will not adversely affect desired biological properties, such as decarboxylase activity) can be determined as described in Bowie et al., Science (1990) 247: 1306 1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

As used herein, "control element" means a transcriptional control element. Control elements include promoters and enhancers. The term "promoter element," "promoter," or "promoter sequence" refers to a DNA sequence that functions as a switch that activates the expression of a gene. If the gene is activated, it is said to be transcribed or participating in transcription. Transcription involves the synthesis of mRNA from the gene. A promoter, therefore, serves as a transcriptional regulatory element and also provides a site for initiation of transcription of the gene into mRNA. Control elements interact specifically with cellular proteins involved in transcription (Maniatis et al., Science 236:1237, 1987).

As used herein, the term "ester synthase" means a peptide capable of producing fatty esters. More specifically, an ester synthase is a peptide which converts a thioester to a fatty ester. In a preferred embodiment, the ester synthase converts a thioester (e.g., acyl-CoA) to a fatty ester.

In an alternate embodiment, an ester synthase uses a thioester and an alcohol as substrates to produce a fatty ester. Ester synthases are capable of using short and long chain thioesters as substrates. In addition, ester synthases are capable of using short and long chain alcohols as substrates.

Non-limiting examples of ester synthases are wax synthases, wax-ester synthases, acyl CoA:alcohol transacylases, acyltransferases, and fatty acyl-coenzyme A:fatty alcohol acyltransferases. Exemplary ester synthases are classified in enzyme classification number EC 2.3.1.75. Exemplary GenBank Accession Numbers are provided in FIG. 40.

As used herein, the term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. In a preferred embodiment, the fatty acid is made from a fatty acid biosynthetic pathway.

As used herein, the term "fatty acid biosynthetic pathway" means a biosynthetic pathway that produces fatty acids. The fatty acid biosynthetic pathway includes fatty acid enzymes that can be engineered, as described herein, to produce fatty acids, and in some embodiments can be expressed with additional enzymes to produce fatty acids having desired carbon chain characteristics.

As used herein, the term "fatty acid derivative" means products made in part from the fatty acid biosynthetic pathway of the production host organism. "Fatty acid derivative"

also includes products made in part from acyl-ACP or acyl-ACP derivatives. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include for example, fatty acids, acyl-CoA, fatty aldehyde, short and long chain alcohols, hydrocarbons, fatty alcohols, and esters (e.g., waxes, fatty acid esters, or fatty esters).

As used herein, the term "fatty acid derivative enzymes" means all enzymes that may be expressed or overexpressed in the production of fatty acid derivatives. These enzymes are collectively referred to herein as fatty acid derivative enzymes. These enzymes may be part of the fatty acid biosynthetic pathway. Non-limiting examples of fatty acid derivative enzymes include fatty acid synthases, thioesterases, acyl-CoA synthases, acyl-CoA reductases, alcohol dehydrogenases, alcohol acyltransferases, fatty alcohol-forming acyl-CoA reductase, ester synthases, aldehyde biosynthetic polypeptides, and alkane biosynthetic polypeptides. Fatty acid derivative enzymes convert a substrate into a fatty acid derivative. In some examples, the substrate may be a fatty acid derivative which the fatty acid derivative enzyme converts into a different fatty acid derivative.

As used herein, the term "fatty alcohol forming peptides" means a peptide capable of catalyzing the conversion of acyl-CoA to fatty alcohol, including fatty alcohol forming acyl-CoA reductase (FAR, EC 1.1.1.*), acyl-CoA reductase (EC 1.2.1.50), or alcohol dehydrogenase (EC 1.1.1.1). Additionally, one of ordinary skill in the art will appreciate that some fatty alcohol forming peptides will catalyze other reactions as well. For example, some acyl-CoA reductase peptides will accept other substrates in addition to fatty acids. Such non-specific peptides are, therefore, also included. Nucleic acid sequences encoding fatty alcohol forming peptides are known in the art, and such peptides are publicly available. Exemplary GenBank Accession Numbers are provided in FIG. 40.

As used herein, "fatty acid enzyme" means any enzyme involved in fatty acid biosynthesis. Fatty acid enzymes can be expressed or overexpressed in host cells to produce fatty acids. Non-limiting examples of fatty acid enzymes include fatty acid synthases and thioesterases.

As used herein, the term "fatty ester" means an ester. In a preferred embodiment, a fatty ester is any ester made from a fatty acid, for example a fatty acid ester. In one embodiment, a fatty ester contains an A side (i.e., the carbon chain attached to the carboxylate oxygen) and a B side (i.e., the carbon chain comprising the parent carboxylate). In a preferred embodiment, when the fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied in the fermentation broth in instances where the fatty ester is produced by an organism. Alternatively, a carboxylic acid, such as a fatty acid or acetic acid, can be supplied exogenously in instances where the fatty ester is produced by an organism that can also produce alcohol.

The carbon chains comprising the A side or B side can be of any length. In one embodiment, the A side of the ester is at least about 1, 2, 3, 4, 5, 6, 7, 8, 10, 12, 14, 16, or 18 carbons in length. The B side of the ester is at least about 4, 6, 8, 10, 12, 14, 16, 18, 20, 22, 24, or 26 carbons in length. The A side and/or the B side can be straight or branched chain. The branched chains may have one or more points of branching. In addition, the branched chains may include cyclic branches. Furthermore, the A side and/or B side can be saturated or unsaturated. If unsaturated, the A side and/or B side can have one or more points of unsaturation.

In one embodiment, the fatty ester is produced biosynthetically. In this embodiment, first the fatty acid is "activated." Non-limiting examples of "activated" fatty acids are acyl-CoA, acyl-ACP, and acyl phosphate. Acyl-CoA can be a direct product of fatty acid biosynthesis or degradation. In addition, acyl-CoA can be synthesized from a free fatty acid, a CoA, or an adenosine nucleotide triphosphate (ATP). An example of an enzyme which produces acyl-CoA is acyl-CoA synthase After the fatty acid is activated, it can be readily transferred to a recipient nucleophile. Exemplary nucleophiles are alcohols, thiols, or phosphates.

In one embodiment, the fatty ester is a wax. The wax can be derived from a long chain alcohol and a long chain fatty acid. In another embodiment, the fatty ester can be derived from a fatty acyl-thioester and an alcohol. In another embodiment, the fatty ester is a fatty acyl thioester, for example fatty acyl Coenzyme A (CoA). In other embodiments, the fatty ester is a fatty acyl panthothenate, an acyl carrier protein (ACP), or a fatty phosphate ester. Fatty esters have many uses. For example, fatty esters can be used as a biofuel.

As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence that is aligned for comparison purposes is at least about 30%, preferably at least about 40%, more preferably at least about 50%, even more preferably at least about 60%, and even more preferably at least about 70%, at least about 80%, at least about 90%, or about 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), J. Mol. Biol. 48:444 453, algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5.

As used herein, a "host cell" is a cell used to produce a product described herein (e.g., an aldehyde or alkane described herein). A host cell can be modified to express or overexpress selected genes or to have attenuated expression of selected genes. Non-limiting examples of host cells include plant, animal, human, bacteria, yeast, or filamentous fungi cells.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either method can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions unless otherwise specified.

The term "isolated" as used herein with respect to nucleic acids, such as DNA or RNA, refers to molecules separated from other DNAs or RNAs, respectively, that are present in the natural source of the nucleic acid. Moreover, an "isolated nucleic acid" includes nucleic acid fragments, such as fragments that are not naturally occurring. The term "isolated" is also used herein to refer to polypeptides, which are isolated from other cellular proteins, and encompasses both purified endogenous polypeptides and recombinant polypeptides. The term "isolated" as used herein also refers to a nucleic acid or polypeptide that is substantially free of cellular material, viral material, or culture medium when produced by recombinant DNA techniques. The term "isolated" as used herein also refers to a nucleic acid or polypeptide that is substantially free of chemical precursors or other chemicals when chemically synthesized.

As used herein, the "level of expression of a gene in a cell" refers to the level of mRNA, pre-mRNA nascent transcript(s), transcript processing intermediates, mature mRNA(s), and/or degradation products encoded by the gene in the cell.

As used herein, the term "microorganism" means prokaryotic and eukaryotic microbial species from the domains Archaea, Bacteria and Eucarya, the latter including yeast and filamentous fungi, protozoa, algae, or higher Protista. The term "microbial cell", as used herein, means a cell from a microorganism.

As used herein, the term "nucleic acid" refers to polynucleotides, such as deoxyribonucleic acid (DNA), and, where appropriate, ribonucleic acid (RNA). The term also includes analogs of either RNA or DNA made from nucleotide analogs, and, as applicable to the embodiment being described, single (sense or antisense) and double-stranded polynucleotides, ESTs, chromosomes, cDNAs, mRNAs, and rRNAs.

As used herein, the term "operably linked" means that a selected nucleotide sequence (e.g., encoding a polypeptide described herein) is in proximity with a promoter to allow the promoter to regulate expression of the selected nucleotide sequence. In addition, the promoter is located upstream of the selected nucleotide sequence in terms of the direction of transcription and translation. By "operably linked" is meant that a nucleotide sequence and a regulatory sequence(s) are connected in such a way as to permit gene expression when the appropriate molecules (e.g., transcriptional activator proteins) are bound to the regulatory sequence(s).

The term "or" is used herein to mean, and is used interchangeably with, the term "and/or," unless context clearly indicates otherwise.

As used herein, "overexpress" means to express or cause to be expressed a nucleic acid, polypeptide, or hydrocarbon in a cell at a greater concentration than is normally expressed in a corresponding wild-type cell. For example, a polypeptide can be "overexpressed" in a recombinant host cell when the polypeptide is present in a greater concentration in the recombinant host cell compared to its concentration in a non-recombinant host cell of the same species.

As used herein, "partition coefficient" or "P," is defined as the equilibrium concentration of a compound in an organic phase divided by the concentration at equilibrium in an aqueous phase (e.g., fermentation broth). In one embodiment of a bi-phasic system described herein, the organic phase is formed by the aldehyde or alkane during the production process. However, in some examples, an organic phase can be provided, such as by providing a layer of octane, to facilitate product separation. When describing a two phase system, the partition characteristics of a compound can be described as log P. For example, a compound with a log P of 1 would partition 10:1 to the organic phase. A compound with a log P of −1 would partition 1:10 to the organic phase. By choosing an appropriate fermentation broth and organic phase, an aldehyde or alkane with a high log P value can separate into the organic phase even at very low concentrations in the fermentation vessel.

As used herein, the term "purify," "purified," or "purification" means the removal or isolation of a molecule from its environment by, for example, isolation or separation. "Substantially purified" molecules are at least about 60% free, preferably at least about 75% free, and more preferably at least about 90% free from other components with which they are associated. As used herein, these terms also refer to the removal of contaminants from a sample. For example, the removal of contaminants can result in an increase in the percentage of aldehydes or alkanes in a sample. For example, when aldehydes or alkanes are produced in a host cell, the aldehydes or alkanes can be purified by the removal of host cell proteins. After purification, the percentage of aldehydes or alkanes in the sample is increased.

The terms "purify," "purified," and "purification" do not require absolute purity. They are relative terms. Thus, for example, when aldehydes or alkanes are produced in host cells, a purified aldehyde or purified alkane is one that is substantially separated from other cellular components (e.g., nucleic acids, polypeptides, lipids, carbohydrates, or other hydrocarbons). In another example, a purified aldehyde or purified alkane preparation is one in which the aldehyde or alkane is substantially free from contaminants, such as those that might be present following fermentation. In some embodiments, an aldehyde or an alkane is purified when at least about 50% by weight of a sample is composed of the aldehyde or alkane. In other embodiments, an aldehyde or an alkane is purified when at least about 60%, 70%, 80%, 85%, 90%, 92%, 95%, 98%, or 99% or more by weight of a sample is composed of the aldehyde or alkane.

As used herein, the term "recombinant polypeptide" refers to a polypeptide that is produced by recombinant DNA techniques, wherein generally DNA encoding the expressed polypeptide or RNA is inserted into a suitable expression vector and that is in turn used to transform a host cell to produce the polypeptide or RNA.

As used herein, the term "substantially identical" (or "substantially homologous") is used to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities.

As used herein, the term "synthase" means an enzyme which catalyzes a synthesis process. As used herein, the term synthase includes synthases, synthetases, and ligases.

As used herein, the term "transfection" means the introduction of a nucleic acid (e.g., via an expression vector) into a recipient cell by nucleic acid-mediated gene transfer.

As used herein, "transformation" refers to a process in which a cell's genotype is changed as a result of the cellular uptake of exogenous nucleic acid. This may result in the transformed cell expressing a recombinant form of an RNA or polypeptide. In the case of antisense expression from the transferred gene, the expression of a naturally-occurring form of the polypeptide is disrupted.

As used herein, a "transport protein" is a polypeptide that facilitates the movement of one or more compounds in and/or out of a cellular organelle and/or a cell.

As used herein, a "variant" of polypeptide X refers to a polypeptide having the amino acid sequence of polypeptide X in which one or more amino acid residues is altered. The variant may have conservative changes or nonconservative changes. Guidance in determining which amino acid residues may be substituted, inserted, or deleted without affecting biological activity may be found using computer programs well known in the art, for example, LASERGENE software (DNASTAR).

The term "variant," when used in the context of a polynucleotide sequence, may encompass a polynucleotide sequence related to that of a gene or the coding sequence thereof. This definition may also include, for example, "allelic," "splice," "species," or "polymorphic" variants. A splice variant may have significant identity to a reference polynucleotide, but will generally have a greater or fewer number of polynucleotides due to alternative splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species.

As used herein, the term "vector" refers to a nucleic acid molecule capable of transporting another nucleic acid to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids," which refer generally to circular double stranded DNA loops that, in their vector form, are not bound to the chromosome. In the present specification, "plasmid" and "vector" are used interchangeably, as the plasmid is the most commonly used form of vector. However, also included are such other forms of expression vectors that serve equivalent functions and that become known in the art subsequently hereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

BRIEF DESCRIPTION OF THE DRAWINGS

FIG. 1A is a GC/MS trace of hydrocarbons produced by *Prochlorococcus marinus* CCMP1986 cells. FIG. 1B is a mass fragmentation pattern of the peak at 7.55 min of FIG. 1A.

FIG. 4A is a GC/MS trace of hydrocarbons produced by *Synechocystic* sp. PCC6803 cells. FIG. 4B is a mass fragmentation pattern of the peak at 7.36 min of FIG. 4A.

FIG. 15 is a GC/MS trace of hydrocarbons produced by *E. coli* MG1655 cells expressing *Synechococcus elongatus* PCC7942 YP_400611 (Synpcc7942_1594) (SEQ ID NO:65) and *Gloeobacter violaceus* PCC7421 gll3146 (NP_926092) (SEQ ID NO:15).

FIG. 16 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Prochlorococcus marinus* MIT9313 PMT1231 (NP_895059) (SEQ ID NO:49).

FIG. 19 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Synechococcus* sp. RS9917 RS9917_09941 (ZP_01079772) (SEQ ID NO:52).

FIG. 20 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Synechococcus* sp. RS9917 RS9917_12945 (ZP_01080370) (SEQ ID NO:53).

FIG. 21 is a GC/MS trace of hydrocarbons produced by *E. coli* MG1655 cells expressing *Synechococcus elongatus* PCC7942 YP_400611 (Synpcc7942_1594) (SEQ ID NO:65) and *Cyanothece* sp. ATCC51142 cce_0778 (YP_001802195) (SEQ ID NO:27).

FIG. 22 is a GC/MS trace of hydrocarbons produced by *E. coli* MG1655 cells expressing *Synechococcus elongatus* PCC7942 YP_400611 (Synpcc7942_1594) (SEQ ID NO:65) and *Cyanothece* sp. PCC7425 Cyan7425_0398 (YP_002481151) (SEQ ID NO:29).

FIG. 24A is a GC/MS trace of hydrocarbons produced by *E. coli* MG1655 cells expressing *Prochlorococcus marinus* CCMP1986 PMM0533 (NP_892651) (SEQ ID NO:71). FIG. 24B is a GC/MS trace of hydrocarbons produced by *E. coli* MG1655 cells expressing *Prochlorococcus marinus* CCMP1986 PMM0533 (NP_892651) (SEQ ID NO:71) and *Prochlorococcus mariunus* CCMP1986 PMM0532 (NP_892650) (SEQ ID NO:19).

FIG. 29A is a representation of the three-dimensional structure of a class I ribonuclease reductase subunit β protein, RNRβ. FIG. 29B is a representation of the three-dimensional structure of *Prochlorococcus marinus* MIT9313 PMT1231 (NP_895059) (SEQ ID NO:17). FIG. 29C is a representation of the three-dimensional structure of the active site of *Prochlorococcus marinus* MIT9313 PMT1231 (NP_895059) (SEQ ID NO:17).

FIG. 31 depicts GC/MS traces of hydrocarbons produced in vitro using *Nostoc punctiforme* PCC73102 Npun02004178 (ZP_00108838) (SEQ ID NO:6) and octadecanal (A); Npun02004178 (ZP_00108838) (SEQ ID NO:6), octadecanal, spinach ferredoxin reductase, and NADPH (B); octadecanal, spinach ferredoxin, spinach ferredoxin reductase, and NADPH(C); or Npun02004178 (ZP_00108838) (SEQ ID NO:6), spinach ferredoxin, and spinach ferredoxin (D).

FIG. 38A-38D is a list of examples of homologs of *Synechococcus elongatus* PCC7942 YP_400610 (Synpcc7942_1593) (SEQ ID NO:1) from a metagenomic database.

FIG. 39A-39D is a list of examples of homologs of *Synechococcus elongatus* PCC7942 YP_400611 (Synpcc7942_1594) (SEQ ID NO:65) from a metagenomic database.

FIG. 40A-40T is a table identifying various genes that can be expressed, overexpressed, or attenuated to increase production of particular substrates.

DETAILED DESCRIPTION

Figure 2A:
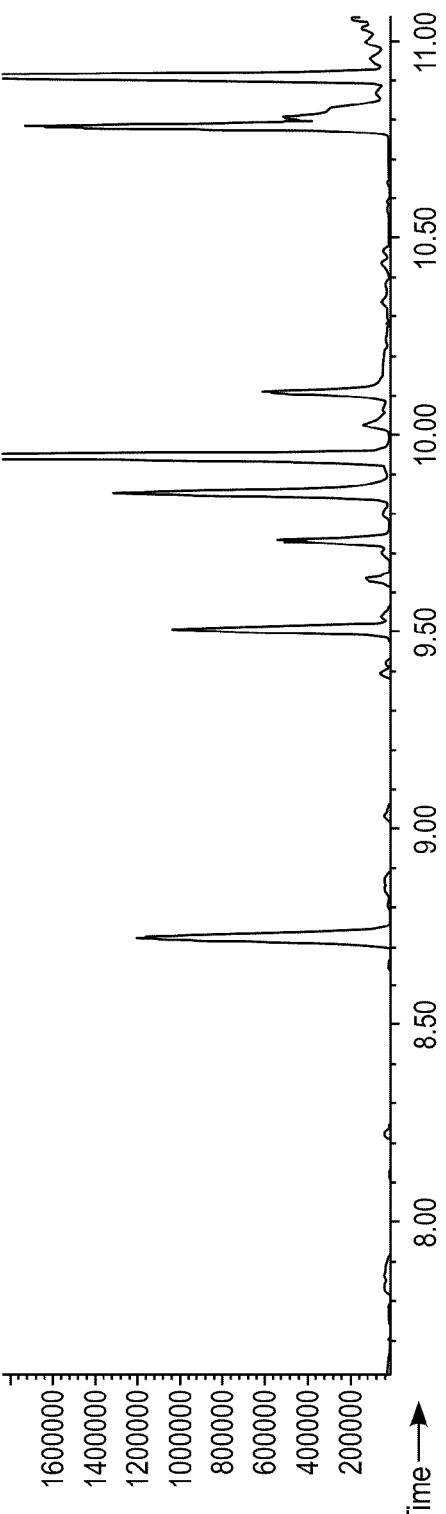
FIG. 2A is a GC/MS trace of hydrocarbons produced by *Nostoc punctiforme* PCC73102 cells.

The invention provides compositions and methods of producing aldehydes, fatty alcohols, and hydrocarbons (such as alkanes, alkenes, and alkynes) from substrates, for example, an acyl-ACP, a fatty acid, an acyl-CoA, a fatty aldehyde, or a fatty alcohol substrate (e.g., as described in PCT/US08/058788, specifically incorporated by reference herein). Such aldehydes, alkanes, and alkenes are useful as biofuels (e.g., substitutes for gasoline, diesel, jet fuel, etc.), specialty chemicals (e.g., lubricants, fuel additive, etc.), or feedstock for further chemical conversion (e.g., fuels, polymers, plastics, textiles, solvents, adhesives, etc.). The invention is based, in part, on the identification of genes that are involved in aldehyde, alkane, and alkene biosynthesis.

Such alkane and alkene biosynthetic genes include, for example, *Synechococcus elongatus* PCC7942 Synpcc7942_1593 (SEQ ID NO:1), *Synechocystis* sp. PCC6803 sll0208 (SEQ ID NO:3), *Nostoc punctiforme* PCC 73102 Npun02004178 (SEQ ID NO:5), *Nostoc* sp. PCC 7120 alr5283 (SEQ ID NO:7), *Acaryochloris marina* MBIC11017 AM1_4041 (SEQ ID NO:9), *Thermosynechococcus elongatus* BP-1 tll1313 (SEQ ID NO:11), *Synechococcus* sp. JA-3-3A CYA_0415 (SEQ ID NO:13), *Gloeobacter violaceus* PCC 7421 gll3146 (SEQ ID NO:15), *Prochlorococcus marinus* MIT9313 PM123 (SEQ ID NO:17), *Prochlorococcus marinus* subsp. *pastoris* str. CCMP1986 PMM0532 (SEQ ID NO:19), *Prochlorococcus marinus* str. NATL2A PMN2A_1863 (SEQ ID NO:21), *Synechococcus* sp. RS9917 RS9917_09941 (SEQ ID NO:23), *Synechococcus* sp. RS9917 RS9917_12945 (SEQ ID NO:25), *Cyanothece* sp. ATCC51142 cce_0778 (SEQ ID NO:27), *Cyanothece* sp. PCC7245 Cyan7425DRAFT_1220 (SEQ ID NO:29), *Cyanothece* sp. PCC7245 cce_0778 (SEQ ID NO:31), *Anabaena variabilis* ATCC29413 YP_323043 (Ava2533) (SEQ ID NO:33), and *Synechococcus elongatus* PCC6301 YP_170760 (syc0050_d) (SEQ ID NO:35). Other alkane and alkene biosynthetic genes are listed in Table 1 and FIG. 38.

Aldehyde biosynthetic genes include, for example, *Synechococcus elongatus* PCC7942 Synpcc7942_1594 (SEQ ID NO:65), *Synechocystis* sp. PCC6803 sll0209 (SEQ ID NO:67), *Cyanothece* sp. ATCC51142 cce_1430 (SEQ ID NO:69), *Prochlorococcus marinus* subsp. *pastoris* str. CCMP1986 PMM0533 (SEQ ID NO:71), *Gloeobacter violaceus* PCC7421 NP_96091 (gll3145) (SEQ ID NO:73), *Nostoc punctiforme* PCC73102 ZP_00108837 (Npun02004176) (SEQ ID NO:75), *Anabaena variabilis* ATCC29413 YP_323044 (Ava_2534) (SEQ ID NO:77), *Synechococcus elongatus* PCC6301 YP_170761 (syc0051_d) (SEQ ID NO:79), and *Nostoc* sp. PCC 7120 alr5284 (SEQ ID NO:81). Other aldehyde biosynthetic genes are listed in Table 1 and FIG. 39.

Using the methods described herein, aldehydes, fatty alcohols, alkanes, and alkenes can be prepared using one or more aldehyde, alkane, and/or alkene biosynthetic genes or polypeptides described herein, or variants thereof, utilizing host cells or cell-free methods.

TABLE 1

Aldehyde and alkane biosynthetic gene homologs in cyanobacterial genomes

| Cyanobacterium | Alkane Biosynth. Gene accession number | % ID | Aldehyde Biosynth. Gene accession number | % ID |
|---|---|---|---|---|
| *Synechococcus elongatus* PCC 7942 | YP_400610 | 100 | YP_400611 | 100 |
| *Synechococcus elongatus* PCC 6301 | YP_170760 | 100 | YP_170761 | 100 |
| *Microcoleus chthonoplastes* PCC 7420 | EDX75019 | 77 | EDX74978 | 70 |
| *Arthrospira maxima* CS-328 | EDZ94963 | 78 | EDZ94968 | 68 |
| *Lyngbya* sp. PCC 8106 | ZP_01619575 | 77 | ZP_01619574 | 69 |
| *Nodularia spumigena* CCY9414 | ZP_01628096 | 77 | ZP_01628095 | 70 |
| *Trichodesmium erythraeum* IMS101 | YP_721979 | 76 | YP_721978 | 69 |
| *Microcystis aeruginosa* NIES-843 | YP_001660323 | 75 | YP_001660322 | 68 |
| *Microcystis aeruginosa* PCC 7806 | CAO90780 | 74 | CAO90781 | 67 |
| *Nostoc* sp. PCC 7120 | NP_489323 | 74 | NP_489324 | 72 |
| *Nostoc azollae* 0708 | EEG05692 | 73 | EEG05693 | 70 |
| *Anabaena variabilis* ATCC 29413 | YP_323043 | 74 | YP_323044 | 73 |
| *Crocosphaera watsonii* WH 8501 | ZP_00514700 | 74 | ZP_00516920 | 67 |
| *Synechocystis* sp. PCC 6803 | NP_442147 | 72 | NP_442146 | 68 |
| *Synechococcus* sp. PCC 7335 | EDX86803 | 73 | EDX87870 | 67 |
| *Cyanothece* sp. ATCC 51142 | YP_001802195 | 73 | YP_001802846 | 67 |
| *Cyanothece* sp. CCY0110 | ZP_01728578 | 72 | ZP_01728620 | 68 |
| *Nostoc punctiforme* PCC 73102 | ZP_00108838 | 72 | ZP_00108837 | 71 |
| *Acaryochloris marina* MBIC11017 | YP_001518340 | 71 | YP_001518341 | 66 |
| *Cyanothece* sp. PCC 7425 | YP_002481151 | 71 | YP_002481152 | 70 |
| *Cyanothece* sp. PCC 8801 | ZP_02941459 | 70 | ZP_02942716 | 69 |
| *Thermosynechococcus elongatus* BP-1 | NP_682103 | 70 | NP_682102 | 70 |
| *Synechococcus* sp. JA-2-3B'a(2-13) | YP_478639 | 68 | YP_478638 | 63 |
| *Synechococcus* sp. RCC307 | YP_001227842 | 67 | YP_001227841 | 64 |
| *Synechococcus* sp. WH 7803 | YP_001224377 | 68 | YP_001224378 | 65 |
| *Synechococcus* sp. WH 8102 | NP_897829 | 70 | NP_897828 | 65 |
| *Synechococcus* sp. WH 7805 | ZP_01123214 | 68 | ZP_01123215 | 65 |
| uncultured marine type-A *Synechococcus* GOM 3O12 | ABD96376 | 70 | ABD96375 | 65 |
| *Synechococcus* sp. JA-3-3Ab | YP_473897 | 68 | YP_473896 | 62 |
| uncultured marine type-A *Synechococcus* GOM 3O6 | ABD96328 | 70 | ABD96327 | 65 |
| uncultured marine type-A *Synechococcus* GOM 3M9 | ABD96275 | 68 | ABD96274 | 65 |
| *Synechococcus* sp. CC9311 | YP_731193 | 63 | YP_731192 | 63 |
| uncultured marine type-A *Synechococcus* 5B2 | ABB92250 | 69 | ABB92249 | 64 |
| *Synechococcus* sp. WH 5701 | ZP_01085338 | 66 | ZP_01085337 | 67 |
| *Gloeobacter violaceus* PCC 7421 | NP_926092 | 63 | NP_926091 | 67 |
| *Synechococcus* sp. RS9916 | ZP_01472594 | 69 | ZP_01472595 | 66 |
| *Synechococcus* sp. RS9917 | ZP_01079772 | 68 | ZP_01079773 | 65 |
| *Synechococcus* sp. CC9605 | YP_381055 | 66 | YP_381056 | 66 |
| *Cyanobium* sp. PCC 7001 | EDY39806 | 64 | EDY38361 | 64 |
| *Prochlorococcus marinus* str. MIT 9303 | YP_001016795 | 63 | YP_001016797 | 66 |
| *Prochlorococcus marinus* str. MIT9313 | NP_895059 | 63 | NP_895058 | 65 |
| *Synechococcus* sp. CC9902 | YP_377637 | 66 | YP_377636 | 65 |
| *Prochlorococcus marinus* str. MIT 9301 | YP_001090782 | 62 | YP_001090783 | 62 |
| *Synechococcus* sp. BL107 | ZP_01469468 | 65 | ZP_01469469 | 65 |
| *Prochlorococcus marinus* str. AS9601 | YP_001008981 | 62 | YP_001008982 | 61 |
| *Prochlorococcus marinus* str. MIT9312 | YP_397029 | 62 | YP_397030 | 61 |
| *Prochlorococcus marinus* subsp. *pastoris* str. CCMP1986 | NP_892650 | 60 | NP_892651 | 63 |
| *Prochlorococcus marinus* str. MIT 9211 | YP_001550420 | 61 | YP_001550421 | 63 |
| *Cyanothece* sp. PCC 7425 | YP_002483683 | 59 | — | |
| *Prochlorococcus marinus* str. NATL2A | YP_293054 | 59 | YP_293055 | 62 |
| *Prochlorococcus marinus* str. NATL1A | YP_001014415 | 59 | YP_001014416 | 62 |
| *Prochlorococcus marinus* subsp. *marinus* str. CCMP1375 | NP_874925 | 59 | NP_874926 | 64 |
| *Prochlorococcus marinus* str. MIT 9515_05961 | YP_001010912 | 57 | YP_001010913 | 63 |
| *Prochlorococcus marinus* str. MIT 9215_06131 | YP_001483814 | 59 | YP_001483815 | 62 |
| *Synechococcus* sp. RS9917 | ZP_01080370 | 43 | — | |
| uncultured marine type-A *Synechococcus* GOM 5D20 | | | ABD96480 | 65 |

Aldehyde, Alkane, and Alkene Biosynthetic Genes and Variants

The methods and compositions described herein include, for example, alkane or alkene biosynthetic genes having the nucleotide sequence of SEQ ID NO:1, 3, 5, 7, 9, 11, 13, 15, 17, 19, 21, 23, 25, 27, 29, 31, 33, or 35, as well as polynucleotide variants thereof. In some instances, the alkane or alkene biosynthetic gene encodes one or more of the amino acid motifs described herein. For example, the alkane or alkene biosynthetic gene can encode a polypeptide comprising SEQ ID NO:37, 38, 39, 41, 42, 43, or 44. The alkane or alkene biosynthetic gene can also include a polypeptide comprising SEQ ID NO:40 and also any one of SEQ ID NO:37, 38, or 39.

The methods and compositions described herein also include, for example, aldehyde biosynthetic genes having the nucleotide sequence of SEQ ID NO:65, 67, 69, 71, 73, 75, 77, 79, or 81, as well as polynucleotide variants thereof. In some instances, the aldehyde biosynthetic gene encodes one or more of the amino acid motifs described herein. For example, the aldehyde biosynthetic gene can encode a polypeptide comprising SEQ ID NO:54, 55, 56, 57, 58, 59, 60, 61, 62, 63, or 64.

The variants can be naturally occurring or created in vitro. In particular, such variants can be created using genetic engineering techniques, such as site directed mutagenesis, random chemical mutagenesis, Exonuclease III deletion procedures, and standard cloning techniques. Alternatively, such variants, fragments, analogs, or derivatives can be created using chemical synthesis or modification procedures.

Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., *Technique* 1:11-15, 1989; and Caldwell et al., *PCR Methods Applic.* 2:28-33, 1992). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized (e.g., an aldehyde or alkane biosynthetic polynucleotide sequence), are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized (e.g., an aldehyde or alkane biosynthetic polynucleotide sequence), 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., *Science* 241:53-57, 1988. Briefly, in such procedures a plurality of double stranded oligonucleotides bearing one or more mutations to be introduced into the cloned DNA are synthesized and inserted into the cloned DNA to be mutagenized (e.g., an aldehyde or alkane biosynthetic polynucleotide sequence). Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408.

Still another method of generating variants is sexual PCR mutagenesis. In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, *PNAS, USA* 91:10747-10751, 1994.

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., an aldehyde or alkane biosynthetic polynucleotide sequence) in one of these strains will eventually generate random mutations within the DNA. Mutator strains suitable for use for in vivo mutagenesis are described in, for example, PCT Publication No. WO 91/16427.

Variants can also be generated using cassette mutagenesis. In cassette mutagenesis, a small region of a double stranded DNA molecule is replaced with a synthetic oligonucleotide "cassette" that differs from the native sequence. The oligonucleotide often contains a completely and/or partially randomized native sequence.

Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., *PNAS, USA* 89:7811-7815, 1992.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., *Biotech. Res.* 11:1548-1552, 1993. Random and site-directed mutagenesis are described in, for example, Arnold, *Curr. Opin. Biotech.* 4:450-455, 1993.

In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

Polynucleotide variants also include nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. (See, e.g., Summerton et al., *Antisense Nucleic Acid Drug Dev.* (1997) 7:187-195; and Hyrup et al., *Bioorgan. Med. Chem.* (1996) 4:5-23.) In addition, the deoxyphosphate backbone can be replaced with, for example, a phosphorothioate or phosphorodithioate backbone, a phosphoroamidite, or an alkyl phosphotriester backbone.

The aldehyde and alkane biosynthetic polypeptides Synpcc7942_1594 (SEQ ID NO:66) and Synpcc7942_1593 (SEQ ID NO:2) have homologs in other cyanobacteria (non-limiting examples are depicted in Table 1). Thus, any polynucleotide sequence encoding a homolog listed in Table 1, or a variant thereof, can be used as an aldehyde or alkane biosynthetic polynucleotide in the methods described herein. Each cyanobacterium listed in Table 1 has copies of both genes. The level of sequence identity of the gene products ranges from 61% to 73% for Synpcc7942_1594 (SEQ ID NO:66) and from 43% to 78% for Synpcc7942_1593 (SEQ ID NO:2).

Further homologs of the aldehyde biosynthetic polypeptide Synpcc7942_1594 (SEQ ID NO:66) are listed in FIG. 39, and any polynucleotide sequence encoding a homolog listed in FIG. 39, or a variant thereof, can be used as an aldehyde biosynthetic polynucleotide in the methods described herein. Further homologs of the alkane biosynthetic polypeptide Synpcc7942_1593 (SEQ ID NO:2) are listed in FIG. 38, and any polynucleotide sequence encoding a homolog listed in FIG. 38, or a variant thereof, can be used as an alkane biosynthetic polynucleotide in the methods described herein.

In certain instances, an aldehyde, alkane, and/or alkene biosynthetic gene is codon optimized for expression in a particular host cell. For example, for expression in E. coli, one or more codons can be optimized as described in, e.g., Grosjean et al., Gene 18:199-209 (1982).

Aldehyde, Alkane, and Alkene Biosynthetic Polypeptides and Variants

The methods and compositions described herein also include alkane or alkene biosynthetic polypeptides having the amino acid sequence of SEQ ID NO:2, 4, 6, 8, 10, 12, 14, 16, 18, 20, 22, 24, 26, 28, 30, 32, 34, or 36, as well as polypeptide variants thereof. In some instances, an alkane or alkene biosynthetic polypeptide is one that includes one or more of the amino acid motifs described herein. For example, the alkane or alkene biosynthetic polypeptide can include the amino acid sequence of SEQ ID NO:37, 38, 39, 41, 42, 43, or 44. The alkane or alkene biosynthetic polypeptide can also include the amino acid sequence of SEQ ID NO:40 and also any one of SEQ ID NO:37, 38, or 39.

The methods and compositions described herein also include aldehyde biosynthetic polypeptides having the amino acid sequence of SEQ ID NO:66, 68, 70, 72, 74, 76, 78, 80, or 82, as well as polypeptide variants thereof. In some instances, an aldehyde biosynthetic polypeptide is one that includes one or more of the amino acid motifs described herein. For example, the aldehyde biosynthetic polypeptide can include the amino acid sequence of SEQ ID NO:54, 55, 56, 57, 58, 59, 60, 61, 62, 63, or 64.

Aldehyde, alkane, and alkene biosynthetic polypeptide variants can be variants in which one or more amino acid residues are substituted with a conserved or non-conserved amino acid residue (preferably a conserved amino acid residue). Such substituted amino acid residue may or may not be one encoded by the genetic code.

Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

Other polypeptide variants are those in which one or more amino acid residues include a substituent group. Still other polypeptide variants are those in which the polypeptide is associated with another compound, such as a compound to increase the half-life of the polypeptide (e.g., polyethylene glycol).

Additional polypeptide variants are those in which additional amino acids are fused to the polypeptide, such as a leader sequence, a secretory sequence, a proprotein sequence, or a sequence which facilitates purification, enrichment, or stabilization of the polypeptide.

In some instances, an alkane or alkene biosynthetic polypeptide variant retains the same biological function as a polypeptide having the amino acid sequence of SEQ ID NO:2, 4, 6, 8, 10, 12, 14, 16, 18, 20, 22, 24, 26, 28, 30, 32, 34, or 36 (e.g., retains alkane or alkene biosynthetic activity) and has an amino acid sequence substantially identical thereto.

In other instances, the alkane or alkene biosynthetic polypeptide variants have at least about 50%, at least about 55%, at least about 60%, at least about 65%, at least about 70%, at least about 75%, at least about 80%, at least about 85%, at least about 90%, at least about 95%, or more than about 95% homology to the amino acid sequence of SEQ ID NO:2, 4, 6, 8, 10, 12, 14, 16, 18, 20, 22, 24, 26, 28, 30, 32, 34, or 36. In another embodiment, the polypeptide variants include a fragment comprising at least about 5, 10, 15, 20, 25, 30, 35, 40, 50, 75, 100, or 150 consecutive amino acids thereof.

In some instances, an aldehyde biosynthetic polypeptide variant retains the same biological function as a polypeptide having the amino acid sequence of SEQ ID NO:66, 68, 70, 72, 74, 76, 78, 80, or 82 (e.g., retains aldehyde biosynthetic activity) and has an amino acid sequence substantially identical thereto.

In yet other instances, the aldehyde biosynthetic polypeptide variants have at least about 50%, at least about 55%, at least about 60%, at least about 65%, at least about 70%, at least about 75%, at least about 80%, at least about 85%, at least about 90%, at least about 95%, or more than about 95% homology to the amino acid sequence of SEQ ID NO:66, 68, 70, 72, 74, 76, 78, 80, or 82. In another embodiment, the polypeptide variants include a fragment comprising at least about 5, 10, 15, 20, 25, 30, 35, 40, 50, 75, 100, or 150 consecutive amino acids thereof.

The polypeptide variants or fragments thereof can be obtained by isolating nucleic acids encoding them using techniques described herein or by expressing synthetic nucleic acids encoding them. Alternatively, polypeptide variants or fragments thereof can be obtained through biochemical enrichment or purification procedures. The sequence of polypeptide variants or fragments can be determined by proteolytic digestion, gel electrophoresis, and/or microsequencing. The sequence of the alkane or alkene biosynthetic polypeptide variants or fragments can then be compared to the amino acid sequence of SEQ ID NO:2, 4, 6, 8, 10, 12, 14, 16, 18, 20, 22, 24, 26, 28, 30, 32, 34, or 36 using any of the programs described herein. The sequence of the aldehyde biosynthetic polypeptide variants or fragments can be compared to the amino acid sequence of SEQ ID NO:66, 68, 70, 72, 74, 76, 78, 80, or 82 using any of the programs described herein.

The polypeptide variants and fragments thereof can be assayed for aldehyde-, fatty alcohol-, alkane-, and/or alkene-producing activity using routine methods. For example, the polypeptide variants or fragment can be contacted with a substrate (e.g., a fatty acid derivative substrate or other substrate described herein) under conditions that allow the polypeptide variant to function. A decrease in the level of the substrate or an increase in the level of an aldehyde, alkane, or alkene can be measured to determine aldehyde-, fatty alcohol-, alkane-, or alkene-producing activity, respectively.

Anti-Aldehyde, Anti-Fatty Alcohol, Anti-Alkane, and Anti-Alkene Biosynthetic Polypeptide Antibodies The aldehyde, fatty alcohol, alkane, and alkene biosynthetic polypeptides described herein can also be used to produce antibodies directed against aldehyde, fatty alcohol, alkane, and alkene biosynthetic polypeptides. Such antibodies can be used, for example, to detect the expression of an aldehyde, fatty alcohol, alkane, or alkene biosynthetic polypeptide using methods known in the art. The antibody can be, e.g., a polyclonal antibody; a monoclonal antibody or antigen binding fragment thereof; a modified antibody such as a chimeric antibody, reshaped antibody, humanized antibody, or fragment thereof (e.g., Fab', Fab, F(ab')$_2$); or a biosynthetic antibody, e.g., a single chain antibody, single domain antibody (DAB), Fv, single chain Fv (scFv), or the like.

Methods of making and using polyclonal and monoclonal antibodies are described, e.g., in Harlow et al., *Using Antibodies: A Laboratory Manual: Portable Protocol I*. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition).

Substrates

The compositions and methods described herein can be used to produce aldehydes, fatty alcohols, alkanes, and/or alkenes from an appropriate substrate. While not wishing to be bound by a particular theory, it is believed that the alkane or alkene biosynthetic polypeptides described herein produce alkanes or alkenes from substrates via a decarbonylation mechanism. In some instances, the substrate is a fatty acid derivative, e.g., a fatty aldehyde, and an alkane having particular branching patterns and carbon chain length can be produced from a fatty acid derivative, e.g., a fatty aldehyde, having those particular characteristics. In other instances, the substrate is an unsaturated fatty acid derivative, e.g., an unsaturated fatty aldehyde, and an alkene having particular branching patterns and carbon chain length can be produced from an unsaturated fatty acid derivative, e.g., an unsaturated fatty aldehyde, having those particular characteristics.

While not wishing to be bound by a particular theory, it is believed that the aldehyde biosynthetic polypeptides described herein produce aldehydes from substrates via a reduction mechanism. In certain instances, the substrate is an acyl-ACP.

While not wishing to be bound by a particular theory, it is believed that the fatty alcohols described herein are produced from substrates via a reduction mechanism. In certain instances, the substrate is a fatty aldehyde.

Accordingly, each step within a biosynthetic pathway that leads to the production of these substrates can be modified to produce or overproduce the substrate of interest. For example, known genes involved in the fatty acid biosynthetic pathway, the fatty aldehyde pathway, and the fatty alcohol pathway can be expressed, overexpressed, or attenuated in host cells to produce a desired substrate (see, e.g., PCT/US08/058788, specifically incorporated by reference herein). Exemplary genes are provided in FIG. 40.

Synthesis of Substrates

Fatty acid synthase (FAS) is a group of polypeptides that catalyze the initiation and elongation of acyl chains (Marrakchi et al., *Biochemical Society*, 30:1050-1055, 2002). The acyl carrier protein (ACP) along with the enzymes in the FAS pathway control the length, degree of saturation, and branching of the fatty acid derivatives produced. The fatty acid biosynthetic pathway involves the precursors acetyl-CoA and malonyl-CoA. The steps in this pathway are catalyzed by enzymes of the fatty acid biosynthesis (fab) and acetyl-CoA carboxylase (acc) gene families (see, e.g., Heath et al., *Prog. Lipid Res.* 40(6):467-97 (2001)).

Host cells can be engineered to express fatty acid derivative substrates by recombinantly expressing or overexpressing acetyl-CoA and/or malonyl-CoA synthase genes. For example, to increase acetyl-CoA production, one or more of the following genes can be expressed in a host cell: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, and fabF. Exemplary GenBank accession numbers for these genes are: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179). Additionally, the expression levels of fadE, gpsA, ldhA, pflb, adhE, pta, poxB, ackA, and/or ackB can be attenuated or knocked-out in an engineered host cell by transformation with conditionally replicative or non-replicative plasmids containing null or deletion mutations of the corresponding genes or by substituting promoter or enhancer sequences. Exemplary GenBank accession numbers for these genes are: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

Malonyl-CoA overexpression can be effected by introducing accABCD (e.g., accession number AAC73296, EC 6.4.1.2) into a host cell. Fatty acids can be further overexpressed in host cells by introducing into the host cell a DNA sequence encoding a lipase (e.g., accession numbers CAA89087, CAA98876).

In addition, inhibiting PlsB can lead to an increase in the levels of long chain acyl-ACP, which will inhibit early steps in the pathway (e.g., accABCD, fabH, and fabI). The plsB (e.g., accession number AAC77011) D311E mutation can be used to increase the amount of available acyl-CoA.

In addition, a host cell can be engineered to overexpress a sfa gene (suppressor of fabA, e.g., accession number AAN79592) to increase production of monounsaturated fatty acids (Rock et al., *J. Bacteriology* 178:5382-5387, 1996).

In some instances, host cells can be engineered to express, overexpress, or attenuate expression of a thioesterase to increase fatty acid substrate production. The chain length of a fatty acid substrate is controlled by thioesterase. In some instances, a tes or fat gene can be overexpressed. In other instances, $C_{10}$ fatty acids can be produced by attenuating thioesterase $C_{18}$ (e.g., accession numbers AAC73596 and P0ADA1), which uses $C_{10}$-ACP, and expressing thioesterase $C_{10}$ (e.g., accession number Q39513), which uses $C_{10}$-ACP.

This results in a relatively homogeneous population of fatty acids that have a carbon chain length of 10. In yet other instances, $C_{14}$ fatty acids can be produced by attenuating endogenous thioesterases that produce non-$C_{14}$ fatty acids and expressing the thioesterases, that use $C_{14}$-ACP (for example, accession number Q39473). In some situations, $C_{12}$ fatty acids can be produced by expressing thioesterases that use $C_{12}$-ACP (for example, accession number Q41635) and attenuating thioesterases that produce non-$C_{12}$ fatty acids. Acetyl-CoA, malonyl-CoA, and fatty acid overproduction can be verified using methods known in the art, for example, by using radioactive precursors, HPLC, and GC-MS subsequent to cell lysis. Non-limiting examples of thioesterases that can be used in the methods described herein are listed in Table 2.

This reaction can be catalyzed by a branched-chain α-keto acid dehydrogenase complex (bkd; EC 1.2.4.4.) (Denoya et al., *J. Bacteria* 177:3504, 1995), which consists of E1α/β (decarboxylase), E2 (dihydrolipoyl transacylase), and E3 (dihydrolipoyl dehydrogenase) subunits. These branched-chain α-keto acid dehydrogenase complexes are similar to pyruvate and α-ketoglutarate dehydrogenase complexes. Any microorganism that possesses brFAs and/or grows on branched-chain amino acids can be used as a source to isolate bkd genes for expression in host cells, for example, *E. coli*. Furthermore, *E. coli* has the E3 component as part of its pyruvate dehydrogenase complex (lpd, EC 1.8.1.4, GenBank accession NP_414658). Thus, it can be sufficient to express only the E1 α/β and E2 bkd genes. Table 3 lists non-limiting examples of

TABLE 2

Thioesterases

| Accession Number | Source Organism | Gene | Preferential product produced |
|---|---|---|---|
| AAC73596 | *E. coli* | tesA without leader sequence | $C_{18:1}$ |
| AAC73555 | *E. coli* | tesB | |
| Q41635, AAA34215 | *Umbellularia california* | fatB | $C_{12:0}$ |
| Q39513; AAC49269 | *Cuphea hookeriana* | fatB2 | $C_{8:0}$-$C_{10:0}$ |
| AAC49269; AAC72881 | *Cuphea hookeriana* | fatB3 | $C_{14:0}$-$C_{16:0}$ |
| Q39473, AAC49151 | *Cinnamonum camphorum* | fatB | $C_{14:0}$ |
| CAA85388 | *Arabidopsis thaliana* | fatB [M141T]* | $C_{16:1}$ |
| NP_189147; NP_193041 | *Arabidopsis thaliana* | fatA | $C_{18:1}$ |
| CAC39106 | *Bradyrhiizobium japonicum* | fatA | $C_{18:1}$ |
| AAC72883 | *Cuphea hookeriana* | fatA | $C_{18:1}$ |
| AAL79361 | *Helianthus annus* | fatA1 | |

*Mayer et al., BMC Plant Biology 7: 1-11, 2007

Formation of Branched Aldehydes, Fatty Alcohols, Alkanes, and Alkenes

Aldehydes, fatty alcohols, alkanes, an alkenes can be produced that contain branch points by using branched fatty acid derivatives as substrates. For example, although *E. coli* naturally produces straight chain fatty acid derivatives (sFAs), *E. coli* can be engineered to produce branched chain fatty acid derivatives (brFAs) by introducing and expressing or overexpressing genes that provide branched precursors in the *E. coli* (e.g., bkd, ilv, icm, and fab gene families). Additionally, a host cell can be engineered to express or overexpress genes encoding proteins for the elongation of brFAs (e.g., ACP, FabF, etc.) and/or to delete or attenuate the corresponding host cell genes that normally lead to sFAs.

The first step in forming brFAs is the production of the corresponding α-keto acids by a branched-chain amino acid aminotransferase. Host cells may endogenously include genes encoding such enzymes or such genes can be recombinantly introduced. *E. coli*, for example, endogenously expresses such an enzyme, IlvE (EC 2.6.1.42; GenBank accession YP_026247). In some host cells, a heterologous branched-chain amino acid aminotransferase may not be expressed. However, *E. coli* IlvE or any other branched-chain amino acid aminotransferase (e.g., IlvE from *Lactococcus lactis* (GenBank accession AAF34406), IlvE from *Pseudomonas putida* (GenBank accession NP_745648), or IlvE from *Streptomyces coelicolor* (GenBank accession NP_629657)), if not endogenous, can be introduced and recombinantly expressed.

The second step is the oxidative decarboxylation of the α-ketoacids to the corresponding branched-chain acyl-CoA.

bkd genes from several microorganisms that can be recombinantly introduced and expressed in a host cell to provide branched-chain acyl-CoA precursors.

TABLE 3

Bkd genes from selected microorganisms

| Organism | Gene | GenBank Accession # |
|---|---|---|
| *Streptomyces coelicolor* | bkdA1 (E1α) | NP_628006 |
| | bkdB1 (E1β) | NP_628005 |
| | bkdC1 (E2) | NP_638004 |
| *Streptomyces coelicolor* | bkdA2 (E1α) | NP_733618 |
| | bkdB2 (E1β) | NP_628019 |
| | bkdC2 (E2) | NP_628018 |
| *Streptomyces avermitilis* | bkdA (E1a) | BAC72074 |
| | bkdB (E1b) | BAC72075 |
| | bkdC (E2) | BAC72076 |
| *Streptomyces avermitilis* | bkdF (E1α) | BAC72088 |
| | bkdG (E1β) | BAC72089 |
| | bkdH (E2) | BAC72090 |
| *Bacillus subtilis* | bkdAA (E1α) | NP_390288 |
| | bkdAB (E1β) | NP_390288 |
| | bkdB (E2) | NP_390288 |
| *Pseudomonas putida* | bkdA1 (E1α) | AAA65614 |
| | bkdA2 (E1β) | AAA65615 |
| | bkdC (E2) | AAA65617 |

In another example, isobutyryl-CoA can be made in a host cell, for example in *E. coli*, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, *J. Bacteriol.* 179:5157, 1997). Crotonyl-CoA is an intermediate in fatty acid biosynthesis in *E. coli* and other microorganisms. Non-limiting examples of ccr and icm genes from selected microorganisms are listed in Table 4.

TABLE 4

Ccr and icm genes from selected microorganisms

| Organism | Gene | GenBank Accession # |
|---|---|---|
| Streptomyces coelicolor | Ccr | NP_630556 |
|  | icmA | NP_629554 |
|  | icmB | NP_630904 |
| Streptomyces cinnamonensis | ccr | AAD53915 |
|  | icmA | AAC08713 |
|  | icmB | AJ246005 |

In addition to expression of the bkd genes, the initiation of brFA biosynthesis utilizes β-ketoacyl-acyl-carrier-protein synthase III (FabH, EC 2.3.1.41) with specificity for branched chain acyl-CoAs (Li et al., J. Bacteriol. 187:3795-3799, 2005). Non-limiting examples of such FabH enzymes are listed in Table 5. fabH genes that are involved in fatty acid biosynthesis of any brFA-containing microorganism can be expressed in a host cell. The Bkd and FabH enzymes from host cells that do not naturally make brFA may not support brFA production. Therefore, bkd and fabH can be expressed recombinantly. Vectors containing the bkd and fabH genes can be inserted into such a host cell. Similarly, the endogenous level of Bkd and FabH production may not be sufficient to produce brFA. In this case, they can be overexpressed. Additionally, other components of the fatty acid biosynthesis pathway can be expressed or overexpressed, such as acyl carrier proteins (ACPs) and 3-ketoacyl-acyl-carrier-protein synthase II (fabF, EC 2.3.1.41) (non-limiting examples of candidates are listed in Table 5). In addition to expressing these genes, some genes in the endogenous fatty acid biosynthesis pathway can be attenuated in the host cell (e.g., the E. coli genes fabH (GenBank accession #NP_415609) and/or fabF (GenBank accession #NP_415613)).

TABLE 5

FabH, ACP and fabF genes from selected microorganisms with brFAs

| Organism | Gene | GenBank Accession # |
|---|---|---|
| Streptomyces coelicolor | fabH1 | NP_626634 |
|  | ACP | NP_626635 |
|  | fabF | NP_626636 |
| Streptomyces avermitilis | fabH3 | NP_823466 |
|  | fabC3 (ACP) | NP_823467 |
|  | fabF | NP_823468 |
| Bacillus subtilis | fabH_A | NP_389015 |
|  | fabH_B | NP_388898 |
|  | ACP | NP_389474 |
|  | fabF | NP_389016 |
| Stenotrophomonas maltophilia | SmalDRAFT_0818 (FabH) | ZP_01643059 |
|  | SmalDRAFT_0821 (ACP) | ZP_01643063 |
|  | SmalDRAFT_0822 (FabF) | ZP_01643064 |
| Legionella pneumophila | FabH | YP_123672 |
|  | ACP | YP_123675 |
|  | fabF | YP_123676 |

Formation of Cyclic Aldehydes, Fatty Alcohols, Alkanes, and Alkenes

Cyclic aldehydes, fatty alcohols, alkanes, and alkenes can be produced by using cyclic fatty acid derivatives as substrates. To produce cyclic fatty acid derivative substrates, genes that provide cyclic precursors (e.g., the ans, chc, and plm gene families) can be introduced into the host cell and expressed to allow initiation of fatty acid biosynthesis from cyclic precursors. For example, to convert a host cell, such as E. coli, into one capable of synthesizing w-cyclic fatty acid derivatives (cyFA), a gene that provides the cyclic precursor cyclohexylcarbonyl-CoA (CHC-CoA) (Cropp et al., Nature Biotech. 18:980-983, 2000) can be introduced and expressed in the host cell. Non-limiting examples of genes that provide CHC-CoA in E. coli include: ansJ, ansK, ansL, chcA, and anaI from the ansatrienin gene cluster of Streptomyces collinus (Chen et al., Eur. J. Biochem. 261: 98-107, 1999) or plmJ, plmK, plmL, chcA, and plmM from the phoslactomycin B gene cluster of Streptomyces sp. HK803 (Palaniappan et al., J. Biol. Chem. 278:35552-35557, 2003) together with the chcB gene (Patton et al., Biochem. 39:7595-7604, 2000) from S. collinus, S. avermitilis, or S. coelicolor (see Table 6). The genes listed in Table 5 can then be expressed to allow initiation and elongation of ω-cyclic fatty acids. Alternatively, the homologous genes can be isolated from microorganisms that make cyFA and expressed in a host cell (e.g., E. coli).

TABLE 6

Genes for the synthesis of CHC-CoA

| Organism | Gene | GenBank Accession # |
|---|---|---|
| Streptomyces collinus | ansJK | U72144* |
|  | ansL |  |
|  | chcA |  |
|  | ansM |  |
|  | chcB | AF268489 |
| Streptomyces sp. HK803 | pmlJK | AAQ84158 |
|  | pmlL | AAQ84159 |
|  | chcA | AAQ84160 |
|  | pmlM | AAQ84161 |
| Streptomyces coelicolor | chcB/caiD | NP_629292 |
| Streptomyces avermitilis | chcB/caiD | NP_629292 |

*Only chcA is annotated in GenBank entry U72144, ansJKLM are according to Chen et al. (Eur. J. Biochem. 261: 98-107, 1999).

The genes listed in Table 5 (fabH, ACP, and fabF) allow initiation and elongation of ω-cyclic fatty acid derivatives because they have broad substrate specificity. If the coexpression of any of these genes with the genes listed in Table 6 does not yield cyFA, then fabH, ACP, and/or fabF homologs from microorganisms that make cyFAs (e.g., those listed in Table 7) can be isolated (e.g., by using degenerate PCR primers or heterologous DNA sequence probes) and coexpressed.

TABLE 7

Non-limiting examples of microorganisms that contain ω-cyclic fatty acids

| Organism | Reference |
|---|---|
| Curtobacterium pusillum | ATCC19096 |
| Alicyclobacillus acidoterrestris | ATCC49025 |
| Alicyclobacillus acidocaldarius | ATCC27009 |
| Alicyclobacillus cycloheptanicus* | Moore, J. Org. Chem. 62: pp. 2173, 1997 |

*Uses cycloheptylcarbonyl-CoA and not cyclohexylcarbonyl-CoA as precursor for cyFA biosynthesis.

Aldehyde, Fatty Alcohol, and Alkene Saturation Levels

The degree of saturation in fatty acid derivatives can be controlled by regulating the degree of saturation of fatty acid derivative intermediates. The sfa, gns, and fab families of genes can be expressed or overexpressed to control the saturation of fatty acids. FIG. 40 lists non-limiting examples of genes in these gene families that may be used in the methods and host cells described herein.

Host cells can be engineered to produce unsaturated fatty acids by engineering the host cell to overexpress fabB or by growing the host cell at low temperatures (e.g., less than 37° C.). FabB has preference to cis-δ3decenoyl-ACP and results in unsaturated fatty acid production in *E. coli*. Overexpression of fabB results in the production of a significant percentage of unsaturated fatty acids (de Mendoza et al., *J. Biol. Chem.* 258:2098-2101, 1983). The gene fabB may be inserted into and expressed in host cells not naturally having the gene. These unsaturated fatty acid derivatives can then be used as intermediates in host cells that are engineered to produce fatty acid derivatives, such as fatty aldehydes, fatty alcohols, or alkenes.

In other instances, a repressor of fatty acid biosynthesis, for example, fabR (GenBank accession NP_418398), can be deleted, which will also result in increased unsaturated fatty acid production in *E. coli* (Zhang et al., *J. Biol. Chem.* 277: 15558, 2002). Similar deletions may be made in other host cells. A further increase in unsaturated fatty acid derivatives may be achieved, for example, by overexpressing fabM (trans-2, cis-3-decenoyl-ACP isomerase, GenBank accession DAA05501) and controlled expression of fabK (trans-2-enoyl-ACP reductase II, GenBank accession NP_357969) from *Streptococcus pneumoniae* (Marrakchi et al., *J. Biol. Chem.* 277: 44809, 2002), while deleting *E. coli* fabI (trans-2-enoyl-ACP reductase, GenBank accession NP_415804). In some examples, the endogenous fabF gene can be attenuated, thus increasing the percentage of palmitoleate (C16:1) produced.

Other Substrates

Other substrates that can be used to produce aldehydes, fatty alcohols, alkanes, and alkenes in the methods described herein are acyl-ACP, acyl-CoA, a fatty aldehyde, or a fatty alcohol, which are described in, for example, PCT/US08/058788. Exemplary genes that can be altered to express or overexpress these substrates in host cells are listed in FIG. 40. Other exemplary genes are described in PCT/US08/058788.

Genetic Engineering of Host Cells to Produce Aldehydes, Fatty Alcohols, Alkanes, and Alkenes Various host cells can be used to produce aldehydes, fatty alcohols, alkanes, and/or alkenes, as described herein. A host cell can be any prokaryotic or eukaryotic cell. For example, a polypeptide described herein can be expressed in bacterial cells (such as *E. coli*), insect cells, yeast or mammalian cells (such as Chinese hamster ovary cells (CHO) cells, COS cells, VERO cells, BHK cells, HeLa cells, Cv1 cells, MDCK cells, 293 cells, 3T3 cells, or PC12 cells). Other exemplary host cells include cells from the members of the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Schizosaccharomyces, Yarrowia,* or *Streptomyces*. Yet other exemplary host cells can be a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, a *Bacillus amyloliquefaciens* cell, a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhizomucor miehei* cell, a *Mucor michei* cell, a *Streptomyces lividans* cell, a *Streptomyces murinus* cell, or an *Actinomycetes* cell.

Other nonlimiting examples of host cells are those listed in Table 1.

In a preferred embodiment, the host cell is an *E. coli* cell. In a more preferred embodiment, the host cell is from *E. coli* strains B, C, K, or W. Other suitable host cells are known to those skilled in the art.

Various methods well known in the art can be used to genetically engineer host cells to produce aldehydes, fatty alcohols, alkanes and/or alkenes. The methods include the use of vectors, preferably expression vectors, containing a nucleic acid encoding an aldehyde, fatty alcohol, alkane, and/or alkene biosynthetic polypeptide described herein, or a polypeptide variant or fragment thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell and are thereby replicated along with the host genome. Moreover, certain vectors, such as expression vectors, are capable of directing the expression of genes to which they are operatively linked. In general, expression vectors used in recombinant DNA techniques are often in the form of plasmids. However, other forms of expression vectors, such as viral vectors (e.g., replication defective retroviruses, adenoviruses, and adeno-associated viruses), can also be used.

The recombinant expression vectors described herein include a nucleic acid described herein in a form suitable for expression of the nucleic acid in a host cell. The recombinant expression vectors can include one or more control sequences, selected on the basis of the host cell to be used for expression. The control sequence is operably linked to the nucleic acid sequence to be expressed. Such control sequences are described, for example, in Goeddel, Gene Expression Technology: Methods in Enzymology 185, Academic Press, San Diego, Calif. (1990). Control sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors described herein can be introduced into host cells to produce polypeptides, including fusion polypeptides, encoded by the nucleic acids as described herein.

Recombinant expression vectors can be designed for expression of an aldehyde, fatty alcohol, alkane, and/or alkene biosynthetic polypeptide or variant in prokaryotic or eukaryotic cells (e.g., bacterial cells, such as *E. coli*, insect cells (using baculovirus expression vectors), yeast cells, or mammalian cells). Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example, by using T7 promoter regulatory sequences and T7 polymerase.

Expression of polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech Inc; Smith et al., *Gene* (1988) 67:31-40), pMAL (New England Biolabs, Beverly, Mass.), and pRITS (Pharmacia, Piscataway, N.J.), which fuse glutathione S-transferase (GST), maltose E binding protein, or protein A, respectively, to the target recombinant polypeptide.

Examples of inducible, non-fusion *E. coli* expression vectors include pTrc (Amann et al., *Gene* (1988) 69:301-315) and pET 11d (Studier et al., Gene Expression Technology Methods in Enzymology 185, Academic Press, San Diego, Calif. (1990) 60-89). Target gene expression from the pTrc vector relies on host RNA polymerase transcription from a hybrid tip-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host cell with an impaired capacity to proteolytically cleave the recombinant polypeptide (see Gottesman, Gene Expression Technology: Methods in Enzymology 185, Academic Press, San Diego, Calif. (1990) 119-128). Another strategy is to alter the nucleic acid sequence to be inserted into an expression vector so that the individual codons for each amino acid are those preferentially utilized in the host cell (Wada et al., *Nucleic Acids Res.* (1992) 20:2111-2118). Such alteration of nucleic acid sequences can be carried out by standard DNA synthesis techniques.

In another embodiment, the host cell is a yeast cell. In this embodiment, the expression vector is a yeast expression vector. Examples of vectors for expression in yeast *S. cerevisiae* include pYepSec1 (Baldari et al., *EMBO J.* (1987) 6:229-234), pMFa (Kurj an et al., *Cell* (1982) 30:933-943), pJRY88 (Schultz et al., *Gene* (1987) 54:113-123), pYES2 (Invitrogen Corporation, San Diego, Calif.), and picZ (Invitrogen Corp, San Diego, Calif.).

Alternatively, a polypeptide described herein can be expressed in insect cells using baculovirus expression vectors. Baculovirus vectors available for expression of proteins in cultured insect cells (e.g., Sf 9 cells) include, for example, the pAc series (Smith et al., *Mol. Cell. Biol.* (1983) 3:2156-2165) and the pVL series (Lucklow et al., *Virology* (1989) 170:31-39).

In yet another embodiment, the nucleic acids described herein can be expressed in mammalian cells using a mammalian expression vector. Examples of mammalian expression vectors include pCDM8 (Seed, *Nature* (1987) 329:840) and pMT2PC (Kaufman et al., *EMBO J.* (1987) 6:187-195). When used in mammalian cells, the expression vector's control functions can be provided by viral regulatory elements.

For example, commonly used promoters are derived from polyoma, Adenovirus 2, cytomegalovirus and Simian Virus 40. Other suitable expression systems for both prokaryotic and eukaryotic cells are described in chapters 16 and 17 of Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989.

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to antibiotics) can be introduced into the host cells along with the gene of interest. Selectable markers include those that confer resistance to drugs, such as ampacillin, kanamycin, chloramphenicol, or tetracycline. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) can be introduced into the host cells along with the gene of interest. Preferred selectable markers include those which confer resistance to drugs, such as G418, hygromycin, and methotrexate. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

In certain methods, an aldehyde biosynthetic polypeptide and an alkane or alkene biosynthetic polypeptide are co-expressed in a single host cell. In alternate methods, an aldehyde biosynthetic polypeptide and an alcohol dehydrogenase polypeptide are co-expressed in a single host cell.

Transport Proteins

Transport proteins can export polypeptides and hydrocarbons (e.g., aldehydes, alkanes, and/or alkenes) out of a host cell. Many transport and efflux proteins serve to excrete a wide variety of compounds and can be naturally modified to be selective for particular types of hydrocarbons.

Non-limiting examples of suitable transport proteins are ATP-Binding Cassette (ABC) transport proteins, efflux proteins, and fatty acid transporter proteins (FATP). Additional non-limiting examples of suitable transport proteins include the ABC transport proteins from organisms such as *Caenorhabditis elegans, Arabidopsis thalania, Alkaligenes*

*eutrophus*, and *Rhodococcus erythropolis*. Exemplary ABC transport proteins that can be used are listed in FIG. 40 (e.g., CER5, AtMRP5, AmiS2, and AtPGP1). Host cells can also be chosen for their endogenous ability to secrete hydrocarbons. The efficiency of hydrocarbon production and secretion into the host cell environment (e.g., culture medium, fermentation broth) can be expressed as a ratio of intracellular product to extracellular product. In some examples, the ratio can be about 5:1, 4:1, 3:1, 2:1, 1:1, 1:2, 1:3, 1:4, or 1:5.

Fermentation

The production and isolation of aldehydes, fatty alcohols, alkanes and/or alkenes can be enhanced by employing beneficial fermentation techniques. One method for maximizing production while reducing costs is increasing the percentage of the carbon source that is converted to hydrocarbon products.

During normal cellular lifecycles, carbon is used in cellular functions, such as producing lipids, saccharides, proteins, organic acids, and nucleic acids. Reducing the amount of carbon necessary for growth-related activities can increase the efficiency of carbon source conversion to product. This can be achieved by, for example, first growing host cells to a desired density (for example, a density achieved at the peak of the log phase of growth). At such a point, replication checkpoint genes can be harnessed to stop the growth of cells. Specifically, quorum sensing mechanisms (reviewed in Camilli et al., *Science* 311:1113, 2006; Venturi *FEMS Microbio. Rev.* 30:274-291, 2006; and Reading et al., *FEMS Microbiol. Lett.* 254:1-11, 2006) can be used to activate checkpoint genes, such as p53, p21, or other checkpoint genes.

Genes that can be activated to stop cell replication and growth in *E. coli* include umuDC genes. The overexpression of umuDC genes stops the progression from stationary phase to exponential growth (Murli et al., *J. of Bact.* 182:1127, 2000). UmuC is a DNA polymerase that can carry out translesion synthesis over non-coding lesions—the mechanistic basis of most UV and chemical mutagenesis. The umuDC gene products are involved in the process of translesion synthesis and also serve as a DNA sequence damage checkpoint. The umuDC gene products include UmuC, UmuD, umuD', UmuD'$_2$C, UmuD'$_2$, and UmuD$_2$. Simultaneously, product-producing genes can be activated, thus minimizing the need for replication and maintenance pathways to be used while an aldehyde, alkane and/or alkene is being made. Host cells can also be engineered to express umuC and umuD from E. coli in pBAD24 under the prpBCDE promoter system through de novo synthesis of this gene with the appropriate end-product production genes.

The percentage of input carbons converted to aldehydes, fatty alcohols, alkanes and/or alkenes can be a cost driver. The more efficient the process is (i.e., the higher the percentage of input carbons converted to aldehydes, fatty alcohols, alkanes and/or alkenes), the less expensive the process will be. For oxygen-containing carbon sources (e.g., glucose and other carbohydrate based sources), the oxygen must be released in the form of carbon dioxide. For every 2 oxygen atoms released, a carbon atom is also released leading to a maximal theoretical metabolic efficiency of approximately 34% (w/w) (for fatty acid derived products). This figure, however, changes for other hydrocarbon products and carbon sources. Typical efficiencies in the literature are approximately less than 5%. Host cells engineered to produce aldehydes, alkanes and/or alkenes can have greater than about 1, 3, 5, 10, 15, 20, 25, and 30% efficiency. In one example, host cells can exhibit an efficiency of about 10% to about 25%. In other examples, such host cells can exhibit an efficiency of about 25% to about 30%. In other examples, host cells can exhibit greater than 30% efficiency.

The host cell can be additionally engineered to express recombinant cellulosomes, such as those described in PCT application number PCT/US2007/003736. These cellulosomes can allow the host cell to use cellulosic material as a carbon source. For example, the host cell can be additionally engineered to express invertases (EC 3.2.1.26) so that sucrose can be used as a carbon source. Similarly, the host cell can be engineered using the teachings described in U.S. Pat. Nos. 5,000,000; 5,028,539; 5,424,202; 5,482,846; and 5,602,030; so that the host cell can assimilate carbon efficiently and use cellulosic materials as carbon sources.

In one example, the fermentation chamber can enclose a fermentation that is undergoing a continuous reduction. In this instance, a stable reductive environment can be created. The electron balance can be maintained by the release of carbon dioxide (in gaseous form). Efforts to augment the NAD/H and NADP/H balance can also facilitate in stabilizing the electron balance. The availability of intracellular NADPH can also be enhanced by engineering the host cell to express an NADH:NADPH transhydrogenase. The expression of one or more NADH:NADPH transhydrogenases converts the NADH produced in glycolysis to NADPH, which can enhance the production of aldehydes, alkanes and/or alkenes.

For small scale production, the engineered host cells can be grown in batches of, for example, around 100 mL, 500 mL, 1 L, 2 L, 5 L, or 10 L; fermented; and induced to express desired aldehydes, fatty alcohols, alkanes and/or alkenes based on the specific genes encoded in the appropriate plasmids. For example, *E. coli* BL21(DE3) cells harboring pBAD24 (with ampicillin resistance and the aldehyde, fatty alcohol, alkane, or alkene synthesis pathway) as well as pUMVC1 (with kanamycin resistance and the acetyl CoA/malonyl CoA overexpression system) can be incubated overnight in 2 L flasks at 37° C. shaken at >200 rpm in 500 mL LB medium supplemented with 75 mg/mL ampicillin and 50 mg/mL kanamycin until cultures reach an OD$_{600}$ of >0.8. Upon achieving an OD$_{600}$ of >0.8, the cells can be supplemented with 25 mM sodium propionate (pH 8.0) to activate the engineered gene systems for production and to stop cellular proliferation by activating UmuC and UmuD proteins. Induction can be performed for 6 hrs at 30° C. After incubation, the media can be examined for aldehydes, fatty alcohols, alkanes and/or alkenes using GC-MS.

For large scale production, the engineered host cells can be grown in batches of 10 L, 100 L, 1000 L, or larger; fermented; and induced to express desired aldehydes, fatty alcohols, alkanes and/or alkenes based on the specific genes encoded in the appropriate plasmids. For example, *E. coli* BL21(DE3) cells harboring pBAD24 (with ampicillin resistance and the aldehyde and/or alkane synthesis pathway) as well as pUMVC1 (with kanamycin resistance and the acetyl-CoA/malonyl-CoA overexpression system) can be incubated from a 500 mL seed culture for 10 L fermentations (5 L for 100 L fermentations, etc.) in LB media (glycerol free) with 50 mg/mL kanamycin and 75 mg/mL ampicillin at 37° C., and shaken at >200 rpm until cultures reach an OD$_{600}$ of >0.8 (typically 16 hrs). Media can be continuously supplemented to maintain 25 mM sodium proprionate (pH 8.0) to activate the engineered gene systems for production and to stop cellular proliferation by activating umuC and umuD proteins. Media can be continuously supplemented with glucose to maintain a concentration 25 g/100 mL.

After the first hour of induction, aliquots of no more than 10% of the total cell volume can be removed each hour and allowed to sit without agitation to allow the aldehydes, alkanes and/or alkenes to rise to the surface and undergo a spontaneous phase separation. The aldehyde, fatty alcohols, alkane and/or alkene component can then be collected, and the aqueous phase returned to the reaction chamber. The reaction chamber can be operated continuously. When the $OD_{600}$ drops below 0.6, the cells can be replaced with a new batch grown from a seed culture.

Producing Aldehydes, Fatty Alcohols, Alkanes and Alkenes Using Cell-Free Methods In some methods described herein, an aldehyde, fatty alcohols, alkane and/or alkene can be produced using a purified polypeptide described herein and a substrate described herein. For example, a host cell can be engineered to express aldehyde, fatty alcohols, alkane and/or alkene biosynthetic polypeptide or variant as described herein. The host cell can be cultured under conditions suitable to allow expression of the polypeptide. Cell free extracts can then be generated using known methods. For example, the host cells can be lysed using detergents or by sonication. The expressed polypeptides can be purified using known methods. After obtaining the cell free extracts, substrates described herein can be added to the cell free extracts and maintained under conditions to allow conversion of the substrates to aldehydes, fatty alcohols, alkanes and/or alkenes. The aldehydes, fatty alcohols, alkanes and/or alkenes can then be separated and purified using known techniques.

Post-Production Processing

The aldehydes, fatty alcohols, alkanes and/or alkenes produced during fermentation can be separated from the fermentation media. Any known technique for separating aldehydes, fatty alcohols, alkanes and/or alkenes from aqueous media can be used. One exemplary separation process is a two phase (bi-phasic) separation process. This process involves fermenting the genetically engineered host cells under conditions sufficient to produce an aldehyde, fatty alcohols, alkane and/or alkene, allowing the aldehyde, fatty alcohols, alkane and/or alkene to collect in an organic phase, and separating the organic phase from the aqueous fermentation broth. This method can be practiced in both a batch and continuous fermentation setting.

Bi-phasic separation uses the relative immiscibility of aldehydes, fatty alcohols, alkanes and/or alkenes to facilitate separation. Immiscible refers to the relative inability of a compound to dissolve in water and is defined by the compound's partition coefficient. One of ordinary skill in the art will appreciate that by choosing a fermentation broth and organic phase, such that the aldehyde, alkane and/or alkene being produced has a high log P value, the aldehyde, alkane and/or alkene can separate into the organic phase, even at very low concentrations, in the fermentation vessel.

The aldehydes, fatty alcohols, alkanes and/or alkenes produced by the methods described herein can be relatively immiscible in the fermentation broth, as well as in the cytoplasm. Therefore, the aldehyde, fatty alcohols, alkane and/or alkene can collect in an organic phase either intracellularly or extracellularly. The collection of the products in the organic phase can lessen the impact of the aldehyde, fatty alcohols, alkane and/or alkene on cellular function and can allow the host cell to produce more product.

The methods described herein can result in the production of homogeneous compounds wherein at least about 60%, 70%, 80%, 90%, or 95% of the aldehydes, fatty alcohols, alkanes and/or alkenes produced will have carbon chain lengths that vary by less than about 6 carbons, less than about 4 carbons, or less than about 2 carbons. These compounds can also be produced with a relatively uniform degree of saturation. These compounds can be used directly as fuels, fuel additives, specialty chemicals, starting materials for production of other chemical compounds (e.g., polymers, surfactants, plastics, textiles, solvents, adhesives, etc.), or personal care product additives. These compounds can also be used as feedstock for subsequent reactions, for example, hydrogenation, catalytic cracking (via hydrogenation, pyrolisis, or both), to make other products.

In some embodiments, the aldehydes, fatty alcohols, alkanes and/or alkenes produced using methods described herein can contain between about 50% and about 90% carbon; or between about 5% and about 25% hydrogen. In other embodiments, the aldehydes, fatty alcohols, alkanes and/or alkenes produced using methods described herein can contain between about 65% and about 85% carbon; or between about 10% and about 15% hydrogen.

Fuel Compositions and Specialty Chemical Compositions

The aldehydes, fatty alcohols, alkanes and/or alkenes described herein can be used as or converted into a fuel or as a specialty chemical. One of ordinary skill in the art will appreciate that, depending upon the intended purpose of the fuel or specialty chemical, different aldehydes, fatty alcohols, alkanes and/or alkenes can be produced and used. For example, a branched aldehyde, fatty alcohol, alkane and/or alkene may be desirable for automobile fuel that is intended to be used in cold climates. In addition, when the aldehydes, fatty alcohols, alkanes and/or alkenes described herein are used as a feedstock for fuel or specialty chemical production, one of ordinary skill in the art will appreciate that the characteristics of the aldehyde, fatty alcohol, alkane and/or alkene feedstock will affect the characteristics of the fuel or specialty chemical produced. Hence, the characteristics of the fuel or specialty chemical product can be selected for by producing particular aldehydes, fatty alcohols, alkanes and/or alkenes for use as a feedstock.

Using the methods described herein, biofuels having desired fuel qualities can be produced from aldehydes, fatty alcohols, alkanes and/or alkenes. Biologically produced aldehydes, fatty alcohols, alkanes and/or alkenes represent a new source of biofuels, which can be used as jet fuel, diesel, or gasoline. Some biofuels made using aldehydes, fatty alcohols, alkanes and/or alkenes have not been produced from renewable sources and are new compositions of matter. These new fuels or specialty chemicals can be distinguished from fuels or specialty chemicals derived from petrochemical carbon on the basis of dual carbon-isotopic fingerprinting. Additionally, the specific source of biosourced carbon (e.g., glucose vs. glycerol) can be determined by dual carbon-isotopic fingerprinting (see, e.g., U.S. Pat. No. 7,169,588, in particular col. 4, line 31, to col. 6, line 8).

The aldehydes, fatty alcohols, alkanes and/or alkenes and the associated biofuels, specialty chemicals, and mixtures can be distinguished from their petrochemical derived counterparts on the basis of $^{14}C$ ($f_M$) and dual carbon-isotopic fingerprinting. In some examples, the aldehyde, fatty alcohol, alkane and/or alkene in the biofuel composition can have a fraction of modern carbon ($f_M$ $^{14}C$) of, for example, at least about 1.003, 1.010, or 1.5.

In some examples, a biofuel composition can be made that includes aldehydes, fatty alcohols, alkanes and/or alkenes having $\delta^{13}C$ of from about −15.4 to about −10.9, where the aldehydes, fatty alcohols, alkanes and/or alkenes account for at least about 85% of biosourced material (i.e., derived from a renewable resource, such as biomass, cellulosic materials, and sugars) in the composition.

The ability to distinguish these biologically derived products is beneficial in tracking these materials in commerce. For example, fuels or specialty chemicals comprising both biologically derived and petroleum-based carbon isotope profiles can be distinguished from fuels and specialty chemicals made only of petroleum-based materials. Thus, the aldehydes, fatty alcohols, alkanes and/or alkenes described herein can be followed in commerce or identified in commerce as a biofuel on the basis of their unique profile. In addition, other competing materials can be identified as being biologically derived or derived from a petrochemical source.

Fuel additives are used to enhance the performance of a fuel or engine. For example, fuel additives can be used to alter the freezing/gelling point, cloud point, lubricity, viscosity, oxidative stability, ignition quality, octane level, and/or flash point. In the United States, all fuel additives must be registered with Environmental Protection Agency. The names of fuel additives and the companies that sell the fuel additives are publicly available by contacting the EPA or by viewing the agency's website. One of ordinary skill in the art will appreciate that the aldehyde- and/or alkane-based biofuels described herein can be mixed with one or more fuel additives to impart a desired quality.

The aldehyde, fatty alcohols, alkane and/or alkene-based biofuels described herein can be mixed with other fuels, such as various alcohols, such as ethanol and butanol, and petroleum-derived products, such as gasoline, diesel, or jet fuel.

In some examples, the mixture can include at least about 10%, 15%, 20%, 30%, 40%, 50%, or 60% by weight of the aldehyde, fatty alcohols, alkane, or alkene. In other examples, a biofuel composition can be made that includes at least about 5%, 10%, 20%, 30%, 40%, 50%, 60%, 70%, 80%, 85%, 90% or 95% of an aldehyde, fatty alcohols, alkane, or alkene that includes a carbon chain that is 8, 10, 12, 13, 14, 15, 16, 17, 18, 19, 20, 21 or 22 carbons in length. Such biofuel compositions can additionally include at least one additive selected from a cloud point lowering additive that can lower the cloud point to less than about 5° C., or 0° C.; a surfactant; a microemulsion; at least about 5%, 10%, 15%, 20%, 30%, 40%, 50%, 60%, 70%, 80%, 85%, 90%, or 95% diesel fuel from triglycerides; petroleum-derived gasoline; or diesel fuel from petroleum.

EXAMPLES

The invention is further described in the following examples, which do not limit the scope of the invention described in the claims.

Example 1

Detection and Verification of Alkane Biosynthesis in Selected Cyanobacteria

Seven cyanobacteria, whose complete genome sequences are publicly available, were selected for verification and/or detection of alkane biosynthesis: *Synechococcus elongatus* PCC7942, *Synechococcus elongatus* PCC6301, *Anabaena variabilis* ATCC29413, *Synechocystis* sp. PCC6803, *Nostoc punctiforme* PCC73102, *Gloeobacter violaceus* ATCC 29082, and *Prochlorococcus marinus* CCMP1986. Only the first three cyanobacterial strains from this list had previously been reported to contain alkanes (Han et al., *J. Am. Chem. Soc.* 91:5156-5159 (1969); Fehler et al., *Biochem.* 9:418-422 (1970)). The strains were grown photoautotrophically in shake flasks in 100 mL of the appropriate media (listed in Table 8) for 3-7 days at 30° C. at a light intensity of approximately 3,500 lux. Cells were extracted for alkane detection as follows: cells from 1 mL culture volume were centrifuged for 1 min at 13,000 rpm, the cell pellets were resuspended in methanol, vortexed for 1 min and then sonicated for 30 min. After centrifugation for 3 min at 13,000 rpm, the supernatants were transferred to fresh vials and analyzed by GC-MS. The samples were analyzed on either 30 m DP-5 capillary column (0.25 mm internal diameter) or a 30 m high temperature DP-5 capillary column (0.25 mm internal diameter) using the following method.

After a 1 µL splitless injection (inlet temperature held at 300° C.) onto the GC/MS column, the oven was held at 100° C. for 3 mins. The temperature was ramped up to 320° C. at a rate of 20° C./min. The oven was held at 320° C. for an additional 5 min. The flow rate of the carrier gas helium was 1.3 mL/min. The MS quadrapole scanned from 50 to 550 m/z. Retention times and fragmentation patterns of product peaks were compared with authentic references to confirm peak identity.

Out of the seven strains, six produced mainly heptadecane and one produced pentadecane (*P. marinus* CCMP1986); one of these strains produced methyl-heptadecane in addition to heptadecane (*A. variabilis* ATCC29413) (see Table 8). Therefore, alkane biosynthesis in three previously reported cyanobacteria was verified, and alkane biosynthesis was detected in four cyanobacteria that were not previously known to produce alkanes: *P. marinus* CCMP1986 (see FIG. 1), *N. punctiforme* PCC73102 (see FIG. 2), *G. violaceus* ATCC 29082 (see FIG. 3) and *Synechocystis* sp. PCC6803 (see FIG. 4).

FIG. 1A depicts the GC/MS trace of *Prochlorococcus marinus* CCMP1986 cells extracted with methanol. The peak at 7.55 min had the same retention time as pentadecane (Sigma). In FIG. 1B, the mass fragmentation pattern of the pentadecane peak is shown. The 212 peak corresponds to the molecular weight of pentadecane.

Figure 2B:
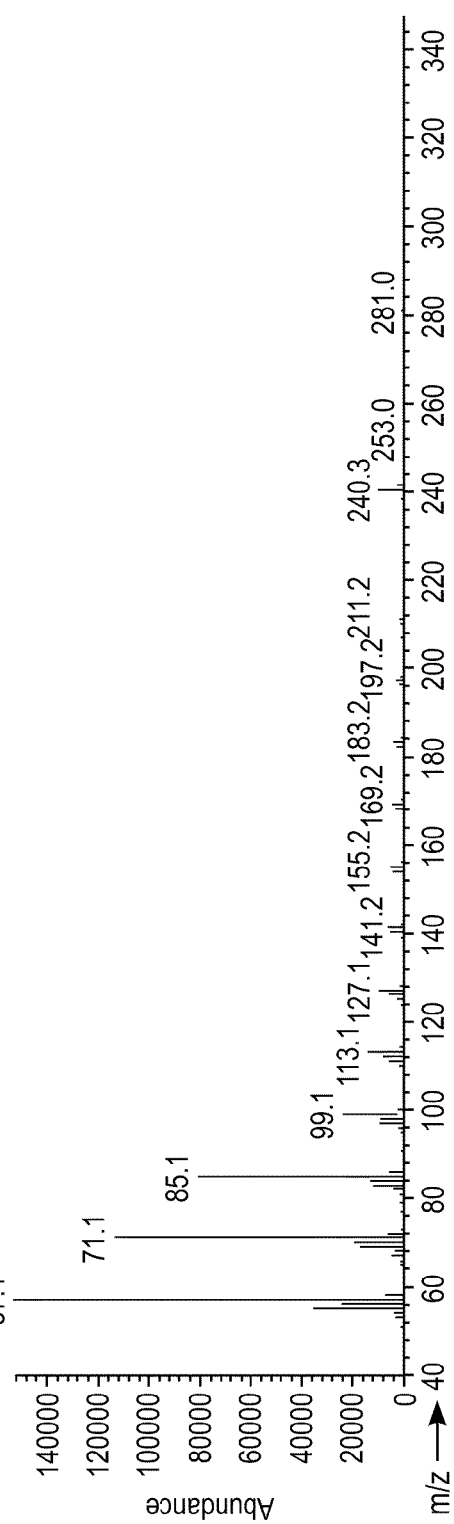
FIG. 2B is a mass fragmentation pattern of the peak at 8.73 min of FIG. 2A.

FIG. 2A depicts the GC/MS trace of *Nostoc punctiforme* PCC73102 cells extracted with methanol. The peak at 8.73 min has the same retention time as heptadecane (Sigma). In FIG. 2B, the mass fragmentation pattern of the heptadecane peak is shown. The 240 peak corresponds to the molecular weight of heptadecane.

Figure 3A:
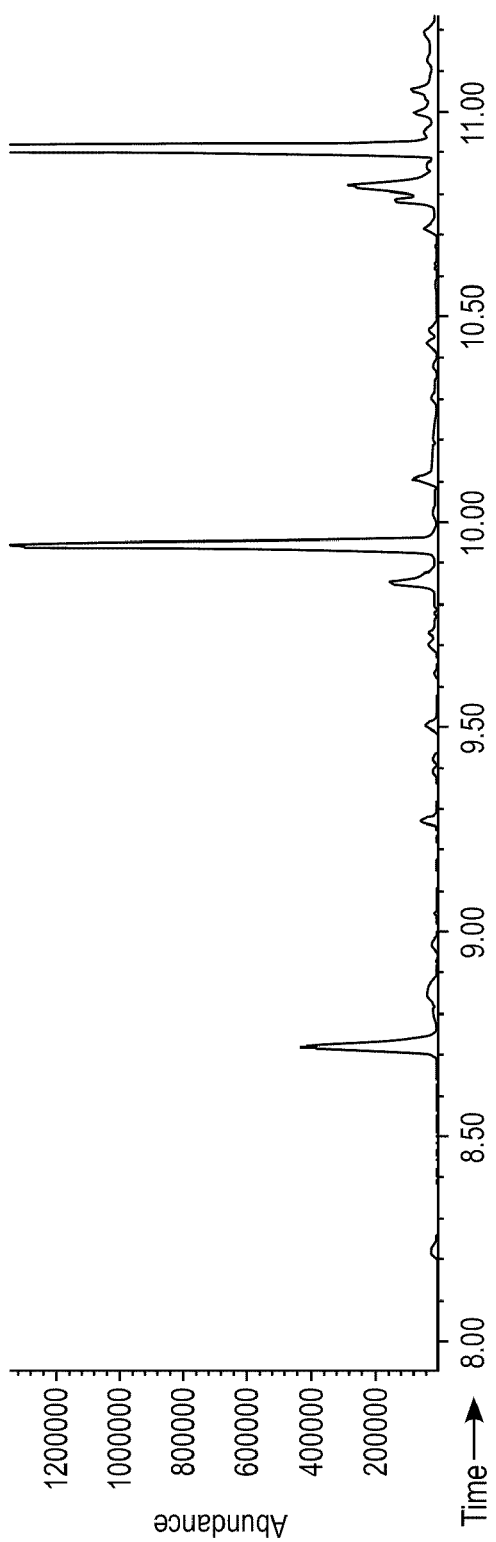
FIG. 3A is a GC/MS trace of hydrocarbons produced by *Gloeobacter violaceus* ATCC29082 cells.
Figure 3B:
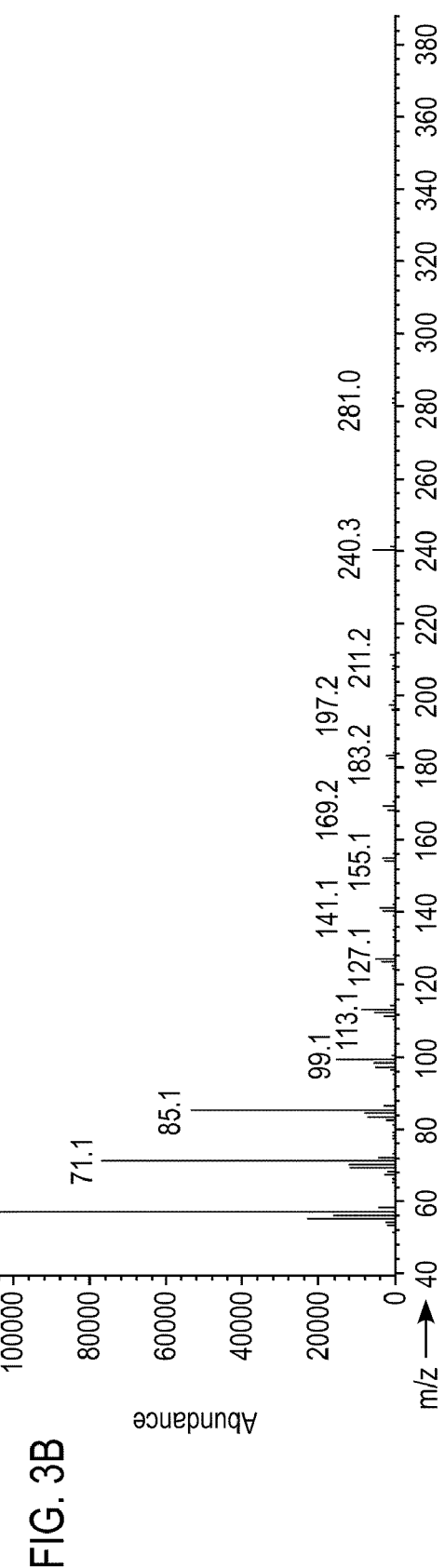
FIG. 3B is a mass fragmentation pattern of the peak at 8.72 min of FIG. 3A.

FIG. 3A depicts the GC/MS trace of *Gloeobacter violaceus* ATCC29082 cells extracted with methanol. The peak at 8.72 min has the same retention time as heptadecane (Sigma). In FIG. 3B, the mass fragmentation pattern of the heptadecane peak is shown. The 240 peak corresponds to the molecular weight of heptadecane.

FIG. 4A depicts the GC/MS trace of *Synechocystic* sp. PCC6803 cells extracted with methanol. The peak at 7.36 min has the same retention time as heptadecane (Sigma). In FIG. 4B, the mass fragmentation pattern of the heptadecane peak is shown. The 240 peak corresponds to the molecular weight of heptadecane.

TABLE 8

Hydrocarbons detected in selected cyanobacteria

| Cyanobacterium | ATCC# | Genome | Medium | Alkanes reported | verified [2] |
|---|---|---|---|---|---|
| *Synechococcus elongatus* PCC7942 | 27144 | 2.7 Mb | BG-11 | C17:0 | C17:0, C15:0 |
| *Synechococcus elongatus* PCC6301 | 33912 | 2.7 Mb | BG-11 | C17:0 | C17:0, C15:0 |
| *Anabaena variabilis* | 29413 | 6.4 Mb | BG-11 | C17:0, 7-or 8-Me-C17:0 | C17:0, Me-C17:0 |
| *Synechocystis* sp. PCC6803 | 27184 | 3.5 Mb | BG-11 | — | C17:0, C15:0 |
| *Prochlorococcus marinus* CCMP1986 [1] | — | 1.7 Mb | — | — | C15:0 |
| *Nostoc punctiforme* PCC73102 | 29133 | 9.0 Mb | ATCC819 | — | C17:0 |
| *Gloeobacter violaceus* | 29082 | 4.6 Mb | BG11 | — | C17:0 |

[1] cells for extraction were a gift from Jacob Waldbauer (MIT)
[2] major hydrocarbon is in bold Genomic analysis yielded two genes that were present in the alkane-producing strains. The *Synechococcus elongatus* PCC7942 homologs of these genes are depicted in Table 9 and are Synpcc7942_1593 (SEQ ID NO:1) and Synpcc7942_1594 (SEQ ID NO:65).

TABLE 9

Alkane-producing cyanobacterial genes

| Gene Object ID | Locus Tag | Genbank accession | Gene Name | Length | COG | Pfam | InterPro | Notes |
|---|---|---|---|---|---|---|---|---|
| 637800026 | Synpcc7942_1593 | YP_400610 | hypothetical protein | 231 aa | — | pfam02915 | IPR009078 IPR003251 | ferritin/ribonucleotide reductase-like rubreryhtrin |
| 637800027 | Synpcc7942_1594 | YP_400611 | hypothetical protein | 341 aa | COG5322 | pfam00106 | IPR000408 IPR016040 IPR002198 | predicted dehydrogenase NAD(P)-binding short chain dehydrogenase |

Example 2

Deletion of the sll0208 and sll0209 Genes in *Synechocystis* sp. PCC6803 Leads to Loss of Alkane Biosynthesis The genes encoding the putative decarbonylase (sll0208; NP_442147) (SEQ ID NO:3) and aldehyde-generating enzyme (sll0209; NP_442146) (SEQ ID NO:67) of *Synechocystis* sp. PCC6803 were deleted as follows. Approximately 1 kb of upstream and downstream flanking DNA were amplified using primer sll0208/9-KO1 (CGCGGATCCCT-TGATTCTACTGCGGCAGT (SEQ ID NO: 95)) with primer sll0208/9-KO2 (CACGCACCTAGGTTCACACTC-CCATGGTATAACAGGGGCGTTGGACTCCTGTG (SEQ ID NO: 96)) and primer sll0208/9-KO3 (GTTATACCATGG-GAGTGTGAACCTAGGTGCGTGGCCGA-CAGGATAGGGCGTGT (SEQ ID NO: 97)) with primer sll0208/9-KO4 (CGCGGATCCAACGCATCCTCAC-TAGTCGGG (SEQ ID NO: 98)), respectively. The PCR products were used in a cross-over PCR with primers sll0208/9-KO1 and sll0208/9-KO4 to amplify the approximately 2 kb sll0208/sll0209 deletion cassette, which was cloned into the BamHI site of the cloning vector pUC19. A kanamycin resistance cassette (aph, KanR) was then amplified from plasmid pRL27 (Larsen et al., *Arch. Microbiol.* 178:193 (2002)) using primers Kan-aph-F (CATGCCATGGAAAGCCACGTTGT-GTCTCAAAATCTCTG (SEQ ID NO: 99)) and Kan-aph-R (CTAGTCTAGAGCGCTGAGGTCTGCCTCGTGAA (SEQ ID NO: 100)), which was then cut with NcoI and XbaI and cloned into the NcoI and AvrII sites of the sll0208/sll0209 deletion cassette, creating a sll0208/sll0209-deletion KanR-insertion cassette in pUC19. The cassette-containing vector, which does not replicate in cyanobacteria, was transfoniied into *Synechocystis* sp. PCC6803 (Zang et al., 2007, J. Microbiol., vol. 45, pp. 241) and transformants (e.g., chromosomal integrants by double-homologous recombination) were selected on BG-11 agar plates containing 100 μg/mL Kanamycin in a light-equipped incubator at 30° C. Kanamycin resistant colonies were restreaked once and then subjected to genotypic analysis using PCR with diagnostic primers.

Confirmed deletion-insertion mutants were cultivated in 12 mL of BG11 medium with 50 μg/mL Kanamycin for 4 days at 30° C. in a light-equipped shaker-incubator. 1 mL of broth was then centrifuged (1 min at 13,000 g) and the cell pellets were extracted with 0.1 mL methanol. After extraction, the samples were again centrifuged and the supernatants were subjected to GC-MS analysis as described in Example 1.

Figures 5A, 5B:
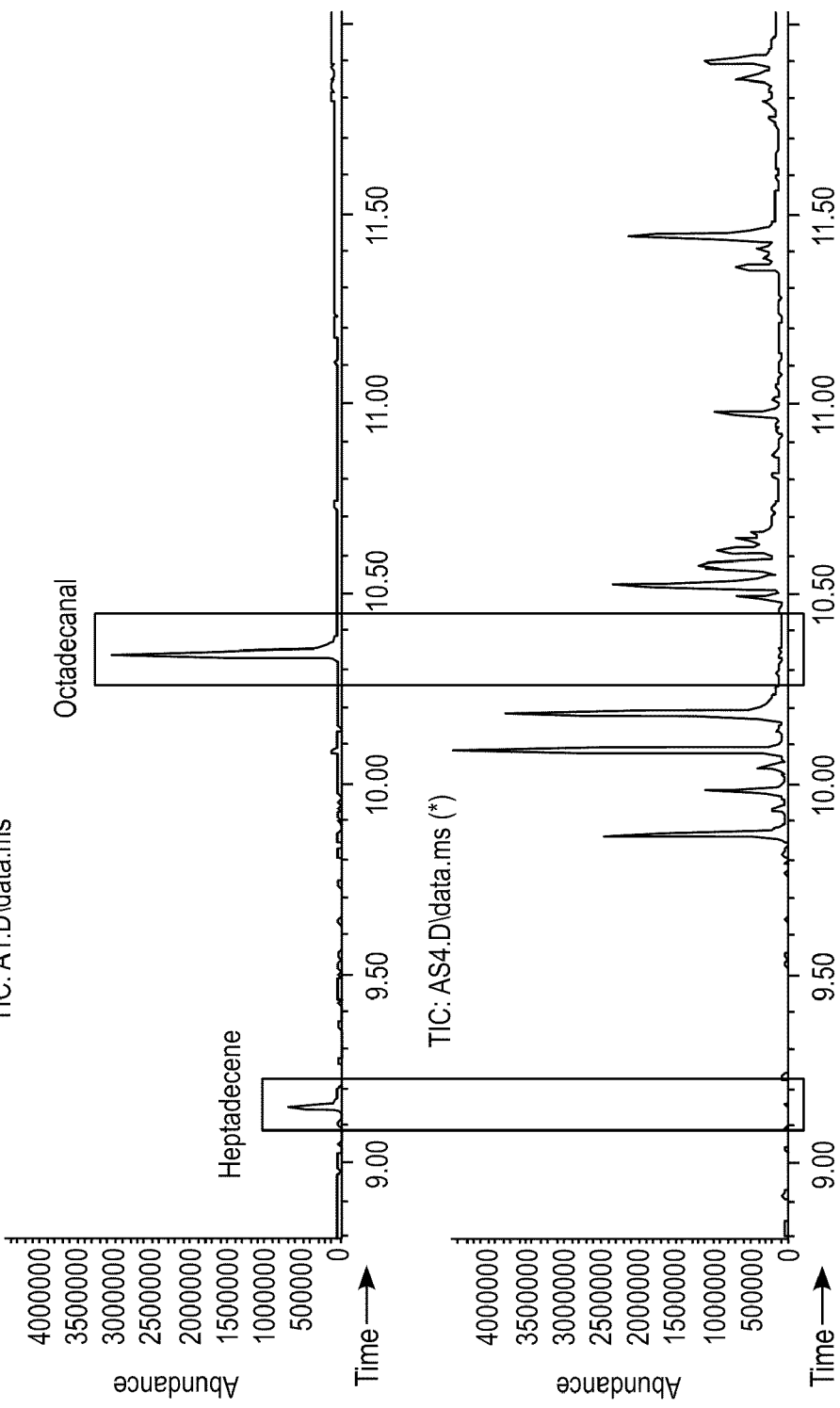
FIG. 5A is a GC/MS trace of hydrocarbons produced by *Synechocystis* sp. PCC6803 wild type cells.
FIG. 5B is a GC/MS trace of hydrocarbons produced by *Synechocystis* sp. PCC6803 cells with a deletion of the sll0208 and sll0209 genes.

As shown in FIG. 5, the *Synechocystis* sp. PCC6803 strains in which the sll0208 and sll0209 genes were deleted lost their ability to produce heptadecene and octadecenal. This result demonstrates that the sll0208 and sll0209 genes in *Synechocystis* sp. PCC6803 and the orthologous genes in other cyanobacteria (see Table 1) are responsible for alkane and fatty aldehyde biosynthesis in these organisms.

Example 3

Production of Fatty Aldehydes and Fatty Alcohols in *E. coli* Through Heterologous Expression of *Synechococcus elongatus* PCC7942 orf1594

The genomic DNA encoding *Synechococcus elongatus* PCC7942 orf1594 (YP_400611; putative aldehyde-generating enzyme) (SEQ ID NO:65) was amplified and cloned into the NcoI and EcoRI sites of vector OP-80 (pCL1920 derivative) under the control of the $P_{trc}$ promoter. The resulting construct ("OP80-PCC7942_1594") was transformed into *E. coli* MG1655 and the cells were grown at 37° C. in M9 minimal media with 1% (w/v) glucose as carbon source and supplemented with 100 μg/mL spectinomycin. When the culture reached $OD_{600}$ of 0.8-1.0, it was induced with 1 mM IPTG and cells were grown for an additional 18-20 h at 37° C. Cells from 0.5 mL of culture were extracted with 0.5 mL of ethyl acetate. After sonication for 60 min, the sample was centrifuged at 15,000 rpm for 5 min. The solvent layer was analyzed by GC-MS as described in Example 1.

Figure 6A:
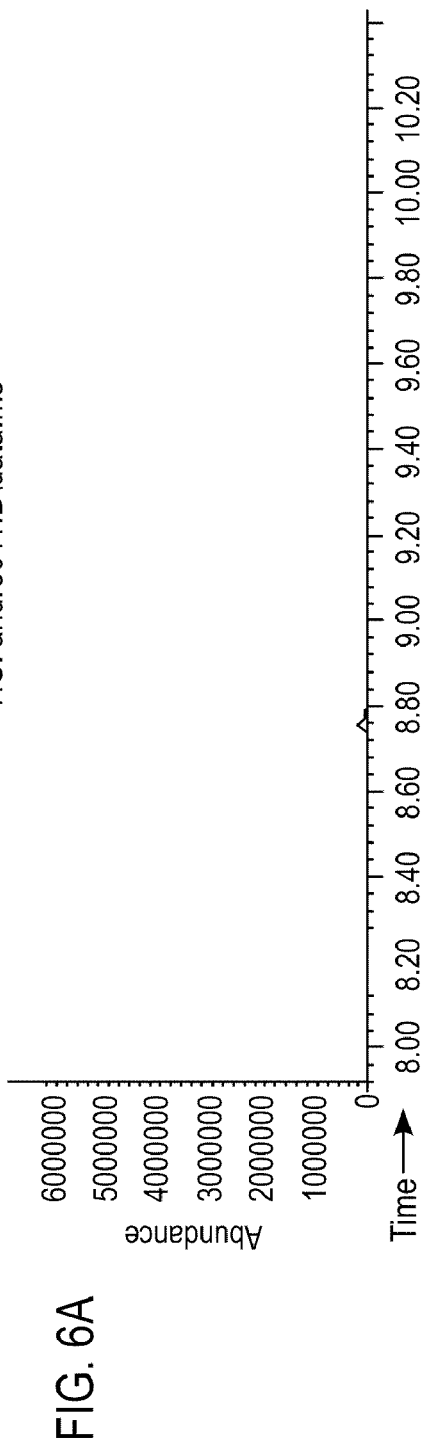
FIG. 6A is a GC/MS trace of hydrocarbons produced by *E. coli* MG1655 wild type cells.
Figure 6B:
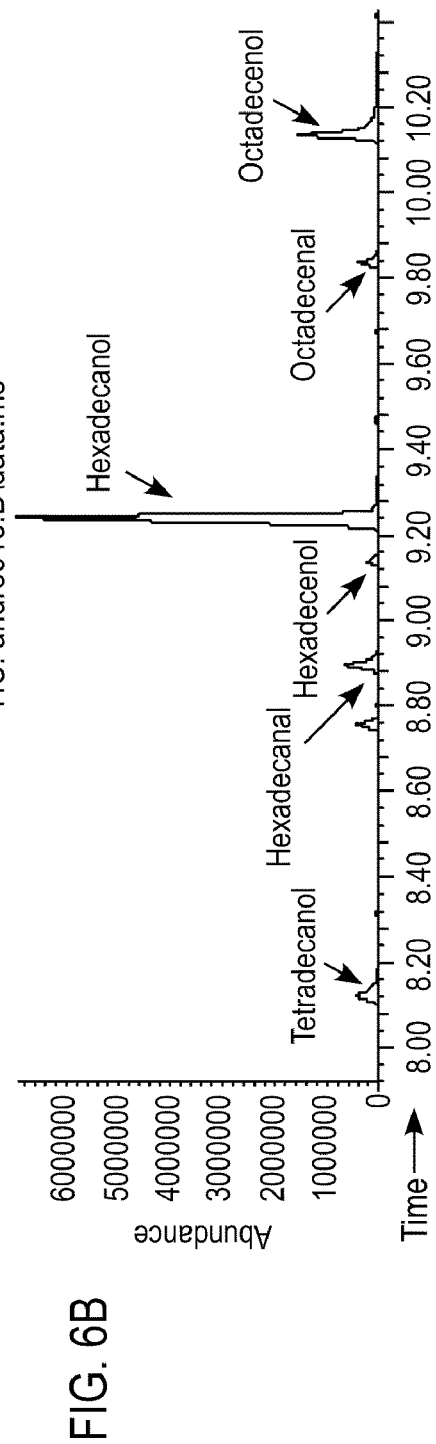
FIG. 6B is a GC/MS trace of hydrocarbons produced by *E. coli* MG1655 cells expressing *Synechococcus elongatus* PCC7942 YP_400611 (Synpcc7942_1594) (SEQ ID NO:65).

As shown in FIG. 6, *E. coli* cells transformed with the *Synechococcus elongatus* PCC7942 orf1594-bearing vector produced the following fatty aldehydes and fatty alcohols: hexadecanal, octadecenal, tetradecenol, hexadecenol, hexadecanol and octadecenol. This result indicates that PCC7942 orf1594 (i) generates aldehydes in-vivo as possible substrates for decarbonylation and (ii) may reduce acyl-ACPs as substrates, which are the most abundant form of activated fatty acids in wild type *E. coli* cells. Therefore, the enzyme was named Acyl-ACP reductase. In-vivo, the fatty aldehydes apparently are further reduced to the corresponding fatty alcohols by an endogenous *E. coli* aldehyde reductase activity.

Example 4

Production of Fatty Aldehydes and Fatty Alcohols in *E. coli* Through Heterologous Expression of *Cyanothece* sp. ATCC51142 cce_1430

The genomic DNA encoding *Cyanothece* sp. ATCC51142 cce_1430 (YP_001802846; putative aldehyde-generating enzyme) (SEQ ID NO:69) was amplified and cloned into the NcoI and EcoRI sites of vector OP-80 (pCL1920 derivative) under the control of the $P_{trc}$ promoter. The resulting construct was transformed into *E. coli* MG1655 and the cells were grown at 37° C. in M9 minimal media with 1% (w/v) glucose as carbon source and supplemented with 100 μg/mL spectinomycin. The cells were cultured and extracted as in Example 3 and analyzed by GC-MS as described in Example 26.

Figure 7:
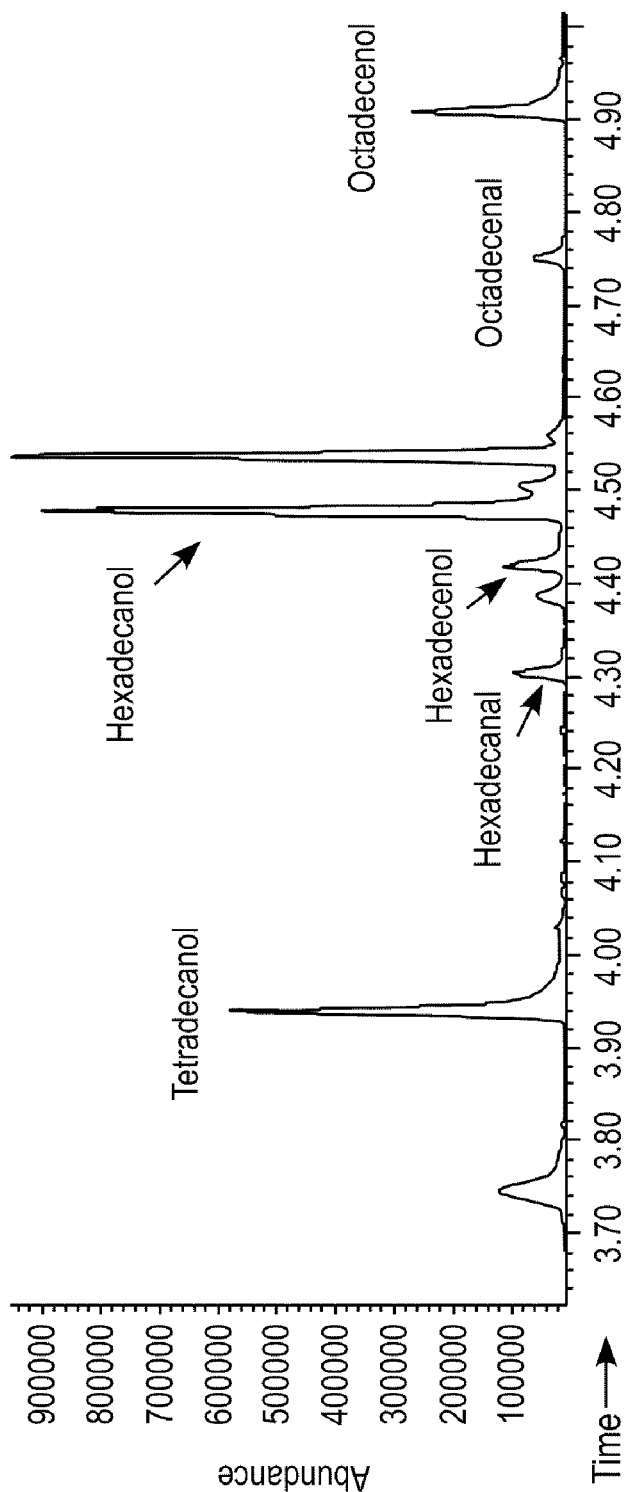
FIG. 7 is a GC/MS trace of hydrocarbons produced by *E. coli* cells expressing *Cyanothece* sp. ATCC51142 cce_1430 (YP_001802846) (SEQ ID NO:69).

As shown in FIG. 7, *E. coli* cells transformed with the *Cyanothece* sp. ATCC51142 cce_1430-bearing vector produced the following fatty aldehydes and fatty alcohols: hexadecanal, octadecenal, tetradecenol, hexadecenol, hexadecanol and octadecenol. This result indicates that ATCC51142 cce_1430 (i) generates aldehydes in-vivo as possible substrates for decarbonylation and (ii) may reduce acyl-ACPs as substrates, which are the most abundant form of activated fatty acids in wild type *E. coli* cells. Therefore, this enzyme is also an Acyl-ACP reductase.

Example 5

Production of Alkanes and Alkenes in *E. coli* Through Heterologous Expression of *Synechococcus elongatus* PCC7942 orf1594 and *Synechococcus elongatus* PCC7942 orf1593

The genomic DNA encoding *Synechococcus elongatus* PCC7942 orf1593 (YP_400610; putative decarbonylase) (SEQ ID NO:1) was amplified and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 μg/mL spectinomycin and 100 μg/mL carbenicillin. The cells were cultured and extracted as in Example 3 and analyzed by GC-MS as described in Example 1.

Figure 8A:
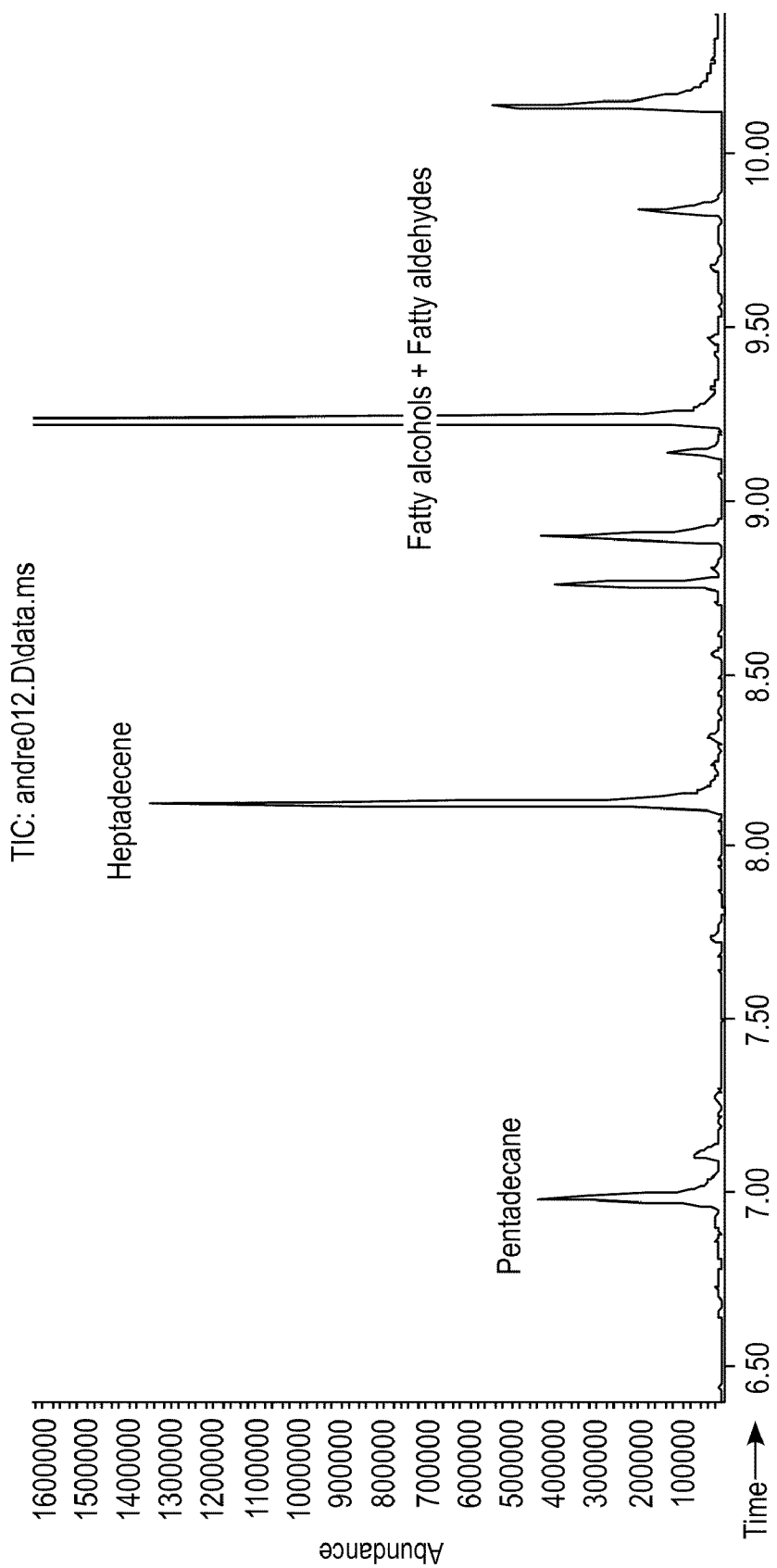
FIG. 8A is a GC/MS trace of hydrocarbons produced by *E. coli* cells expressing *Synechococcus elongatus* PCC7942 YP_400611 (Synpcc7942_1594) (SEQ ID NO:65) and *Synechococcus elongatus* PCC7942 YP_400610 (Synpcc7942_1593) (SEQ ID NO:1).
Figure 8B:
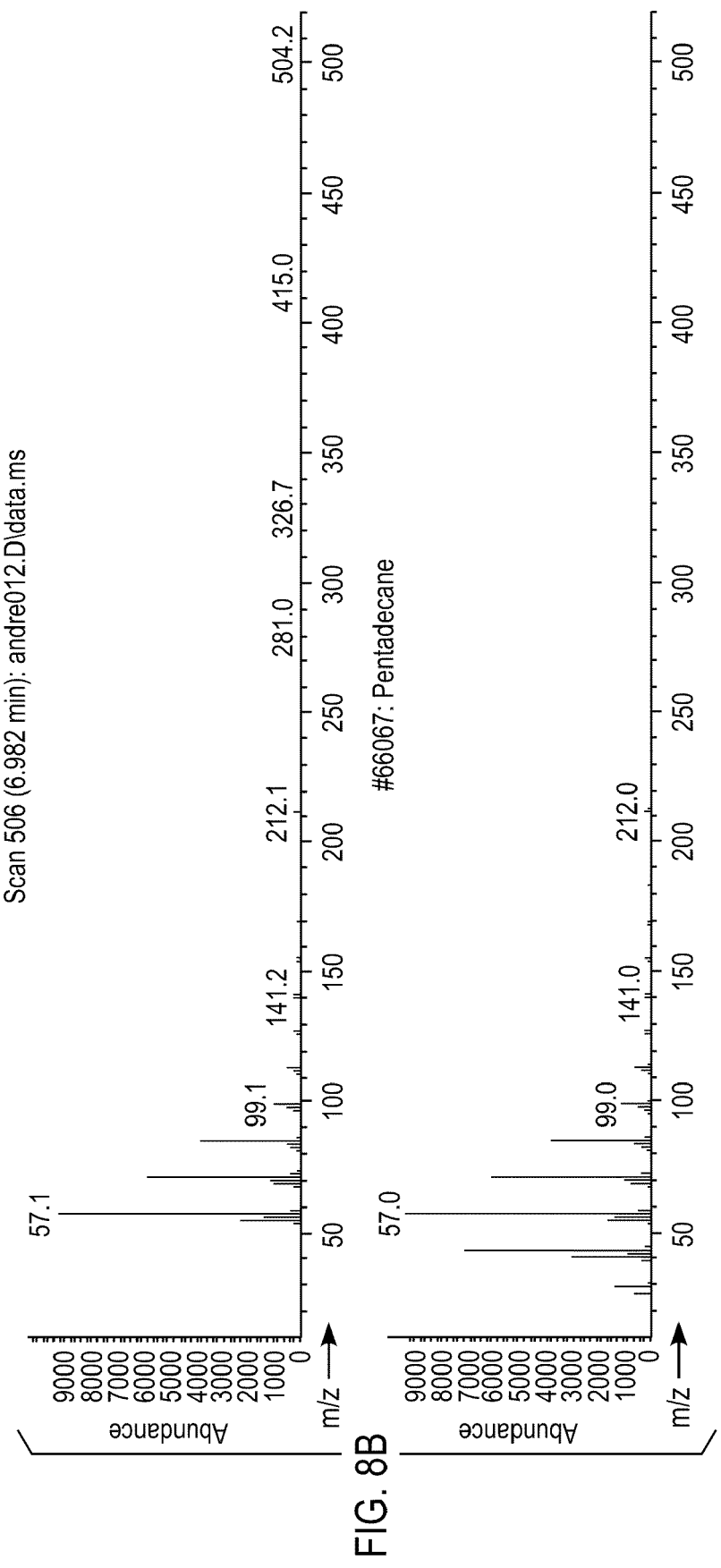
FIG. 8B depicts mass fragmentation patterns of the peak at 6.98 min of FIG. 8A and of pentadecane.
Figure 8C:
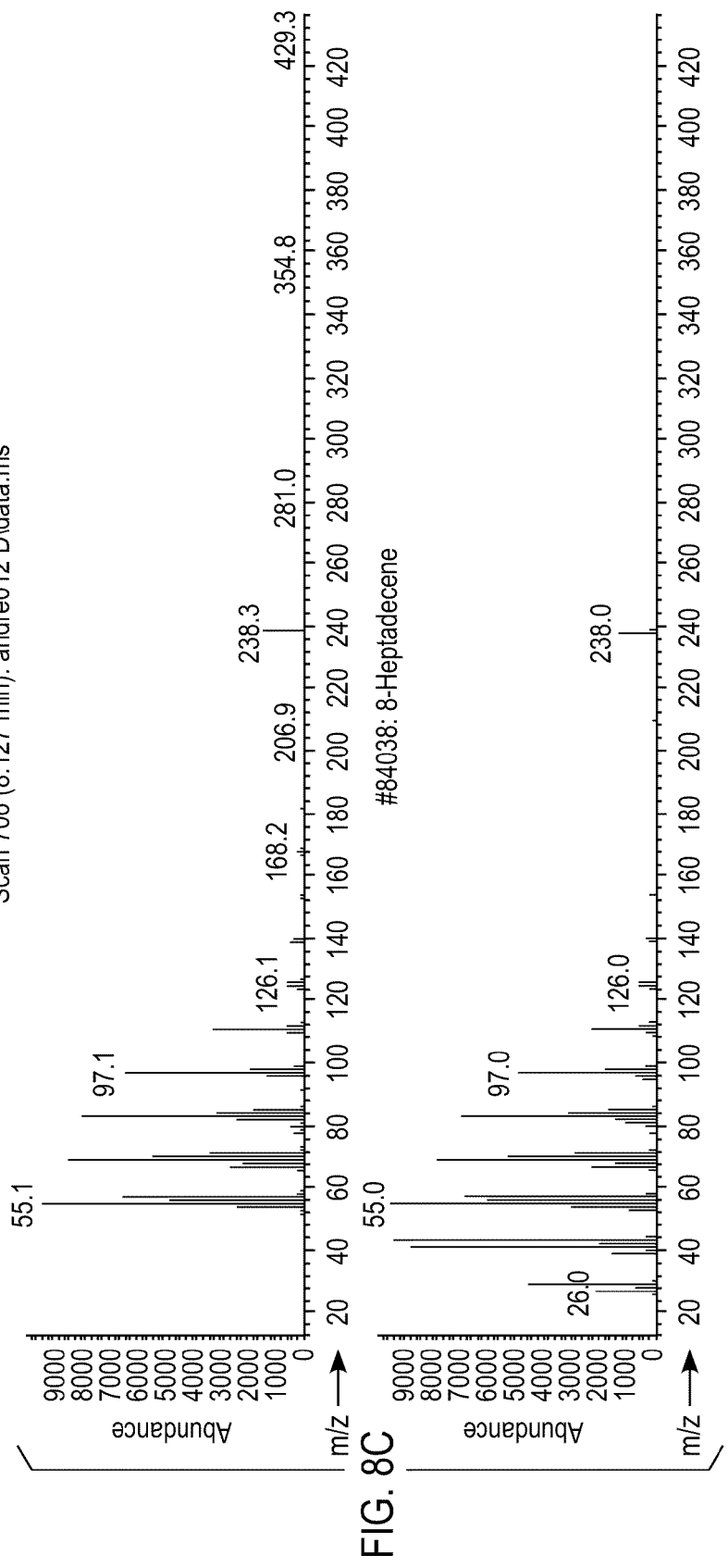
FIG. 8C depicts mass fragmentation patterns of the peak at 8.12 min of FIG. 8A and of 8-heptadecene.

As shown in FIG. 8, *E. coli* cells cotransformed with the *S. elongatus* PCC7942_1594 and *S. elongatus* PCC7942_1593-bearing vectors produced the same fatty aldehydes and fatty alcohols as in Example 3, but also pentadecane and heptadecene. This result indicates that PCC7942_1593 in *E. coli* converts hexadecanal and octadecenal to pentadecane and heptadecene, respectively, and therefore is an active fatty aldehyde decarbonylase.

Example 6

Production of Alkanes and Alkenes in *E. coli* Through Heterologous Expression of *Synechococcus elongatus* PCC7942 orf1594 and *Nostoc punctiforme* PCC73102 Npun02004178

The genomic DNA encoding *Nostoc punctiforme* PCC73102 Npun02004178 (ZP_00108838; putative decarbonylase) (SEQ ID NO:5) was amplified and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 μg/mL spectinomycin and 100 μg/mL carbenicillin. The cells were cultured and extracted as in Example 3 and analyzed by GC-MS as described in Example 1.

Figure 9:
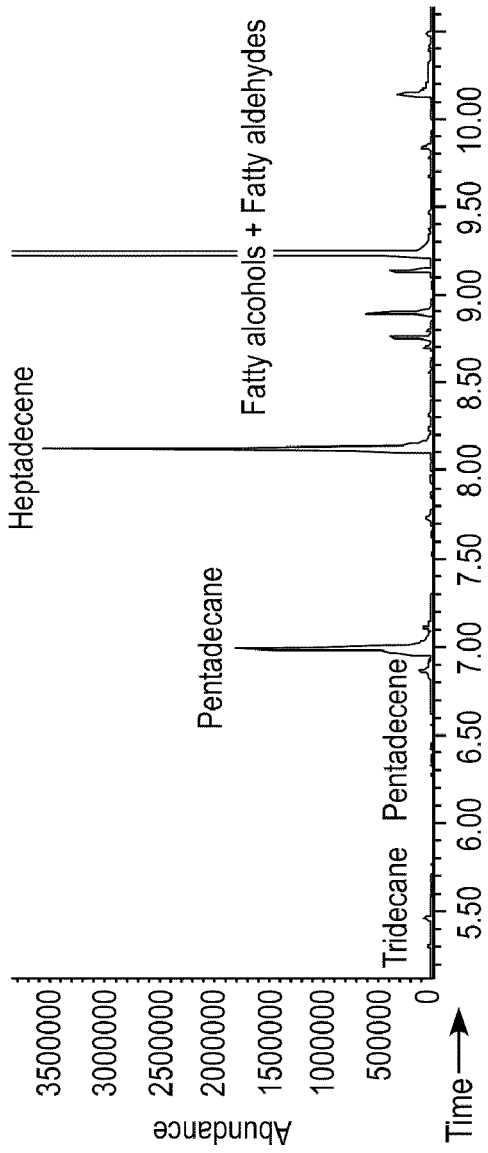
FIG. 9 is a GC/MS trace of hydrocarbons produced by *E. coli* MG1655 cells expressing *Synechococcus elongatus* PCC7942 YP_400611 (Synpcc7942_1594) (SEQ ID NO:65) and *Nostoc punctiforme* PCC73102 Npun02004178 (ZP_00108838) (SEQ ID NO:5).

As shown in FIG. 9, *E. coli* cells cotransformed with the *S. elongatus* PCC7942_1594 and *N. punctiforme* PCC73102 Npun02004178-bearing vectors produced the same fatty aldehydes and fatty alcohols as in Example 3, but also tridecane, pentadecene, pentadecane and heptadecene. This result indicates that Npun02004178 in *E. coli* converts tetradecanal, hexadecenal, hexadecanal and octadecenal to tridecane, pentadecene, pentadecane and heptadecene, respectively, and therefore is an active fatty aldehyde decarbonylase.

Example 7

Production of Alkanes and Alkenes in *E. coli* Through Heterologous Expression of *Synechococcus elongatus* PCC7942 orf1594 and *Synechocystis* sp. PCC6803 sll0208

The genomic DNA encoding *Synechocystis* sp. PCC6803 sll0208 (NP_442147; putative decarbonylase) (SEQ ID NO:3) was amplified and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 μg/mL spectinomycin and 100 μg/mL carbenicillin. The cells were cultured and extracted as in Example 3 and analyzed by GC-MS as described in Example 1.

Figure 10:
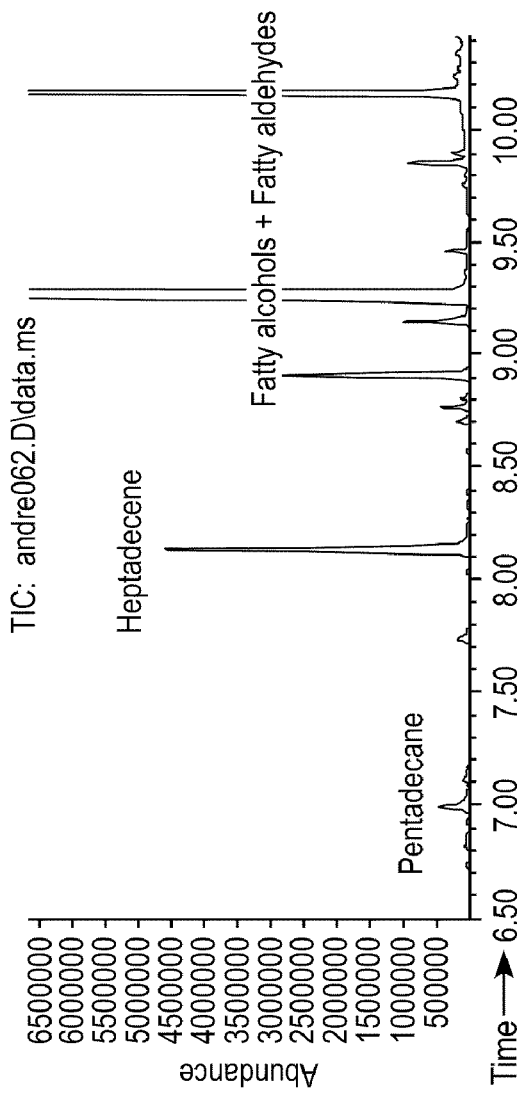
FIG. 10 is a GC/MS trace of hydrocarbons produced by *E. coli* MG1655 cells expressing *Synechococcus elongatus* PCC7942 YP_400611 (Synpcc7942_1594) (SEQ ID NO:65) and *Synechocystis* sp. PCC6803 sll0208 (NP_442147) (SEQ ID NO:3).

As shown in FIG. 10, *E. coli* cells cotransformed with the *S. elongatus* PCC7942_1594 and *Synechocystis* sp. PCC6803 sll0208-bearing vectors produced the same fatty aldehydes and fatty alcohols as in Example 3, but also pentadecane and heptadecene. This result indicates that Npun02004178 in *E. coli* converts hexadecanal and octadecenal to pentadecane and heptadecene, respectively, and therefore is an active fatty aldehyde decarbonylase.

Example 8

Production of Alkanes and Alkenes in *E. coli* Through Heterologous Expression of *Synechococcus elongatus* PCC7942 orf1594 and *Nostoc* sp. PCC7210 alr5283

The genomic DNA encoding *Nostoc* sp. PCC7210 alr5283 (NP_489323; putative decarbonylase) (SEQ ID NO:7) was amplified and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 1.

Figure 11:
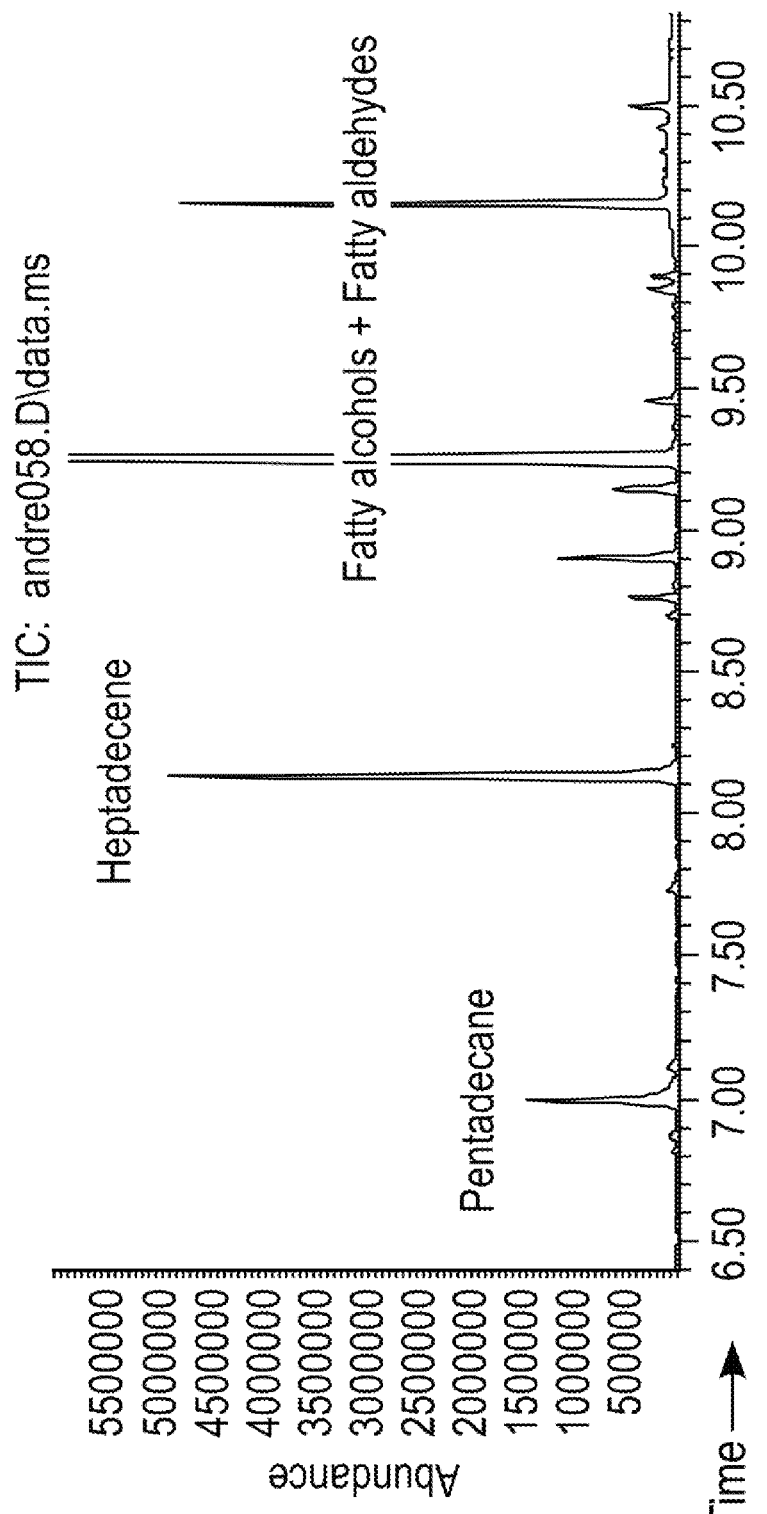
FIG. 11 is a GC/MS trace of hydrocarbons produced by *E. coli* MG1655 cells expressing *Synechococcus elongatus* PCC7942 YP_400611 (Synpcc7942_1594) (SEQ ID NO:65) and *Nostoc* sp. PCC7210 alr5283 (NP_489323) (SEQ ID NO:7).

As shown in FIG. 11, *E. coli* cells cotransformed with the *S. elongatus* PCC7942_1594 and *Nostoc* sp. PCC7210 alr5283-bearing vectors produced the same fatty aldehydes and fatty alcohols as in Example 3, but also pentadecane and heptadecene. This result indicates that alr5283 in *E. coli* converts hexadecanal and octadecenal to pentadecane and heptadecene, respectively, and therefore is an active fatty aldehyde decarbonylase.

Example 9

Production of Alkanes and Alkenes in *E. coli* Through Heterologous Expression of *Synechococcus elongatus* PCC7942 orf1594 and *Acaryochloris marina* MBIC11017 AM1_4041

The genomic DNA encoding *Acaryochloris marina* MBIC11017 AM1_4041 (YP_001518340; putative decarbonylase) (SEQ ID NO:9) was codon optimized for expression in *E. coli* (SEQ ID NO:46), synthesized, and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

Figure 12:
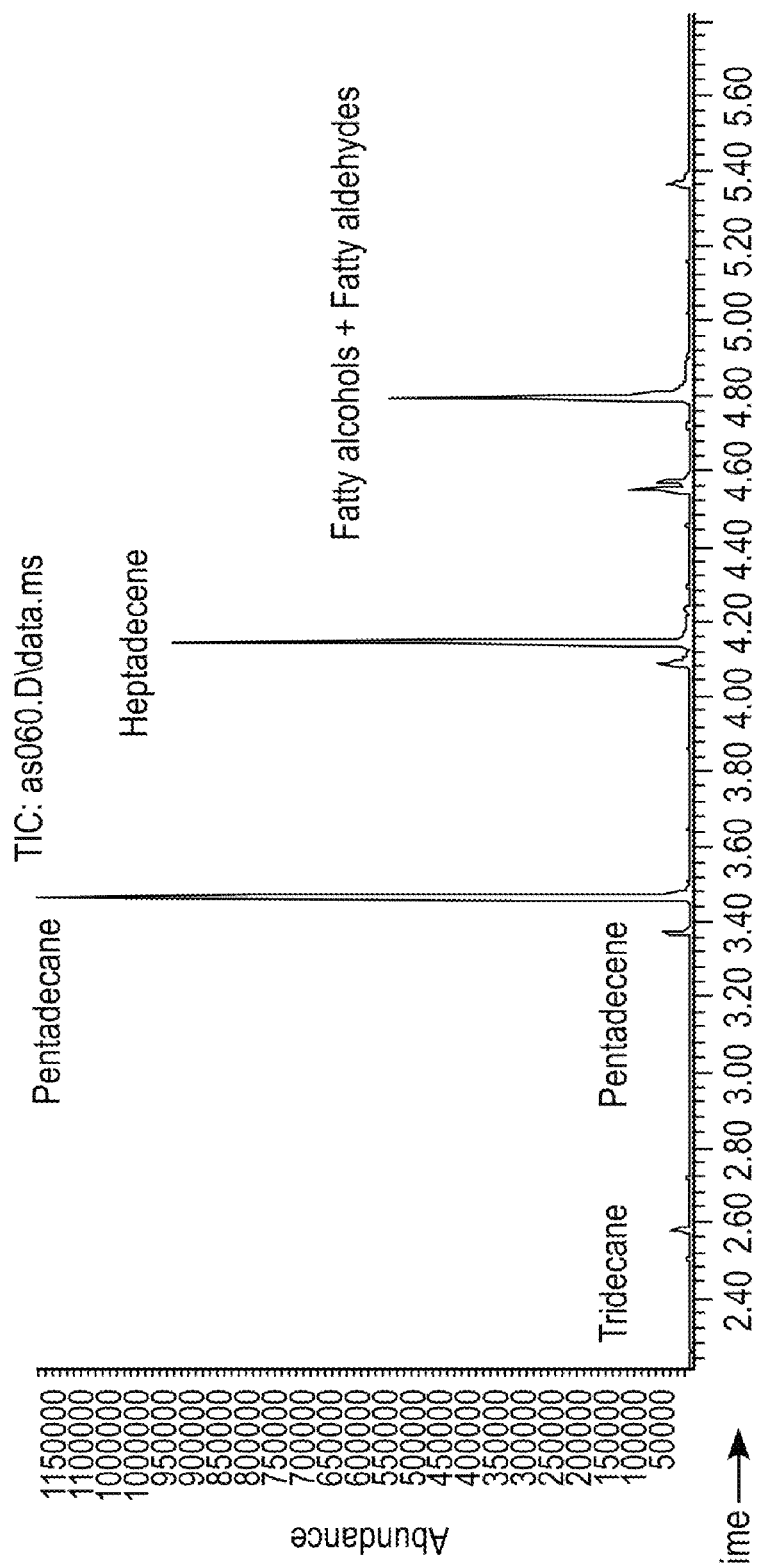
FIG. 12 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Acaryochloris marina* MBIC11017 AM1_4041 (YP_001518340) (SEQ ID NO:46).

As shown in FIG. 12, *E. coli* cells cotransformed with the *S. elongatus* PCC7942_1594 and *A. marina* MBIC11017 AM1_4041-bearing vectors produced the same fatty aldehydes and fatty alcohols as in Example 3, but also tridecane, pentadecene, pentadecane and heptadecene. This result indicates that AM1_4041 in *E. coli* converts tetradecanal, hexadecenal, hexadecanal and octadecenal to tridecane, pentadecene, pentadecane and heptadecene, respectively, and therefore is an active fatty aldehyde decarbonylase.

Example 10

Production of Alkanes and Alkenes in *E. coli* Through Heterologous Expression of *Synechococcus elongatus* PCC7942 orf1594 and *Thermosynechococcus elongatus* BP-1 tll1313

The genomic DNA encoding *Thermosynechococcus elongatus* BP-1 tll1313 (NP_682103; putative decarbonylase) (SEQ ID NO:11) was codon optimized for expression in *E. coli* (SEQ ID NO:47), synthesized, and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

Figure 13:
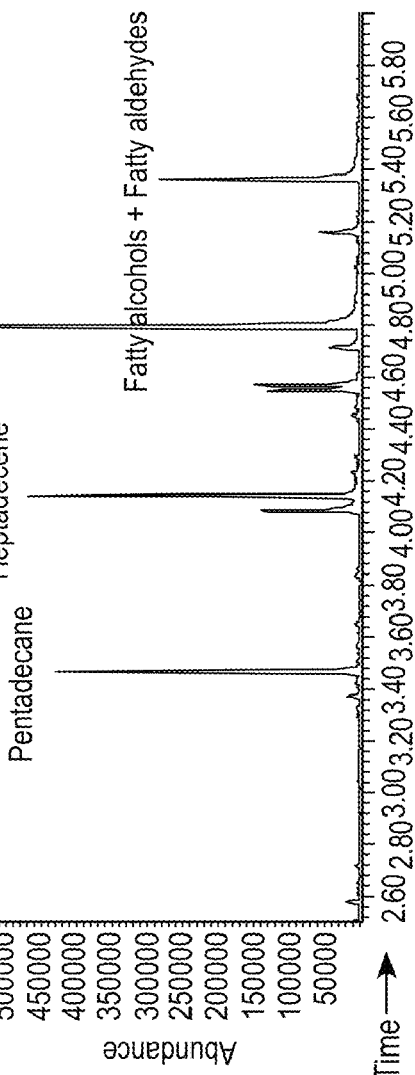
FIG. 13 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Thermosynechococcus elongatus* BP-1 tll1313 (NP_682103) (SEQ ID NO:47).

As shown in FIG. 13, *E. coli* cells cotransformed with the *S. elongatus* PCC7942_1594 and *T. elongatus* BP-1 tll1313-bearing vectors produced the same fatty aldehydes and fatty alcohols as in Example 3, but also pentadecane and heptadecene. This result indicates that tll1313 in *E. coli* converts hexadecanal and octadecenal to pentadecane and heptadecene, respectively, and therefore is an active fatty aldehyde decarbonylase.

Example 11

Production of Alkanes and Alkenes in *E. coli* Through Heterologous Expression of *Synechococcus elongatus* PCC7942 orf1594 and *Synechococcus* sp. JA-3-3Ab CYA_0415

The genomic DNA encoding *Synechococcus* sp. JA-3-3Ab CYA_0415 (YP_473897; putative decarbonylase) (SEQ ID NO:13) was codon optimized for expression in *E. coli* (SEQ ID NO:48), synthesized, and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

Figure 14:
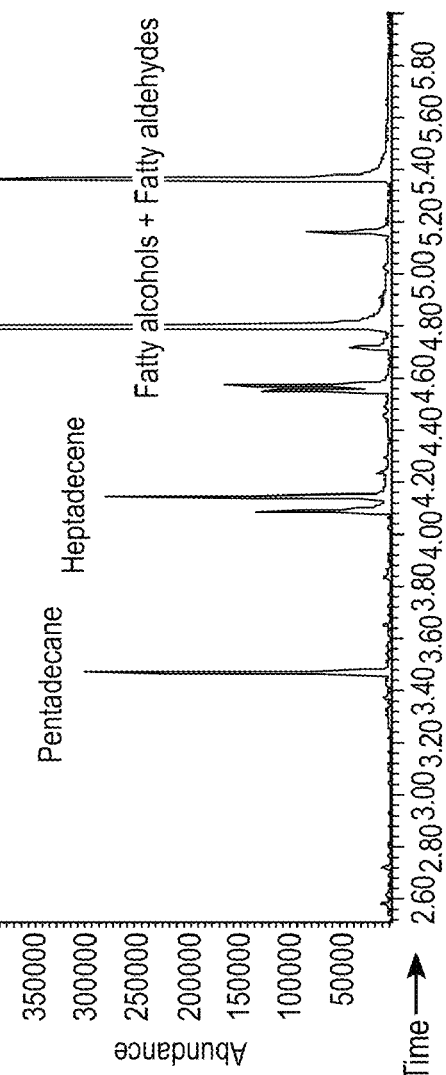
FIG. 14 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Synechococcus* sp. JA-3-3Ab CYA_0415 (YP_473897) (SEQ ID NO:48).

As shown in FIG. 14, *E. coli* cells cotransformed with the *S. elongatus* PCC7942_1594 and *Synechococcus* sp. JA-3-3Ab CYA_0415-bearing vectors produced the same fatty aldehydes and fatty alcohols as in Example 3, but also pentadecane and heptadecene. This result indicates that Npun02004178 in *E. coli* converts hexadecanal and octadecenal to pentadecane and heptadecene, respectively, and therefore is an active fatty aldehyde decarbonylase.

Example 12

Production of Alkanes and Alkenes in *E. coli* Through Heterologous Expression of *Synechococcus elongatus* PCC7942 orf1594 and *Gloeobacter violaceus* PCC7421 gll3146

The genomic DNA encoding *Gloeobacter violaceus* PCC7421 gll3146 (NP_926092; putative decarbonylase) (SEQ ID NO:15) was amplified and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 1.

As shown in FIG. 15, *E. coli* cells cotransformed with the *S. elongatus* PCC7942_1594 and *G. violaceus* PCC7421 gll3146-bearing vectors produced the same fatty aldehydes and fatty alcohols as in Example 3, but also pentadecane and heptadecene. This result indicates that gll3146 in *E. coli* converts hexadecanal and octadecenal to pentadecane and heptadecene, respectively, and therefore is an active fatty aldehyde decarbonylase.

Example 13

Production of Alkanes and Alkenes in *E. coli* Through Heterologous Expression of *Synechococcus elongatus* PCC7942 orf1594 and *Prochlorococcus marinus* MIT9313 PMT1231

The genomic DNA encoding *Prochlorococcus marinus* MIT9313 PMT1231 (NP_895059; putative decarbonylase) (SEQ ID NO:17) was codon optimized for expression in *E. coli* (SEQ ID NO:49), synthesized, and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

As shown in FIG. 16, *E. coli* cells cotransformed with the *S. elongatus* PCC7942_1594 and *P. marinus* MIT9313 PMT1231-bearing vectors produced the same fatty aldehydes and fatty alcohols as in Example 3, but also pentadecane and heptadecene. This result indicates that PMT1231 in *E. coli* converts hexadecanal and octadecenal to pentadecane and heptadecene, respectively, and therefore is an active fatty aldehyde decarbonylase.

Example 14

Production of Alkanes and Alkenes in *E. coli* Through Heterologous Expression of *Synechococcus elongatus* PCC7942 orf1594 and *Prochlorococcus marinus* CCMP1986 PMM0532

The genomic DNA encoding *Prochlorococcus marinus* CCMP1986 PMM0532 (NP_892650; putative decarbonylase) (SEQ ID NO:19) was amplified and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 1.

Figure 17:
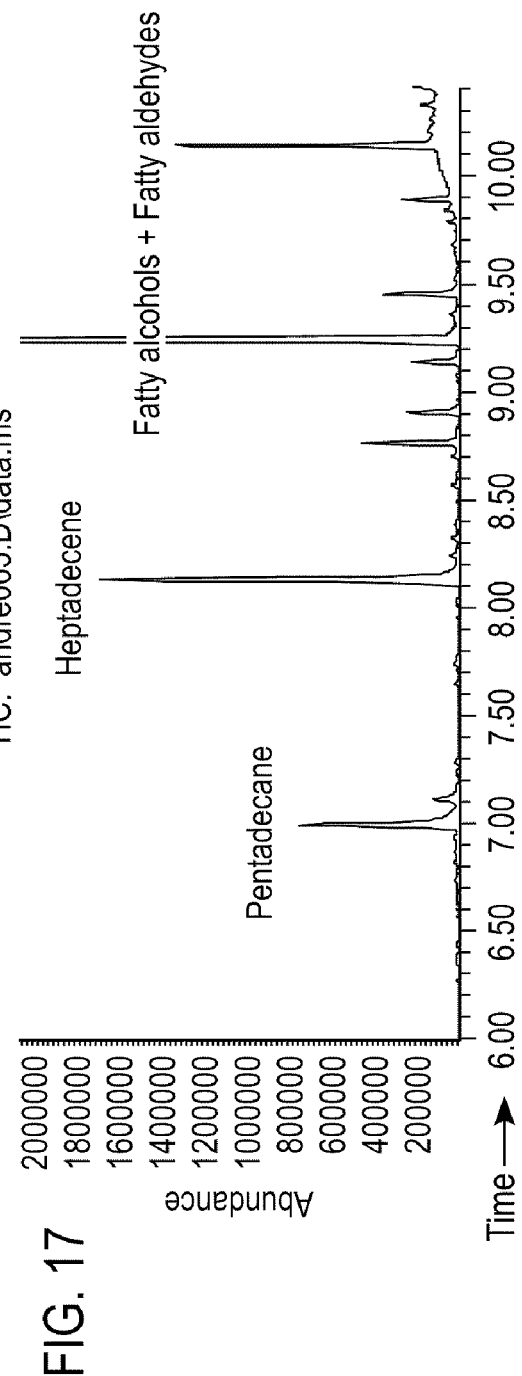
FIG. 17 is a GC/MS trace of hydrocarbons produced by *E. coli* MG1655 cells expressing *Synechococcus elongatus* PCC7942 YP_400611 (Synpcc7942_1594) (SEQ ID NO:65) and *Prochlorococcus marinus* CCMP1986 PMM0532 (NP_892650) (SEQ ID NO:19).

As shown in FIG. 17, *E. coli* cells cotransformed with the *S. elongatus* PCC7942_1594 and *P. marinus* CCMP1986 PMM0532-bearing vectors produced the same fatty aldehydes and fatty alcohols as in Example 3, but also pentadecane and heptadecene. This result indicates that PMM0532 in *E. coli* converts hexadecanal and octadecenal to pentadecane and heptadecene, respectively, and therefore is an active fatty aldehyde decarbonylase.

Example 15

Production of Alkanes and Alkenes in *E. coli* Through Heterologous Expression of *Synechococcus elongatus* PCC7942 orf1594 and *Prochlorococcus mariunus* NATL2A PMN2A_1863

The genomic DNA encoding *Prochlorococcus mariunus* NATL2A PMN2A_1863 (YP_293054; putative decarbonylase) (SEQ ID NO:21) was codon optimized for expression in *E. coli* (SEQ ID NO:51), synthesized, and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

Figure 18:
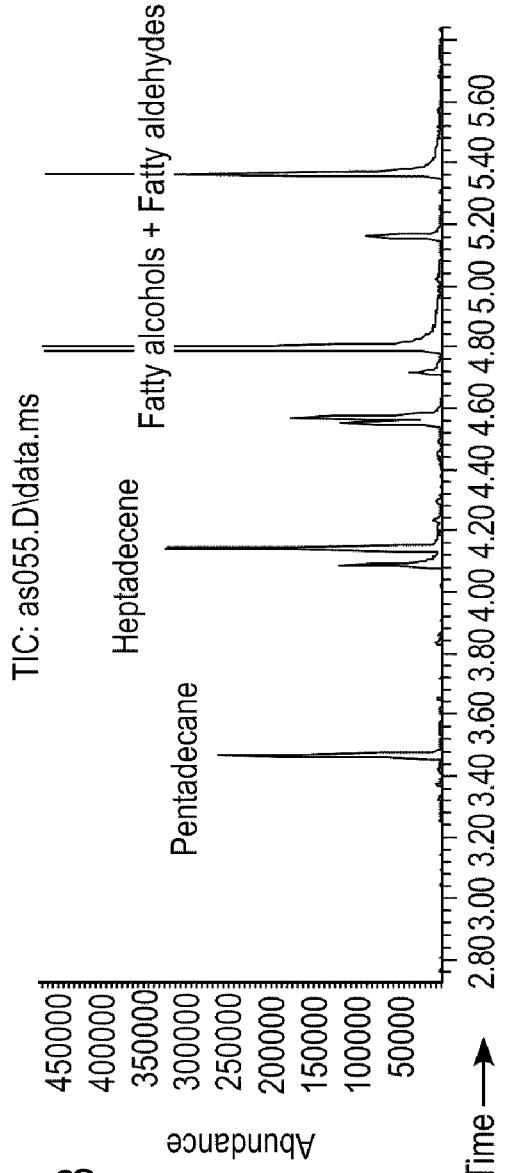
FIG. 18 is a GC/MS trace of hydrocarbons produced by *E. coli* MG1655 cells expressing *Synechococcus elongatus* PCC7942 YP_400611 (Synpcc7942_1594) (SEQ ID NO:65) and codon-optimized *Prochlorococcus mariunus* NATL2A PMN2A_1863 (YP_293054) (SEQ ID NO:51).

As shown in FIG. 18, *E. coli* cells cotransformed with the *S. elongatus* PCC7942_1594 and *P. mariunus* NATL2A PMN2A_1863-bearing vectors produced the same fatty aldehydes and fatty alcohols as in Example 3, but also pentadecane and heptadecene. This result indicates that PMN2A_1863 in *E. coli* converts hexadecanal and octadecenal to pentadecane and heptadecene, respectively, and therefore is an active fatty aldehyde decarbonylase.

Example 16

Production of Alkanes and Alkenes in *E. coli* Through Heterologous Expression of *Synechococcus elongatus* PCC7942 orf1594 and *Synechococcus* sp. RS9917 RS9917_09941

The genomic DNA encoding *Synechococcus* sp. RS9917 RS9917_09941 (ZP_01079772; putative decarbonylase) (SEQ ID NO:23) was codon optimized for expression in *E. coli* (SEQ ID NO:52), synthesized, and cloned into the NdeI and XhoI sites of vector OP-183 (pACYC derivative) under the control of the $P_t$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

As shown in FIG. 19, *E. coli* cells cotransformed with the *S. elongatus* PCC7942_ 1594 and *Synechococcus* sp. RS9917 RS9917_09941-bearing vectors produced the same fatty aldehydes and fatty alcohols as in Example 3, but also pentadecane and heptadecene. This result indicates that RS9917_09941 in *E. coli* converts hexadecanal and octadecenal to pentadecane and heptadecene, respectively, and therefore is an active fatty aldehyde decarbonylase.

Example 17

Production of Alkanes and Alkenes in *E. coli* Through Heterologous Expression of *Synechococcus elongatus* PCC7942 orf1594 and *Synechococcus* sp. RS9917 RS9917_12945

The genomic DNA encoding *Synechococcus* sp. RS9917 RS9917_12945 (ZP_01080370; putative decarbonylase) (SEQ ID NO:25) was codon optimized for expression in *E. coli* (SEQ ID NO:53), synthesized, and cloned into the NdeI and XhoI sites of vector OP-183 (pACYC derivative) under the control of the $P_t$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

As shown in FIG. 20, *E. coli* cells cotransformed with the *S. elongatus* PCC7942_1594 and *Synechococcus* sp. RS9917 RS9917_12945-bearing vectors produced the same fatty aldehydes and fatty alcohols as in Example 3, but also pentadecane and heptadecene. This result indicates that RS9917_12945 in *E. coli* converts hexadecanal and octadecenal to pentadecane and heptadecene, respectively, and therefore is an active fatty aldehyde decarbonylase.

Example 18

Production of Alkanes and Alkenes in *E. coli* Through Heterologous Expression of *Synechococcus elongatus* PCC7942 orf1594 and *Cyanothece* sp. ATCC51142 cce_0778

The genomic DNA encoding *Cyanothece* sp. ATCC51142 cce_0778 (YP_001802195; putative decarbonylase) (SEQ ID NO:27) was synthesized and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

As shown in FIG. 21, *E. coli* cells cotransformed with the *S. elongatus* PCC7942_1594 and *Cyanothece* sp. ATCC51142 cce_0778-bearing vectors produced the same fatty aldehydes and fatty alcohols as in Example 3, but also tridecane, pentadecene, pentadecane and heptadecene. This result indicates that ATCC51142 cce_0778 in *E. coli* converts tetradecanal, hexadecenal, hexadecanal and octadecenal to tridecane, pentadecene, pentadecane and heptadecene, respectively, and therefore is an active fatty aldehyde decarbonylase.

Example 19

Production of Alkanes and Alkenes in *E. coli* Through Heterologous Expression of *Synechococcus elongatus* PCC7942 orf1594 and *Cyanothece* sp. PCC7425 Cyan7425_0398

The genomic DNA encoding *Cyanothece* sp. PCC7425 Cyan7425_0398 (YP_002481151; putative decarbonylase) (SEQ ID NO:29) was synthesized and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

As shown in FIG. 22, *E. coli* cells cotransformed with the *S. elongatus* PCC7942_1594 and *Cyanothece* sp. PCC7425 Cyan7425_0398-bearing vectors produced the same fatty aldehydes and fatty alcohols as in Example 3, but also tridecane, pentadecene, pentadecane and heptadecene. This result indicates that Cyan7425_0398 in *E. coli* converts tetradecanal, hexadecenal, hexadecanal and octadecenal to tridecane, pentadecene, pentadecane and heptadecene, respectively, and therefore is an active fatty aldehyde decarbonylase.

Example 20

Production of Alkanes and Alkenes in *E. coli* Through Heterologous Expression of *Synechococcus elongatus* PCC7942 orf1594 and *Cyanothece* sp. PCC7425 Cyan7425_2986

The genomic DNA encoding *Cyanothece* sp. PCC7425 Cyan7425_2986 (YP_002483683; putative decarbonylase) (SEQ ID NO:31) was synthesized and cloned into the NdeI and XhoI sites of vector OP-183 (pACYC derivative) under the control of the $P_{trc}$ promoter. The resulting construct was cotransformed with OP80-PCC7942_1594 into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

Figure 23:
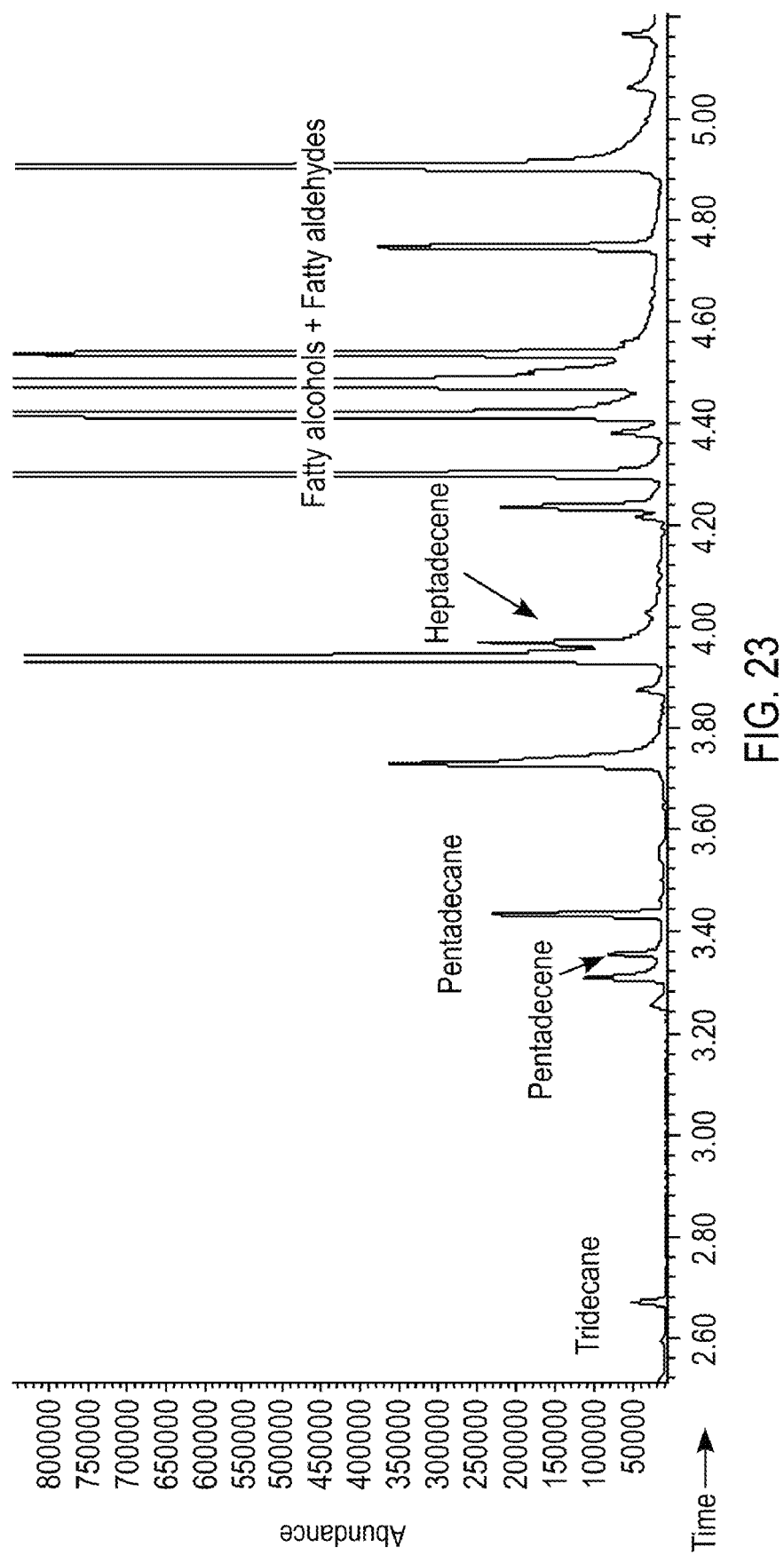
FIG. 23 is a GC/MS trace of hydrocarbons produced by *E. coli* MG1655 cells expressing *Synechococcus elongatus* PCC7942 YP_400611 (Synpcc7942_1594) (SEQ ID NO:65) and *Cyanothece* sp. PCC7425 Cyan7425_2986 (YP_002483683) (SEQ ID NO:31).

As shown in FIG. 23, *E. coli* cells cotransformed with the *S. elongatus* PCC7942_1594 and *Cyanothece* sp. PCC7425 Cyan7425_2986-bearing vectors produced the same fatty aldehydes and fatty alcohols as in Example 3, but also tridecane, pentadecene, pentadecane and heptadecene. This result indicates that Cyan7425_2986 in *E. coli* converts tetradecanal, hexadecenal, hexadecanal and octadecenal to tridecane, pentadecene, pentadecane and heptadecene, respectively, and therefore is an active fatty aldehyde decarbonylase.

Example 21

Production of Alkanes and Alkenes in *E. coli* Through Heterologous Expression of *Prochlorococcus marinus* CCMP1986 PMM0533 and *Prochlorococcus mariunus* CCMP1986 PMM0532

The genomic DNA encoding *P. mariunus* CCMP1986 PMM0533 (NP_892651; putative aldehyde-generating enzyme) (SEQ ID NO:71) and *Prochlorococcus mariunus* CCMP1986 PMM0532 (NP_892650; putative decarbonylase) (SEQ ID NO:19) were amplified and cloned into the NcoI and EcoRI sites of vector OP-80 and the NdeI and XhoI sites of vector OP-183, respectively. The resulting constructs were separately transformed and cotransformed into *E. coli* MG1655 and the cells were grown at 37° C. in M9 minimal media supplemented with 100 µg/mL spectinomycin and 100 µg/mL carbenicillin. The cells were cultured and extracted as in Example 3 and analyzed by GC-MS as described in Example 26.

As shown in FIG. 24A, *E. coli* cells transformed with only the *P. mariunus* CCMP1986 PMM0533-bearing vector did not produce any fatty aldehydes or fatty alcohols. However, *E. coli* cells cotransformed with PMM0533 and PMM0532-bearing vectors produced hexadecanol, pentadecane and heptadecene (FIG. 24B). This result indicates that PMM0533 only provides fatty aldehyde substrates for the decarbonylation reaction when it interacts with a decarbonylase, such as PMM0532.

Example 22

Production of Alkanes and Alkenes in a Fatty Acyl-CoA-Producing *E. coli* Strain Through Heterologous Expression of *Synechococcus elongatus* PCC7942 orf1594 and *Acaryochloris marina* MBIC11017 AM1_4041

The genomic DNA encoding *Acaryochloris marina* MBIC11017 AM1_4041 (YP_001518340; putative fatty aldehyde decarbonylase) (SEQ ID NO:9) was synthesized and cloned into the NdeI and XhoI sites of vector OP-183 (pACYC derivative) under the control of the P$_{trc}$ promoter. The resulting construct was cotransformed with OP80-PCC7942__1594 into *E. coli* MG1655 ΔfadE lacZ::P$_{trc}$'tesA-fadD. This strain expresses a cytoplasmic version of the *E. coli* thioesterase, 'TesA, and the *E. coli* acyl-CoA synthetase, FadD, under the control of the P$_{trc}$ promoter, and therefore produces fatty acyl-CoAs. The cells were grown at 37° C. in M9 minimal media supplemented with 100 μg/mL spectinomycin and 100 μg/mL carbenicillin. The cells were cultured and extracted as in Example 3 and analyzed by GC-MS as described in Example 1.

Figures 25A, 25B:
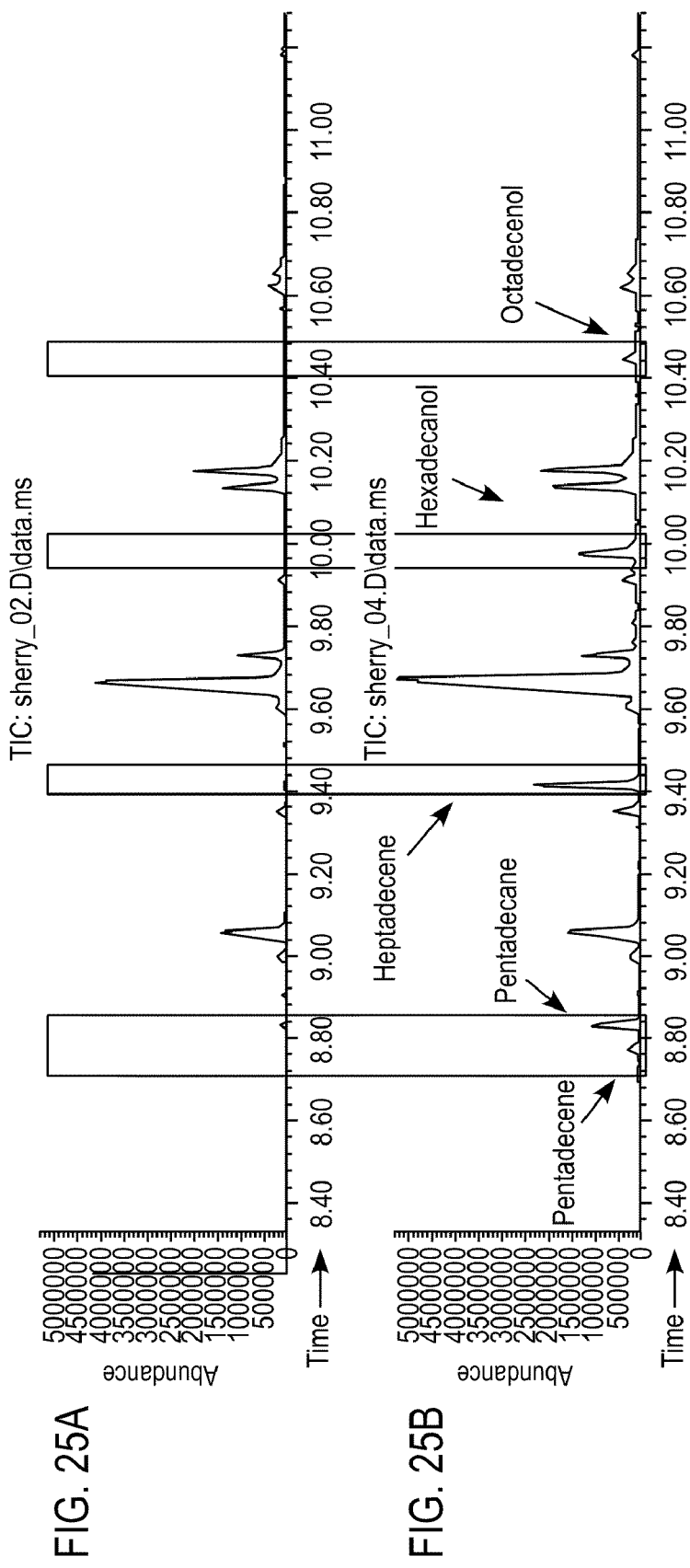
FIG. 25A is a GC/MS trace of hydrocarbons produced by *E. coli* MG1655 ΔfadE lacZ::P$_{trc}$ 'tesA-fadD cells.
FIG. 25B is a GC/MS trace of hydrocarbons produced by *E. coli* MG1655 ΔfadE lacZ::P$_{trc}$ 'tesA-fadD cells expressing *Synechococcus elongatus* PCC7942 YP_400611 (Synpcc7942_1594) (SEQ ID NO:65) and *Acaryochloris marina* MBIC11017 AM1_4041 (YP_001518340) (SEQ ID NO:9).

As shown in FIG. 25, these *E. coli* cells cotransformed with *S. elongatus* PCC7942__1594 and *A. marina* MBIC11017 AM1__4041 also produced alkanes and fatty alcohols. This result indicates that *S. elongatus* PCC7942__1594 is able to use acyl-CoA as a substrate to produce hexadecenal, hexadecanal and octadecenal, which is then converted into pentadecene, pentadecane and heptadecene, respectively, by *A. marina* MBIC11017 AM1__4041.

Example 23

Production of Alkanes and Alkenes in a Fatty Acyl-CoA-Producing *E. coli* Strain Through Heterologous Expression of *Synechocystis* sp. PCC6803 sll0209 and *Synechocystis* sp. PCC6803 sll0208

The genomic DNA encoding *Synechocystis* sp. PCC6803 sll0208 (NP__442147; putative fatty aldehyde decarbonylase) (SEQ ID NO:3) was synthesized and cloned into the NdeI and XhoI sites of vector OP-183 (pACYC derivative) under the control of the P$_{trc}$ promoter. The genomic DNA encoding *Synechocystis* sp. PCC6803 sll0209 (NP__442146; acyl-ACP reductase) (SEQ ID NO:67) was synthesized and cloned into the NcoI and EcoRI sites of vector OP-183 (pACYC derivative) under the control of the P$_{trc}$ promoter. The resulting constructs were cotransformed with into *E. coli* MG1655 ΔfadE lacZ::P$_{trc}$ tesA-fadD. This strain expresses a cytoplasmic version of the *E. coli* thioesterase, 'TesA, and the *E. coli* acyl-CoA synthetase, FadD, under the control of the P$_{trc}$ promoter, and therefore produces fatty acyl-CoAs. The cells were grown at 37° C. in M9 minimal media supplemented with 100 μg/mL spectinomycin and 100 μg/mL carbenicillin. The cells were cultured and extracted as in Example 3 and analyzed by GC-MS as described in Example 26.

Figures 26A, 26B:
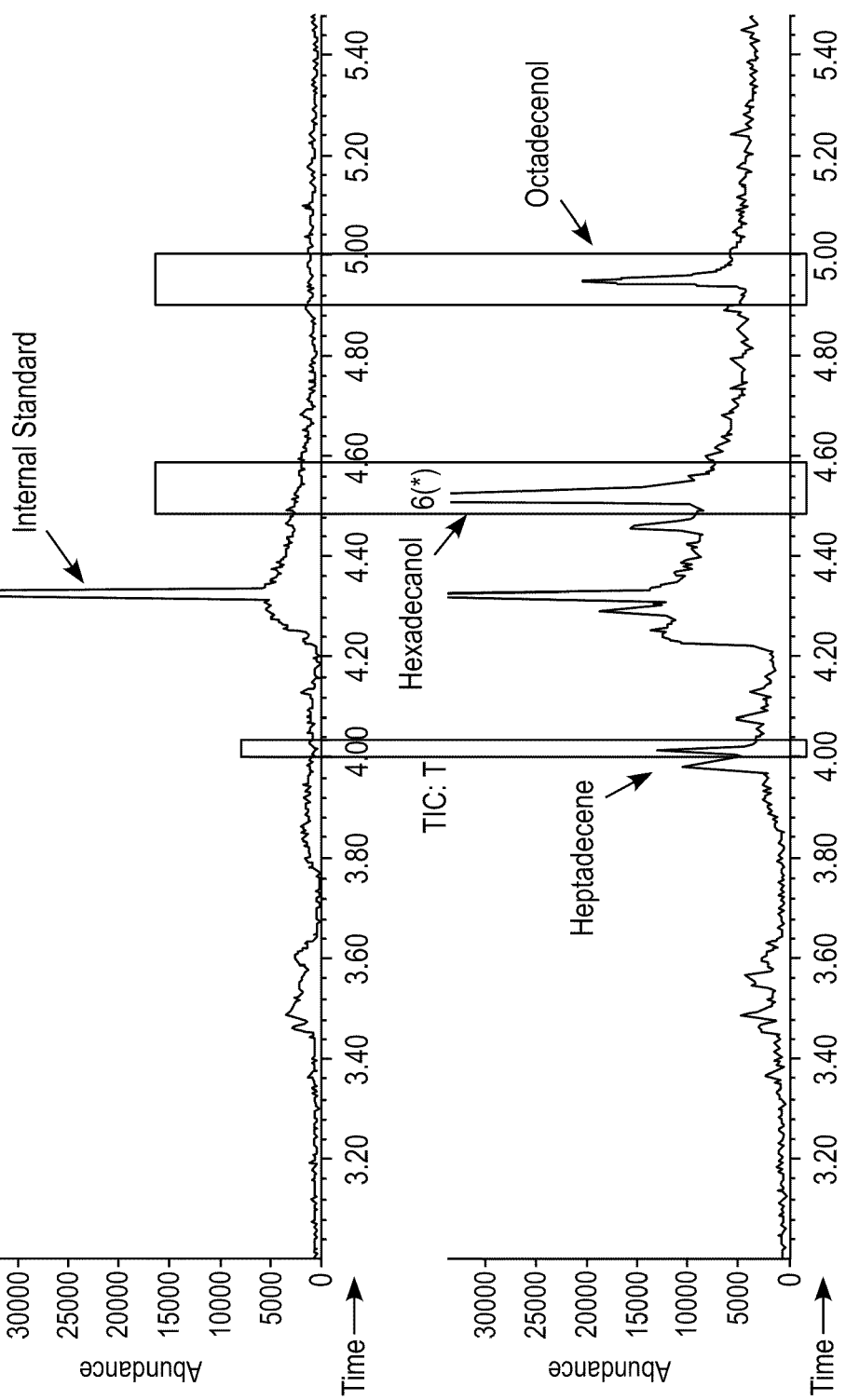
FIG. 26A is a GC/MS trace of hydrocarbons produced by *E. coli* MG1655 ΔfadE lacZ::P$_{trc}$ 'tesA-fadD cells expressing *Synechocystis* sp. PCC6803 sll0209 (NP_442146) (SEQ ID NO:67).
FIG. 26B is a GC/MS trace of hydrocarbons produced by *E. coli* MG1655 ΔfadE lacZ::P$_{trc}$ 'tesA-fadD cells expressing *Synechocystis* sp. PCC6803 sll0209 (NP_442146) (SEQ ID NO:67) and *Synechocystis* sp. PCC6803 sll0208 (NP_442147) (SEQ ID NO:3).

As shown in FIG. 26, these *E. coli* cells transformed with *Synechocystis* sp. PCC6803 sll0209 did not produce any fatty aldehydes or fatty alcohols. However, when cotransformed with *Synechocystis* sp. PCC6803 sll0208 and sll0209, they produced alkanes, fatty aldehydes and fatty alcohols. This result indicates that *Synechocystis* sp. PCC6803 sll0209 is able to use acyl-CoA as a substrate to produce fatty aldehydes such as tetradecanal, hexadecanal and octadecenal, but only when coexpressed with a fatty aldehyde decarbonylase. The fatty aldehydes apparently are further reduced to the corresponding fatty alcohols, tetradecanol, hexadecanol and octadecenol, by an endogenous *E. coli* aldehyde reductase activity. In this experiment, octadecenal was converted into heptadecene by *Synechocystis* sp. PCC6803 sll0208.

Example 24

Production of Alkanes and Alkenes in a Fatty Aldehyde-Producing *E. coli* Strain Through Heterologous Expression of *Nostoc Punctiforme* PCC73102 Npun02004178 and Several of its Homologs The genomic DNA encoding *Nostoc punctiforme* PCC73102 Npun02004178 (ZP__00108838; putative fatty aldehyde decarbonylase) (SEQ ID NO:5) was amplified and cloned into the NdeI and XhoI sites of vector OP-183 (pACYC derivative) under the control of the P$_{trc}$ promoter. The genomic DNA encoding *Mycobacterium smegmatis* strain MC2 155 orf MSMEG__5739 (YP__889972, putative carboxylic acid reductase) (SEQ ID NO:85) was amplified and cloned into the NcoI and EcoRI sites of vector OP-180 (pCL1920 derivative) under the control of the P$_{trc}$ promoter. The two resulting constructs were cotransformed into *E. coli* MG1655 ΔfadD lacZ::P$_{trc}$-'tesA. In this strain, fatty aldehydes were provided by MSMEG__5739, which reduces free fatty acids (formed by the action of 'TesA) to fatty aldehydes. The cells were grown at 37° C. in M9 minimal media supplemented with 100 μg/mL spectinomycin and 100 μg/mL carbenicillin. The cells were cultured and extracted as in Example 3 and analyzed by GC-MS as described in Example 1.

Figures 27A, 27B:
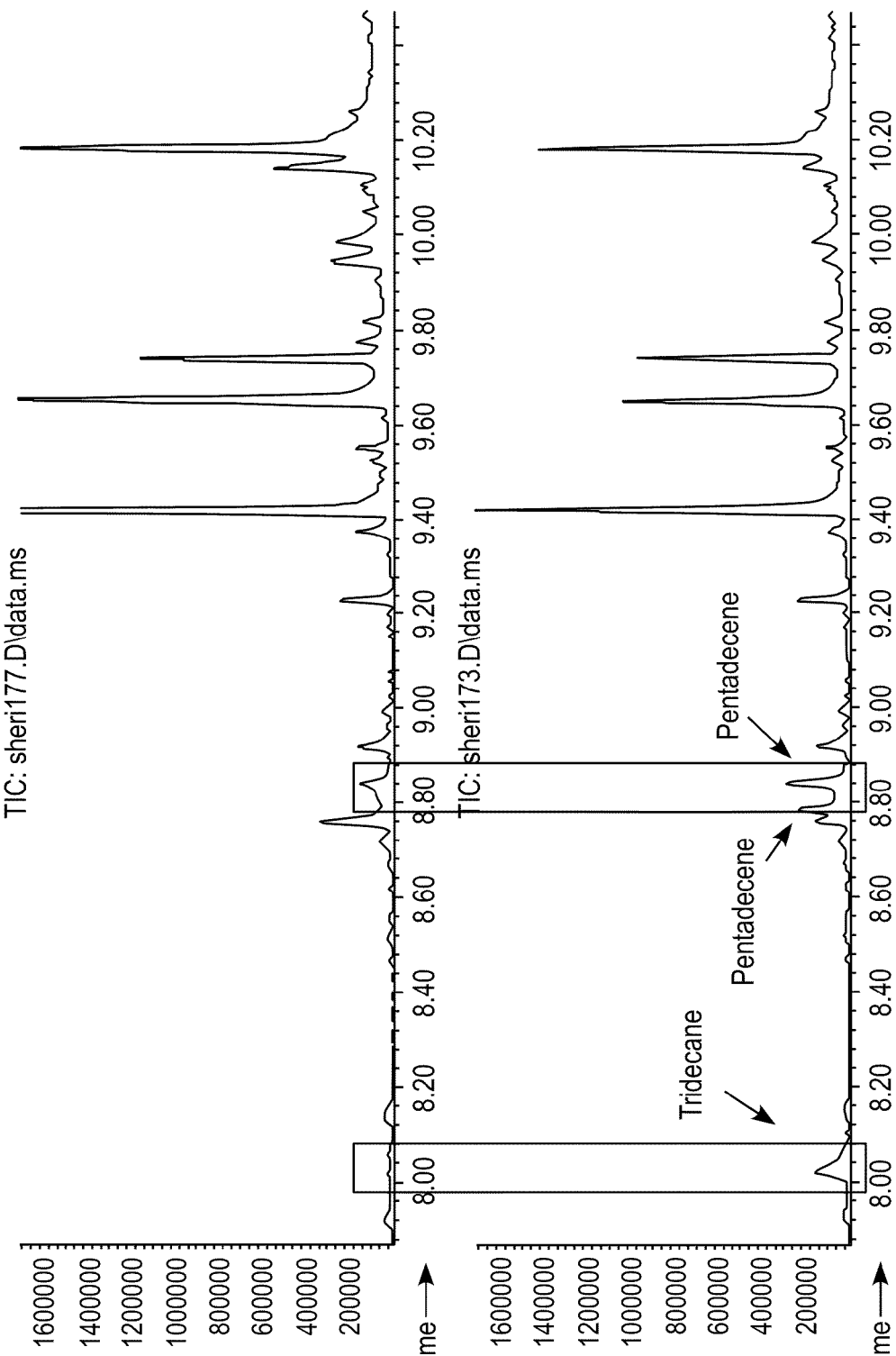
FIG. 27A is a GC/MS trace of hydrocarbons produced by *E. coli* MG1655 ΔfadD lacZ::P$_{trc}$-'tesA cells expressing *M. smegmatis* strain MC2 155 MSMEG_5739 (YP_889972) (SEQ ID NO:85).
FIG. 27B is a GC/MS trace of hydrocarbons produced by *E. coli* MG1655 ΔfadD lacZ::P$_{trc}$-'tesA cells expressing *M. smegmatis* strain MC2 155 MSMEG_5739 (YP_889972) (SEQ ID NO:85) and *Nostoc punctiforme* PCC73102 Npun02004178 (ZP_00108838) (SEQ ID NO:5).
Figure 28:
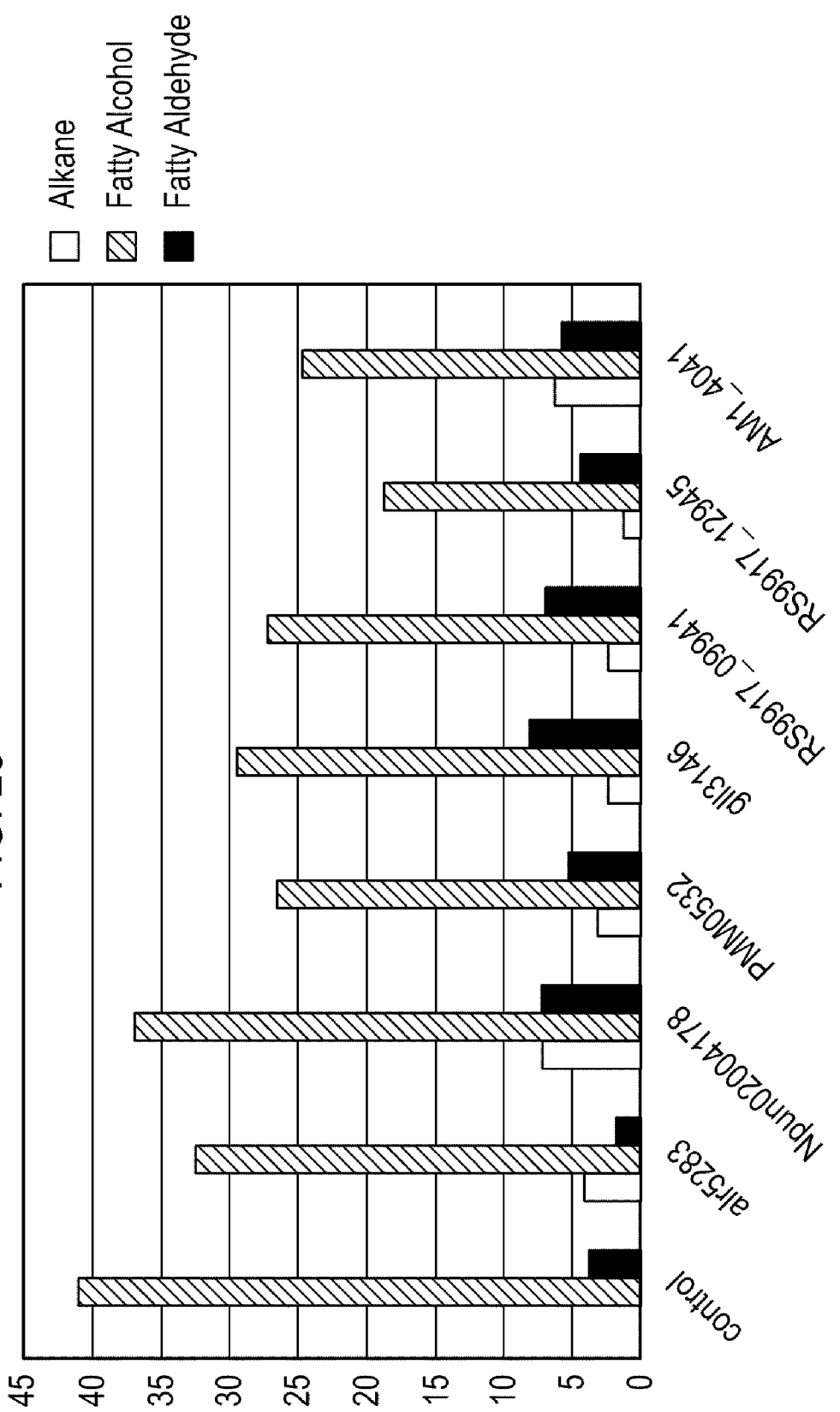
FIG. 28 is a graphic representation of hydrocarbons produced by *E. coli* MG1655 ΔfadD lacZ::P$_{trc}$-'tesA cells expressing *M. smegmatis* strain MC2 155 MSMEG_5739 (YP_889972) (SEQ ID NO:85) either alone or in combination with *Nostoc* sp. PCC7120 alr5283 (SEQ ID NO:7), *Nostoc punctiforme* PCC73102 Npun02004178 (SEQ ID NO:5), *P. mariunus* CCMP1986 PMM0532 (SEQ ID NO:19), *G. violaceus* PCC7421 gll3146 (SEQ ID NO:15), *Synechococcus* sp. RS9917_09941 (SEQ ID NO:23), *Synechococcus* sp. RS9917_12945 (SEQ ID NO:25), or *A. marina* MBIC11017 AM1_4041 (SEQ ID NO:9).

As shown in FIG. 27, these *E. coli* cells cotransformed with the *N. punctiforme* PCC73102 Npun02004178 and *M. smegmatis* strain MC2 155 MSMEG__5739-bearing vectors produced tridecane, pentadecene and pentadecane. This result indicates that Npun02004178 in *E. coli* converts tetradecanal, hexadecenal and hexadecanal provided by the carboxylic acid reductase MSMEG__5739 to tridecane, pentadecene and pentadecane. As shown in FIG. 28, in the same experimental set-up, the following fatty aldehyde decarbonylases also converted fatty aldehydes provided by MSMEG__5739 to the corresponding alkanes when expressed in *E. coli* MG1655 ΔfadD lacZ::P$_{trc}$-'tesA: *Nostoc* sp. PCC7210 alr5283 (SEQ ID NO:7), *P. mariunus* CCMP1986 PMM0532 (SEQ ID NO:19), *G. violaceus* PCC7421 gll3146 (SEQ ID NO:15), *Synechococcus* sp. RS9917__09941 (SEQ ID NO:23), *Synechococcus* sp. RS9917__12945 (SEQ ID NO:25), and *A. marina* MBIC11017 AM1__4041 (SEQ ID NO:9).

Example 25

Cyanobacterial Fatty Aldehyde Decarbonylases Belong to the Class of Non-Heme Diiron Proteins. Site-Directed Mutagenesis of Conserved Histidines to Phenylalanines in *Nostoc punctiforme* PCC73102 Npun02004178 does not Abolish its Catalytic Function As discussed in Example 13, the hypothetical protein PMT1231 from *Prochlorococcus marinus* MIT9313 (SEQ ID NO:18) is an active fatty aldehyde decarbonylase. Based on the three-dimensional structure of PMT1231, which is available at 1.8 Å resolution (pdb2OC5A) (see FIG. 29B), cyanobacterial fatty aldehyde decarbonylases have structural similarity with non-heme diiron proteins, in particular with class I ribonuclease reductase subunit β proteins, RNRβ (Stubbe and Riggs-Gelasco, TIBS 1998, vol. 23., pp. 438) (see FIG. 29A). Class Ia and Ib RNRβ contains a diferric tyrosyl radical that mediates the catalytic activity of RNRα (reduction of ribonucleotides to deoxyribonucleotides). In *E. coli* RNRβ, this tyrosine is in position 122 and is in close proximity to one of the active site's iron molecules. Structural alignment showed that PMT1231 contained a phenylalanine in the same position as RNRb tyr122, suggesting a different catalytic mechanism for cyanobacterial fatty aldehyde decarbonylases. However, an alignment of all decarbonylases showed that two tyrosine residues were completely conserved in all sequences, tyr135 and tyr138 with respect to PMT1231, with tyr135 being in close proximity (5.5 Å) to one of the active site iron molecules (see FIG. 29C). To examine whether either of the two conserved tyrosine residues is involved in the catalytic mechanism of cyanobacterial fatty aldehyde decarbonylases, these residues were replaced with phenylalanine in Npun02004178 (tyr 123 and tyr126) as follows.

The genomic DNA encoding *S. elongatus* PCC7942 ORF1594 (SEQ ID NO:65) was cloned into the NcoI and EcoRI sites of vector OP-80 (pCL1920 derivative) under the control of the $P_{trc}$ promoter. The genomic DNA encoding *N. punctiforme* PCC73102 Npun02004178 (SEQ ID NO:5) was also cloned into the NdeI and XhoI sites of vector OP-183 (pACYC177 derivative) under the control of the $P_{trc}$ promoter. The latter construct was used as a template to introduce a mutation at positions 123 and 126 of the decarbonylase protein, changing the tyrosines to phenylalanines using the primers gttttgcgatcgcagcatttaacatttacatccccgttgccgacg and gttttgcgatcgcagcatataacattttcatccccgttgccgacg, respectively. The resulting constructs were then transformed into *E. coli* MG1655. The cells were grown at 37° C. in M9 minimal media supplemented with 1% glucose (w/v), and 100 μg/mL carbenicillin and spectinomycin. The cells were cultured and extracted as in Example 3.

Figure 30A:
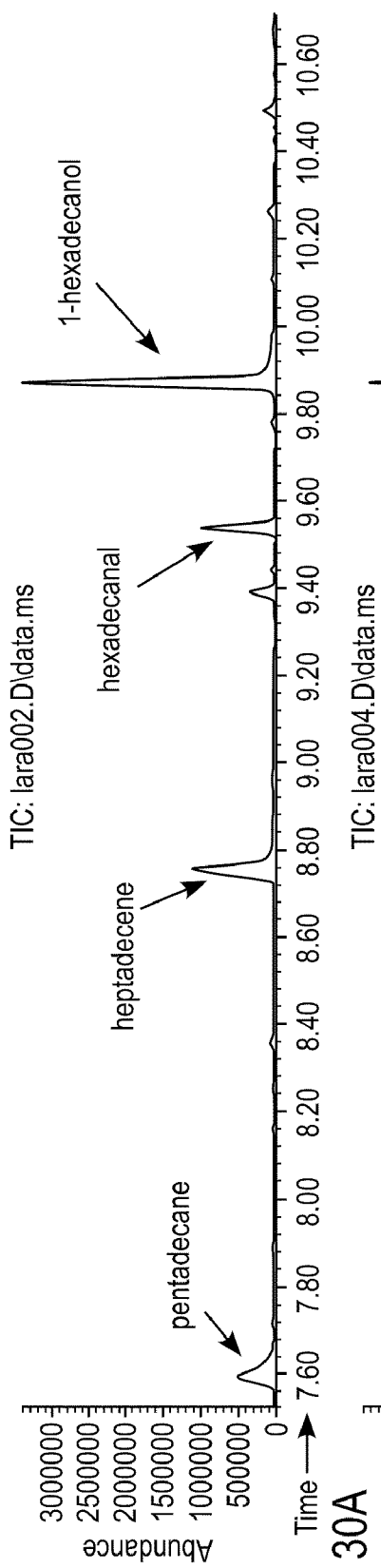
FIG. 30A is a GC/MS trace of hydrocarbons produced by *E. coli* MG1655 cells expressing *Nostoc punctiforme* PCC73102 Npun02004178 (ZP_00108838) (SEQ ID NO:5).
Figure 30B:
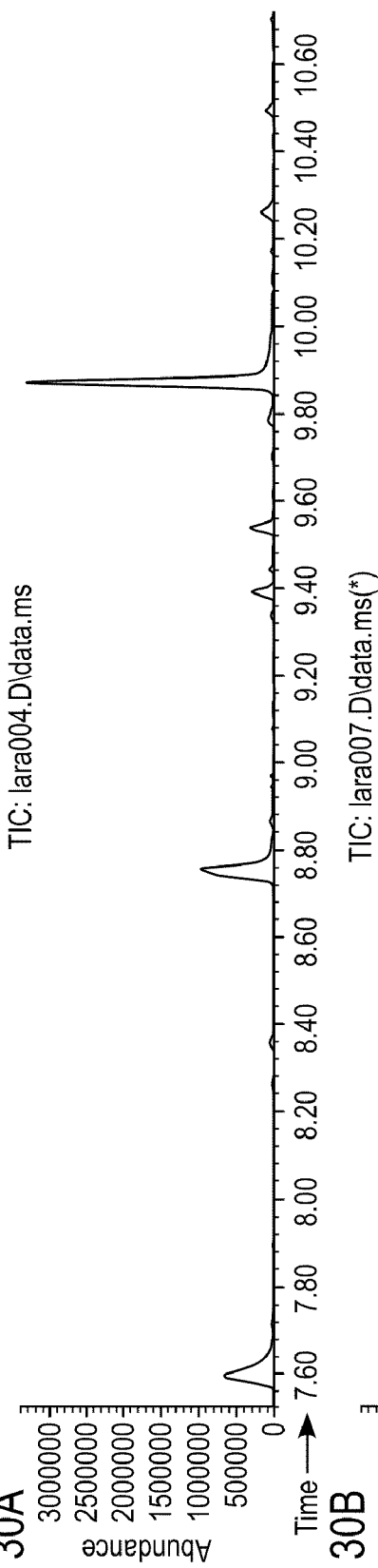
FIG. 30B is a GC/MS trace of hydrocarbons produced by *E. coli* MG1655 cells expressing *Nostoc punctiforme* PCC73102 Npun02004178 (ZP_00108838) Y123F variant.
Figure 30C:
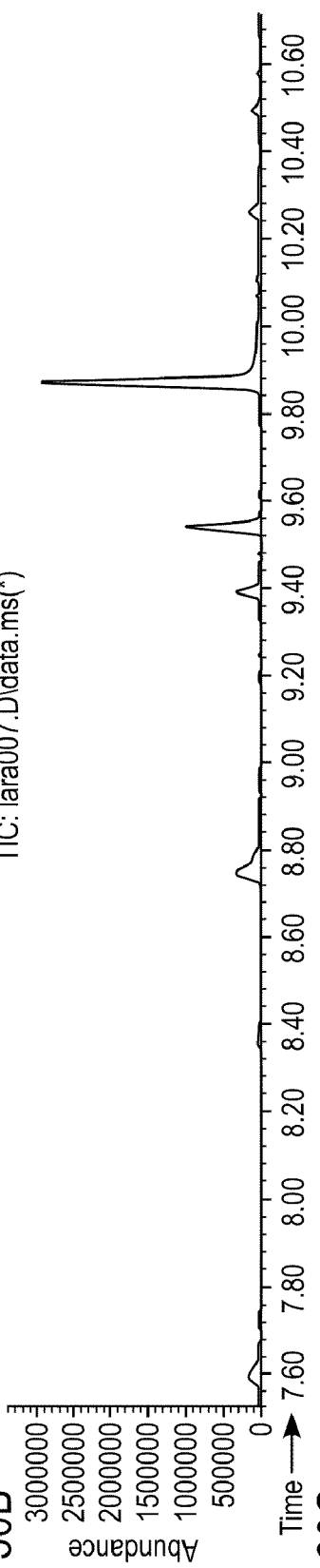
FIG. 30C is a GC/MS trace of hydrocarbons produced by *E. coli* MG1655 cells expressing *Nostoc punctiforme* PCC73102 Npun02004178 (ZP_00108838) Y126F variant.

As shown in FIG. 30, the two Npun02004178 Tyr to Phe protein variants were active and produced alkanes when coexpressed with *S. elongatus* PCC7942 ORF1594. This result indicates that in contrast to class Ia and Ib RNRβ proteins, the catalytic mechanism of fatty aldehyde decarbonylases does not involve a tyrosyl radical.

Example 26

Biochemical Characterization of *Nostoc punctiforme* PCC73102 Npun02004178

The genomic DNA encoding *N. punctiforme* PCC73102 Npun02004178 (SEQ ID NO:5) was cloned into the NdeI and XhoI sites of vector pET-15b under the control of the T7 promoter. The resulting Npun02004178 protein contained an N-terminal His-tag. An *E. coli* BL21 strain (DE3) (Invitrogen) was transformed with the plasmid by routine chemical transformation techniques. Protein expression was carried out by first inoculating a colony of the *E. coli* strain in 5 mL of LB media supplemented with 100 mg/L of carbenicillin and shaken overnight at 37° C. to produce a starter culture. This starter cultures was used to inoculate 0.5 L of LB media supplemented with 100 mg/L of carbenecillin. The culture was shaken at 37° C. until an $OD_{600}$ value of 0.8 was reached, and then IPTG was added to a final concentration of 1 mM. The culture was then shaken at 37° C. for approximately 3 additional h. The culture was then centrifuged at 3,700 rpm for 20 min at 4° C. The pellet was then resuspended in 10 mL of buffer containing 100 mM sodium phosphate buffer at pH 7.2 supplemented with Bacterial ProteaseArrest (GBiosciences). The cells were then sonicated at 12 W on ice for 9 s with 1.5 s of sonication followed by 1.5 s of rest. This procedure was repeated 5 times with one min intervals between each sonication cycle. The cell free extract was centrifuged at 10,000 rpm for 30 min at 4° C. 5 mL of Ni-NTA (Qiagen) was added to the supernatant and the mixture was gently stirred at 4° C. The slurry was passed over a column removing the resin from the lysate. The resin was then washed with 30 mL of buffer containing 100 mM sodium phosphate buffer at pH 7.2 plus 30 mM imidazole. Finally, the protein was eluted with 10 mL of 100 mM sodium phosphate buffer at pH 7.2 plus 250 mM imidazole. The protein solution was dialyzed with 200 volumes of 100 mM sodium phosphate buffer at pH 7.2 with 20% glycerol. Protein concentration was determined using the Bradford assay (Biorad). 5.6 mg/mL of Npun02004178 protein was obtained.

To synthesize octadecanal for the decarbonylase reaction, 500 mg of octadecanol (Sigma) was dissolved in 25 mL of dichloromethane. Next, 200 mg of pyridinium chlorochromate (TCI America) was added to the solution and stirred overnight. The reaction mixture was dried under vacuum to remove the dichloromethane. The remaining products were resuspended in hexane and filtered through Whatman filter paper. The filtrate was then dried under vacuum and resuspended in 5 mL of hexane and purified by silica flash chromatography. The mixture was loaded onto the gravity fed column in hexane and then washed with two column volumes of hexane. The octadecanal was then eluted with an 8:1 mixture of hexane and ethyl acetate. Fractions containing octadecanal were pooled and analyzed using the GC/MS methods described below. The final product was 95% pure as determined by this method.

To test Npun02004178 protein for decarbonylation activity, the following enzyme assays were set-up. 200 μL reactions were set up in 100 mM sodium phosphate buffer at pH 7.2 with the following components at their respective final concentrations: 30 μM of purified Npun02004178 protein, 200 μM octadecanal, 0.11 μg/mL spinach ferredoxin (Sigma), 0.05 units/mL spinach ferredoxin reductase (Sigma), and 1 mM NADPH (Sigma). Negative controls included the above reaction without Npun02004178, the above reaction without octadecanal, and the above reaction without spinach ferredoxin, ferredoxin reductase and NADPH. Each reaction was incubated at 37° C. for 2 h before being extracted with 100 μL ethyl acetate. Samples were analyzed by GC/MS using the following parameters: run time: 13.13 min; column. HP-5-MS Part No. 190915-433E (length of 30 meters; I.D.: 0.25 mm narrowbore; film: 0.25 iM); inject: 1 íl Agilent 6850 inlet; inlet: 300 C splitless; carrier gas: helium; flow: 1.3 mL/min; oven temp: 75° C. hold 5 min, 320 at 40° C./min, 320 hold 2 min; det: Agilent 5975B VL MSD; det. temp: 330° C.; scan: 50-550 M/Z. Heptadecane from Sigma was used as an authentic reference for determining compound retention time and fragmentation pattern.

As shown in FIG. 31, in-vitro conversion of octadecanal to heptadecane was observed in the presence of Npun02004178. The enzymatic decarbonylation of octadecanal by Npun02004178 was dependent on the addition of spinach ferredoxin reductase, ferredoxin and NADPH.

Next, it was determined whether cyanobaterial ferredoxins and ferredoxin reductases can replace the spinach proteins in the in-vitro fatty aldehyde decarbonylase assay. The following four genes were cloned separately into the NdeI and XhoI sites of pET-15b: *N. punctiforme* PCC73102 Npun02003626 (ZP_00109192, ferredoxin oxidoreductase petH without the n-terminal allophycocyanin linker domain) (SEQ ID NO:87), *N. punctiforme* PCC73102 Npun02001001 (ZP_00111633, ferredoxin 1) (SEQ ID NO:89), *N. punctiforme* PCC73102 Npun02003530 (ZP_00109422, ferredoxin 2) (SEQ ID NO:91) and *N. punctiforme* PCC73102 Npun02003123 (ZP_00109501, ferredoxin 3) (SEQ ID NO:93). The four proteins were expressed and purified as described above. 1 mg/mL of each ferredoxin and 4 mg/mL of the ferredoxin oxidoreductase was obtained. The three cyanobacterial ferredoxins were tested with the cyanobacterial ferredoxin oxidoreductase using the enzymatic set-up described earlier with the following changes. The final concentration of the ferredoxin reductase was 60 µg/mL and the ferredoxins were at 50 µg/mL. The extracted enzymatic reactions were by GC/MS using the following parameters: run time: 6.33 min; column. J&W 122-5711 DB-5ht (length of 15 meters; I.D.: 0.25 mm narrowbore; film: 0.10nM); inject: 1 µL Agilent 6850 inlet; inlet: 300° C. splitless; carrier gas: helium; flow: 1.3 mL/min; oven temp: 100° C. hold 0.5 min, 260 at 30° C./min, 260 hold 0.5 min; det: Agilent 5975B VL MSD; det. temp: 230° C.; scan: 50-550 M/Z.

Figure 32:
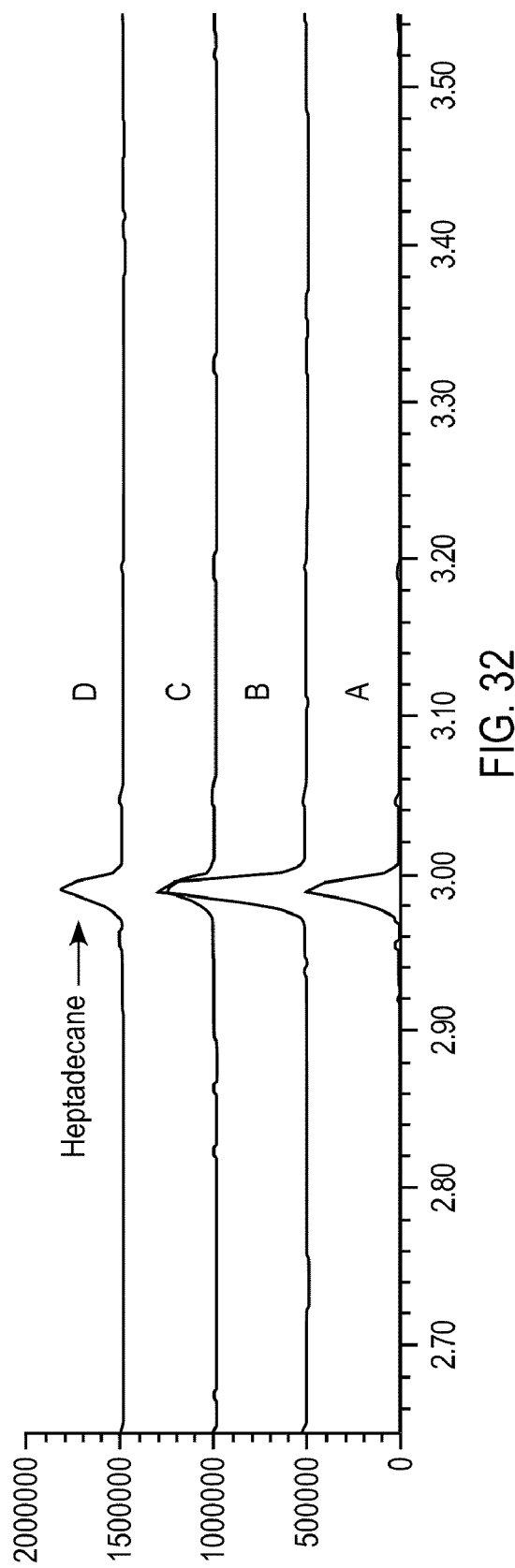
FIG. 32 depicts GC/MS traces of hydrocarbons produced in vitro using *Nostoc punctiforme* PCC73102 Npun02004178 (ZP_00108838) (SEQ ID NO:6), NADPH, octadecanal, and either (A) spinach ferredoxin and spinach ferredoxin reductase; (B) *N. punctiforme* PCC73102 Npun02003626 (ZP_00109192) (SEQ ID NO:88) and *N. punctiforme* PCC73102 Npun02001001 (ZP_00111633) (SEQ ID NO:90); (C) Npun02003626 (ZP_00109192) (SEQ ID NO:88) and *N. punctiforme* PCC73102 Npun02003530 (ZP_00109422) (SEQ ID NO:92); or (D) Npun02003626 (ZP_00109192) (SEQ ID NO:88) and *N. punctiforme* PCC73102 Npun02003123 (ZP_00109501) (SEQ ID NO:94).

As shown in FIG. 32, Npun02004178-dependent in-vitro conversion of octadecanal to heptadecane was observed in the presence of NADPH and the cyanobacterial ferredoxin oxidoreductase and any of the three cyanobacterial ferredoxins.

Example 27

Biochemical Characterization of *Synechococcus elongatus* PCC7942 orf1594

The genomic DNA encoding *S. elongatus* PCC7492 orf1594 (SEQ ID NO:65) was cloned into the NcoI and XhoI sites of vector pET-28b under the control of the T7 promoter. The resulting PCC7942_orf1594 protein contained a C-terminal His-tag. An *E. coli* BL21 strain (DE3) (Invitrogen) was transformed with the plasmid and PCC7942_orf1594 protein was expressed and purified as described in Example 22. The protein solution was stored in the following buffer: 50 mM sodium phosphate, pH 7.5, 100 mM NaCl, 1 mM THP, 10% glycerol. Protein concentration was determined using the Bradford assay (Biorad). 2 mg/mL of PCC7942_orf1594 protein was obtained.

To test PCC7942_orf1594 protein for acyl-ACP or acyl-CoA reductase activity, the following enzyme assays were set-up. 100 µL reactions were set-up in 50 mM Tris-HCl buffer at pH 7.5 with the following components at their respective final concentrations: 10 µM of purified PCC7942_orf1594 protein, 0.01-1 mM acyl-CoA or acyl-ACP, 2 mM $MgCl_2$, 0.2-2 mM NADPH. The reactions were incubated for 1 h at 37° C. and where stopped by adding 100 µL ethyl acetate (containing 5 mg/l 1-octadecene as internal standard). Samples were vortexed for 15 min and centrifuged at max speed for 3 min for phase separation. 80 µL of the top layer were transferred into GC glass vials and analyzed by GC/MS as described in Example 26. The amount of aldehyde formed was calculated based on the internal standard.

Figure 33A:
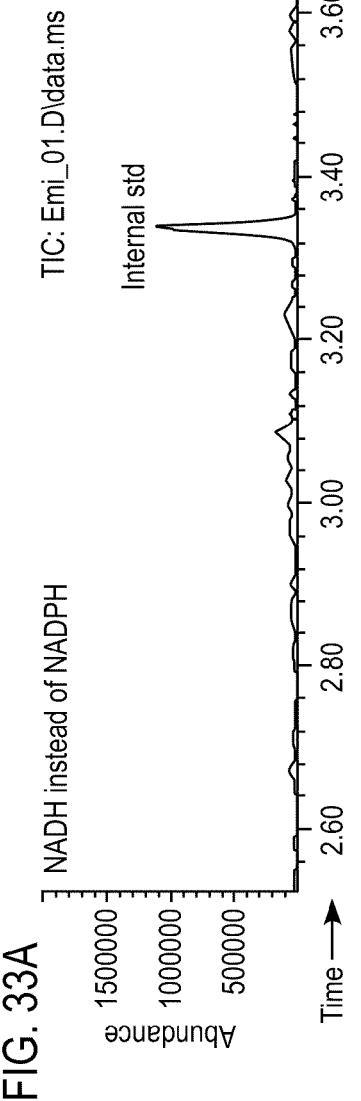
FIG. 33A is a GC/MS trace of hydrocarbons produced in vitro using octadecanoyl-CoA, *Synechococcus elongatus* PCC7942 YP_400611 (Synpcc7942_1594) (SEQ ID NO:66), NADH, and $Mg^{2+}$.
Figure 33B:
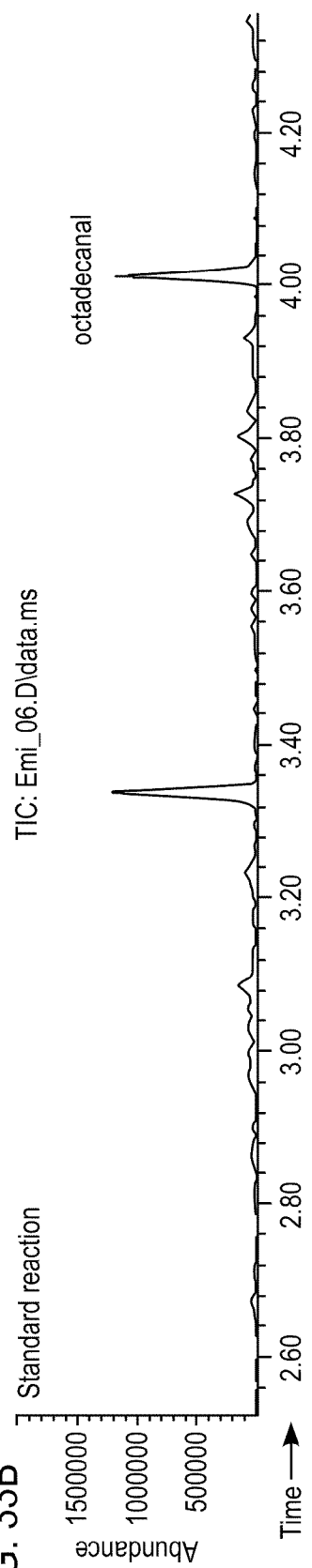
FIG. 33B is a GC/MS trace of hydrocarbons produced in vitro using octadecanoyl-CoA, *Synechococcus elongatus* PCC7942 YP_400611 (Synpcc7942_1594) (SEQ ID NO:66), NADPH, and $Mg^{2+}$.
Figure 33C:
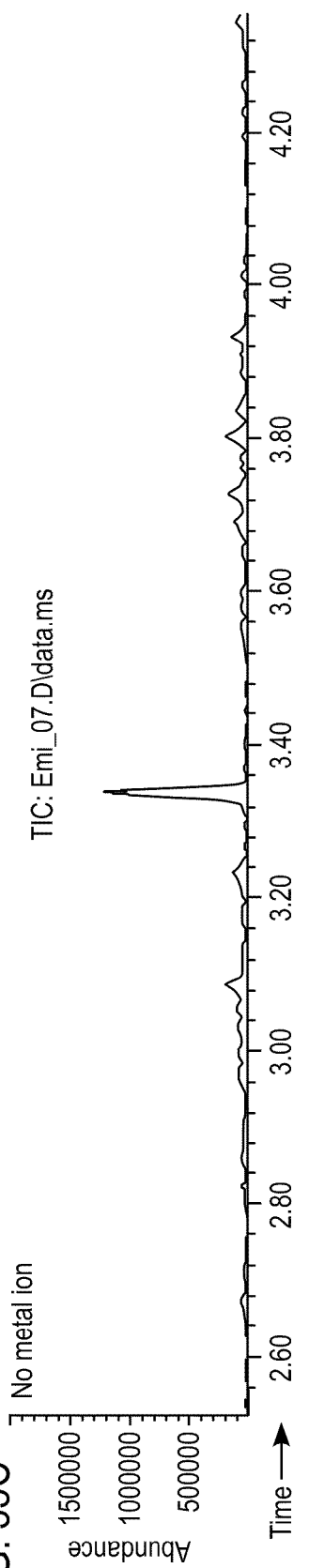
FIG. 33C is a GC/MS trace of hydrocarbons produced in vitro using octadecanoyl-CoA, *Synechococcus elongatus* PCC7942 YP_400611 (Synpcc7942_1594) (SEQ ID NO:66) and NADPH.

As shown in FIG. 33, PCC7942_orf1594 was able to reduce octadecanoyl-CoA to octadecanal. Reductase activity required divalent cations such as $Mg^{2+}$, $Mn^{2+}$ or $Fe^{2+}$ and NADPH as electron donor. NADH did not support reductase activity. PCC7942_orf1594 was also able to reduce octadecenoyl-CoA and octadecenoyl-ACP to octadecenal. The $K_m$ values for the reduction of octadecanoyl-CoA, octadecenoyl-CoA and octadecenoyl-ACP in the presence of 2 mM NADPH were determined as 45±20 µM, 82±22 µM and 7.8±2 µM, respectively. These results demonstrate that PCC7942_orf1594, in vitro, reduces both acyl-CoAs and acyl-ACPs and that the enzyme apparently has a higher affinity for acyl-ACPs as compared to acyl-CoAs. The $K_m$ value for NADPH in the presence of 0.5 mM octadecanoyl-CoA for PCC7942_orf1594 was determined as 400±80 µM.

Next, the stereospecific hydride transfer from NADPH to a fatty aldehyde catalyzed by PCC7942_orf1594 was examined Deutero-NADPH was prepared according to the following protocol. 5 mg of $NADP^+$ and 3.6 mg of D-glucose-1-d was added to 2.5 mL of 50 mM sodium phosphate buffer (pH 7.0). Enzymatic production of labeled NADPH was initiated by the addition of 5 units of glucose dehydrogenase from either *Bacillus megaterium* (USB Corporation) for the production of R-(4-$^2$H)NADPH or *Thermoplasma acidophilum* (Sigma) for the production of S-(4-$^2$H)NADPH. The reaction was incubated for 15 min at 37° C., centrifuge-filtered using a 10 KDa MWCO Amicon Ultra centrifuge filter (Millipore), flash frozen on dry ice, and stored at −80° C.

Figure 34A:
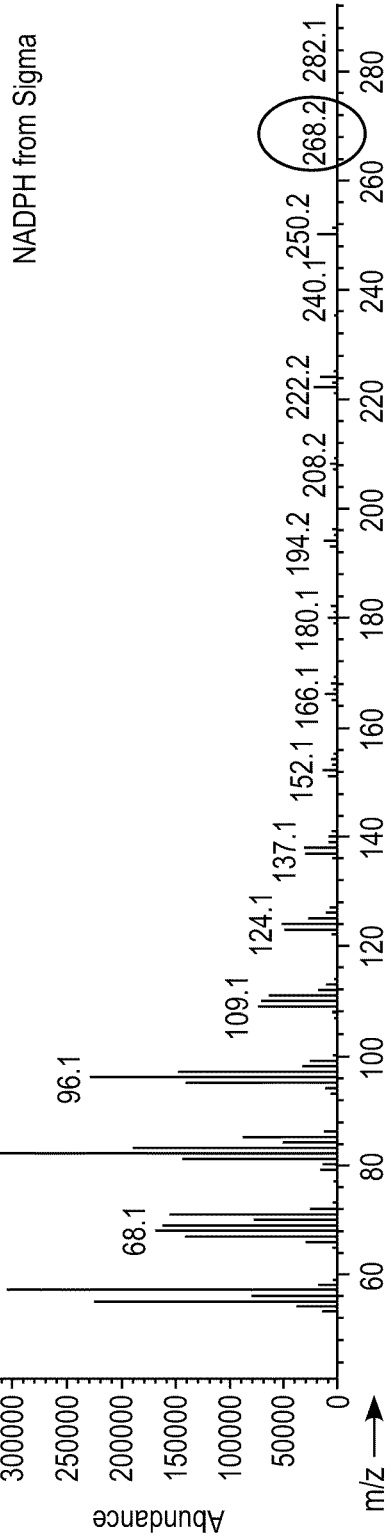
FIG. 34A is a GC/MS trace of hydrocarbons produced in vitro using octadecanoyl-CoA, labeled NADPH, *Synechococcus elongatus* PCC7942 YP_400611 (Synpcc7942_1594) (SEQ ID NO:66), and unlabeled NADPH.
Figure 34B:
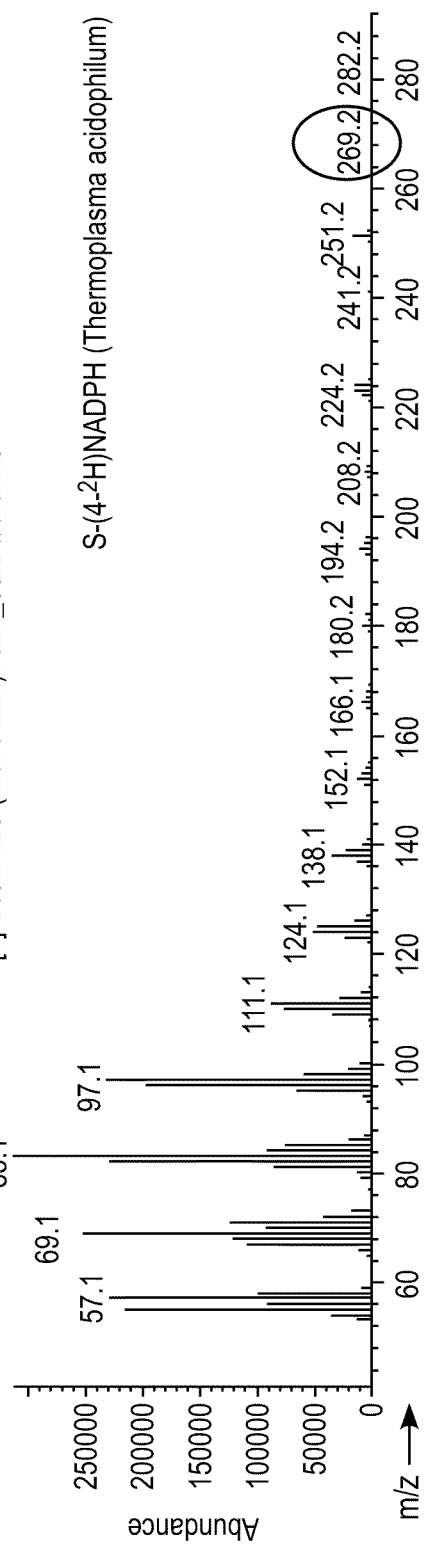
FIG. 34B is a GC/MS trace of hydrocarbons produced in vitro using octadecanoyl-CoA, labeled NADPH, *Synechococcus elongatus* PCC7942 YP_400611 (Synpcc7942_1594) (SEQ ID NO:66), and S-(4-$^2$H)NADPH.
Figure 34C:
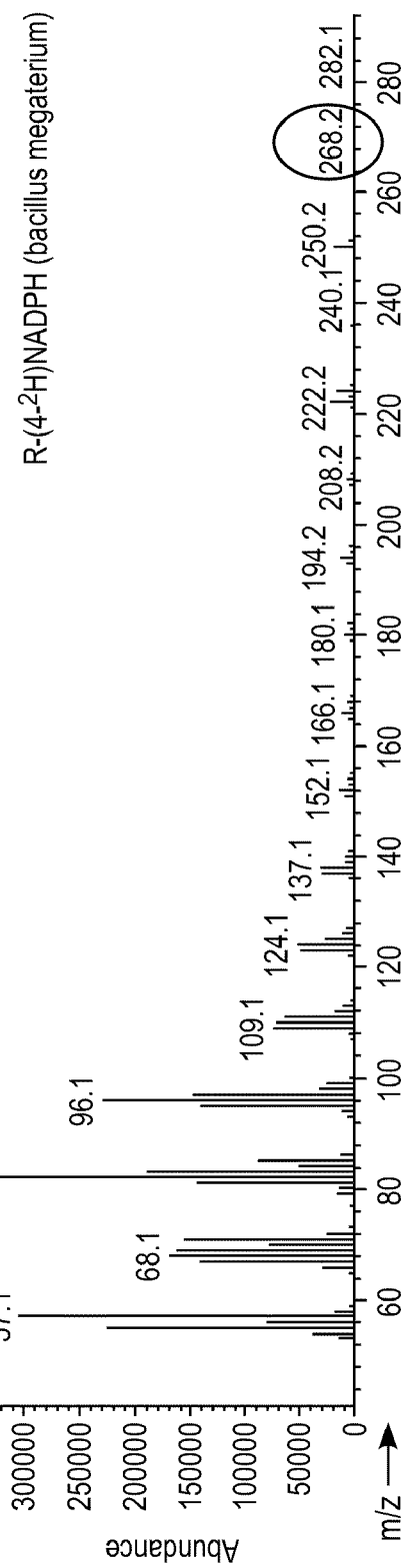
FIG. 34C is a GC/MS trace of hydrocarbons produced in vitro using octadecanoyl-CoA, labeled NADPH, *Synechococcus elongatus* PCC7942 YP_400611 (Synpcc7942_1594) (SEQ ID NO:66), and R-(4-$^2$H)NADPH.

The in vitro assay reaction contained 50 mM Tris-HCl (pH 7.5), 10 µM of purified PCC7942_orf1594 protein, 1 mM octadecanoyl-CoA, 2 mM $MgCl_2$, and 50 µL deutero-NADPH (prepared as described above) in a total volume of 100 µL. After a 1 h incubation, the product of the enzymatic reaction was extracted and analyzed as described above. The resulting fatty aldehyde detected by GC/MS was octadecanal (see FIG. 34). Because hydride transfer from NADPH is stereospecific, both R-(4-$^2$H)NADPH and S-(4-$^2$H)NADPH were synthesized. Octadecanal with a plus one unit mass was observed using only the S-(4-$^2$H)NADPH. The fact that the fatty aldehyde was labeled indicates that the deuterated hydrogen has been transferred from the labeled NADPH to the labeled fatty aldehyde. This demonstrates that NADPH is used in this enzymatic reaction and that the hydride transfer catalyzed by PCC7942_orf1594 is stereospecific.

Example 28

Intracellular and Extracellular Production of Fatty Aldehydes and Fatty Alcohols in *E. coli* Through Heterologous Expression of *Synechococcus elongatus* PCC7942 orf1594

The genomic DNA encoding *Synechococcus elongatus* PCC7942 orf1594 (YP_400611; acyl-ACP reductase) (SEQ ID NO:65) was amplified and cloned into the NcoI and EcoRI sites of vector OP-80 (pCL1920 derivative) under the control of the $P_{trc}$ promoter. The resulting construct was cotransformed into E. coli MG1655 ΔfadE and the cells were grown at 37° C. in 15 mL Che-9 minimal media with 3% (w/v) glucose as carbon source and supplemented with 100 µg/mL spectinomycin and carbenicillin, respectively. When the culture reached $OD_{600}$ of 0.8-1.0, it was induced with 1 mM IPTG and cells were grown for an additional 24-48 h at 37° C. Che-9 minimal medium is defined as: 6 g/L $Na_2HPO_4$, 3 g/L $KH_2PO_4$, 0.5 g/L NaCl, 2 g/L $NH_4Cl$, 0.25 g/L $MgSO_4·7H_2O$, 11 mg/L $CaCl_2$, 27 mg/L $Fe_3Cl×6H_2O$, 2 mg/L $ZnCl×4H_2O$, 2 mg/L $Na_2MoO_4×2H_2O$, 1.9 mg/L $CuSO_4×5H_2O$, 0.5 mg/L $H_3BO_3$, 1 mg/L thiamine, 200 mM Bis-Tris (pH 7.25) and 0.1% (v/v) Triton-X100. When the culture reached $OD_{600}$ of 1.0-1.2, it was induced with 1 mM IPTG and cells were allowed to grow for an additional 40 hrs at 37° C. Cells from 0.5 mL of culture were extracted with 0.5 mL of ethyl acetate for total hydrocarbon production as described in Example 26. Additionally, cells and supernatant were separated by centrifugation (4,000 g at RT for 10 min) and extracted separately.

Figure 35:
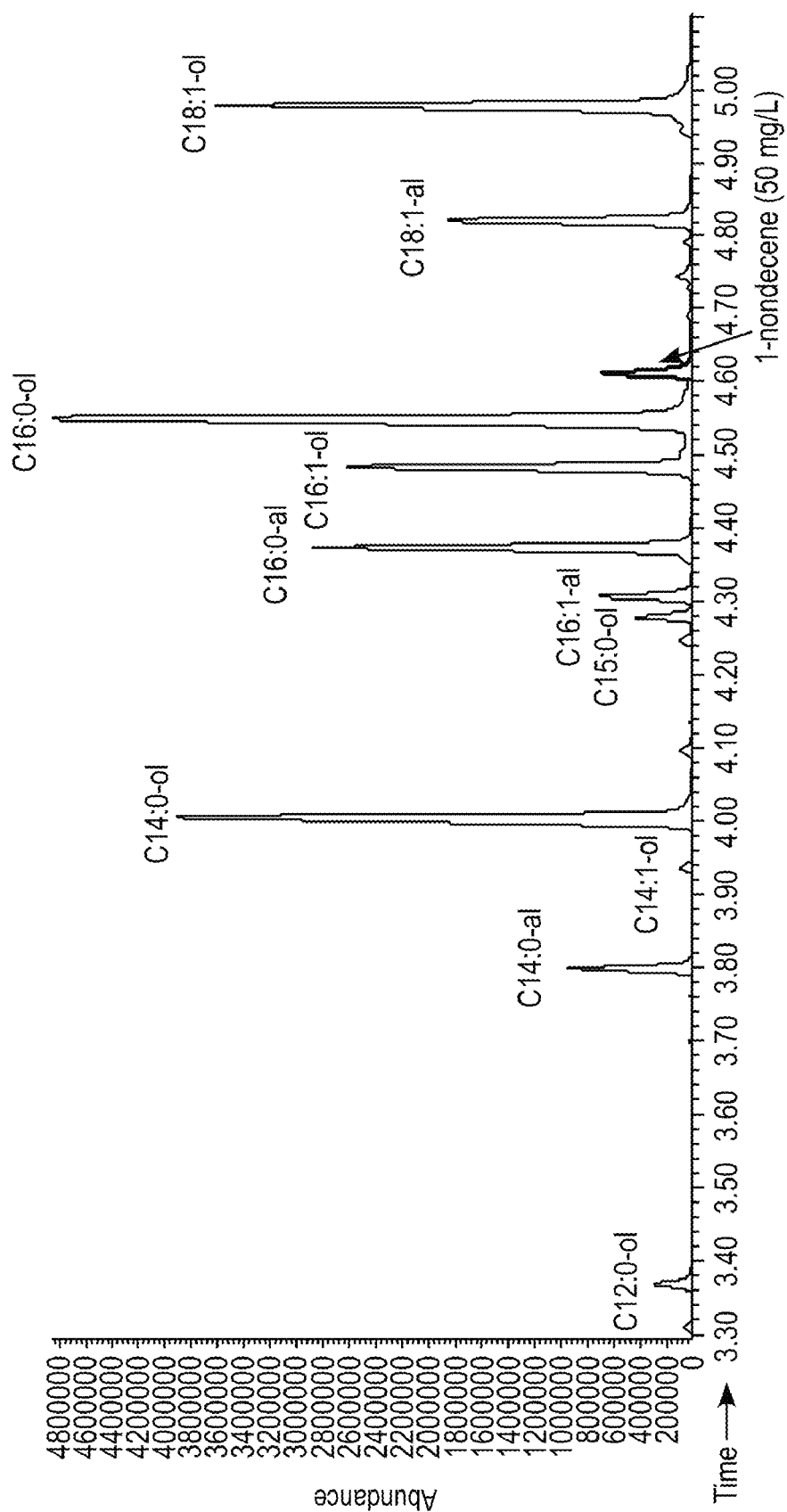
FIG. 35 is a GC/MS trace of hydrocarbons in the cell-free supernatant produced by *E. coli* MG1655 ΔfadE cells in Che-9 media expressing *Synechococcus elongatus* PCC7942 YP_400611 (Synpcc7942_1594) (SEQ ID NO:65).

The culture produced 620 mg/L fatty aldehydes (tetradecanal, heptadecenal, heptadecanal and octadecenal) and 1670 mg/L fatty alcohols (dodecanol, tetradecenol, tetradecanol, heptadecenol, heptadecanol and octadecenol). FIG. 35 shows the chromatogram of the extracted supernatant. It was determined that 73% of the fatty aldehydes and fatty alcohols were in the cell-free supernatant.

Example 29

Intracellular and Extracellular Production of Alkanes and Alkenes in *E. coli* Through Heterologous Expression of *Synechococcus elongatus* PCC7942 orf1594 and *Nostoc punctiforme* PCC73102 Npun02004178

The genomic DNA encoding *Synechococcus elongatus* PCC7942 orf1594 (YP_400611; acyl-ACP reductase) (SEQ ID NO:65) was amplified and cloned into the NcoI and EcoRI sites of vector OP-80 (pCL1920 derivative) under the control of the P$_{trc}$ promoter. The genomic DNA encoding *Nostoc punctiforme* PCC73102 Npun02004178 (ZP_00108838; fatty aldehyde decarbonylase) (SEQ ID NO:5) was amplified and cloned into the NdeI and XhoI sites of vector OP-183 (pACYC derivative) under the control of the P$_{trc}$ promoter. The resulting constructs were cotransformed into *E. coli* MG1655 ΔfadE and the cells were grown at 37° C. in 15 mL Che9 minimal media with 3% (w/v) glucose as carbon source and supplemented with 100 μg/mL spectinomycin and carbenicillin, respectively. The cells were grown, separated from the broth, extracted, and analyzed as described in Example 28.

Figure 36:
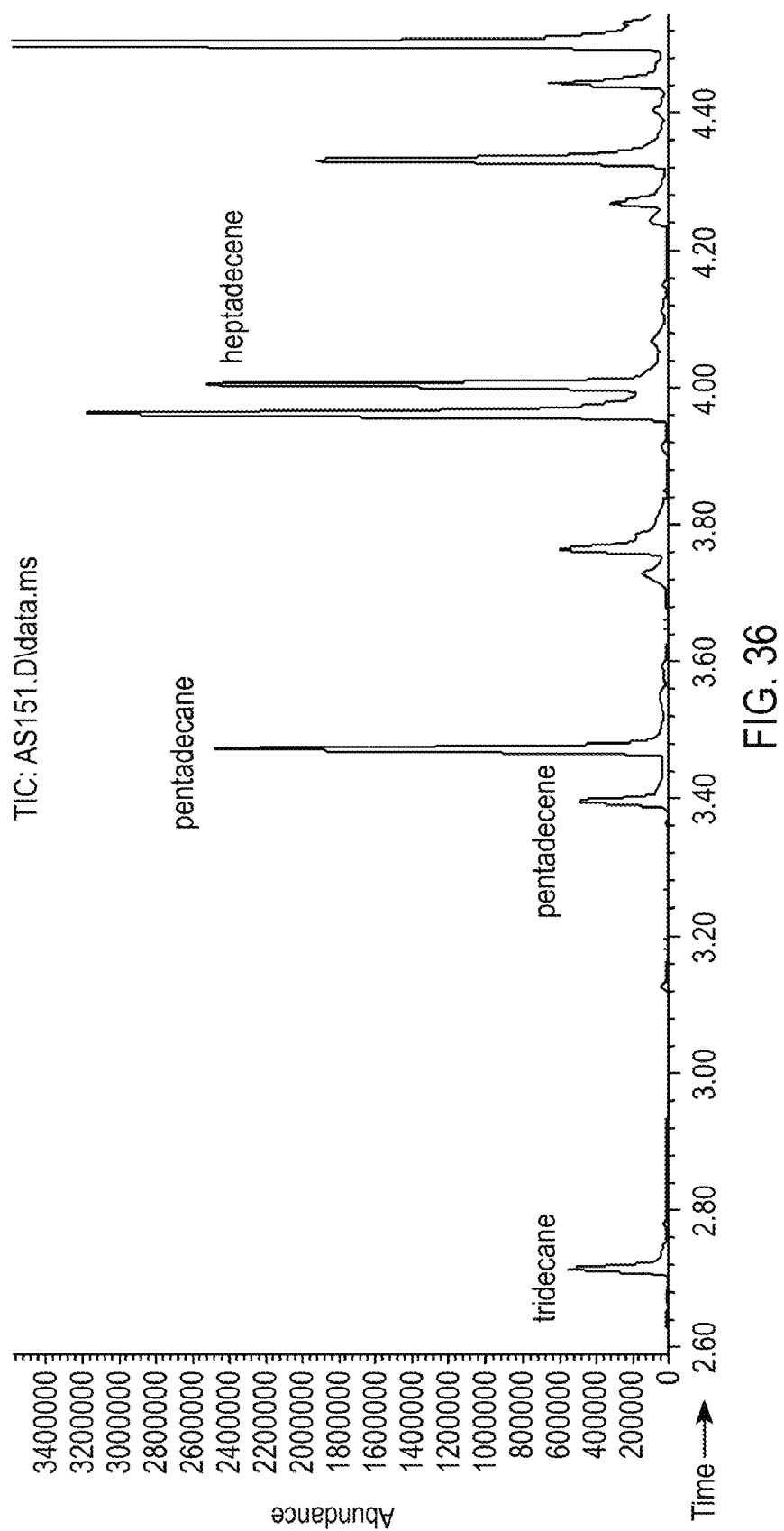
FIG. 36 is a GC/MS trace of hydrocarbons in the cell-free supernatant produced by *E. coli* MG1655 ΔfadE cells in Che-9 media expressing *Synechococcus elongatus* PCC7942 YP_400611 (Synpcc7942_1594) (SEQ ID NO:65) and *Nostoc punctiforme* PCC73102 Npun02004178 (ZP_00108838) (SEQ ID NO:5).

The culture produced 323 mg/L alkanes and alkenes (tridecane, pentadecene, pentadecane and heptadecene), 367 mg/L fatty aldehydes (tetradecanal, heptadecenal, heptadecanal and octadecenal) and 819 mg/L fatty alcohols (tetradecanol, heptadecenol, heptadecanol and octadecenol). FIG. 36 shows the chromatogram of the extracted supernatant. It was determined that 86% of the alkanes, alkenes, fatty aldehydes and fatty alcohols were in the cell-free supernatant.

Example 30

Production of Alkanes and Alkenes in *E. coli* Through Heterologous Expression of *Nostoc* sp. PCC7210 alr5284 and *Nostoc* sp. PCC7210 alr5283

The genomic DNA encoding *Nostoc* sp. PCC7210 alr5284 (NP_489324; putative aldehyde-generating enzyme) (SEQ ID NO:81) was amplified and cloned into the NcoI and EcoRI sites of vector OP-80 (pCL1920 derivative) under the control of the P$_{trc}$ promoter. The genomic DNA encoding *Nostoc* sp. PCC7210 alr5283 (NP_489323; putative decarbonylase) (SEQ ID NO:7) was amplified and cloned into the NdeI and XhoI sites of vector OP-183 (pACYC derivative) under the control of the P$_{trc}$ promoter. The resulting constructs were cotransformed into *E. coli* MG1655 and the cells were grown at 37° C. in 15 mL Che9 minimal media with 3% (w/v) glucose as carbon source and supplemented with 100 μg/mL spectinomycin and carbenicillin, respectively (as described in Example 28). Cells from 0.5 mL of culture were extracted and analyzed as described in Example 3 and analyzed by GC-MS as described in Example 26.

Figure 37:
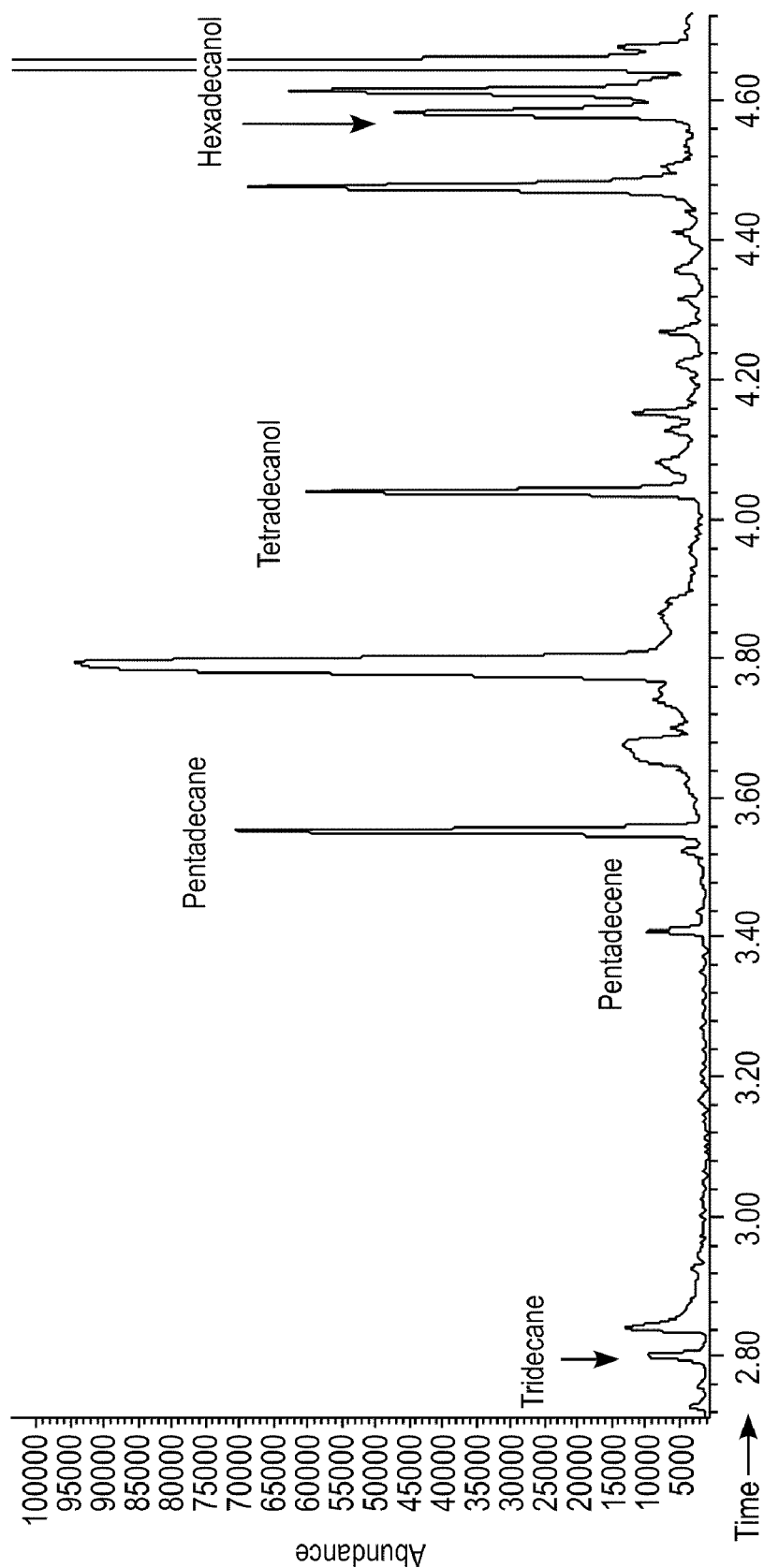
FIG. 37 is a GC/MS trace of hydrocarbons produced by *E. coli* MG1655 cells expressing *Nostoc* sp. PCC7120 alr5283 (NP_489323) (SEQ ID NO:7) and *Nostoc* sp. PCC7120 alr5284 (NP_489324) (SEQ ID NO:81).

As shown in FIG. 37, *E. coli* cells cotransformed with the *Nostoc* sp. PCC7210 alr5284 and *Nostoc* sp. PCC7210 alr5283-bearing vectors produced tridecane, pentadecene, pentadecane, tetradecanol and hexadecanol. This result indicates that coexpression of *Nostoc* sp. PCC7210 alr5284 and alr5283 is sufficient for *E. coli* to produce fatty alcohols, alkanes and alkenes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing an alkane or alkene from an engineered microorganism, the method comprising,
expressing a first gene encoding an acyl-ACP reductase that catalyzes the conversion of acyl ACP to a fatty aldehyde in said engineered microorganism;
expressing a second gene encoding a decarbonylase that catalyzes the conversion of a fatty aldehyde to an alkane or alkene in said engineered microorganism;
culturing said engineered microorganism in a culture media containing a carbohydrate carbon source under conditions effective to produce an alkane or alkene in the cell-free supernatant.

2. The method according to claim 1, wherein said acyl-ACP reductase has a higher affinity for acyl-ACP as compared to acyl-CoA.

3. The method of claim 1, wherein the engineered microorganism is selected from the group consisting of a yeast, a fungi, a filamentous fungi, an algae and a bacteria.

4. The method of claim 3, wherein the bacteria is $E.$ $coli$.

5. The method of claim 1, wherein the alkane or alkene comprises a $C_{13}$ to $C_{21}$ alkane or alkene.

6. A cell culture comprising an engineered microorganism wherein an acyl-ACP reductase that catalyzes the conversion of acyl ACP to a fatty aldehyde and a decarbonylase that catalyzes the conversion of a fatty aldehyde to an alkane or alkene are overexpressed in said engineered microorganism and an alkane or alkene is produced in the cell culture when said engineered microorganism is cultured in medium containing a carbon source under conditions effective to express said acyl-ACP reductase and said decarbonylase.

7. The cell culture according to claim 6, wherein the engineered microorganism is selected from the group consisting of a yeast, a fungi, a filamentous fungi, an algae and a bacteria.

8. The cell culture according to claim 7, wherein the bacteria is $E.$ $coli$.

9. The cell culture according to claim 6, wherein the alkane or alkene comprises a $C_{13}$ to $C_{21}$ alkane or alkene.

10. The cell culture according to claim 6, wherein the alkane or alkene is selected from the group consisting of tridecane, methyltridecane, nonadecane, methylnonadecane, heptadecane, methylheptadecane, pentadecane, methylpentadecane, pentadecene, heptadecene, methylpentadecane, and methylheptadecene.

11. The cell culture according to claim 6, comprising an alkane or alkene having a $\delta^{13}C$ of about −15.4 or greater.

12. The cell culture according to claim 6, comprising an alkane or alkene having an $f_M{}^{14}C$ of at least about 1.003.

* * * * *

SEQUENCE LISTING

<160> NUMBER OF SEQ ID NOS: 100

<210> SEQ ID NO 1
<211> LENGTH: 696
<212> TYPE: DNA
<213> ORGANISM: Synechococcus elongatus

<400> SEQUENCE: 1

```
atgccgcagc ttgaagccag ccttgaactg gactttcaaa gcgagtccta caaagacgct      60
tacagccgca tcaacgcgat cgtgattgaa ggcgaacaag aggcgttcga caactacaat     120
cgccttgctg agatgctgcc cgaccagcgg gatgagcttc acaagctagc caagatggaa     180
cagcgccaca tgaaaggctt tatggcctgt ggcaaaaatc tctccgtcac tcctgacatg     240
ggttttgccc agaaattttt cgagcgcttg cacgagaact tcaaagcggc ggctgcggaa     300
ggcaaggtcg tcacctgcct actgattcaa tcgctaatca tcgagtgctt tgcgatcgcg     360
gcttacaaca tctacatccc agtggcggat gcttttgccc gcaaaatcac ggaggggggtc     420 gtgcgcgacg aatacctgca ccgcaacttc ggtgaagagt ggctgaaggc gaatttttgat     480 gcttccaaag ccgaactgga agaagccaat cgtcagaacc tgcccttggt ttggctaatg     540
ctcaacgaag tggccgatga tgctcgcgaa ctcgggatgg agcgtgagtc gctcgtcgag     600
gactttatga ttgcctacgg tgaagctctg gaaaacatcg gcttcacaac gcgcgaaatc     660
```

```
atgcgtatgt ccgcctatgg ccttgcggcc gtttga                               696
```

<210> SEQ ID NO 2
<211> LENGTH: 231
<212> TYPE: PRT
<213> ORGANISM: Synechococcus elongatus

<400> SEQUENCE: 2

```
Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30

Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80

Gly Phe Ala Gln Lys Phe Phe Glu Arg Leu His Glu Asn Phe Lys Ala
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190

Met Glu Arg Glu Ser Leu Val Glu Asp Phe Met Ile Ala Tyr Gly Glu
        195                 200                 205

Ala Leu Glu Asn Ile Gly Phe Thr Thr Arg Glu Ile Met Arg Met Ser
    210                 215                 220

Ala Tyr Gly Leu Ala Ala Val
225                 230
```

<210> SEQ ID NO 3
<211> LENGTH: 696
<212> TYPE: DNA
<213> ORGANISM: Synechocystis sp.

<400> SEQUENCE: 3

```
atgcccgagc ttgctgtccg caccgaattt gactattcca gcgaaattta caaagacgcc    60
tatagccgca tcaacgccat tgtcattgaa ggcgaacagg aagcctacag caactaccct   120
cagatggcgg aactcttgcc ggaagacaaa gaagagttga cccgcttggc caaaatggaa   180
aaccgccata aaaaggtttt ccaagcctgt ggcaacaacc tccaagtgaa ccctgatatg   240
ccctatgccc aggaattttt cgccggtctc catggcaatt ccagcacgc ttttagcgaa    300 gggaaagttg ttacctgttt attgatccag gctttgatta tcgaagcttt tgcgatcgcc   360
gcctataaca tatatatccc tgtggcggac gactttgctc ggaaaatcac tgagggcgta   420
gtcaaggacg aatacacccca cctcaactac ggggaagaat ggctaaaggc caactttgcc   480
```

```
accgctaagg aagaactgga gcaggccaac aaagaaaacc tacccttagt gtggaaaatg    540
ctcaaccaag tgcaggggga cgccaaggta ttgggcatgg aaaaagaagc cctagtggaa    600
gattttatga tcagctacgg cgaagccctc agtaacatcg gcttcagcac cagggaaatt    660
atgcgtatgt cttcctacgg tttggccgga gtctag                              696
```

<210> SEQ ID NO 4
<211> LENGTH: 231
<212> TYPE: PRT
<213> ORGANISM: Synechocystis sp.

<400> SEQUENCE: 4

```
Met Pro Glu Leu Ala Val Arg Thr Glu Phe Asp Tyr Ser Ser Glu Ile
1               5                   10                  15

Tyr Lys Asp Ala Tyr Ser Arg Ile Asn Ala Ile Val Ile Glu Gly Glu
            20                  25                  30

Gln Glu Ala Tyr Ser Asn Tyr Leu Gln Met Ala Glu Leu Leu Pro Glu
        35                  40                  45

Asp Lys Glu Glu Leu Thr Arg Leu Ala Lys Met Glu Asn Arg His Lys
    50                  55                  60

Lys Gly Phe Gln Ala Cys Gly Asn Asn Leu Gln Val Asn Pro Asp Met
65                  70                  75                  80

Pro Tyr Ala Gln Glu Phe Phe Ala Gly Leu His Gly Asn Phe Gln His
                85                  90                  95

Ala Phe Ser Glu Gly Lys Val Val Thr Cys Leu Leu Ile Gln Ala Leu
            100                 105                 110

Ile Ile Glu Ala Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Thr His Leu Asn Tyr Gly Glu Glu Trp Leu Lys Ala Asn Phe Ala
145                 150                 155                 160

Thr Ala Lys Glu Glu Leu Glu Gln Ala Asn Lys Glu Asn Leu Pro Leu
                165                 170                 175

Val Trp Lys Met Leu Asn Gln Val Gln Gly Asp Ala Lys Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Arg Met Ser
    210                 215                 220

Ser Tyr Gly Leu Ala Gly Val
225                 230
```

<210> SEQ ID NO 5
<211> LENGTH: 699
<212> TYPE: DNA
<213> ORGANISM: Nostoc punctiforme

<400> SEQUENCE: 5

```
atgcagcagc ttacagacca atctaaagaa ttagatttca gagcgaaac atacaaagat     60 gcttatagcc ggattaatgc gatcgtgatt gaggggaac aagaagccca tgaaaattac    120
atcacactag cccaactgct gccagaatct catgatgaat tgattcgcct atccaagatg    180
gaaagccgcc ataagaaagg atttgaagct tgtgggcgca atttagctgt taccccagat    240
ttgcaatttg ccaaagagtt tttctccggc ctacaccaaa attttcaaac agctgccgca    300
gaagggaaag tggttacttg tctgttgatt cagtctttaa ttattgaatg ttttgcgatc    360
```

```
gcagcatata acatttacat ccccgttgcc gacgatttcg cccgtaaaat tactgaagga    420
gtagttaaag aagaatacag ccacctcaat tttggagaag tttggttgaa agaacacttt    480
gcagaatcca aagctgaact tgaacttgca atcgccaga acctacccat cgtctggaaa    540
atgctcaacc aagtagaagg tgatgccac acaatggcaa tggaaaaaga tgctttggta    600
gaagacttca tgattcagta tggtgaagca ttgagtaaca ttggttttc gactcgcgat    660 attatgcgct tgtcagccta cggactcata ggtgcttaa                          699
```

<210> SEQ ID NO 6
<211> LENGTH: 232
<212> TYPE: PRT
<213> ORGANISM: Nostoc punctiforme

<400> SEQUENCE: 6

```
Met Gln Gln Leu Thr Asp Gln Ser Lys Glu Leu Asp Phe Lys Ser Glu
1               5                   10                  15

Thr Tyr Lys Asp Ala Tyr Ser Arg Ile Asn Ala Ile Val Ile Glu Gly
                20                  25                  30

Glu Gln Glu Ala His Glu Asn Tyr Ile Thr Leu Ala Gln Leu Leu Pro
            35                  40                  45

Glu Ser His Asp Glu Leu Ile Arg Leu Ser Lys Met Glu Ser Arg His
        50                  55                  60

Lys Lys Gly Phe Glu Ala Cys Gly Arg Asn Leu Ala Val Thr Pro Asp
65                  70                  75                  80

Leu Gln Phe Ala Lys Glu Phe Phe Ser Gly Leu His Gln Asn Phe Gln
                85                  90                  95

Thr Ala Ala Ala Glu Gly Lys Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160

Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205

Glu Ala Leu Ser Asn Ile Gly Phe Ser Thr Arg Asp Ile Met Arg Leu
    210                 215                 220

Ser Ala Tyr Gly Leu Ile Gly Ala
225                 230
```

<210> SEQ ID NO 7
<211> LENGTH: 696
<212> TYPE: DNA
<213> ORGANISM: Nostoc sp.

<400> SEQUENCE: 7

```
atgcagcagg ttgcagccga tttagaaatt gatttcaaga gcgaaaaata taagatgcc     60 tatagtcgca taaatgcgat cgtgattgaa ggggaacaag aagcatacga gaattacatt    120
caactatccc aactgctgcc agacgataaa gaagacctaa ttcgcctctc gaaaatggaa    180
```

-continued

```
agccgtcaca aaaaaggatt tgaagcttgt ggacggaacc tacaagtatc accagatatg    240
gagtttgcca agaattctt tgctggacta cacggtaact tccaaaaagc ggcggctgaa     300
ggtaaaatcg ttacctgtct attgattcag tccctgatta ttgaatgttt tgcgatcgcc    360
gcatacaata tctacattcc cgttgctgac gattttgctc gtaaaatcac tgagggtgta    420
gtcaaagatg aatacagcca cctcaacttc ggcgaagttt ggttacagaa aaattttgcc    480
caatccaaag cagaattaga agaagctaat cgtcataatc ttcccatagt ttggaaaatg    540
ctcaatcaag tcgcggatga tgccgcagtc ttagctatgg aaaagaagc cctagtcgaa     600 gattttatga ttcagtacgg cgaagcgtta agtaatattg gcttcacaac cagagatatt    660
atgcggatgt cagcctacgg acttacagca gcttaa                              696
```

<210> SEQ ID NO 8
<211> LENGTH: 231
<212> TYPE: PRT
<213> ORGANISM: Nostoc sp.

<400> SEQUENCE: 8

```
Met Gln Gln Val Ala Ala Asp Leu Glu Ile Asp Phe Lys Ser Glu Lys
1               5                   10                  15

Tyr Lys Asp Ala Tyr Ser Arg Ile Asn Ala Ile Val Ile Glu Gly Glu
            20                  25                  30

Gln Glu Ala Tyr Glu Asn Tyr Ile Gln Leu Ser Gln Leu Leu Pro Asp
        35                  40                  45

Asp Lys Glu Asp Leu Ile Arg Leu Ser Lys Met Glu Ser Arg His Lys
    50                  55                  60

Lys Gly Phe Glu Ala Cys Gly Arg Asn Leu Gln Val Ser Pro Asp Met
65                  70                  75                  80

Glu Phe Ala Lys Glu Phe Ala Gly Leu His Gly Asn Phe Gln Lys
                85                  90                  95

Ala Ala Ala Glu Gly Lys Ile Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Ser His Leu Asn Phe Gly Glu Val Trp Leu Gln Lys Asn Phe Ala
145                 150                 155                 160

Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Ala Val Leu Ala
            180                 185                 190

Met Glu Lys Glu Ala Leu Val Glu Asp Phe Met Ile Gln Tyr Gly Glu
        195                 200                 205

Ala Leu Ser Asn Ile Gly Phe Thr Thr Arg Asp Ile Met Arg Met Ser
    210                 215                 220

Ala Tyr Gly Leu Thr Ala Ala
225                 230
```

<210> SEQ ID NO 9
<211> LENGTH: 696
<212> TYPE: DNA
<213> ORGANISM: Acaryochloris marina
<400> SEQUENCE: 9

```
atgccccaaa ctcaggctat ttcagaaatt gacttctata gtgacaccta caaagatgct    60
```

-continued

```
tacagtcgta ttgacggcat tgtgatcgaa ggtgagcaag aagcgcatga aaactatatt    120
cgtcttggcg aaatgctgcc tgagcaccaa gacgacttta tccgcctgtc aagatggaa    180 gcccgtcata agaaagggtt tgaagcctgc ggtcgcaact aaaagtaac ctgcgatcta    240 gactttgccc ggcgtttctt ttccgactta cacaagaatt ttcaagatgc tgcagctgag    300
gataaagtgc caacttgctt agtgattcag tccttgatca ttgagtgttt tgcgatcgca    360
gcttacaaca tctatatccc cgtcgctgat gactttgccc gtaagattac agagtctgtg    420
gttaaggatg agtatcaaca cctcaattat ggtgaagagt ggcttaaagc tcacttcgat    480
gatgtgaaag cagaaatcca agaagctaat cgcaaaaacc tccccatcgt ttggagaatg    540
ctgaacgaag tggacaagga tgcggccgtt ttaggaatgg aaaaagaagc cctggttgaa    600
gacttcatga tccagtatgg tgaagccctt agcaatattg gtttctctac aggcgaaatt    660
atgcggatgt ctgcctatgg tcttgtggct gcgtaa                             696
```

<210> SEQ ID NO 10
<211> LENGTH: 231
<212> TYPE: PRT
<213> ORGANISM: Acaryochloris marina

<400> SEQUENCE: 10

```
Met Pro Gln Thr Gln Ala Ile Ser Glu Ile Asp Phe Tyr Ser Asp Thr
1               5                   10                  15

Tyr Lys Asp Ala Tyr Ser Arg Ile Asp Gly Ile Val Ile Glu Gly Glu
            20                  25                  30

Gln Glu Ala His Glu Asn Tyr Ile Arg Leu Gly Glu Met Leu Pro Glu
        35                  40                  45

His Gln Asp Asp Phe Ile Arg Leu Ser Lys Met Glu Ala Arg His Lys
    50                  55                  60

Lys Gly Phe Glu Ala Cys Gly Arg Asn Leu Lys Val Thr Cys Asp Leu
65                  70                  75                  80

Asp Phe Ala Arg Arg Phe Phe Ser Asp Leu His Lys Asn Phe Gln Asp
                85                  90                  95

Ala Ala Ala Glu Asp Lys Val Pro Thr Cys Leu Val Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Ser Val Val Lys Asp Glu
    130                 135                 140

Tyr Gln His Leu Asn Tyr Gly Glu Glu Trp Leu Lys Ala His Phe Asp
145                 150                 155                 160

Asp Val Lys Ala Glu Ile Gln Glu Ala Asn Arg Lys Asn Leu Pro Ile
                165                 170                 175

Val Trp Arg Met Leu Asn Glu Val Asp Lys Asp Ala Ala Val Leu Gly
            180                 185                 190

Met Glu Lys Glu Ala Leu Val Glu Asp Phe Met Ile Gln Tyr Gly Glu
        195                 200                 205

Ala Leu Ser Asn Ile Gly Phe Ser Thr Gly Glu Ile Met Arg Met Ser
    210                 215                 220

Ala Tyr Gly Leu Val Ala Ala
225                 230
```

<210> SEQ ID NO 11
<211> LENGTH: 696
<212> TYPE: DNA

<213> ORGANISM: Thermosynechococcus elongatus

<400> SEQUENCE: 11

```
atgacaacgg ctaccgctac acctgttttg gactaccata gcgatcgcta caaggatgcc    60
tacagccgca ttaacgccat tgtcattgaa ggtgaacagg aagctcacga taactatatc   120
gatttagcca agctgctgcc acaacaccaa gaggaactca cccgccttgc caagatggaa   180
gctcgccaca aaaaggggtt tgaggcctgt ggtcgcaacc tgagcgtaac gccagatatg   240
gaatttgcca agccttcttt gaaaaactg cgcgctaact ttcagagggc tctggcggag   300
ggaaaaactg cgacttgtct tctgattcaa gctttgatca tcgaatcctt tgcgatcgcg   360
gcctacaaca tctacatccc aatggcggat cctttcgccc gtaaaattac tgagagtgtt   420
gttaaggacg aatacagcca cctcaacttt ggcgaaatct ggctcaagga acactttgaa   480
agcgtcaaag gagagctcga agaagccaat cgcgccaatt tacccttggt ctggaaaatg   540
ctcaaccaag tggaagcaga tgccaaagtg ctcggcatgg aaaaagatgc ccttgtggaa   600
gacttcatga ttcagtacag tggtgcccta gaaaatatcg gctttaccac ccgcgaaatt   660
atgaagatgt cagtttatgg cctcactggg gcataa                             696
```

<210> SEQ ID NO 12
<211> LENGTH: 231
<212> TYPE: PRT
<213> ORGANISM: Thermosynechococcus elongatus

<400> SEQUENCE: 12

```
Met Thr Thr Ala Thr Ala Thr Pro Val Leu Asp Tyr His Ser Asp Arg
  1               5                  10                  15

Tyr Lys Asp Ala Tyr Ser Arg Ile Asn Ala Ile Val Ile Glu Gly Glu
             20                  25                  30

Gln Glu Ala His Asp Asn Tyr Ile Asp Leu Ala Lys Leu Leu Pro Gln
         35                  40                  45

His Gln Glu Glu Leu Thr Arg Leu Ala Lys Met Glu Ala Arg His Lys
     50                  55                  60

Lys Gly Phe Glu Ala Cys Gly Arg Asn Leu Ser Val Thr Pro Asp Met
 65                  70                  75                  80

Glu Phe Ala Lys Ala Phe Phe Glu Lys Leu Arg Ala Asn Phe Gln Arg
                 85                  90                  95

Ala Leu Ala Glu Gly Lys Thr Ala Thr Cys Leu Leu Ile Gln Ala Leu
            100                 105                 110

Ile Ile Glu Ser Phe Ala Ile Ala Ala Tyr Asn Ile Tyr Ile Pro Met
        115                 120                 125

Ala Asp Pro Phe Ala Arg Lys Ile Thr Glu Ser Val Val Lys Asp Glu
    130                 135                 140

Tyr Ser His Leu Asn Phe Gly Glu Ile Trp Leu Lys Glu His Phe Glu
145                 150                 155                 160

Ser Val Lys Gly Glu Leu Glu Ala Asn Arg Ala Asn Leu Pro Leu
                165                 170                 175

Val Trp Lys Met Leu Asn Gln Val Glu Ala Asp Ala Lys Val Leu Gly
            180                 185                 190

Met Glu Lys Asp Ala Leu Val Glu Asp Phe Met Ile Gln Tyr Ser Gly
        195                 200                 205

Ala Leu Glu Asn Ile Gly Phe Thr Thr Arg Glu Ile Met Lys Met Ser
    210                 215                 220

Val Tyr Gly Leu Thr Gly Ala
225                 230
```

<210> SEQ ID NO 13
<211> LENGTH: 732
<212> TYPE: DNA
<213> ORGANISM: Synechococcus sp.

<400> SEQUENCE: 13

```
atggccccag cgaacgtcct gcccaacacc cccccgtccc ccactgatgg gggcggcact      60
gccctagact acagcagccc aaggtatcgg caggcctact cccgcatcaa cggtattgtt     120
atcgaaggcg aacaagaagc ccacgacaac tacctcaagc tggccgaaat gctgccggaa     180
gctgcagagg agctgcgcaa gctggccaag atggaattgc gccacatgaa aggcttccag     240
gcctgcggca aaaacctgca ggtggaaccc gatgtggagt ttgcccgcgc ctttttcgcg     300
cccttgcggg acaatttcca aagcgccgca gcggcagggg atctggtctc ctgttttgtc     360
attcagtctt tgatcatcga gtgctttgcc attgccgcct acaacatcta catcccggtt     420
gccgatgact ttgcccgcaa gatcaccgag ggggtagtta aggacgagta tctgcacctc     480
aattttgggg agcgctggct gggcgagcac tttgccgagg ttaaagccca gatcgaagca     540
gccaacgccc aaaatctgcc tctagttcgg cagatgctgc agcaggtaga ggcggatgtg     600
gaagccattt acatggatcg cgaggccatt gtagaagact tcatgatcgc ctacggcgag     660
gccctggcca gcatcggctt caacacccgc gaggtaatgc cctctcggc ccagggtctg     720
cgggccgcct ga                                                        732
```

<210> SEQ ID NO 14
<211> LENGTH: 243
<212> TYPE: PRT
<213> ORGANISM: Synechococcus sp.

<400> SEQUENCE: 14

Met Ala Pro Ala Asn Val Leu Pro Asn Thr Pro Ser Pro Thr Asp
1               5                   10                  15

Gly Gly Gly Thr Ala Leu Asp Tyr Ser Ser Pro Arg Tyr Arg Gln Ala
            20                  25                  30

Tyr Ser Arg Ile Asn Gly Ile Val Ile Glu Gly Glu Gln Glu Ala His
        35                  40                  45

Asp Asn Tyr Leu Lys Leu Ala Glu Met Leu Pro Glu Ala Ala Glu Glu
    50                  55                  60

Leu Arg Lys Leu Ala Lys Met Glu Leu Arg His Met Lys Gly Phe Gln
65                  70                  75                  80

Ala Cys Gly Lys Asn Leu Gln Val Glu Pro Asp Val Glu Phe Ala Arg
                85                  90                  95

Ala Phe Phe Ala Pro Leu Arg Asp Asn Phe Gln Ser Ala Ala Ala Ala
            100                 105                 110

Gly Asp Leu Val Ser Cys Phe Val Ile Gln Ser Leu Ile Ile Glu Cys
        115                 120                 125

Phe Ala Ile Ala Ala Tyr Asn Ile Tyr Ile Pro Val Ala Asp Asp Phe
    130                 135                 140

Ala Arg Lys Ile Thr Glu Gly Val Val Lys Asp Glu Tyr Leu His Leu
145                 150                 155                 160

Asn Phe Gly Glu Arg Trp Leu Gly Glu His Phe Ala Glu Val Lys Ala
                165                 170                 175

Gln Ile Glu Ala Ala Asn Ala Gln Asn Leu Pro Leu Val Arg Gln Met
            180                 185                 190

Leu Gln Gln Val Glu Ala Asp Val Glu Ala Ile Tyr Met Asp Arg Glu

```
                 195                 200                 205
Ala Ile Val Glu Asp Phe Met Ile Ala Tyr Gly Glu Ala Leu Ala Ser
    210                 215                 220

Ile Gly Phe Asn Thr Arg Glu Val Met Arg Leu Ser Ala Gln Gly Leu
225                 230                 235                 240

Arg Ala Ala

<210> SEQ ID NO 15
<211> LENGTH: 708
<212> TYPE: DNA
<213> ORGANISM: Gloeobacter violaceus

<400> SEQUENCE: 15
gtgaaccgaa ccgcaccgtc cagcgccgcg cttgattacc gctccgacac ctaccgcgat     60
gcgtactccc gcatcaatgc catcgtcctt gaaggcgagc gggaagccca cgccaactac    120 cttacccctcg ctgagatgct gccggaccat gccgaggcgc tcaaaaaact ggccgcgatg    180
gaaaatcgcc acttcaaagg cttccagtcc tgcgcccgca acctcgaagt cacgccggac    240
gacccgtttg caaggccta cttcgaacag ctcgacggca actttcagca ggcggcggca    300
gaaggtgacc ttaccacctg catggtcatc caggcactga tcatcgagtg cttcgcaatt    360
gcggcctaca cgtctacat tccggtggcc gacgcgtttg cccgcaaggt gaccgagggc    420
gtcgtcaagg acgagtacac ccacctcaac tttgggcagc agtggctcaa agagcgcttc    480
gtgaccgtgc gcgagggcat cgagcgcgcc aacgcccaga tctgcccat cgtctggcgg    540 atgctcaacg ccgtcgaagc ggacaccgaa gtgctgcaga tggataaaga agcgatcgtc    600 gaagactta tgatcgccta cggtgaagcc ttgggcgaca tcggtttttc gatgcgcgac    660
gtgatgaaga tgtccgcccg cggccttgcc tctgccccc gccagtga               708

<210> SEQ ID NO 16
<211> LENGTH: 235
<212> TYPE: PRT
<213> ORGANISM: Gloeobacter violaceus

<400> SEQUENCE: 16

Met Asn Arg Thr Ala Pro Ser Ser Ala Ala Leu Asp Tyr Arg Ser Asp
1               5                   10                  15

Thr Tyr Arg Asp Ala Tyr Ser Arg Ile Asn Ala Ile Val Leu Glu Gly
                20                  25                  30

Glu Arg Glu Ala His Ala Asn Tyr Leu Thr Leu Ala Glu Met Leu Pro
            35                  40                  45

Asp His Ala Glu Ala Leu Lys Lys Leu Ala Ala Met Glu Asn Arg His
        50                  55                  60

Phe Lys Gly Phe Gln Ser Cys Ala Arg Asn Leu Glu Val Thr Pro Asp
65                  70                  75                  80

Asp Pro Phe Ala Arg Ala Tyr Phe Glu Gln Leu Asp Gly Asn Phe Gln
                85                  90                  95

Gln Ala Ala Ala Glu Gly Asp Leu Thr Thr Cys Met Val Ile Gln Ala
            100                 105                 110

Leu Ile Ile Glu Cys Phe Ala Ile Ala Ala Tyr Asn Val Tyr Ile Pro
        115                 120                 125

Val Ala Asp Ala Phe Ala Arg Lys Val Thr Glu Gly Val Val Lys Asp
    130                 135                 140

Glu Tyr Thr His Leu Asn Phe Gly Gln Gln Trp Leu Lys Glu Arg Phe
145                 150                 155                 160
```

```
Val Thr Val Arg Glu Gly Ile Glu Arg Ala Asn Ala Gln Asn Leu Pro
                165                 170                 175

Ile Val Trp Arg Met Leu Asn Ala Val Glu Ala Asp Thr Glu Val Leu
            180                 185                 190

Gln Met Asp Lys Glu Ala Ile Val Glu Asp Phe Met Ile Ala Tyr Gly
        195                 200                 205

Glu Ala Leu Gly Asp Ile Gly Phe Ser Met Arg Asp Val Met Lys Met
    210                 215                 220

Ser Ala Arg Gly Leu Ala Ser Ala Pro Arg Gln
225                 230                 235

<210> SEQ ID NO 17
<211> LENGTH: 732
<212> TYPE: DNA
<213> ORGANISM: Prochlorococcus marinus

<400> SEQUENCE: 17
atgcctacgc ttgagatgcc tgtggcagct gttcttgaca gcactgttgg atcttcagaa      60
gccctgccag acttcacttc agatagatat aaggatgcat acagcagaat caacgcaata     120
gtcattgagg gcgaacagga agcccatgac aattacatcg cgattggcac gctgcttccc     180
gatcatgtcg aagagctcaa gcggcttgcc aagatggaga tgaggcacaa gaagggcttt     240
acagcttgcg gcaagaacct tggcgttgag gctgacatgg acttcgcaag ggagtttttt     300 gctccttttgc gtgacaactt ccagacagct ttagggcagg ggaaaacacc tacatgcttg     360
ctgatccagg cgctcttgat tgaagccttt gctatttcgg cttatcacac ctatatccct     420
gtttctgacc cctttgctcg caagattact gaaggtgtcg tgaaggacga gtacacacac     480
ctcaattatg gcgaggcttg gctcaaggcc aatctggaga gttgccgtga ggagttgctt     540
gaggccaatc gcgagaacct gcctctgatt cgccggatgc ttgatcaggt agcaggtgat     600
gctgccgtgc tgcagatgga taaggaagat ctgattgagg atttcttaat cgcctaccag     660
gaatctctca ctgagattgg ctttaacact cgtgaaatta cccgtatggc agcggcagct     720
cttgtgagct ga                                                         732

<210> SEQ ID NO 18
<211> LENGTH: 243
<212> TYPE: PRT
<213> ORGANISM: Prochlorococcus marinus

<400> SEQUENCE: 18

Met Pro Thr Leu Glu Met Pro Val Ala Ala Val Leu Asp Ser Thr Val
1               5                   10                  15

Gly Ser Ser Glu Ala Leu Pro Asp Phe Thr Ser Asp Arg Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ala Ile Gly Thr Leu Leu Pro Asp His Val Glu
    50                  55                  60

Glu Leu Lys Arg Leu Ala Lys Met Glu Met Arg His Lys Lys Gly Phe
65                  70                  75                  80

Thr Ala Cys Gly Lys Asn Leu Gly Val Glu Ala Asp Met Asp Phe Ala
                85                  90                  95

Arg Glu Phe Phe Ala Pro Leu Arg Asp Asn Phe Gln Thr Ala Leu Gly
            100                 105                 110

Gln Gly Lys Thr Pro Thr Cys Leu Leu Ile Gln Ala Leu Leu Ile Glu
        115                 120                 125
```

Ala Phe Ala Ile Ser Ala Tyr His Thr Tyr Ile Pro Val Ser Asp Pro
            130                 135                 140

Phe Ala Arg Lys Ile Thr Glu Gly Val Val Lys Asp Glu Tyr Thr His
145                 150                 155                 160

Leu Asn Tyr Gly Glu Ala Trp Leu Lys Ala Asn Leu Glu Ser Cys Arg
                165                 170                 175

Glu Glu Leu Leu Glu Ala Asn Arg Glu Asn Leu Pro Leu Ile Arg Arg
            180                 185                 190

Met Leu Asp Gln Val Ala Gly Asp Ala Ala Val Leu Gln Met Asp Lys
            195                 200                 205

Glu Asp Leu Ile Glu Asp Phe Leu Ile Ala Tyr Gln Glu Ser Leu Thr
210                 215                 220

Glu Ile Gly Phe Asn Thr Arg Glu Ile Thr Arg Met Ala Ala Ala Ala
225                 230                 235                 240

Leu Val Ser

<210> SEQ ID NO 19
<211> LENGTH: 717
<212> TYPE: DNA
<213> ORGANISM: Prochlorococcus marinus

<400> SEQUENCE: 19
atgcaaacac tcgaatctaa taaaaaaact aatctagaaa attctattga tttacccgat     60
tttactactg attcttacaa agacgcttat agcaggataa atgcaatagt tattgaaggt    120
gaacaagagg ctcatgataa ttacatttcc ttagcaacat taattcctaa cgaattagaa    180
gagttaacta aattagcgaa aatggagctt aagcacaaaa gaggctttac tgcatgtgga    240
agaaatctag gtgttcaagc tgacatgatt tttgctaaag aattcttttc caaattacat    300
ggtaattttc aggttgcgtt atctaatggc aagacaacta catgcctatt aatacaggca    360
attttaattg aagcttttgc tatatccgcg tatcacgttt acataagagt tgctgatcct    420
ttcgcgaaaa aaattaccca aggtgttgtt aaagatgaat atcttcattt aaattatgga    480
caagaatggc taaagaaaaa tttagcgact tgtaaagatg agctaatgga agcaaataag    540
gttaaccttc cattaatcaa gaagatgtta gatcaagtct cggaagatgc ttcagtacta    600
gctatggata gggaagaatt aatggaagaa ttcatgattg cctatcagga cactctcctt    660
gaaataggtt tagataatag agaaattgca agaatggcaa tggctgctat agtttaa      717

<210> SEQ ID NO 20
<211> LENGTH: 238
<212> TYPE: PRT
<213> ORGANISM: Prochlorococcus marinus

<400> SEQUENCE: 20

Met Gln Thr Leu Glu Ser Asn Lys Lys Thr Asn Leu Glu Asn Ser Ile
1               5                   10                  15

Asp Leu Pro Asp Phe Thr Thr Asp Ser Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Ala Thr Leu Ile Pro Asn Glu Leu Glu Glu Leu Thr Lys
    50                  55                  60

Leu Ala Lys Met Glu Leu Lys His Lys Arg Gly Phe Thr Ala Cys Gly
65                  70                  75                  80

Arg Asn Leu Gly Val Gln Ala Asp Met Ile Phe Ala Lys Glu Phe Phe

```
              85                  90                  95
Ser Lys Leu His Gly Asn Phe Gln Val Ala Leu Ser Asn Gly Lys Thr
            100                 105                 110

Thr Thr Cys Leu Leu Ile Gln Ala Ile Leu Ile Glu Ala Phe Ala Ile
        115                 120                 125

Ser Ala Tyr His Val Tyr Ile Arg Val Ala Asp Pro Phe Ala Lys Lys
    130                 135                 140

Ile Thr Gln Gly Val Val Lys Asp Glu Tyr Leu His Leu Asn Tyr Gly
145                 150                 155                 160

Gln Glu Trp Leu Lys Glu Asn Leu Ala Thr Cys Lys Asp Glu Leu Met
                165                 170                 175

Glu Ala Asn Lys Val Asn Leu Pro Leu Ile Lys Lys Met Leu Asp Gln
            180                 185                 190

Val Ser Glu Asp Ala Ser Val Leu Ala Met Asp Arg Glu Glu Leu Met
        195                 200                 205

Glu Glu Phe Met Ile Ala Tyr Gln Asp Thr Leu Leu Glu Ile Gly Leu
    210                 215                 220

Asp Asn Arg Glu Ile Ala Arg Met Ala Met Ala Ala Ile Val
225                 230                 235

<210> SEQ ID NO 21
<211> LENGTH: 726
<212> TYPE: DNA
<213> ORGANISM: Prochlorococcus marinus

<400> SEQUENCE: 21
atgcaagctt ttgcatccaa caatttaacc gtagaaaaag aagagctaag ttctaactct      60
cttccagatt tcacctcaga atcttacaaa gatgcttaca gcagaatcaa tgcagttgta     120
attgaagggg agcaagaagc ttattctaat tttcttgatc tcgctaaatt gattcctgaa     180
catgcagatg agcttgtgag gctagggaag atggagaaaa agcatatgaa tggttttgt     240 gcttgcggga gaaatcttgc tgtaaagcct gatatgcctt ttgcaaagac cttttttctca    300 aaactccata taattttttt agaggctttc aaagtaggag atacgactac ctgtctccta    360
attcaatgca tcttgattga atcttttgca atatccgcat atcacgttta tacgtgtt      420 gctgatccat cgccaaaaag aatcacagag ggtgttgtcc aagatgaata cttgcatttg    480
aactatggtc aagaatggct taaggccaat ctagagacag ttaagaaaga tcttatgagg    540
gctaataagg aaaacttgcc tcttataaag tccatgctcg atgaagtttc aaacgacgcc    600
gaagtccttc atatggataa agaagagtta atggaggaat ttatgattgc ttatcaagat    660
tcccttcttg aaataggtct tgataataga gaaattgcaa gaatggctct tgcagcggtg    720
atataa                                                               726

<210> SEQ ID NO 22
<211> LENGTH: 241
<212> TYPE: PRT
<213> ORGANISM: Prochlorococcus marinus

<400> SEQUENCE: 22

Met Gln Ala Phe Ala Ser Asn Asn Leu Thr Val Glu Lys Glu Glu Leu
1               5                   10                  15

Ser Ser Asn Ser Leu Pro Asp Phe Thr Ser Glu Ser Tyr Lys Asp Ala
            20                  25                  30

Tyr Ser Arg Ile Asn Ala Val Val Ile Glu Gly Glu Gln Glu Ala Tyr
        35                  40                  45
```

```
Ser Asn Phe Leu Asp Leu Ala Lys Leu Ile Pro Glu His Ala Asp Glu
 50                  55                  60

Leu Val Arg Leu Gly Lys Met Glu Lys Lys His Met Asn Gly Phe Cys
 65                  70                  75                  80

Ala Cys Gly Arg Asn Leu Ala Val Lys Pro Asp Met Pro Phe Ala Lys
                 85                  90                  95

Thr Phe Phe Ser Lys Leu His Asn Asn Phe Leu Glu Ala Phe Lys Val
            100                 105                 110

Gly Asp Thr Thr Thr Cys Leu Leu Ile Gln Cys Ile Leu Ile Glu Ser
        115                 120                 125

Phe Ala Ile Ser Ala Tyr His Val Tyr Ile Arg Val Ala Asp Pro Phe
    130                 135                 140

Ala Lys Arg Ile Thr Glu Gly Val Val Gln Asp Glu Tyr Leu His Leu
145                 150                 155                 160

Asn Tyr Gly Gln Glu Trp Leu Lys Ala Asn Leu Glu Thr Val Lys Lys
                165                 170                 175

Asp Leu Met Arg Ala Asn Lys Glu Asn Leu Pro Leu Ile Lys Ser Met
            180                 185                 190

Leu Asp Glu Val Ser Asn Asp Ala Glu Val Leu His Met Asp Lys Glu
        195                 200                 205

Glu Leu Met Glu Glu Phe Met Ile Ala Tyr Gln Asp Ser Leu Leu Glu
    210                 215                 220

Ile Gly Leu Asp Asn Arg Glu Ile Ala Arg Met Ala Leu Ala Ala Val
225                 230                 235                 240

Ile

<210> SEQ ID NO 23
<211> LENGTH: 732
<212> TYPE: DNA
<213> ORGANISM: Synechococcus sp.

<400> SEQUENCE: 23
atgccgaccc ttgagacgtc tgaggtcgcc gttcttgaag actcgatggc ttcaggctcc    60
cggctgcctg atttcaccag cgaggcttac aaggacgcct acagccgcat caatgcgatc   120
gtgatcgagg gtgagcagga agcgcacgac aactacatcg ccctcggcac gctgatcccc   180
gagcagaagg atgagctggc ccgtctcgcc cgcatggaga tgaagcacat gaaggggttc   240
acctcctgtg ccgcaatctc ggcgtggag gcagaccttc cctttgctaa ggaattcttc   300
gccccctgc acgggaactt ccaggcagct ctccaggagg caaggtggt gacctgcctg   360
ttgattcagg cgctgctgat tgaagcgttc gccatttccg cctatcacat ctacatcccg   420
gtggcggatc ccttcgctcg caagatcact gaaggtgtgg tgaaggatga gtacacccac   480
ctcaattacg gccaggaatg gctgaaggcc aattttgagg ccagcaagga tgagctgatg   540
gaggccaaca aggccaatct gcctctgatc cgctcgatgc tggagcaggt ggcagccgac   600
gccgccgtgc tgcagatgga aaaggaagat ctgatcgaag atttcctgat cgcttaccag   660
gaggccctct gcgagatcgg tttcagctcc cgtgacattg ctcgcatggc cgccgctgcc   720
ctcgcggtct ga                                                        732

<210> SEQ ID NO 24
<211> LENGTH: 243
<212> TYPE: PRT
<213> ORGANISM: Synechococcus sp.

<400> SEQUENCE: 24
```

```
Met Pro Thr Leu Glu Thr Ser Glu Val Ala Val Leu Glu Asp Ser Met
1               5                   10                  15

Ala Ser Gly Ser Arg Leu Pro Asp Phe Thr Ser Glu Ala Tyr Lys Asp
            20                  25                  30

Ala Tyr Ser Arg Ile Asn Ala Ile Val Ile Glu Gly Glu Gln Glu Ala
            35                  40                  45

His Asp Asn Tyr Ile Ala Leu Gly Thr Leu Ile Pro Glu Gln Lys Asp
        50                  55                  60

Glu Leu Ala Arg Leu Ala Arg Met Glu Met Lys His Met Lys Gly Phe
65                  70                  75                  80

Thr Ser Cys Gly Arg Asn Leu Gly Val Glu Ala Asp Leu Pro Phe Ala
            85                  90                  95

Lys Glu Phe Phe Ala Pro Leu His Gly Asn Phe Gln Ala Ala Leu Gln
            100                 105                 110

Glu Gly Lys Val Val Thr Cys Leu Leu Ile Gln Ala Leu Leu Ile Glu
            115                 120                 125

Ala Phe Ala Ile Ser Ala Tyr His Ile Tyr Ile Pro Val Ala Asp Pro
        130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Glu Ala Ser Lys
            165                 170                 175

Asp Glu Leu Met Glu Ala Asn Lys Ala Asn Leu Pro Leu Ile Arg Ser
            180                 185                 190

Met Leu Glu Gln Val Ala Ala Asp Ala Ala Val Leu Gln Met Glu Lys
            195                 200                 205

Glu Asp Leu Ile Glu Asp Phe Leu Ile Ala Tyr Gln Glu Ala Leu Cys
210                 215                 220

Glu Ile Gly Phe Ser Ser Arg Asp Ile Ala Arg Met Ala Ala Ala Ala
225                 230                 235                 240

Leu Ala Val
```

<210> SEQ ID NO 25
<211> LENGTH: 681
<212> TYPE: DNA
<213> ORGANISM: Synechococcus sp.

<400> SEQUENCE: 25

| | | | | | |
|---|---|---|---|---|---|
| atgacccagc | tcgactttgc | cagtgcggcc | taccgcgagg | cctacagccg | gatcaacggc | 60 |
| gttgtgattg | tgggcgaagg | tctcgccaat | cgccatttcc | agatgttggc | gcggcgcatt | 120 |
| cccgctgatc | gcgacgagct | gcagcggctc | ggacgcatgg | agggagacca | tgccagcgcc | 180 |
| tttgtgggct | gtggtcgcaa | cctcggtgtg | gtggccgatc | tgccctggc | ccggcgcctg | 240 |
| tttcagcccc | tccatgatct | gttcaaacgc | cacgaccacg | acggcaatcg | ggccgaatgc | 300 |
| ctggtgatcc | aggggttgat | cgtggaatgt | tcgccgtgg | cggcttaccg | ccactacctg | 360 |
| ccggtggccg | atgcctacgc | ccggccgatc | accgcagcgg | tgatgaacga | tgaatcggaa | 420 |
| cacctcgact | acgctgagac | ctggctgcag | cgccatttcg | atcaggtgaa | ggcccgggtc | 480 |
| agcgcggtgg | tggtggaggc | gttgccgctc | accctggcga | tgttgcaatc | gcttgctgca | 540 |
| gacatgcgac | agatcggcat | ggatccggtg | gagaccctgg | ccagcttcag | tgaactgttt | 600 |
| cgggaagcgt | tggaatcggt | ggggtttgag | gctgtggagg | ccaggcgact | gctgatgcga | 660 |
| gcggccgccc | ggatggtctg | a | | | | 681 |

<210> SEQ ID NO 26
<211> LENGTH: 226
<212> TYPE: PRT
<213> ORGANISM: Synechococcus sp.

<400> SEQUENCE: 26

Met Thr Gln Leu Asp Phe Ala Ser Ala Ala Tyr Arg Glu Ala Tyr Ser
1               5                   10                  15

Arg Ile Asn Gly Val Val Ile Val Gly Glu Gly Leu Ala Asn Arg His
            20                  25                  30

Phe Gln Met Leu Ala Arg Arg Ile Pro Ala Asp Arg Asp Glu Leu Gln
        35                  40                  45

Arg Leu Gly Arg Met Glu Gly Asp His Ala Ser Ala Phe Val Gly Cys
    50                  55                  60

Gly Arg Asn Leu Gly Val Val Ala Asp Leu Pro Leu Ala Arg Arg Leu
65                  70                  75                  80

Phe Gln Pro Leu His Asp Leu Phe Lys Arg His Asp His Asp Gly Asn
                85                  90                  95

Arg Ala Glu Cys Leu Val Ile Gln Gly Leu Ile Val Glu Cys Phe Ala
            100                 105                 110

Val Ala Ala Tyr Arg His Tyr Leu Pro Val Ala Asp Ala Tyr Ala Arg
        115                 120                 125

Pro Ile Thr Ala Ala Val Met Asn Asp Glu Ser Glu His Leu Asp Tyr
    130                 135                 140

Ala Glu Thr Trp Leu Gln Arg His Phe Asp Gln Val Lys Ala Arg Val
145                 150                 155                 160

Ser Ala Val Val Glu Ala Leu Pro Leu Thr Leu Ala Met Leu Gln
                165                 170                 175

Ser Leu Ala Ala Asp Met Arg Gln Ile Gly Met Asp Pro Val Glu Thr
            180                 185                 190

Leu Ala Ser Phe Ser Glu Leu Phe Arg Glu Ala Leu Glu Ser Val Gly
        195                 200                 205

Phe Glu Ala Val Glu Ala Arg Arg Leu Leu Met Arg Ala Ala Ala Arg
    210                 215                 220

Met Val
225

<210> SEQ ID NO 27
<211> LENGTH: 696
<212> TYPE: DNA
<213> ORGANISM: Cyanothece sp.

<400> SEQUENCE: 27
atgcaagagc ttgctttacg ctcagagctt gattttaaca gcgaaaccta taaagatgct      60
tacagtcgca tcaatgctat tgtcattgaa ggggaacaag aagcctatca aaattatctt     120
gatatggcgc aacttctccc agaagacgag gctgagttaa ttcgtctctc caagatggaa     180
aaccgtcaca aaaaaggctt tcaagcctgt ggcaagaatt tgaatgtgac cccagatatg     240
gactacgctc aacaatttttt tgctgaactt catggcaact tccaaaaggc aaaagccgaa     300
ggcaaaattg tcacttgctt attaattcaa tctttgatca tcgaagcctt tgcgatcgcc     360
gcttataata tttatattcc tgtggcagat ccctttgctc gtaaaatcac cgaagggta      420 gttaaggatg aatataccca cctcaatttt ggggaagtct ggttaaaaga gcattttgaa     480
gcctctaaag cagaattaga agacgcaaat aaagaaaatt tacccttgt ttggcaaatg      540 ctcaaccaag ttgaaaaaga tgccgaagtg ttagggatgg agaaagaagc cttagtggaa     600

```
gatttcatga ttagttatgg agaagcttta agtaatattg gtttctctac ccgtgagatc    660
atgaaaatgt ctgcttacgg gctacgggct gcttaa                              696
```

<210> SEQ ID NO 28
<211> LENGTH: 231
<212> TYPE: PRT
<213> ORGANISM: Cyanothece sp.

<400> SEQUENCE: 28

```
Met Gln Glu Leu Ala Leu Arg Ser Glu Leu Asp Phe Asn Ser Glu Thr
1               5                   10                  15

Tyr Lys Asp Ala Tyr Ser Arg Ile Asn Ala Ile Val Ile Glu Gly Glu
            20                  25                  30

Gln Glu Ala Tyr Gln Asn Tyr Leu Asp Met Ala Gln Leu Leu Pro Glu
        35                  40                  45

Asp Glu Ala Glu Leu Ile Arg Leu Ser Lys Met Glu Asn Arg His Lys
    50                  55                  60

Lys Gly Phe Gln Ala Cys Gly Lys Asn Leu Asn Val Thr Pro Asp Met
65                  70                  75                  80

Asp Tyr Ala Gln Gln Phe Phe Ala Glu Leu His Gly Asn Phe Gln Lys
                85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Thr His Leu Asn Phe Gly Glu Val Trp Leu Lys Glu His Phe Glu
145                 150                 155                 160

Ala Ser Lys Ala Glu Leu Glu Asp Ala Asn Lys Glu Asn Leu Pro Leu
                165                 170                 175

Val Trp Gln Met Leu Asn Gln Val Glu Lys Asp Ala Glu Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Lys Met Ser
    210                 215                 220

Ala Tyr Gly Leu Arg Ala Ala
225                 230
```

<210> SEQ ID NO 29
<211> LENGTH: 696
<212> TYPE: DNA
<213> ORGANISM: Cyanothece sp.

<400> SEQUENCE: 29

```
atgcctcaag tgcagtcccc atcggctata gacttctaca gtgagaccta ccaggatgct    60
tacagccgca ttgatgcgat cgtgatcgag ggagaacagg aagcccacga caattacctg   120
aagctgacgg aactgctgcc ggattgtcaa gaagatctgg tccggctggc caaaatggaa   180
gcccgtcaca aaaagggtt tgaagcttgt ggccgcaatc tcaaggtcac acccgatatg   240
gagtttgctc aacagttctt tgctgacctg cacaacaatt ccagaaagc tgctgcggcc   300 aacaaaattg ccacctgtct ggtgatccag gccctgatta ttgagtgctt tgccatcgcc   360
gcttataaca tctatattcc tgtcgctgat gactttgccc gcaaaattac cgaaaacgtg   420
gtcaaagacg aatacaccca cctcaacttt ggtgaagagt ggctcaaagc taactttgat   480
```

```
agccagcggg aagaagtgga agcggccaac cgggaaaacc tgccgatcgt ctggcggatg      540
ctcaatcagg tagagactga tgctcacgtt ttaggtatgg aaaaagaggc tttagtggaa      600
agcttcatga tccaatatgg tgaagccctg gaaaatattg gtttctcgac ccgtgagatc      660
atgcgcatgt ccgtttacgg cctctctgcg gcataa                                696
```

<210> SEQ ID NO 30
<211> LENGTH: 231
<212> TYPE: PRT
<213> ORGANISM: Cyanothece sp.

<400> SEQUENCE: 30

```
Met Pro Gln Val Gln Ser Pro Ser Ala Ile Asp Phe Tyr Ser Glu Thr
1               5                   10                  15

Tyr Gln Asp Ala Tyr Ser Arg Ile Asp Ala Ile Val Ile Glu Gly Glu
                20                  25                  30

Gln Glu Ala His Asp Asn Tyr Leu Lys Leu Thr Glu Leu Leu Pro Asp
            35                  40                  45

Cys Gln Glu Asp Leu Val Arg Leu Ala Lys Met Glu Ala Arg His Lys
        50                  55                  60

Lys Gly Phe Glu Ala Cys Gly Arg Asn Leu Lys Val Thr Pro Asp Met
65                  70                  75                  80

Glu Phe Ala Gln Gln Phe Phe Ala Asp Leu His Asn Asn Phe Gln Lys
                85                  90                  95

Ala Ala Ala Ala Asn Lys Ile Ala Thr Cys Leu Val Ile Gln Ala Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Asn Val Val Lys Asp Glu
    130                 135                 140

Tyr Thr His Leu Asn Phe Gly Glu Glu Trp Leu Lys Ala Asn Phe Asp
145                 150                 155                 160

Ser Gln Arg Glu Glu Val Glu Ala Ala Asn Arg Glu Asn Leu Pro Ile
                165                 170                 175

Val Trp Arg Met Leu Asn Gln Val Glu Thr Asp Ala His Val Leu Gly
            180                 185                 190

Met Glu Lys Glu Ala Leu Val Glu Ser Phe Met Ile Gln Tyr Gly Glu
        195                 200                 205

Ala Leu Glu Asn Ile Gly Phe Ser Thr Arg Glu Ile Met Arg Met Ser
    210                 215                 220

Val Tyr Gly Leu Ser Ala Ala
225                 230
```

<210> SEQ ID NO 31
<211> LENGTH: 702
<212> TYPE: DNA
<213> ORGANISM: Cyanothece sp.

<400> SEQUENCE: 31

```
atgtctgatt gcgccacgaa cccagccctc gactattaca gtgaaaccta ccgcaatgct      60
taccggcggg tgaacggtat tgtgattgaa ggcgagaagc aagcctacga caactttatc     120
cgcttagctg agctgctccc agagtatcaa gcggaattaa cccgtctggc taaaatggaa     180
gcccgccacc agaagagctt tgttgcctgt ggcaaaatc tcaaggttag cccggactta      240
gactttgcgg cacagttttt tgctgaactg catcaaattt ttgcatctgc agcaaatgcg     300
```

```
ggccaggtgg ctacctgtct ggttgtgcaa gccctgatca ttgaatgctt tgcgatcgcc    360
gcctacaata cctatttgcc agtagcggat gaatttgccc gtaaagtcac cgcatccgtt    420
gttcaggacg agtacagcca cctaaacttt ggtgaagtct ggctgcagaa tgcgtttgag    480
cagtgtaaag acgaaattat cacagctaac cgtcttgctc tgccgctgat ctggaaaatg    540
ctcaaccagg tgacaggcga attgcgcatt ctgggcatgg acaaagcttc tctggtagaa    600
gactttagca ctcgctatgg agaggccctg ggccagattg gtttcaaact atctgaaatt    660
ctctccctgt ccgttcaggg tttacaggcg gttacgcctt ag                      702
```

```
<210> SEQ ID NO 32
<211> LENGTH: 233
<212> TYPE: PRT
<213> ORGANISM: Cyanothece sp.

<400> SEQUENCE: 32
```

```
Met Ser Asp Cys Ala Thr Asn Pro Ala Leu Asp Tyr Tyr Ser Glu Thr
1               5                   10                  15

Tyr Arg Asn Ala Tyr Arg Arg Val Asn Gly Ile Val Ile Glu Gly Glu
            20                  25                  30

Lys Gln Ala Tyr Asp Asn Phe Ile Arg Leu Ala Glu Leu Leu Pro Glu
        35                  40                  45

Tyr Gln Ala Glu Leu Thr Arg Leu Ala Lys Met Glu Ala Arg His Gln
    50                  55                  60

Lys Ser Phe Val Ala Cys Gly Gln Asn Leu Lys Val Ser Pro Asp Leu
65                  70                  75                  80

Asp Phe Ala Ala Gln Phe Phe Ala Glu Leu His Gln Ile Phe Ala Ser
                85                  90                  95

Ala Ala Asn Ala Gly Gln Val Ala Thr Cys Leu Val Val Gln Ala Leu
            100                 105                 110

Ile Ile Glu Cys Phe Ala Ile Ala Ala Tyr Asn Thr Tyr Leu Pro Val
        115                 120                 125

Ala Asp Glu Phe Ala Arg Lys Val Thr Ala Ser Val Val Gln Asp Glu
    130                 135                 140

Tyr Ser His Leu Asn Phe Gly Glu Val Trp Leu Gln Asn Ala Phe Glu
145                 150                 155                 160

Gln Cys Lys Asp Glu Ile Ile Thr Ala Asn Arg Leu Ala Leu Pro Leu
                165                 170                 175

Ile Trp Lys Met Leu Asn Gln Val Thr Gly Glu Leu Arg Ile Leu Gly
            180                 185                 190

Met Asp Lys Ala Ser Leu Val Glu Asp Phe Ser Thr Arg Tyr Gly Glu
        195                 200                 205

Ala Leu Gly Gln Ile Gly Phe Lys Leu Ser Glu Ile Leu Ser Leu Ser
    210                 215                 220

Val Gln Gly Leu Gln Ala Val Thr Pro
225                 230
```

```
<210> SEQ ID NO 33
<211> LENGTH: 696
<212> TYPE: DNA
<213> ORGANISM: Anabaena variabilis

<400> SEQUENCE: 33
atgcagcagg ttgcagccga tttagaaatc gatttcaaga gcgaaaaata taaagatgcc     60
tatagtcgca taaatgcgat cgtgattgaa ggggaacaag aagcatatga gaattacatt    120
caactatccc aactgctgcc agacgataaa gaagacctaa ttcgcctctc gaaaatggaa    180
```

```
agtcgccaca aaaaaggatt tgaagcttgt ggacggaacc tgcaagtatc cccagacata    240
gagttcgcta agaattcttt tgccgggcta cacggtaatt tccaaaaagc ggcagctgaa    300
ggtaaagttg tcacttgcct attgattcaa tccctgatta ttgaatgttt tgcgatcgcc    360
gcatacaata tctacatccc cgtggctgac gatttcgccc gtaaaatcac tgagggtgta    420
gttaaagatg aatacagtca cctcaacttc ggcgaagttt ggttacagaa aaatttcgct    480
caatcaaaag cagaactaga agaagctaat cgtcataatc ttcccatagt ctggaaaatg    540
ctcaatcaag ttgccgatga tgcggcagtc ttagctatgg aaaaagaagc cctagtggaa    600
gattttatga ttcagtacgg cgaagcacta agtaatattg gcttcacaac cagagatatt    660
atgcggatgt cagcctacgg actcacagca gcttaa                               696
```

<210> SEQ ID NO 34
<211> LENGTH: 231
<212> TYPE: PRT
<213> ORGANISM: Anabaena variabilis

<400> SEQUENCE: 34

```
Met Gln Gln Val Ala Ala Asp Leu Glu Ile Asp Phe Lys Ser Glu Lys
1               5                   10                  15

Tyr Lys Asp Ala Tyr Ser Arg Ile Asn Ala Ile Val Ile Glu Gly Glu
            20                  25                  30

Gln Glu Ala Tyr Glu Asn Tyr Ile Gln Leu Ser Gln Leu Leu Pro Asp
        35                  40                  45

Asp Lys Glu Asp Leu Ile Arg Leu Ser Lys Met Glu Ser Arg His Lys
    50                  55                  60

Lys Gly Phe Glu Ala Cys Gly Arg Asn Leu Gln Val Ser Pro Asp Ile
65                  70                  75                  80

Glu Phe Ala Lys Glu Phe Phe Ala Gly Leu His Gly Asn Phe Gln Lys
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Ser His Leu Asn Phe Gly Glu Val Trp Leu Gln Lys Asn Phe Ala
145                 150                 155                 160

Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Ala Val Leu Ala
            180                 185                 190

Met Glu Lys Glu Ala Leu Val Glu Asp Phe Met Ile Gln Tyr Gly Glu
        195                 200                 205

Ala Leu Ser Asn Ile Gly Phe Thr Thr Arg Asp Ile Met Arg Met Ser
    210                 215                 220

Ala Tyr Gly Leu Thr Ala Ala
225                 230
```

<210> SEQ ID NO 35
<211> LENGTH: 765
<212> TYPE: DNA
<213> ORGANISM: Synechococcus elongatus

<400> SEQUENCE: 35

```
gtgcgtaccc cctgggatcc accaaatccc acattctccc tctcatccgt gtcaggagac    60
cgcagactca tgccgcagct tgaagccagc cttgaactgg actttcaaag cgagtcctac   120
aaagacgctt acagccgcat caacgcgatc gtgattgaag cgaacaaga ggcgttcgac    180 aactacaatc gccttgctga gatgctgccc gaccagcggg atgagcttca caagctagcc   240
aagatggaac agcgccacat gaaaggcttt atggcctgtg gcaaaaatct ctccgtcact   300
cctgacatgg gttttgccca gaaattttc gagcgcttgc acgagaactt caaagcggcg   360
gctgcggaag gcaaggtcgt cacctgccta ctgattcaat cgctaatcat cgagtgcttt   420
gcgatcgcgg cttacaacat ctacatccca gtggcggatg cttttgcccg caaaatcacg   480
gagggggtcg tgcgcgacga atacctgcac cgcaacttcg gtgaagagtg gctgaaggcg   540
aattttgatg cttccaaagc cgaactggaa gaagccaatc gtcagaacct gcccttggtt   600
tggctaatgc tcaacgaagt ggccgatgat gctcgcgaac tcgggatgga gcgtgagtcg   660
ctcgtcgagg actttatgat tgcctacggt gaagctctgg aaaacatcgg cttcacaacg   720
cgcgaaatca tgcgtatgtc cgcctatggc cttgcggccg tttga                   765
```

<210> SEQ ID NO 36
<211> LENGTH: 254
<212> TYPE: PRT
<213> ORGANISM: Synechococcus elongatus

<400> SEQUENCE: 36

```
Met Arg Thr Pro Trp Asp Pro Pro Asn Pro Thr Phe Ser Leu Ser Ser
1               5                   10                  15

Val Ser Gly Asp Arg Arg Leu Met Pro Gln Leu Glu Ala Ser Leu Glu
            20                  25                  30

Leu Asp Phe Gln Ser Glu Ser Tyr Lys Asp Ala Tyr Ser Arg Ile Asn
        35                  40                  45

Ala Ile Val Ile Glu Gly Glu Gln Ala Phe Asp Asn Tyr Asn Arg
    50                  55                  60

Leu Ala Glu Met Leu Pro Asp Gln Arg Asp Glu Leu His Lys Leu Ala
65                  70                  75                  80

Lys Met Glu Gln Arg His Met Lys Gly Phe Met Ala Cys Gly Lys Asn
                85                  90                  95

Leu Ser Val Thr Pro Asp Met Gly Phe Ala Gln Lys Phe Phe Glu Arg
            100                 105                 110

Leu His Glu Asn Phe Lys Ala Ala Ala Ala Glu Gly Lys Val Val Thr
        115                 120                 125

Cys Leu Leu Ile Gln Ser Leu Ile Ile Glu Cys Phe Ala Ile Ala Ala
    130                 135                 140

Tyr Asn Ile Tyr Ile Pro Val Ala Asp Ala Phe Ala Arg Lys Ile Thr
145                 150                 155                 160

Glu Gly Val Val Arg Asp Glu Tyr Leu His Arg Asn Phe Gly Glu Glu
                165                 170                 175

Trp Leu Lys Ala Asn Phe Asp Ala Ser Lys Ala Glu Leu Glu Glu Ala
            180                 185                 190

Asn Arg Gln Asn Leu Pro Leu Val Trp Leu Met Leu Asn Glu Val Ala
        195                 200                 205

Asp Asp Ala Arg Glu Leu Gly Met Glu Arg Glu Ser Leu Val Glu Asp
    210                 215                 220

Phe Met Ile Ala Tyr Gly Glu Ala Leu Glu Asn Ile Gly Phe Thr Thr
225                 230                 235                 240

Arg Glu Ile Met Arg Met Ser Ala Tyr Gly Leu Ala Ala Val
                245                 250
```

245        250

```
<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (17)..(18)
<223> OTHER INFORMATION: Any amino acid

<400> SEQUENCE: 37

Tyr Xaa Xaa Ala Tyr Xaa Arg Xaa Xaa Xaa Xaa Val Xaa Xaa Gly Glu
1               5                   10                  15

Xaa Xaa Ala

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid

<400> SEQUENCE: 38

Leu Xaa Xaa Met Glu Xaa Xaa His Xaa Xaa Xaa Phe Xaa Xaa Cys
1               5                   10                  15

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
```

```
<220> FEATURE:
<221> NAME/KEY: MOD_RES
<222> LOCATION: (6)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 39

Cys Xaa Xaa Xaa Gln Xaa Xaa Xaa Xaa Glu Xaa Phe Ala Xaa Xaa Ala
1               5                   10                  15

Tyr

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(17)
<223> OTHER INFORMATION: Any amino acid

<400> SEQUENCE: 40

Thr Xaa Xaa Val Xaa Xaa Xaa Glu Xaa Xaa His Xaa Xaa Xaa Xaa Xaa
1               5                   10                  15

Xaa Trp Leu

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Arg or Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Ser or Arg
<220> FEATURE:
<221> NAME/KEY: MOD_RES
<222> LOCATION: (8)..(8)
<223> OTHER INFORMATION: Ile or Val
<220> FEATURE:
<221> NAME/KEY: MOD_RES
<222> LOCATION: (9)..(9)
<223> OTHER INFORMATION: Asp or Asn
```

```
<220> FEATURE:
<221> NAME/KEY: MOD_RES
<222> LOCATION: (10)..(10)
<223> OTHER INFORMATION: Gly or Ala
<220> FEATURE:
<221> NAME/KEY: MOD_RES
<222> LOCATION: (11)..(11)
<223> OTHER INFORMATION: Val or Ile
<220> FEATURE:
<221> NAME/KEY: MOD_RES
<222> LOCATION: (13)..(13)
<223> OTHER INFORMATION: Ile or Leu
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(21)
<223> OTHER INFORMATION: Any amino acid
<220> FEATURE:
<221> NAME/KEY: MOD_RES
<222> LOCATION: (22)..(22)
<223> OTHER INFORMATION: Asn or His
<220> FEATURE:
<221> NAME/KEY: MOD_RES
<222> LOCATION: (23)..(23)
<223> OTHER INFORMATION: Tyr or Phe

<400> SEQUENCE: 41

Tyr Xaa Xaa Ala Tyr Xaa Arg Xaa Xaa Xaa Xaa Val Xaa Xaa Gly Glu
1               5                   10                  15

Xaa Xaa Ala Xaa Xaa Xaa Xaa
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala, Ser or Gly
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Arg, Asp or Lys
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Ala, Ser or Gly
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
```

```
<223> OTHER INFORMATION: Ala, Ser or Gly
<220> FEATURE:
<221> NAME/KEY: MOD_RES
<222> LOCATION: (16)..(16)
<223> OTHER INFORMATION: Ala or Gly
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (21)..(21)
<223> OTHER INFORMATION: Val or Ile

<400> SEQUENCE: 42

Leu Xaa Xaa Met Glu Xaa Xaa His Xaa Xaa Xaa Phe Xaa Xaa Cys Xaa
1               5                   10                  15

Xaa Asn Leu Xaa Xaa
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu, Met or Phe
<220> FEATURE:
<221> NAME/KEY: MOD_RES
<222> LOCATION: (3)..(3)
<223> OTHER INFORMATION: Val or Leu
<220> FEATURE:
<221> NAME/KEY: MOD_RES
<222> LOCATION: (4)..(4)
<223> OTHER INFORMATION: Ile or Val
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (8)..(8)
<223> OTHER INFORMATION: Ile, Leu or Met
<220> FEATURE:
<221> NAME/KEY: MOD_RES
<222> LOCATION: (9)..(9)
<223> OTHER INFORMATION: Ile or Val
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(14)
<223> OTHER INFORMATION: Ile or Val
<220> FEATURE:
<221> NAME/KEY: MOD_RES
<222> LOCATION: (15)..(15)
<223> OTHER INFORMATION: Ala or Ser
<220> FEATURE:
<221> NAME/KEY: MOD_RES
<222> LOCATION: (18)..(18)
<223> OTHER INFORMATION: Asn, His or Arg
<220> FEATURE:
<221> NAME/KEY: MOD_RES
```

```
<222> LOCATION: (19)..(19)
<223> OTHER INFORMATION: Any amino acid
<220> FEATURE:
<221> NAME/KEY: MOD_RES
<222> LOCATION: (21)..(21)
<223> OTHER INFORMATION: Ile or Leu

<400> SEQUENCE: 43

Cys Xaa Xaa Xaa Gln Xaa Xaa Xaa Xaa Glu Xaa Phe Ala Xaa Xaa Ala
1               5                   10                  15

Tyr Xaa Xaa Tyr Xaa
            20

<210> SEQ ID NO 44
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Phe or Tyr
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Ile or Val
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(12)
<223> OTHER INFORMATION: Val or Met
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Asp or Glu
<220> FEATURE:
<221> NAME/KEY: MOD_RES
<222> LOCATION: (16)..(16)
<223> OTHER INFORMATION: Tyr or Ser
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(19)
<223> OTHER INFORMATION: Leu or Arg
<220> FEATURE:
<221> NAME/KEY: MOD_RES
<222> LOCATION: (20)..(20)
<223> OTHER INFORMATION: Asn or Asp
<220> FEATURE:
<221> NAME/KEY: MOD_RES
<222> LOCATION: (21)..(21)
<223> OTHER INFORMATION: Tyr or Phe
<220> FEATURE:
```

```
<221> NAME/KEY: MOD_RES
<222> LOCATION: (22)..(22)
<223> OTHER INFORMATION: Ala or Gly
<220> FEATURE:
<221> NAME/KEY: MOD_RES
<222> LOCATION: (23)..(23)
<223> OTHER INFORMATION: Glu or Gln
<220> FEATURE:
<221> NAME/KEY: MOD_RES
<222> LOCATION: (24)..(24)
<223> OTHER INFORMATION: Any amino acid

<400> SEQUENCE: 44

Asp Xaa Xaa Ala Xaa Xaa Xaa Thr Xaa Xaa Val Xaa Xaa Xaa Glu Xaa
1               5                   10                  15

Xaa His Xaa Xaa Xaa Xaa Xaa Xaa Trp Leu
            20                  25

<210> SEQ ID NO 45
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atgcagcaac tgacggatca gagcaaagaa ctggacttca aaagcgaaac ctacaaggac      60
gcgtattctc gtatcaacgc tatcgttatc gagggtgaac aagaagcgca cgagaattac     120
attaccctgg cgcagctgct gcctgaatcc acgatgaac tgattcgtct gagcaaaatg      180
gagtcgcgtc acaaaaaggg ttttgaggcc tgcggtcgta acctggcggt cactccggac    240
ctgcagttcg ctaaggagtt cttcagcggc ctgcatcaaa actttcagac ggcagcggcg    300
gaaggtaagg ttgtcacctg cctgctgatt caaagcctga tcattgagtg tttcgctatc    360
gcagcctata acatttacat cccggtggcg gacgattttg cacgcaagat cactgagggt    420
gtggttaaag aagaatacag ccacctgaac ttcggtgagg tctggttgaa ggagcacttt    480
gcggaaagca aggcggagct ggaattggca atcgtcaaa acctgccgat cgtgtggaaa     540
atgctgaatc aagtggaggg tgatgcacac acgatggcta tggaaaaaga cgctctggtg    600
gaggacttca tgatccagta cggcgaggcg ctgagcaaca ttggctttag cacccgtgac    660
attatgcgcc tgagcgcgta tggcctgatc ggtgcgtaa                            699

<210> SEQ ID NO 46
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atgccgcaaa cgcaagctat tagcgaaatt gatttctatt ctgacaccta aggacgct       60 tactctcgta tcgatggtat cgtgatcgag ggtgagcaag aggcgcatga gaactacatt    120
cgtctgggtg aaatgttgcc tgagcatcaa gacgacttta ccgtttgag caagatggag     180 gcccgtcaca gaagggcttt gaggcttgt ggtcgtaact gaaggtgac ttgcgatctg      240 gacttcgcgc gtcgcttctt ctcggacctg cacaagaact tccaagatgc tgcggccgag    300
gataaagttc cgacctgctt ggttattcag tccctgatca tcgaatgctt cgcgattgca    360
gcgtataaca tttacatccc ggttgccgat gatttcgctc gtaagattac cgagagcgtc    420
```

```
gtcaaggacg aataccagca tctgaactat ggcgaggagt ggctgaaggc ccatttcgac      480
gacgtgaagg ccgagatcca ggaagcaaat cgcaagaatc tgccgatcgt tggcgtatg      540 ctgaacgagg ttgacaagga cgcagcagtg ctgggcatgg agaaggaagc gttggttgaa      600
gacttcatga ttcaatacgg tgaggccctg tccaacattg cttttctac cggcgagatc      660 atgcgtatgt ctgcgtacgg tctggtggca gcctaa                                696
```

<210> SEQ ID NO 47
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgaccaccg cgaccgcaac gccggtgctg gactatcaca gcgaccgcta caaggacgca      60
tacagccgca tcaacgcgat tgtcatcgaa ggtgaacaag aggcccacga caattacatt     120
gatctggcta aactgctgcc tcaacaccaa gaagagctga cccgtctggc gaagatggag     180
gcccgccaca gaagggtttt tgaagcgtgc ggtcgcaatc tgtccgttac cccggatatg     240
gagttcgcga aagcgttctt tgagaagctg cgcgcgaact ttcagcgtgc cctggcggag     300
ggtaagaccg caacctgtct gctgatccag gcgttgatca ttgaatcctt cgcaattgcc     360
gcgtacaaca tttacatccc tatggccgat ccgtttgcgc gcaagattac cgaaagcgtc     420
gtcaaggatg aatactctca cttgaacttt ggcgaaatct ggttgaagga catttcgag     480 agcgtcaagg gcgagttgga ggaagctaac cgtgcgaatc tgccgctggt ttggaagatg     540
ttgaatcagg tcgaggcaga cgcaaaggtc ctgggcatgg agaaggatgc tctggtggaa     600
gactttatga tccagtactc cggtgcgctg gagaacatcg gctttaccac ccgtgaaatc     660
atgaaaatgt ctgtgtatgg cctgaccggc gcgtaa                                696
```

<210> SEQ ID NO 48
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
atggcgcctg caaacgtgct gccaaatacg ccgccgagcc cgaccgatgg tggtggtacg      60
gccctggact acagctctcc gcgttaccgt caggcgtaca gccgtatcaa tggcattgtt     120
atcgaaggcg agcaggaagc gcacgataac tacctgaagt tggcggagat gctgcctgag     180
gctgccgagg aactgcgtaa gctggcaaag atggaattgc gtcacatgaa gggctttcag     240
gcttgcggca agaacttgca ggtggagcct gacgtcgagt ttgcccgcgc tttcttcgcg     300
ccgctgcgcg acaacttcca atccgcagca gcggccggtg atctggtttc ctgtttcgtc     360
atccaaagcc tgatcatcga gtgttttgcg atcgctgcgt ataacattta catcccggtt     420
gcagacgact cgcccgtaa gatcacggag ggcgtggtta aggacgagta tctgcatctg     480
aatttcggcg agcgttggtt gggtgaacac ttcgcagagg ttaaagcaca gatcgaggca     540
gccaatgccc agaacctgcc gctggtgcgc caaatgctgc agcaagttga ggcggacgtc     600
gaggcaatct atatggaccg tgaggcgatc gttgaggatt tcatgattgc ttatggcgaa     660
gcgctggcaa gcattggctt caacacgcgc gaagtgatgc gtctgagcgc acagggcttg     720
```

-continued cgtgcagcat aa                                                     732

<210> SEQ ID NO 49
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgccgacgt tggagatgcc ggtcgctgcg gtcctggaca gcacggtcgg tagctctgag    60
gcgctgccgg actttaccag cgaccgctac aaagacgctt attcgcgtat caacgcgatt   120
gtgatcgagg gtgaacaaga agcccacgac aactacatcg caattggcac cctgttgccg   180
gaccatgtgg aagaactgaa acgtctggcg aaaatggaaa tgcgtcacaa gaaaggtttc   240
accgcgtgcg gtaagaactt gggtgtggaa gccgatatgg acttcgcccg tgagttcttt   300
gccccgttgc gcgacaactt tcaaaccgcg ctgggtcaag caagacccc tacgtgtctg    360 ttgatccaag cgctgctgat gaagcgttc gcgatctcgg cctaccacac ttacattccg    420
gttagcgatc cgttcgcacg taagatcact gaaggtgtcg ttaaggacga atacacccat   480
ctgaactacg gtgaggcatg gctgaaggcg aatctggaga gctgccgcga ggaactgctg    540
gaagcgaacc gtgagaatct gccgctgatc cgccgcatgc tggatcaggt cgcgggcgac    600
gcggcagtcc tgcagatgga taaggaagac ctgatcgaag acttcctgat tgcttaccaa    660
gagagcttga ctgagatcgg ctttaacacg cgtgaaatca cccgtatggc cgcagcggcg   720
ctggtcagct aa                                                      732

<210> SEQ ID NO 50
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atgcaaaccc tggagagcaa caagaaaacc aacctggaaa acagcattga cctgccagat    60
ttcacgacgg acagctacaa ggatgcgtat tcccgtatca atgctatcgt cattgaaggt   120
gaacaggaag cccatgacaa ctatatcagc ctggccaccc tgatcccgaa tgaactggag    180
gaattgacca aactggccaa gatggagctg aaacacaaac gtggctttac ggcatgcggt    240
cgcaatctgg gtgttcaggc cgatatgatc tttgcgaaag agttttttctc taagctgcac    300 ggcaacttcc aagttgcgct gagcaacggt aagacgacca cctgcttgct gatccaggcc    360
atcttgattg aagccttcgc gatttccgcg taccacgtgt acattcgtgt cgcggacccg   420
tttgcgaaaa agattactca aggtgtggtg aaggatgagt acctgcacct gaactatggt    480
caggaatggt tgaaggagaa tctggcaacc tgtaaggacg aactgatgga agcaaacaaa    540
gttaatctgc cgctgattaa gaaaatgctg gatcaggtga gcgaggatgc ctctgtgttg    600
gctatggatc gtgaggagct gatggaggag ttcatgatcg cgtatcagga caccctgttg    660
gaaatcggtc tggacaatcg tgaaattgcg cgtatggcaa tggctgcgat tgtgtaa       717

<210> SEQ ID NO 51
<211> LENGTH: 726
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 51

```
atgcaggcct tcgcaagcaa taacctgacg gtcgaaaagg aagaactgag ctccaatagc      60
ctgccggatt tcaccagcga gagctataag gatgcatact ctcgtatcaa tgccgtggtt     120
atcgaaggtg aacaagaggc ttattctaac tttctggacc tggccaagct gatcccggag     180
cacgccgacg agctggtgcg cttgggtaag atggaaaaga acacatgaa cggcttctgc      240
gcgtgtggtc gtaacttggc agttaaacca gacatgccgt tcgcgaagac gttctttagc     300
aagctgcaca caaatttcct ggaggcgttt aaggtgggcg atacgacgac ctgtttgttg     360
atccaatgca tcttgatcga gtcctttgcc atcagcgcgt accacgtgta cattcgcgtg     420
gcagatccgt ttgccaagcg tatcacgaaa ggtgttgttc aagacgagta cctgcatttg     480
aattacggtc aagagtggct gaaagcgaac ctggagactg tgaagaaaga cctgatgcgc     540
gcgaacaaag agaatctgcc attgattaag tctatgctgg acgaagtctc caacgacgct     600
gaagtgctgc acatggataa agaagagctg atggaagagt ttatgattgc atatcaggac     660
agcctgctgg aaattggcct ggacaaccgc gagatcgcac gcatggcgct ggcagcggtt     720
atttaa                                                                726
```

<210> SEQ ID NO 52
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atgccgaccc tggaaactag cgaggtggca gttctggaag actcgatggc cagcggtagc      60
cgcctgccgg actttaccag cgaggcctat aaggacgcgt atagccgtat caatgcgatc     120
gtgattgaag gcgagcaaga agcgcatgac aactacattg cactgggcac gctgatccca     180
gaacagaagg acgagctggc tcgcctggct cgtatgcgaaa tgaaacacat gaagggcttt     240
accagctgtg gtcgtaacct gggtgtggaa gcggatctgc cgttcgcgaa ggagttcttc     300
gcaccgctgc atggtaactt tcaggcgcg ctgcaggaag gtaaggtggt gacctgtctg      360
ctgattcagg cactgctgat tgaggcgttc gccattagcg cttatcacat ttacattccg     420
gttgctgacc cgtttgcacg caagattacc gaaggtgttg tgaaagacga gtataccccat    480
ctgaactacg gtcaagagtg gttgaaggcg aatttcgaag cctccaaaga cgaactgatg     540
gaagccaaca aggcgaatct gccgctgatc cgttctatgc tggaacaagt cgctgctgat     600
gcggccgtgc tgcaaatgga gaaagaggac ctgattgaag acttcctgat cgcatatcaa     660
gaagctctgt gtgagattgg cttctcgtcc cgtgatatcg cccgcatggc ggcagccgca     720
ctggcggttt aa                                                          732
```

<210> SEQ ID NO 53
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgacccaat ggactttgc atctgcggca taccgtgagg catacagccg tatcaatggt      60
```

```
gtcgttattg ttggcgaggg cctggcgaat cgtcacttcc aaatgctggc gcgtcgcatt      120
ccggcagacc gtgacgaatt gcaacgtttg ggccgcatgg agggtgacca cgcaagcgcc      180
tttgttggtt gcggtcgcaa tctgggtgtg gtcgctgatc tgccgctggc acgccgcctg      240
ttccagccgc tgcatgatct gttcaagcgt cacgaccacg acggtaaccg tgctgaatgc      300
ctggtgatcc agggtctgat tgttgagtgc tttgcggttg ccgcgtatcg tcattacctg      360
ccggtggcag acgcgtatgc ccgtccgatc accgctgcgg ttatgaatga cgagagcgaa      420
cacctggact acgcagaaac ctggctgcag cgccacttcg accaagttaa agcccgcgtg      480
agcgctgtgg ttgtggaggc gctgccgctg acgctggcga tgttgcaaag cctggctgca      540
gatatgcgcc aaatcggcat ggacccggtg gaaacgctgg cgagcttcag cgagctgttt      600
cgtgaagcgc tggaaagcgt tggttttgaa gcggtcgaag cgcgccgttt gctgatgcgt      660
gctgcagctc gtatggttta a                                                681
```

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(26)
<223> OTHER INFORMATION: Any amino acid and this region may encompass 12
      or 13 residues

<400> SEQUENCE: 54

Gly Ala Xaa Gly Asp Ile Gly Ser Xaa Xaa Xaa Xaa Trp Xaa Xaa Xaa
1               5                   10                  15

Xaa Xaa Xaa Xaa Xaa Xaa Xaa Xaa Xaa Xaa Ala Arg
            20                  25

<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Val or Ile
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (17)..(17)
<223> OTHER INFORMATION: Cys or Thr
<220> FEATURE:
<221> NAME/KEY: MOD_RES
<222> LOCATION: (21)..(21)
<223> OTHER INFORMATION: Asp or Ile
<220> FEATURE:
<221> NAME/KEY: MOD_RES
<222> LOCATION: (22)..(22)

```
<223> OTHER INFORMATION: Any amino acid
<220> FEATURE:
<221> NAME/KEY: MOD_RES
<222> LOCATION: (24)..(27)
<223> OTHER INFORMATION: Any amino acid
<220> FEATURE:
<221> NAME/KEY: MOD_RES
<222> LOCATION: (28)..(28)
<223> OTHER INFORMATION: Asp or Glu
<220> FEATURE:
<221> NAME/KEY: MOD_RES
<222> LOCATION: (30)..(30)
<223> OTHER INFORMATION: Ile, Leu or Phe
<220> FEATURE:
<221> NAME/KEY: MOD_RES
<222> LOCATION: (32)..(32)
<223> OTHER INFORMATION: Thr, Ile or Val

<400> SEQUENCE: 55

Ala Thr Val Ala Xaa Xaa Gly Ala Thr Gly Asp Ile Gly Ser Ala Val
1               5                   10                  15

Xaa Arg Trp Leu Xaa Xaa Lys Xaa Xaa Xaa Xaa Xaa Leu Xaa Leu Xaa
            20                  25                  30

Ala Arg

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Lys
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Phe, Leu or Trp
<220> FEATURE:
<221> NAME/KEY: MOD_RES
<222> LOCATION: (5)..(5)
<223> OTHER INFORMATION: Any amino acid

<400> SEQUENCE: 56

Xaa Leu Xaa Xaa Xaa Arg Phe Thr Thr Gly Asn
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(13)
<223> OTHER INFORMATION: Any amino acid

<400> SEQUENCE: 57

Met Phe Gly Leu Ile Gly His Xaa Xaa Xaa Xaa Xaa Xaa Ala
1               5                   10

<210> SEQ ID NO 58
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (3)..(3)
<223> OTHER INFORMATION: Phe, Leu, Val or Met
<220> FEATURE:
<221> NAME/KEY: MOD_RES
<222> LOCATION: (5)..(5)
<223> OTHER INFORMATION: Cys or Ser
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Gln or Val
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Leu or Val
<220> FEATURE:
<221> NAME/KEY: MOD_RES
<222> LOCATION: (13)..(13)
<223> OTHER INFORMATION: Asp or Glu
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (17)..(17)
<223> OTHER INFORMATION: Val or Ile
<220> FEATURE:
<221> NAME/KEY: MOD_RES
<222> LOCATION: (18)..(18)
<223> OTHER INFORMATION: Any amino acid

<400> SEQUENCE: 58

Leu Xaa Xaa Trp Xaa Xaa Ala Pro Pro Xaa Xaa Xaa Xaa Xaa Xaa Xaa
1               5                   10                  15

Xaa Xaa Ser

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
```

```
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid

<400> SEQUENCE: 59

Ser Xaa Xaa Gly Xaa Xaa Ile Xaa Gly Xaa Tyr Xaa Xaa Ser Xaa Phe
1               5                   10                  15

Xaa Pro Glu Met Leu
            20

<210> SEQ ID NO 60
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(20)
<223> OTHER INFORMATION: Any amino acid
<220> FEATURE:
<221> NAME/KEY: MOD_RES
<222> LOCATION: (22)..(23)
<223> OTHER INFORMATION: Any amino acid

<400> SEQUENCE: 60

Lys Xaa Ala Xaa Arg Lys Xaa Xaa Xaa Ala Met Xaa Xaa Xaa Gln Xaa
1               5                   10                  15

Xaa Xaa Xaa Xaa Ile Xaa Xaa Leu Gly Gly Phe
            20                  25

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu, Val or Met
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
```

```
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Asp or Asn
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(9)
<223> OTHER INFORMATION: Val or Ile
<220> FEATURE:
<221> NAME/KEY: MOD_RES
<222> LOCATION: (14)..(14)
<223> OTHER INFORMATION: Leu, Met or Ile

<400> SEQUENCE: 61

Ala Xaa Xaa Xaa Xaa Xaa Xaa Xaa Xaa Trp Val Ala Ser Xaa
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid

<400> SEQUENCE: 62

Pro Xaa Xaa Xaa Xaa Asp Gly Gly Tyr Pro Lys Asn
1               5                   10

<210> SEQ ID NO 63
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(16)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(23)
<223> OTHER INFORMATION: Any amino acid

<400> SEQUENCE: 63

Asn Phe Ser Trp Gly Arg Asn Xaa Ile Xaa Xaa Xaa Xaa Xaa Xaa
1               5                   10                  15

Ile Gly Xaa Xaa Ser Xaa Xaa His Gly
            20                  25

<210> SEQ ID NO 64
<211> LENGTH: 9
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 64

Phe Thr Thr Gly Asn Thr His Thr Ala
1               5

<210> SEQ ID NO 65
<211> LENGTH: 1026
<212> TYPE: DNA
<213> ORGANISM: Synechococcus elongatus

<400> SEQUENCE: 65

```
atgttcggtc ttatcggtca tctcaccagt ttggagcagg cccgcgacgt ttctcgcagg      60
atgggctacg acgaatacgc cgatcaagga ttggagtttt ggagtagcgc tcctcctcaa     120
atcgttgatg aaatcacagt caccagtgcc acaggcaagg tgattcacgg tcgctacatc     180
gaatcgtgtt tcttgccgga aatgctggcg gcgcgccgct tcaaaacagc cacgcgcaaa     240
gttctcaatg ccatgtccca tgcccaaaaa cacggcatcg acatctcggc cttgggggc      300
tttacctcga ttattttcga gaatttcgat ttggccagtt tgcggcaagt gcgcgacact     360
accttggagt ttgaacggtt caccaccggc aatactcaca cggcctacgt aatctgtaga     420
caggtggaag ccgctgctaa aacgctgggc atcgacatta cccaagcgac agtagcggtt     480
gtcggcgcga ctggcgatat cggtagcgct gtctgccgct ggctcgacct caaactgggt     540
gtcggtgatt tgatcctgac ggcgcgcaat caggagcgtt tggataacct gcaggctgaa     600
ctcggccggg gcaagattct gcccttggaa gccgctctgc cggaagctga ctttatcgtg     660
tgggtcgcca gtatgcctca gggcgtagtg atcgacccag caaccctgaa gcaaccctgc     720
gtcctaatcg acgggggcta ccccaaaaac ttgggcagca agtccaagg tgagggcatc      780
tatgtcctca atggcggggt agttgaacat tgcttcgaca tcgactggca gatcatgtcc     840
gctgcagaga tggcgcggcc cgagcgccag atgtttgcct gctttgccga ggcgatgctc     900
ttggaatttg aaggctggca tactaacttc tcctggggcc gcaaccaaat cacgatcgag     960
aagatggaag cgatcggtga ggcatcggtg cgccacggct ccaacccctt ggcattggca    1020
atttga                                                              1026
```

<210> SEQ ID NO 66
<211> LENGTH: 341
<212> TYPE: PRT
<213> ORGANISM: Synechococcus elongatus

<400> SEQUENCE: 66

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala

```
              100                 105                 110
Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
        130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Gly Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340

<210> SEQ ID NO 67
<211> LENGTH: 1023
<212> TYPE: DNA
<213> ORGANISM: Synechocystis sp.

<400> SEQUENCE: 67
atgtttggtc ttattggtca tctcacgagt ttagaacacg cccaagcggt tgctgaagat      60
ttaggctatc ctgagtacgc caaccaaggc ctggattttt ggtgttcggc tcctccccaa     120
gtggttgata tttttcaggt gaaaagtgtg acggggcagg tgattgaagg caaatatgtg     180
gagtcttgct ttttgccgga atgttaacc caacggcgga tcaaagcggc cattcgtaaa     240
atcctcaatg ctatggccct ggcccaaaag gtgggcttgg atattacggc cctgggaggc     300
ttttcttcaa tcgtatttga agaatttaac ctcaagcaaa ataatcaagt ccgcaatgtg     360
gaactagatt ttcagcggtt caccactggt aatacccaca ccgcttatgt gatctgccgt     420
caggtcgagt ctggagctaa acagttgggt attgatctaa gtcaggcaac ggtagcggtt     480
tgtggcgcca cggagatat tggtagcgcc gtatgtcgtt ggttagatag caaacatcaa     540
gttaaggaat tattgctaat tgcccgtaac cgccaaagat tggaaaatct ccaagaggaa     600
ttgggtcggg gcaaaattat ggatttggaa acagccctgc cccaggcaga tattattgtt     660
tgggtggcta gtatgcccaa gggggtagaa attgcggggg aaatgctgaa aaagccctgt     720
ttgattgtgg atgggggcta tcccaagaat ttagacacca gggtgaaagc ggatgggtg     780
```

```
catattctca agggggggat tgtagaacat tcccttgata ttacctggga aattatgaag    840
attgtggaga tggatattcc ctcccggcaa atgttcgcct gttttgcgga ggccattttg    900
ctagagtttg agggctggcg cactaatttt tcctggggcc gcaaccaaat ttccgttaat    960
aaaatggagg cgattggtga agcttctgtc aagcatggct tttgcccttt agtagctctt   1020
tag                                                                 1023
```

<210> SEQ ID NO 68
<211> LENGTH: 340
<212> TYPE: PRT
<213> ORGANISM: Synechocystis sp.

<400> SEQUENCE: 68

```
Met Phe Gly Leu Ile Gly His Leu Thr Ser Leu Glu His Ala Gln Ala
 1               5                  10                  15

Val Ala Glu Asp Leu Gly Tyr Pro Glu Tyr Ala Asn Gln Gly Leu Asp
            20                  25                  30

Phe Trp Cys Ser Ala Pro Pro Gln Val Val Asp Asn Phe Gln Val Lys
        35                  40                  45

Ser Val Thr Gly Gln Val Ile Glu Gly Lys Tyr Val Glu Ser Cys Phe
    50                  55                  60

Leu Pro Glu Met Leu Thr Gln Arg Arg Ile Lys Ala Ala Ile Arg Lys
65                  70                  75                  80

Ile Leu Asn Ala Met Ala Leu Ala Gln Lys Val Gly Leu Asp Ile Thr
                85                  90                  95

Ala Leu Gly Gly Phe Ser Ser Ile Val Phe Glu Glu Phe Asn Leu Lys
            100                 105                 110

Gln Asn Asn Gln Val Arg Asn Val Glu Leu Asp Phe Gln Arg Phe Thr
        115                 120                 125

Thr Gly Asn Thr His Thr Ala Tyr Val Ile Cys Arg Gln Val Glu Ser
    130                 135                 140

Gly Ala Lys Gln Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Ser Lys His Gln Val Lys Glu Leu Leu Leu Ile Ala Arg Asn Arg Gln
            180                 185                 190

Arg Leu Glu Asn Leu Gln Glu Glu Leu Gly Arg Gly Lys Ile Met Asp
        195                 200                 205

Leu Glu Thr Ala Leu Pro Gln Ala Asp Ile Ile Val Trp Val Ala Ser
    210                 215                 220

Met Pro Lys Gly Val Glu Ile Ala Gly Glu Met Leu Lys Lys Pro Cys
225                 230                 235                 240

Leu Ile Val Asp Gly Gly Tyr Pro Lys Asn Leu Asp Thr Arg Val Lys
                245                 250                 255

Ala Asp Gly Val His Ile Leu Lys Gly Gly Ile Val Glu His Ser Leu
            260                 265                 270

Asp Ile Thr Trp Glu Ile Met Lys Ile Val Glu Met Asp Ile Pro Ser
        275                 280                 285

Arg Gln Met Phe Ala Cys Phe Ala Glu Ala Ile Leu Leu Glu Phe Glu
    290                 295                 300

Gly Trp Arg Thr Asn Phe Ser Trp Gly Arg Asn Gln Ile Ser Val Asn
305                 310                 315                 320

Lys Met Glu Ala Ile Gly Glu Ala Ser Val Lys His Gly Phe Cys Pro
```

Leu Val Ala Leu
        340

<210> SEQ ID NO 69
<211> LENGTH: 1023
<212> TYPE: DNA
<213> ORGANISM: Cyanothece sp.

<400> SEQUENCE: 69

```
atgtttggtt taattggtca tcttacaagt ttagaacacg cccactccgt tgctgatgcc      60
tttggctatg gcccatacgc cactcaggga cttgatttgt ggtgttctgc tccaccccaa     120
ttcgtcgagc attttcatgt tactagcatc acaggacaaa ccatcgaagg aaagtatata     180
gaatccgctt tcttaccaga aatgctgata aagcgacgga ttaaagcagc aattcgcaaa     240
atactgaatg cgatggcctt tgctcagaaa aataaccta acatcacagc attaggggc      300
ttttcttcga ttattttga agaatttaat ctcaaagaga atagacaagt tcgtaatgtc     360
tctttagagt ttgatcgctt caccaccgga acacccata ctgcttatat catttgtcgt     420
caagttgaac aggcatccgc taaactaggg attgacttat cccaagcaac ggttgctatt     480
tgcgggggcaa ccggagatat tggcagtgca gtgtgtcgtt ggttagatag aaaaaccgat     540
acccaggaac tattcttaat tgctcgcaat aaagaacgat acaacgact gcaagatgag     600
ttgggacggg gtaaaattat gggattggag gaggctttac ccgaagcaga tattatcgtt     660
tgggtggcga gtatgcccaa aggagtggaa attaatgccg aaactctcaa aaaccctgt     720
ttaattatcg atggtggtta tcctaagaat ttagacacaa aaattaaaca tcctgatgtc     780
catatcctga aagggggaat tgtagaacat tctctagata ttgactggaa gattatggaa     840
actgtcaata tggatgttcc ttctcgtcaa atgtttgctt gttttgccga agccatttta     900
ttagagtttg aacaatggca cactaatttt tcttggggac gcaatcaaat tacagtgact     960
aaaatggaac aaataggaga agcttctgtc aaacatgggt tacaaccgtt gttgagttgg    1020
taa                                                                 1023
```

<210> SEQ ID NO 70
<211> LENGTH: 340
<212> TYPE: PRT
<213> ORGANISM: Cyanothece sp.

<400> SEQUENCE: 70

Met Phe Gly Leu Ile Gly His Leu Thr Ser Leu Glu His Ala His Ser
1               5                   10                  15

Val Ala Asp Ala Phe Gly Tyr Gly Pro Tyr Ala Thr Gln Gly Leu Asp
            20                  25                  30

Leu Trp Cys Ser Ala Pro Pro Gln Phe Val Glu His Phe His Val Thr
        35                  40                  45

Ser Ile Thr Gly Gln Thr Ile Glu Gly Lys Tyr Ile Glu Ser Ala Phe
    50                  55                  60

Leu Pro Glu Met Leu Ile Lys Arg Arg Ile Lys Ala Ala Ile Arg Lys
65                  70                  75                  80

Ile Leu Asn Ala Met Ala Phe Ala Gln Lys Asn Asn Leu Asn Ile Thr
                85                  90                  95

Ala Leu Gly Gly Phe Ser Ser Ile Ile Phe Glu Glu Phe Asn Leu Lys
            100                 105                 110

Glu Asn Arg Gln Val Arg Asn Val Ser Leu Glu Phe Asp Arg Phe Thr
        115                 120                 125

```
Thr Gly Asn Thr His Thr Ala Tyr Ile Ile Cys Arg Gln Val Glu Gln
    130                 135                 140

Ala Ser Ala Lys Leu Gly Ile Asp Leu Ser Gln Ala Thr Val Ala Ile
145                 150                 155                 160

Cys Gly Ala Thr Gly Asp Ile Gly Ser Ala Val Cys Arg Trp Leu Asp
                165                 170                 175

Arg Lys Thr Asp Thr Gln Glu Leu Phe Leu Ile Ala Arg Asn Lys Glu
            180                 185                 190

Arg Leu Gln Arg Leu Gln Asp Glu Leu Gly Arg Gly Lys Ile Met Gly
        195                 200                 205

Leu Glu Glu Ala Leu Pro Glu Ala Asp Ile Ile Val Trp Val Ala Ser
    210                 215                 220

Met Pro Lys Gly Val Glu Ile Asn Ala Glu Thr Leu Lys Lys Pro Cys
225                 230                 235                 240

Leu Ile Ile Asp Gly Gly Tyr Pro Lys Asn Leu Asp Thr Lys Ile Lys
                245                 250                 255

His Pro Asp Val His Ile Leu Lys Gly Gly Ile Val Glu His Ser Leu
            260                 265                 270

Asp Ile Asp Trp Lys Ile Met Glu Thr Val Asn Met Asp Val Pro Ser
        275                 280                 285

Arg Gln Met Phe Ala Cys Phe Ala Glu Ala Ile Leu Leu Glu Phe Glu
    290                 295                 300

Gln Trp His Thr Asn Phe Ser Trp Gly Arg Asn Gln Ile Thr Val Thr
305                 310                 315                 320

Lys Met Glu Gln Ile Gly Glu Ala Ser Val Lys His Gly Leu Gln Pro
                325                 330                 335

Leu Leu Ser Trp
            340

<210> SEQ ID NO 71
<211> LENGTH: 1041
<212> TYPE: DNA
<213> ORGANISM: Prochlorococcus marinus

<400> SEQUENCE: 71
atgtttgggc ttataggtca ttcaactagt tttgaagatg caaaagaaa ggcttcatta      60 ttgggctttg atcatattgc ggatggtgat ttagatgttt ggtgcacagc tccacctcaa    120
ctagttgaaa atgtagaggt taaaagtgct ataggtatat caattgaagg ttcttatatt    180
gattcatgtt tcgttcctga aatgctttca agatttaaaa cggcaagaag aaaagtatta    240
aatgcaatgg aattagctca aaaaaaaggt attaatatta ccgctttggg ggggttcact    300
tctatcatct ttgaaaattt taatctcctt caacataagc agattagaaa cacttcacta    360
gagtgggaaa ggtttacaac tggtaatact catactgcgt gggttatttg caggcaatta    420
gagatgaatg ctcctaaaat aggtattgat cttaaaagcg caacagttgc tgtagttggt    480
gctactggag ataggcag tgctgtttgt cgatggttaa tcaataaaac aggtattggg     540
gaacttcttt tggtagctag gcaaaaggaa cccttggatt ctttgcaaaa ggaattagat    600
ggtggaacta tcaaaaatct agatgaagca ttgcctgaag cagatattgt tgtatgggta    660
gcaagtatgc caaagacaat ggaaatcgat gctaataatc ttaaacaacc atgtttaatg    720
attgatggag ttatccaaa gaatctagat gaaaaatttc aaggaaataa tatacatgtt    780
gtaaaaggag gtatagtaag attcttcaat gatataggtt ggaatatgat ggaactagct    840
gaaatgcaaa atcccagag agaaatgttt gcatgctttg cagaagcaat gattttagaa    900
```

```
tttgaaaaat gtcatacaaa ctttagctgg ggaagaaata atatatctct cgagaaaatg    960
gagtttattg gagctgcttc tgtaaagcat ggcttctctg caattggcct agataagcat   1020
ccaaaagtac tagcagtttg a                                             1041
```

<210> SEQ ID NO 72
<211> LENGTH: 346
<212> TYPE: PRT
<213> ORGANISM: Prochlorococcus marinus

<400> SEQUENCE: 72

```
Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Ile Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Arg Phe Thr Thr Gly
        115                 120                 125

Asn Thr His Thr Ala Trp Val Ile Cys Arg Gln Leu Glu Met Asn Ala
    130                 135                 140

Pro Lys Ile Gly Ile Asp Leu Lys Ser Ala Thr Val Ala Val Val Gly
145                 150                 155                 160

Ala Thr Gly Asp Ile Gly Ser Ala Val Cys Arg Trp Leu Ile Asn Lys
                165                 170                 175

Thr Gly Ile Gly Glu Leu Leu Leu Val Ala Arg Gln Lys Glu Pro Leu
            180                 185                 190

Asp Ser Leu Gln Lys Glu Leu Asp Gly Gly Thr Ile Lys Asn Leu Asp
        195                 200                 205

Glu Ala Leu Pro Glu Ala Asp Ile Val Val Trp Val Ala Ser Met Pro
    210                 215                 220

Lys Thr Met Glu Ile Asp Ala Asn Asn Leu Lys Gln Pro Cys Leu Met
225                 230                 235                 240

Ile Asp Gly Gly Tyr Pro Lys Asn Leu Asp Glu Lys Phe Gln Gly Asn
                245                 250                 255

Asn Ile His Val Val Lys Gly Gly Ile Val Arg Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Val Lys His Gly Phe Ser Ala Ile Gly
                325                 330                 335

Leu Asp Lys His Pro Lys Val Leu Ala Val
            340                 345
```

<210> SEQ ID NO 73
<211> LENGTH: 1053
<212> TYPE: DNA
<213> ORGANISM: Gloeobacter violaceus

<400> SEQUENCE: 73

```
atgtttggcc tgatcggaca cttgaccaat ctttcccatg cccagcgggt cgcccgcgac      60
ctgggctacg acgagtatgc aagccacgac ctcgaattct ggtgcatggc ccctccccag     120
gcggtcgatg aaatcacgat caccagcgtc accggtcagg tgatccacgg tcagtacgtc     180
gaatcgtgct ttctgccgga gatgctcgcc cagggccgct tcaagaccgc catgcgcaag     240
atcctcaatg ccatggccct ggtccagaag cgcggcatcg acattacggc cctgggaggc     300
ttctcgtcga tcatcttcga gaatttcagc ctcgataaat tgctcaacgt ccgcgacatc     360
accctcgaca tccagcgctt caccaccggc aacacccaca cggcctacat cctttgtcag     420
caggtcgagc agggtgcggt acgctacggc atcgatccgg ccaaagcgac cgtggcggta     480
gtcggggcca ccggcgacat cggtagcgcc gtctgccgat ggctcaccga ccgcgccggc     540
atccacgaac tcttgctggt ggcccgcgac gccgaaaggc tcgaccggct gcagcaggaa     600
ctcggcaccg gtcggatcct gccggtcgaa gaagcacttc ccaaagccga catcgtcgtc     660
tgggtcgcct cgatgaacca gggcatggcc atcgaccccg ccggcctgcg caccccctgc     720
ctgctcatcg acggcggcta ccccaagaac atggccggca ccctgcagcg cccgggcatc     780
catatcctcg acggcggcat ggtcgagcac tcgctcgaca tcgactggca gatcatgtcg     840
tttctaaatg tgcccaaccc cgcccgccag ttcttcgcct gcttcgccga gtcgatgctg     900
ctggaattcg aagggcttca cttcaatttt tcctggggcc gcaaccacat caccgtcgag     960
aagatggccc agatcggctc gctgtctaaa aaacatggct tcgtcccct gcttgaaccc    1020
agtcagcgca gcggcgaact cgtacacgga taa                                1053
```

<210> SEQ ID NO 74
<211> LENGTH: 350
<212> TYPE: PRT
<213> ORGANISM: Gloeobacter violaceus

<400> SEQUENCE: 74

```
Met Phe Gly Leu Ile Gly His Leu Thr Asn Leu Ser His Ala Gln Arg
1               5                  10                  15

Val Ala Arg Asp Leu Gly Tyr Asp Glu Tyr Ala Ser His Asp Leu Glu
            20                  25                  30

Phe Trp Cys Met Ala Pro Pro Gln Ala Val Asp Glu Ile Thr Ile Thr
        35                  40                  45

Ser Val Thr Gly Gln Val Ile His Gly Gln Tyr Val Glu Ser Cys Phe
    50                  55                  60

Leu Pro Glu Met Leu Ala Gln Gly Arg Phe Lys Thr Ala Met Arg Lys
65                  70                  75                  80

Ile Leu Asn Ala Met Ala Leu Val Gln Lys Arg Gly Ile Asp Ile Thr
                85                  90                  95

Ala Leu Gly Gly Phe Ser Ser Ile Ile Phe Glu Asn Phe Ser Leu Asp
            100                 105                 110

Lys Leu Leu Asn Val Arg Asp Ile Thr Leu Asp Ile Gln Arg Phe Thr
        115                 120                 125

Thr Gly Asn Thr His Thr Ala Tyr Ile Leu Cys Gln Gln Val Glu Gln
    130                 135                 140
```

```
Gly Ala Val Arg Tyr Gly Ile Asp Pro Ala Lys Ala Thr Val Ala Val
145                 150                 155                 160

Val Gly Ala Thr Gly Asp Ile Gly Ser Ala Val Cys Arg Trp Leu Thr
                165                 170                 175

Asp Arg Ala Gly Ile His Glu Leu Leu Leu Val Ala Arg Asp Ala Glu
            180                 185                 190

Arg Leu Asp Arg Leu Gln Gln Glu Leu Gly Thr Gly Arg Ile Leu Pro
        195                 200                 205

Val Glu Glu Ala Leu Pro Lys Ala Asp Ile Val Val Trp Val Ala Ser
210                 215                 220

Met Asn Gln Gly Met Ala Ile Asp Pro Ala Gly Leu Arg Thr Pro Cys
225                 230                 235                 240

Leu Leu Ile Asp Gly Gly Tyr Pro Lys Asn Met Ala Gly Thr Leu Gln
                245                 250                 255

Arg Pro Gly Ile His Ile Leu Asp Gly Gly Met Val Glu His Ser Leu
            260                 265                 270

Asp Ile Asp Trp Gln Ile Met Ser Phe Leu Asn Val Pro Asn Pro Ala
        275                 280                 285

Arg Gln Phe Phe Ala Cys Phe Ala Glu Ser Met Leu Leu Glu Phe Glu
    290                 295                 300

Gly Leu His Phe Asn Phe Ser Trp Gly Arg Asn His Ile Thr Val Glu
305                 310                 315                 320

Lys Met Ala Gln Ile Gly Ser Leu Ser Lys Lys His Gly Phe Arg Pro
                325                 330                 335

Leu Leu Glu Pro Ser Gln Arg Ser Gly Glu Leu Val His Gly
            340                 345                 350

<210> SEQ ID NO 75
<211> LENGTH: 1020
<212> TYPE: DNA
<213> ORGANISM: Nostoc punctiforme

<400> SEQUENCE: 75
atgtttggtc taattggaca tctgactagt ttagaacacg ctcaagccgt agcccaagaa      60
ttgggatacc cagaatatgc cgatcaaggg ctagactttt ggtgcagcgc cccgccgcaa     120
attgtcgata gtattattgt caccagtgtt actgggcaac aaattgaagg acgatatgta     180
gaatcttgct ttttgccgga aatgctagct agtcgccgca tcaaagccgc aacacggaaa     240
atcctcaacg ctatggccca tgcacagaag cacggcatta acatcacagc tttaggcgga     300
ttttcctcga ttattttga aaactttaag ttagagcagt ttagccaagt ccgaaatatc     360
aagctagagt ttgaacgctt caccacagga aacacgcata ctgcctacat tatttgtaag     420
caggtggaag aagcatccaa acaactggga attaatctat caaacgcgac tgttgcggta     480
tgtggagcaa ctgggggatat tggtagtgcc gttacgcct ggctagatgc gagaacagat     540
gtccaagaac tcctgctaat cgcccgcgat caagaacgtc tcaaagagtt gcaaggcgaa     600
ctggggcggg ggaaaatcat gggtttgaca gaagcactac cccaagccga tgttgtagtt     660
tgggttgcta gtatgcccag aggcgtggaa attgacccca ccactttgaa caaccctgt     720 ttgttgattg atggtggcta tcctaaaaac ttagcaacaa aaattcaata tcctggcgta     780
cacgtgttaa atggtgggat tgtagagcat ccctgata ttgactggaa aattatgaaa     840
atagtcaata tggacgtgcc agcccgtcag ttgtttgcct gttttgccga atcaatgcta     900
ctggaatttg agaagttata cacgaacttt tcgtggggac ggaatcagat taccgtagat     960
aaaatggagc agattggccg ggtgtcagta aaacatggat ttagaccgtt gttggtttag    1020
```

<210> SEQ ID NO 76
<211> LENGTH: 339
<212> TYPE: PRT
<213> ORGANISM: Nostoc punctiforme

<400> SEQUENCE: 76

Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp Ser Ile Ile Val Thr
        35                  40                  45

Ser Val Thr Gly Gln Gln Ile Glu Gly Arg Tyr Val Glu Ser Cys Phe
50                  55                  60

Leu Pro Glu Met Leu Ala Ser Arg Arg Ile Lys Ala Ala Thr Arg Lys
65                  70                  75                  80

Ile Leu Asn Ala Met Ala His Ala Gln Lys His Gly Ile Asn Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Ile Lys Leu Glu Phe Glu Arg Phe Thr
        115                 120                 125

Thr Gly Asn Thr His Thr Ala Tyr Ile Ile Cys Lys Gln Val Glu Glu
130                 135                 140

Ala Ser Lys Gln Leu Gly Ile Asn Leu Ser Asn Ala Thr Val Ala Val
145                 150                 155                 160

Cys Gly Ala Thr Gly Asp Ile Gly Ser Ala Val Thr Arg Trp Leu Asp
                165                 170                 175

Ala Arg Thr Asp Val Gln Glu Leu Leu Leu Ile Ala Arg Asp Gln Glu
            180                 185                 190

Arg Leu Lys Glu Leu Gln Gly Glu Leu Gly Arg Gly Lys Ile Met Gly
        195                 200                 205

Leu Thr Glu Ala Leu Pro Gln Ala Asp Val Val Trp Val Ala Ser
210                 215                 220

Met Pro Arg Gly Val Glu Ile Asp Pro Thr Thr Leu Lys Gln Pro Cys
225                 230                 235                 240

Leu Leu Ile Asp Gly Gly Tyr Pro Lys Asn Leu Ala Thr Lys Ile Gln
                245                 250                 255

Tyr Pro Gly Val His Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
290                 295                 300

Lys Leu Tyr Thr Asn Phe Ser Trp Gly Arg Asn Gln Ile Thr Val Asp
305                 310                 315                 320

Lys Met Glu Gln Ile Gly Arg Val Ser Val Lys His Gly Phe Arg Pro
                325                 330                 335

Leu Leu Val

<210> SEQ ID NO 77
<211> LENGTH: 1020
<212> TYPE: DNA
<213> ORGANISM: Anabaena variabilis

<400> SEQUENCE: 77

```
atgtttggtc taattggaca tctgacaagt ttagaacacg ctcaagcggt agctcaagaa      60
ctgggatacc cagaatacgc cgaccaaggg ctagatttt ggtgcagcgc tccaccgcaa      120
atagttgacc acattaaagt tactagcatt actggtgaaa taattgaagg gaggtatgta     180
gaatcttgct ttttaccaga aatgctagcc agccgtagga ttaaagccgc aacccgcaaa     240
gtcctcaatg ctatggctca tgctcaaaaa catggcattg acatcaccgc tttgggtggt     300
ttctcctcca ttatttttga aaacttcaaa ttggaacagt ttagccaagt tcgtaatgtc     360
acactagagt ttgaacgctt cactacaggc aacactcaca cagcttatat catttgtcgg     420
caggtagaac aagcatcaca acaactcggc attgaactct cccaagcaac agtagctata     480
tgtgggctta ctggtgacat tggtagtgca gttactcgct ggctggatgc caaaacagac     540
gtaaaagaat tactgttaat cgcccgtaat caagaacgtc tccaagagtt gcaaagcgag     600
ttgggacgcg gtaaaatcat gagcctagat gaagcattgc ctcaagctga tattgtagtt     660
tgggtagcta gtatgcctaa aggcgtggaa attaatcctc aagttttgaa acaaccctgt     720
ttattgattg atggtggtta tccgaaaaac ttgggtacaa aagttcagta tcctggtgtt     780
tatgtactga acggaggtat cgtcgaacat tccctagata ttgactggaa aatcatgaaa     840
atagtcaata tggatgtacc tgcacgccaa ttatttgctt gttttgcgga atctatgctc     900
ttggaatttg agaagttgta cacgaacttt tcttggggc gcaatcagat taccgtagac     960
aaaatggagc agattggtca agcatcagtg aaacatgggt ttagaccact gctggtttag    1020
```

<210> SEQ ID NO 78
<211> LENGTH: 339
<212> TYPE: PRT
<213> ORGANISM: Anabaena variabilis

<400> SEQUENCE: 78

```
Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Lys Val Thr
        35                  40                  45

Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190
```

```
Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
225                 230                 235                 240

Leu Leu Ile Asp Gly Gly Tyr Pro Lys Asn Leu Gly Thr Lys Val Gln
            245                 250                 255

Tyr Pro Gly Val Tyr Val Leu Asn Gly Gly Ile Val Glu His Ser Leu
            260                 265                 270

Asp Ile Asp Trp Lys Ile Met Lys Ile Val Asn Met Asp Val Pro Ala
            275                 280                 285

Arg Gln Leu Phe Ala Cys Phe Ala Glu Ser Met Leu Leu Glu Phe Glu
        290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val
```

<210> SEQ ID NO 79
<211> LENGTH: 1026
<212> TYPE: DNA
<213> ORGANISM: Synechococcus elongatus

<400> SEQUENCE: 79

```
atgttcggtc ttatcggtca tctcaccagt ttggagcagg cccgcgacgt ttctcgcagg     60
atgggctacg acgaatacgc cgatcaagga ttggagtttt ggagtagcgc tcctcctcaa    120
atcgttgatg aaatcacagt caccagtgcc acaggcaagg tgattcacgg tcgctacatc    180
gaatcgtgtt tcttgccgga atgctggcg gcgcgccgct tcaaaacagc cacgcgcaaa    240
gttctcaatg ccatgtccca tgcccaaaaa cacggcatcg acatctcggc cttgggggc    300
tttacctcga ttattttcga gaatttcgat ttggccagtt tgcggcaagt gcgcgacact    360
accttggagt ttgaacggtt caccaccggc aatactcaca cggcctacgt aatctgtaga    420
caggtggaag ccgctgctaa aacgctgggc atcgacatta cccaagcgac agtagcggtt    480
gtcggcgcga ctggcgatat cggtagcgct gtctgccgct ggctcgacct caaactgggt    540
gtcggtgatt tgatcctgac ggcgcgcaat caggagcgtt tggataacct gcaggctgaa    600
ctcggccggg gcaagattct gcccttggaa gccgctctgc cggaagctga ctttatcgtg    660
tgggtcgcca gtatgcctca gggcgtagtg atcgacccag caaccctgaa gcaaccctgc    720
gtcctaatcg acgggggcta ccccaaaaac ttgggcagca agtccaaggt tgagggcatc    780
tatgtcctca atggcggggt agttgaacat tgcttcgaca tcgactggca gatcatgtcc    840
gctgcagaga tggcgcggcc cgagcgccag atgtttgcct gctttgccga ggcgatgctc    900
ttggaatttg aaggctggca tactaacttc tcctggggcc gcaaccaaat cacgatcgag    960
aagatggaag cgatcggtga ggcatcggtg cgccacggct tccaacccct ggcattggca   1020
atttga                                                              1026
```

<210> SEQ ID NO 80
<211> LENGTH: 340
<212> TYPE: PRT
<213> ORGANISM: Synechococcus elongatus

<400> SEQUENCE: 80

```
Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala
            340

<210> SEQ ID NO 81
<211> LENGTH: 1020
<212> TYPE: DNA
<213> ORGANISM: Nostoc sp.

<400> SEQUENCE: 81
atgtttggtc taattggaca tctgacaagt ttagaacacg ctcaagcggt agctcaagaa      60
ctgggatacc cagaatacgc cgaccaaggg ctagattttt ggtgtagcgc tccaccgcaa     120
atagttgacc acattaaagt tactagtatt actggtgaaa taattgaagg gaggtatgta     180
```

```
gaatcttgct ttttaccgga gatgctagcc agtcgtcgga ttaaagccgc aacccgcaaa      240
gtcctcaatg ctatggctca tgctcaaaag aatggcattg atatcacagc tttgggtggt      300
ttctcctcca ttattttga aaactttaaa ttggagcagt ttagccaagt tcgtaatgtg       360
acactagagt ttgaacgctt cactacaggc aacactcaca cagcatatat tatttgtcgg      420
caggtagaac aagcatcaca caactcggc attgaactct cccaagcaac agtagctata       480 tgtgggcta ctggtgatat tggtagtgca gttactcgct ggctggatgc taaaacagac       540
gtgaaagaat tgctgttaat cgcccgtaat caagaacgtc tccaagagtt gcaaagcgag      600
ctgggacgcg gtaaaatcat gagccttgat gaagcactgc cccaagctga tatcgtagtt      660
tgggtagcca gtatgcctaa aggtgtggaa attaatcctc aagttttgaa gcaaccctgt      720
ttgctgattg atgggggtta tccgaaaaac ttgggtacaa aagttcagta tcctggtgtt      780
tatgtactga acggcggtat cgtcgaacat tcgctggata ttgactggaa aatcatgaaa      840
atagtcaata tggatgtacc tgcacgccaa ttatttgctt gttttgcgga atctatgctc      900
ttggaatttg agaagttgta cacgaacttt tcttgggggc gcaatcagat taccgtagac      960
aaaatggagc agattggtca agcatcagtg aaacatgggt ttagaccact gctggtttag    1020
```

<210> SEQ ID NO 82
<211> LENGTH: 339
<212> TYPE: PRT
<213> ORGANISM: Nostoc sp.

<400> SEQUENCE: 82

```
Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
                20                  25                  30

Phe Trp Cys Ser Ala Pro Pro Gln Ile Val Asp His Ile Lys Val Thr
            35                  40                  45

Ser Ile Thr Gly Glu Ile Ile Glu Gly Arg Tyr Val Glu Ser Cys Phe
        50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys Asn Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Ile Ala Arg Asn Gln Glu
            180                 185                 190

Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
```

```
                225                 230                 235                 240
Leu Leu Ile Asp Gly Gly Tyr Pro Lys Asn Leu Gly Thr Lys Val Gln
                    245                 250                 255

Tyr Pro Gly Val Tyr Val Leu Asn Gly Gly Ile Val Glu His Ser Leu
                260                 265                 270

Asp Ile Asp Trp Lys Ile Met Lys Ile Val Asn Met Asp Val Pro Ala
                275                 280                 285

Arg Gln Leu Phe Ala Cys Phe Ala Glu Ser Met Leu Leu Glu Phe Glu
                290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val

<210> SEQ ID NO 83
<211> LENGTH: 1026
<212> TYPE: DNA
<213> ORGANISM: Synechococcus elongatus

<400> SEQUENCE: 83
atgtttggtc tgattggtca cctgaccagc ttggaacaag cgcgtgacgt cagccgccgt       60
atgggttatg atgaatacgc tgatcaaggc ctggagtttt ggagcagcgc gccaccgcag      120
atcgtcgatg agatcaccgt gacctccgca accggtaagg tcatccacgg ccgctacatt      180
gagtcctgct tcctgcctga tgctggcagc gctcgccgtt tcaaaacggc cactcgtaag      240
gttctgaatg cgatgtccca tgcgcaaaag catggcattg acattagcgc cttgggcggt      300
tttacgtcga ttatcttcga gaacttcgat ctggcctctt tgcgccaggt cgcgtgacacg     360 accttggagt ttgagcgttt taccacgggt aatacgcaca ccgcttacgt tatctgtcgc      420
caagtcgaag cagcagccaa aaccctgggt attgatatca cccaggccac cgtcgccgtg      480
gtgggtgcta ccggtgatat tggttccgcg gtttgccgtt ggctggatct gaaactgggt      540
gttggcgatc tgatcctgac ggcgcgtaat caggagcgtc tggacaacct gcaagccgag      600
ttgggtcgcg gtaagatcct gccgttggag gcagcgttgc cggaggcaga cttcatcgtc      660
tgggttgcgt ctatgccgca gggtgttgtt atcgacccgg cgaccttgaa acagccgtgc      720
gtgctgattg atggcggcta tccgaaaaac ctgggcagca aggtccaagg cgagggtatc      780
tatgtcctga atgcggtgt ggttgagcat tgcttcgaca ttgactggca gatcatgagc      840
gcagcagaaa tggcgcgtcc ggagcgccaa atgtttgcct gttttgcaga agccatgctg      900
ctggagttcg aaggctggca tacgaatttc agctggggtc gtaatcagat taccattgaa      960
aagatggaag cgattggtga agcaagcgtg cgtcatggtt ttcagccact ggcgctggct     1020
atttaa                                                               1026

<210> SEQ ID NO 84
<211> LENGTH: 1041
<212> TYPE: DNA
<213> ORGANISM: Prochlorococcus marinus

<400> SEQUENCE: 84
atgtttggtc tgattggcca cagcacgagc tttgaggacg caaagcgtaa ggcgagcctg       60
ctgggctttg atcatattgc tgatggcgac ctggacgtct ggtgcacggc acctccgcaa      120
ctggttgaga atgtcgaggt gaaatcggcg attggcattt ccatcgaagg ctcctacatc      180
```

```
gacagctgtt tcgtgccgga gatgttgagc cgtttcaaaa ccgcacgtcg caaagttctg      240
aatgcaatgg agctggcaca aaagaagggc atcaacatca cggcgctggg tggtttcacc      300
agcattatct ttgagaactt caatctgttg cagcataaac agatccgtaa taccagcctg      360
gagtgggaac gctttaccac gggtaacacc cacaccgcgt gggtgatctg ccgccagctg      420
gagatgaatg cgccgaaaat cggtattgac ctgaaaagcg cgacggtggc agttgttggc      480
gcaactggcg acattggttc ggccgtttgt cgctggctga ttaacaagac cggtatcggt      540
gaattgttgc tggtcgctcg ccagaaggag cctctggaca gcctgcaaaa agagctggac      600
ggtggtacga tcaagaacct ggatgaagcg ctgccagaag cggacatcgt cgtctgggtc      660
gcatctatgc cgaaaactat ggaaatcgat gccaacaatc tgaaacaacc gtgcctgatg      720
atcgatggcg gctacccgaa gaacttggat gagaagtttc aaggcaataa catccacgtt      780
gtgaagggtg gtattgtccg tttcttcaat gatatcggtt ggaacatgat ggaactggct      840
gaaatgcaga acccgcaacg tgagatgttc gcttgttttg cggaggccat gattctggag      900
ttcgagaaat gccataccaa tttcagctgg ggtcgcaaca acattagcct ggagaaaatg      960
gagttcatcg cgcgctgcgag cgttaagcac ggcttcagcg cgattggttt ggataaacat     1020
ccgaaggtcc tggcagttta a                                               1041

<210> SEQ ID NO 85
<211> LENGTH: 3522
<212> TYPE: DNA
<213> ORGANISM: Mycobacterium smegmatis

<400> SEQUENCE: 85
atgaccagcg atgttcacga cgccacagac ggcgtcaccg aaaccgcact cgacgacgag       60
cagtcgaccc gccgcatcgc cgagctgtac gccaccgatc ccgagttcgc cgccgccgca      120
ccgttgcccg ccgtggtcga cgcggcgcac aaacccgggc tgcggctggc agagatcctg      180
cagaccctgt tcaccggcta cggtgaccgc ccggcgctgg ataccgcgc  ccgtgaactg      240 gccaccgacg agggcgggcg caccgtgacg cgtctgctgc cgcggttcga caccctcacc      300
tacgcccagg tgtggtcgcg cgtgcaagcg gtcgccgcgg ccctgcgcca aacttcgcg      360 cagccgatct accccggcga cgccgtcgcg acgatcggtt cgcgagtccc cgattacctg      420
acgctggatc tcgtatgcgc ctacctgggc ctcgtgagtc ttccgctgca gcacaacgca      480
ccggtcagcc ggctcgcccc gatcctggcc gaggtcgaac cgcggatcct caccgtgagc      540
gccgaatacc tcgacctcgc agtcgaatcc gtgcgggacg tcaactcggt gtcgcagctc      600
gtggtgttcg accatcaccc cgaggtcgac gaccaccgcg acgcactggc ccgcgcgcgt      660
gaacaactcg ccggcaaggg catcgccgtc accaccctgg acgcgatcgc cgacgagggc      720
gccgggctgc cggccgaacc gatctacacc gccgaccatg atcagcgcct cgcgatgatc      780
ctgtacacct cggggttcca ccggcgcaccc aagggtgcga tgtacaccga ggcgatggtg      840
gcgcggctgt ggaccatgtc gttcatcacg ggtgacccca cgccggtcat caacgtcaac      900
ttcatgccgc tcaaccacct gggcgggcgc atccccattt ccaccgccgt gcagaacggt      960
ggaaccagtt acttcgtacc ggaatccgac atgtccacgc tgttcgagga tctcgcgctg     1020
gtgcgcccga ccgaactcgg cctggttccg cgcgtcgccg acatgctcta ccagcaccac     1080
ctcgccaccg tcgaccgcct ggtcacgcag ggcgccgacg aactgaccgc cgagaagcag     1140
gccggtgccg aactgcgtga gcaggtgctc ggcggacgcg tgatcaccgg attcgtcagc     1200
accgcaccgc tggccgcgga gatgagggcg ttcctcgaca tcaccctggg cgcacacatc     1260
```

```
gtcgacggct acgggctcac cgagaccggc gccgtgacac gcgacggtgt gatcgtgcgg    1320
ccaccggtga tcgactacaa gctgatcgac gttcccgaac tcggctactt cagcaccgac    1380
aagccctacc cgcgtggcga actgctggtc aggtcgcaaa cgctgactcc cgggtactac    1440
aagcgccccg aggtcaccgc gagcgtcttc gaccgggacg gctactacca caccggcgac    1500
gtcatggccg agaccgcacc cgaccacctg gtgtacgtgg accgtcgcaa caacgtcctc    1560
aaactcgcgc agggcgagtt cgtggcggtc gccaacctgg aggcggtgtt ctccggcgcg    1620
gcgctggtgc gccagatctt cgtgtacggc aacagcgagc gcagtttcct tctggccgtg    1680
gtggtcccga cgccggaggc gctcgagcag tacgatccgg ccgcgctcaa ggccgcgctg    1740
gccgactcgc tgcagcgcac cgcacgcgac gccgaactgc aatcctacga ggtgccggcc    1800
gatttcatcg tcgagaccga gccgttcagc gccgccaacg ggctgctgtc gggtgtcgga    1860
aaactgctgc ggcccaacct caaagaccgc tacgggcagc gcctggagca gatgtacgcc    1920
gatatcgcgg ccacgcaggc caaccagttg cgcgaactgc ggcgcgcggc cgccacacaa    1980
ccggtgatcg acaccctcac ccaggccgct gccacgatcc tcggcaccgg gagcgaggtg    2040
gcatccgacg cccacttcac cgacctgggc ggggattccc tgtcggcgct gacactttcg    2100
aacctgctga gcgatttctt cggtttcgaa gttcccgtcg gcaccatcgt gaacccggcc    2160
accaacctcg cccaactcgc ccagcacatc gaggcgcagc gcaccgcggg tgaccgcagg    2220
ccgagtttca ccaccgtgca cggcgcggac gccaccgaga tccgggcgag tgagctgacc    2280
ctggacaagt tcatcgacgc cgaaacgctc cgggccgcac cgggtctgcc caaggtcacc    2340
accgagccac ggacggtgtt gctctcgggc gccaacggct ggctgggccg gttcctcacg    2400
ttgcagtggc tggaacgcct ggcacctgtc ggcggcaccc tcatcacgat cgtgcgggc    2460 cgcgacgacg ccgcggcccg cgcacggctg acccaggcct acgacaccga tcccgagttg    2520
tcccgccgct tcgccgagct ggccgaccgc cacctgcggg tggtcgcggg tgacatcggc    2580
gacccgaatc tgggcctcac acccgagatc tggcaccggc tcgccgccga ggtcgacctg    2640 gtggtcatc cggcagcgct ggtcaaccac gtgctcccct accggcagct gttcggcccc    2700
aacgtcgtgg gcacggccga ggtgatcaag ctggccctca ccgaacggat caagcccgtc    2760
acgtacctgt ccaccgtgtc ggtggccatg gggatccccg acttcgagga ggacggcgac    2820
atccggaccg tgagcccggt gcgcccgctc gacggcggat acgccaacgg ctacggcaac    2880
agcaagtggg ccggcgaggt gctgctgcgg gaggcccacg atctgtgcgg gctgcccgtg    2940
gcgacgttcc gctcggacat gatcctggcg catccgcgct accgcggtca ggtcaacgtg    3000
ccagacatgt tcacgcgact cctgttgagc ctcttgatca ccggcgtcgc gccgcggtcg    3060
ttctacatcg gagacggtga gcgccgcgg gcgcactacc ccggcctgac ggtcgatttc    3120
gtggccgagg cggtcacgac gctcggcgcg cagcagcgcg agggatacgt gtcctacgac    3180
gtgatgaacc cgcacgacga cgggatctcc ctggatgtgt tcgtggactg gctgatccgg    3240
gcgggccatc cgatcgaccg ggtcgacgac tacgacgact gggtgcgtcg gttcgagacc    3300
gcgttgaccg cgcttcccga aagcgccgc gcacagaccg tactgccgct gctgcacgcg    3360
ttccgcgctc cgcaggcacc gttgcgcggc gcacccgaac ccacggaggt gttccacgcc    3420
gcggtgcgca ccgcgaaggt gggccccgga gacatcccgc acctcgacga ggcgctgatc    3480
gacaagtaca tacgcgatct gcgtgagttc ggtctgatct ga                        3522

<210> SEQ ID NO 86
<211> LENGTH: 1173
<212> TYPE: PRT
```

-continued

<213> ORGANISM: Mycobacterium smegmatis

<400> SEQUENCE: 86

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
                20                  25                  30

Asp Pro Glu Phe Ala Ala Ala Pro Leu Pro Ala Val Val Asp Ala
            35                  40                  45

Ala His Lys Pro Gly Leu Arg Leu Ala Glu Ile Leu Gln Thr Leu Phe
        50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
```

```
                    405                 410                 415
Gly Ala His Ile Val Asp Gly Tyr Gly Leu Thr Glu Thr Gly Ala Val
            420                 425                 430
Thr Arg Asp Gly Val Ile Val Arg Pro Val Ile Asp Tyr Lys Leu
            435                 440                 445
Ile Asp Val Pro Glu Leu Gly Tyr Phe Ser Thr Asp Lys Pro Tyr Pro
450                 455                 460
Arg Gly Glu Leu Leu Val Arg Ser Gln Thr Leu Thr Pro Gly Tyr Tyr
465                 470                 475                 480
Lys Arg Pro Glu Val Thr Ala Ser Val Phe Asp Arg Asp Gly Tyr Tyr
            485                 490                 495
His Thr Gly Asp Val Met Ala Glu Thr Ala Pro Asp His Leu Val Tyr
            500                 505                 510
Val Asp Arg Arg Asn Asn Val Leu Lys Leu Ala Gln Gly Glu Phe Val
            515                 520                 525
Ala Val Ala Asn Leu Glu Ala Val Phe Ser Gly Ala Ala Leu Val Arg
            530                 535                 540
Gln Ile Phe Val Tyr Gly Asn Ser Glu Arg Ser Phe Leu Leu Ala Val
545                 550                 555                 560
Val Val Pro Thr Pro Glu Ala Leu Glu Gln Tyr Asp Pro Ala Ala Leu
                565                 570                 575
Lys Ala Ala Leu Ala Asp Ser Leu Gln Arg Thr Ala Arg Asp Ala Glu
            580                 585                 590
Leu Gln Ser Tyr Glu Val Pro Ala Asp Phe Ile Val Glu Thr Glu Pro
            595                 600                 605
Phe Ser Ala Ala Asn Gly Leu Leu Ser Gly Val Gly Lys Leu Leu Arg
610                 615                 620
Pro Asn Leu Lys Asp Arg Tyr Gly Gln Arg Leu Glu Gln Met Tyr Ala
625                 630                 635                 640
Asp Ile Ala Ala Thr Gln Ala Asn Gln Leu Arg Glu Leu Arg Arg Ala
                645                 650                 655
Ala Ala Thr Gln Pro Val Ile Asp Thr Leu Thr Gln Ala Ala Ala Thr
                660                 665                 670
Ile Leu Gly Thr Gly Ser Glu Val Ala Ser Asp Ala His Phe Thr Asp
            675                 680                 685
Leu Gly Gly Asp Ser Leu Ser Ala Leu Thr Leu Ser Asn Leu Leu Ser
            690                 695                 700
Asp Phe Phe Gly Phe Glu Val Pro Val Gly Thr Ile Val Asn Pro Ala
705                 710                 715                 720
Thr Asn Leu Ala Gln Leu Ala Gln His Ile Glu Ala Gln Arg Thr Ala
                725                 730                 735
Gly Asp Arg Arg Pro Ser Phe Thr Thr Val His Gly Ala Asp Ala Thr
                740                 745                 750
Glu Ile Arg Ala Ser Glu Leu Thr Leu Asp Lys Phe Ile Asp Ala Glu
            755                 760                 765
Thr Leu Arg Ala Ala Pro Gly Leu Pro Lys Val Thr Thr Glu Pro Arg
            770                 775                 780
Thr Val Leu Leu Ser Gly Ala Asn Gly Trp Leu Gly Arg Phe Leu Thr
785                 790                 795                 800
Leu Gln Trp Leu Glu Arg Leu Ala Pro Val Gly Gly Thr Leu Ile Thr
                805                 810                 815
Ile Val Arg Gly Arg Asp Asp Ala Ala Ala Arg Ala Arg Leu Thr Gln
            820                 825                 830
```

```
Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
        915                 920                 925

Ala Met Gly Ile Pro Asp Phe Glu Glu Asp Gly Asp Ile Arg Thr Val
    930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
        995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 87
<211> LENGTH: 921
<212> TYPE: DNA
<213> ORGANISM: Nostoc punctiforme

<400> SEQUENCE: 87
atgactcaag cgaaagccaa aaaagaccac ggtgacgttc ctgttaacac ttaccgtccc      60
aatgctccat ttattggcaa ggtaatatct aatgaaccat tagtcaaaga aggtggtatt     120
ggtattgttc aacaccttaa atttgaccta tctggtgggg atttgaagta tatagaaggt     180
```

```
caaagtattg gcattattcc gccaggttta gacaagaacg gcaagcctga aaaactcaga    240
ctatattcca tcgcctcaac tcgtcatggt gatgatgtag atgataagac agtatcactg    300
tgcgtccgcc agttggagta caagcaccca gaaactggcg aaacagtcta cggtgtttgc    360
tctacgcacc tgtgtttcct caagccaggg aagaggtaaa aaattacagg gcctgtgggt    420
aaggaaatgt tgttacccaa tgaccctgat gctaatgtta tcatgatggc tactggaaca    480
ggtattgcgc cgatgcgggc ttacttgtgg cgtcagttta agatgcggaa agagcggct     540 aacccagaat accaatttaa aggattctct tggctaatat ttggcgtacc tacaactcca    600
aaccttttat ataaggaaga actggaagag attcaacaaa aatatcctga aacttccgc     660 ctaactgctg ccatcagccg cgaacagaaa aatccccaag gcggtagaat gtatattcaa    720
gaccgcgtag cagaacatgc tgatgaattg tggcagttga ttaaaaatga aaaaacccac    780
acttacattt gcggtttgcg cggtatggaa gaaggtattg atgcagcctt aactgctgct    840
gctgctaagg aaggcgtaac ctggagtgat taccagaagc aactcaagaa agccggtcgc    900
tggcacgtag aaacttacta a                                              921

<210> SEQ ID NO 88
<211> LENGTH: 437
<212> TYPE: PRT
<213> ORGANISM: Nostoc punctiforme

<400> SEQUENCE: 88

Met Tyr Asn Gln Gly Ala Val Glu Gly Ala Ala Asn Ile Glu Leu Gly
1               5                   10                  15

Ser Arg Ile Phe Val Tyr Glu Val Val Gly Leu Arg Gln Gly Glu Glu
            20                  25                  30

Thr Asp Gln Thr Asn Tyr Pro Ile Arg Lys Ser Gly Ser Val Phe Ile
        35                  40                  45

Arg Val Pro Tyr Asn Arg Met Asn Gln Glu Met Arg Arg Ile Thr Arg
    50                  55                  60

Leu Gly Gly Thr Ile Val Ser Ile Gln Pro Ile Thr Ala Leu Glu Pro
65                  70                  75                  80

Val Asn Gly Lys Ala Ser Phe Gly Asn Ala Thr Ser Val Val Ser Glu
                85                  90                  95

Leu Ala Lys Ser Gly Glu Thr Ala Asn Ser Glu Gly Asn Gly Lys Ala
            100                 105                 110

Thr Pro Val Asn Ala His Ser Ala Glu Glu Gln Asn Lys Asp Lys Lys
        115                 120                 125

Gly Asn Thr Met Thr Gln Ala Lys Ala Lys Lys Asp His Gly Asp Val
    130                 135                 140

Pro Val Asn Thr Tyr Arg Pro Asn Ala Pro Phe Ile Gly Lys Val Ile
145                 150                 155                 160

Ser Asn Glu Pro Leu Val Lys Glu Gly Gly Ile Gly Ile Val Gln His
                165                 170                 175

Leu Lys Phe Asp Leu Ser Gly Gly Asp Leu Lys Tyr Ile Glu Gly Gln
            180                 185                 190

Ser Ile Gly Ile Ile Pro Pro Gly Leu Asp Lys Asn Gly Lys Pro Glu
        195                 200                 205

Lys Leu Arg Leu Tyr Ser Ile Ala Ser Thr Arg His Gly Asp Asp Val
    210                 215                 220

Asp Asp Lys Thr Val Ser Leu Cys Val Arg Gln Leu Glu Tyr Lys His
225                 230                 235                 240

Pro Glu Thr Gly Glu Thr Val Tyr Gly Val Cys Ser Thr His Leu Cys
```

```
                        245                 250                 255
Phe Leu Lys Pro Gly Glu Glu Val Lys Ile Thr Gly Pro Val Gly Lys
                260                 265                 270

Glu Met Leu Leu Pro Asn Asp Pro Asp Ala Asn Val Ile Met Met Ala
            275                 280                 285

Thr Gly Thr Gly Ile Ala Pro Met Arg Ala Tyr Leu Trp Arg Gln Phe
        290                 295                 300

Lys Asp Ala Glu Arg Ala Ala Asn Pro Glu Tyr Gln Phe Lys Gly Phe
305                 310                 315                 320

Ser Trp Leu Ile Phe Gly Val Pro Thr Thr Pro Asn Leu Leu Tyr Lys
                325                 330                 335

Glu Glu Leu Glu Glu Ile Gln Gln Lys Tyr Pro Glu Asn Phe Arg Leu
            340                 345                 350

Thr Ala Ala Ile Ser Arg Glu Gln Lys Asn Pro Gln Gly Gly Arg Met
        355                 360                 365

Tyr Ile Gln Asp Arg Val Ala Glu His Ala Asp Glu Leu Trp Gln Leu
    370                 375                 380

Ile Lys Asn Glu Lys Thr His Thr Tyr Ile Cys Gly Leu Arg Gly Met
385                 390                 395                 400

Glu Glu Gly Ile Asp Ala Ala Leu Thr Ala Ala Ala Lys Glu Gly
                405                 410                 415

Val Thr Trp Ser Asp Tyr Gln Lys Gln Leu Lys Lys Ala Gly Arg Trp
            420                 425                 430

His Val Glu Thr Tyr
        435

<210> SEQ ID NO 89
<211> LENGTH: 300
<212> TYPE: DNA
<213> ORGANISM: Nostoc punctiforme

<400> SEQUENCE: 89
atgccaactt ataaagtgac actaattaac gaggctgaag ggctgaacac aacccttgat    60
gttgaggacg atacctatat tctagacgca gctgaagaag ctggtattga cctgccctac   120
tcttgccgcg ctggtgcttg ctctacttgt gcaggtaaac tcgtatcagg taccgtcgat   180
caaggcgatc aatcattctt agatgacgat caaatagaag ctggatatgt actgacctgt   240
gttgcttacc caacttctaa tgtcacgatc gaaactcaca agaagaaga actctattaa    300

<210> SEQ ID NO 90
<211> LENGTH: 99
<212> TYPE: PRT
<213> ORGANISM: Nostoc punctiforme

<400> SEQUENCE: 90

Met Pro Thr Tyr Lys Val Thr Leu Ile Asn Glu Ala Glu Gly Leu Asn
1               5                   10                  15

Thr Thr Leu Asp Val Glu Asp Asp Thr Tyr Ile Leu Asp Ala Ala Glu
            20                  25                  30

Glu Ala Gly Ile Asp Leu Pro Tyr Ser Cys Arg Ala Gly Ala Cys Ser
        35                  40                  45

Thr Cys Ala Gly Lys Leu Val Ser Gly Thr Val Asp Gln Gly Asp Gln
    50                  55                  60

Ser Phe Leu Asp Asp Gln Ile Glu Ala Gly Tyr Val Leu Thr Cys
65                  70                  75                  80

Val Ala Tyr Pro Thr Ser Asn Val Thr Ile Glu Thr His Lys Glu Glu
```

```
                 85                  90                  95

Glu Leu Tyr

<210> SEQ ID NO 91
<211> LENGTH: 369
<212> TYPE: DNA
<213> ORGANISM: Nostoc punctiforme

<400> SEQUENCE: 91
atgtcccgta catacacaat taaagttcgc gatcgcgcca ctggcaaaac acacaccta     60 aaagtgccag aagaccgtta tatcctgcac actgccgaaa acaaggtgt ggaactaccg    120 ttttcctgtc gcaacggagc ttgcaccgct tgtgctgtga gggtattgtc aggagaaatt    180
tatcaaccag aggcgatcgg attgtcacca gatttacgtc agcaaggtta tgccctgttg    240
tgtgtgagtt atccccgttc tgacttggaa gtagagacac aagacgaaga tgaagtctac    300
gaactccagt ttgggcgcta ttttgctaag gggaaagtta agcgggttt accgttagat    360 gaggaataa                                                            369

<210> SEQ ID NO 92
<211> LENGTH: 122
<212> TYPE: PRT
<213> ORGANISM: Nostoc punctiforme

<400> SEQUENCE: 92

Met Ser Arg Thr Tyr Thr Ile Lys Val Arg Asp Arg Ala Thr Gly Lys
1               5                   10                  15

Thr His Thr Leu Lys Val Pro Glu Asp Arg Tyr Ile Leu His Thr Ala
            20                  25                  30

Glu Lys Gln Gly Val Glu Leu Pro Phe Ser Cys Arg Asn Gly Ala Cys
        35                  40                  45

Thr Ala Cys Ala Val Arg Val Leu Ser Gly Glu Ile Tyr Gln Pro Glu
    50                  55                  60

Ala Ile Gly Leu Ser Pro Asp Leu Arg Gln Gln Gly Tyr Ala Leu Leu
65                  70                  75                  80

Cys Val Ser Tyr Pro Arg Ser Asp Leu Glu Val Glu Thr Gln Asp Glu
                85                  90                  95

Asp Glu Val Tyr Glu Leu Gln Phe Gly Arg Tyr Phe Ala Lys Gly Lys
            100                 105                 110

Val Lys Ala Gly Leu Pro Leu Asp Glu Glu
        115                 120

<210> SEQ ID NO 93
<211> LENGTH: 321
<212> TYPE: DNA
<213> ORGANISM: Nostoc punctiforme

<400> SEQUENCE: 93
atgcccaaaa cttacaccgt agaaatcgat catcaaggca aaattcatac cttgcaagtt     60
cctgaaaatg aaacgatctt atcagttgcc gatgctgctg gtttggaact gccgagttct    120
tgtaatgcag gtgtttgcac aacttgcgcc ggtcaaataa gccagggaac tgtggatcaa    180
actgatggca tgggcgttag tccagattta caaaagcaag ttacgtatt gctttgtgtt    240 gcgaaacccc tttctgattt gaaacttgaa acagaaaagg aagacatagt ttatcagtta    300
caatttggca aagacaaata a                                              321

<210> SEQ ID NO 94
```

```
<211> LENGTH: 106
<212> TYPE: PRT
<213> ORGANISM: Nostoc punctiforme

<400> SEQUENCE: 94

Met Pro Lys Thr Tyr Thr Val Glu Ile Asp His Gln Gly Lys Ile His
1               5                   10                  15

Thr Leu Gln Val Pro Glu Asn Glu Thr Ile Leu Ser Val Ala Asp Ala
                20                  25                  30

Ala Gly Leu Glu Leu Pro Ser Ser Cys Asn Ala Gly Val Cys Thr Thr
            35                  40                  45

Cys Ala Gly Gln Ile Ser Gln Gly Thr Val Asp Gln Thr Asp Gly Met
    50                  55                  60

Gly Val Ser Pro Asp Leu Gln Lys Gln Gly Tyr Val Leu Leu Cys Val
65                  70                  75                  80

Ala Lys Pro Leu Ser Asp Leu Lys Leu Glu Thr Glu Lys Glu Asp Ile
                85                  90                  95

Val Tyr Gln Leu Gln Phe Gly Lys Asp Lys
            100                 105

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgcggatccc ttgattctac tgcggcgagt                                      30

<210> SEQ ID NO 96
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cacgcaccta ggttcacact cccatggtat aacaggggcg ttggactcct gtg            53

<210> SEQ ID NO 97
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gttataccat gggagtgtga acctaggtgc gtggccgaca ggatagggcg tgt            53

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cgcggatcca acgcatcctc actagtcggg                                      30
```

```
<210> SEQ ID NO 99
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
catgccatgg aaagccacgt tgtgtctcaa aatctctg                              38

<210> SEQ ID NO 100
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctagtctaga gcgctgaggt ctgcctcgtg aa                                    32
```